US008680062B2

(12) United States Patent
Segev

(10) Patent No.: US 8,680,062 B2
(45) Date of Patent: Mar. 25, 2014

(54) SYSTEM FOR DELIVERING THERAPEUTIC AGENTS INTO LIVING CELLS AND CELLS NUCLEI

(75) Inventor: David Segev, Mazkeret Batia (IL)

(73) Assignee: Deliversir Ltd., Tel Aviv (IL)

( * ) Notice: Subject to any disclaimer, the term of this patent is extended or adjusted under 35 U.S.C. 154(b) by 1579 days.

(21) Appl. No.: 11/806,609

(22) Filed: Jun. 1, 2007

(65) Prior Publication Data
US 2008/0004234 A1 Jan. 3, 2008

Related U.S. Application Data

(63) Continuation-in-part of application No. 11/320,411, filed on Dec. 29, 2005, now abandoned, which is a continuation-in-part of application No. PCT/US2005/024443, filed on Jul. 6, 2005.

(60) Provisional application No. 60/585,075, filed on Jul. 6, 2004, provisional application No. 60/809,827, filed on Jun. 1, 2006.

(51) Int. Cl.
*C12N 15/11* (2006.01)
*C07H 19/00* (2006.01)
*C07H 21/00* (2006.01)
*C07H 21/02* (2006.01)
*C07H 21/04* (2006.01)

(52) U.S. Cl.
USPC .................. 514/44 R; 536/22.1; 536/23.1

(58) Field of Classification Search
None
See application file for complete search history.

(56) References Cited

U.S. PATENT DOCUMENTS

| | | | |
|---|---|---|---|
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,899,481 A * | 8/1975 | Butti et al. | 536/25.4 |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,666,828 A | 5/1987 | Gusella | |
| 4,683,202 A | 7/1987 | Mullis | |
| 4,801,531 A | 1/1989 | Frossard | |
| 4,873,316 A | 10/1989 | Meade et al. | |
| 4,879,219 A | 11/1989 | Wands et al. | |
| 5,011,771 A | 4/1991 | Bellet et al. | |
| 5,013,830 A | 5/1991 | Ohtsuka et al. | |
| 5,149,797 A | 9/1992 | Pederson et al. | |
| 5,192,659 A | 3/1993 | Simons | |
| 5,220,007 A | 6/1993 | Pederson et al. | |
| 5,225,182 A * | 7/1993 | Sharma | 424/93.71 |
| 5,256,775 A | 10/1993 | Froehler | |
| 5,272,057 A | 12/1993 | Smulson et al. | |
| 5,281,521 A | 1/1994 | Trojanowski et al. | |
| 5,366,878 A | 11/1994 | Pederson et al. | |
| 5,403,711 A | 4/1995 | Walder et al. | |
| 5,491,133 A | 2/1996 | Walder et al. | |
| 5,565,350 A | 10/1996 | Kmiec | |
| 5,571,677 A * | 11/1996 | Gryaznov | 435/6 |
| 5,623,065 A | 4/1997 | Cook et al. | |
| 5,652,355 A | 7/1997 | Metelev et al. | |
| 5,652,356 A | 7/1997 | Agrawal | |
| 5,700,922 A | 12/1997 | Cook | |
| 6,287,335 B1 | 9/2001 | Drasler et al. | |
| 7,169,814 B2 | 1/2007 | Rothbard et al. | |
| 2006/0160763 A1 | 7/2006 | Segev | |
| 2008/0004234 A1 | 1/2008 | Segev | |

FOREIGN PATENT DOCUMENTS

| | | |
|---|---|---|
| WO | WO 99/32619 | 7/1999 |
| WO | WO 99/53050 | 10/1999 |
| WO | WO 03/049772 | 6/2003 |
| WO | WO 2005/123676 | 12/2005 |
| WO | WO 2006/010084 | 1/2006 |

OTHER PUBLICATIONS

International Search and the Written Opinion Dated Mar. 8, 2006 From the International Searching Authority Re. Application No. PCT/UA2005/024443.
International Preliminary Report on Patentability Dated Jan. 18, 2007 From the International Bureau of WIPO Re.: Application No. PCT/US2005/024443.
Official Action Dated Jun. 11, 2008 From the US Patent and Trademark Office Re.: U.S. Appl. No. 11/320,411.
Alpha-Bazin et al. "Europium Cryptate Labeled Deoxyuridine-Triphosphate Analog: Synthesis and Enzymatic Incorporation", Nucleosides, Nucleotides & Nucleic Acids, 19(9): 1463-1474, 2000. Fig. 1.
Baneiji et al. "A Lymphocyte-Specific Cellular Enhancer Is Located Downstream of the Joining Region in Immunoglobulin Heavy Chain Genes", Cell, 33: 729-740, 1983.
Battersby et al. "Quantitative Analysis of Receptors for Adenosine Nucleotides Obtained Via In Vitro From a Library Incorporating a Cationic Nucleotide Analog", Journal of the American Chemical Society, 121(42): 9781-9789, 1999. p. 9788, col. 2, Line 15.

(Continued)

*Primary Examiner* — Cecilia J Tsang
*Assistant Examiner* — Zachary J Miknis
(74) *Attorney, Agent, or Firm* — Pearl Cohen Zedek Latzer Baratz LLP

(57) ABSTRACT

A novel class of oligomeric compounds designed for forming conjugates with biologically active substances and delivering these substances to a desired bodily target are disclosed. Novel conjugates of these oligomeric compounds and biologically active moieties, pharmaceutical compositions containing such conjugates, and uses thereof as delivery systems for delivering the biologically active substances to a desired target are further disclosed. Processes of preparing the conjugates and the oligomeric compounds and novel intermediates designed for and used in these processes are also disclosed.

26 Claims, 15 Drawing Sheets
(9 of 15 Drawing Sheet(s) Filed in Color)

(56) References Cited

OTHER PUBLICATIONS

Byrne et al. "Multiplex Gene Regulation: A Two-Tiered Approach to Transgene Regulation in Transgenic Mice", Proc. Natl. Acad. Sci. USA, 86: 5473-5477, 1989.

Dezhurov et al. "A Comparative Study of the Modification Efficiency of DNA Polymerases and DNA Template by the DNA Primers With Various Photoreactive Groups at Their 3'-Termini", Russian Journal of Bioorganic Chemistry, 29(1): 6672, 2003. p. 67, col. 2.

Di Giusto et al. "Multipotential Electrochemical Detection of Primer Extension Reactions on DNA Self-Assembled Monolayers", Journal of the American Chemical Society, 126(13): 4120-4121, 2004. Fig. 1.

Drachkova et al. "Reagents for Modification of Protein-Nucleic Acid Complexes: II. Site-Specific Photomodification of Mammalian DNA Polymerase β Complexes With Primers Extended by dCTP Exo-N-Substituted Arylazido Derivatives", Russian Journal of Bioorganic Chemistry, 27(3): 173-179, 2001. p. 173-174.

Edlund et al. "Cell-Specific Expression of the Rat Insulin Gene: Evidence for Role of Two Distinct 5$5$^ {\Prime}$ Flanking Elements", Science, 230(4728): 912-916, 1985.

Elbashir et al. "Duplexes of 21—Nucleotide RNAs Mediate RNA Interference in Cultured Mammalian Cells", Nature, 411: 494-498; 2001.

Feigner et al. "Lipofection: A Highly Efficient, Lipid-Mediated DNA-Transfection Procedure", Proc. Natl. Acad. Sci. USA, 84: 7413-7417, 1987.

Hinz et al. "Synthesis and Properties of 2'-Deoxycytidine Triphosphate Carrying c-myc Tag Sequence", Nucleosides, Nucleotides & Nucleic Acids, 19(10-12): 1543-1552, 2000. Chart 1.

Hutvágner et al. "RNAi: Nature Abhors A Double-Strand", Current Opinion in Genetics & Development, 12: 225-232, 2002.

Iverson et al. "Nonenzymatic Sequence-Specific Cleavage of Single-Stranded DNA to Nucleotide Resolution. DNA Methyl Thioether Probes", Journal of the American Chemical Society, 109(4): 1241-1243, 1987. Fig.1.

Jansons et al. "$N^2$-(p-n-Octylphenyl)dGTP: Synthesis and Inhibitory Activity Against DNA Polymerases", Nucleosides & Nucleotides, 15(1-3): 669-682, 1996. Scheme on p. 672.

Kolpashchnikov et al. "New Reagents for Directed Modification of Biopolymers: Photoaffinity Modification of Tte DNA Polymerase", Russian Journal of Bioorganic Chemistry, 25(2): 110-117, 1999. Scheme on p. 111.

Korshunova et al. "Trifluoromethyldiazirine-Containing dUTP: Synthesis and Application in DNA/Protein Crosslinking", Nucleosides & Nucleotides, 18(4&5): 1097-1098, 1999.

Kuwahara et al. "Substrate Properties of C5-Substituted Pyrimidine 2'- Deoxynucleoside 5'-Triphosphates for Thermostable DNA Polymerases During PCR", Bioorganic & Medicinal Chemistry Letters, 13(21): 3735-3738, 2003. Scheme 1, Fig. 1.

Lee et al. "Enhancing the Catalytic Repertoire of Nucleic Acids: A Systematic Study of Linker Length and Rigidity", Nucleic Acids Research, 29(7): 1565-1573, 2001. Fig.2.

Lohmann et al. "Silencing of Developmental Genes in Hydra", Developmental Biology, 214: 211-214,1999. Online: www.idealibrary.com.

Mishell et al. "Selected Methods in Cellular Immunology", Freeman & Co., p. I-XIV, 1980.

Obayashi et al. "Enzymatic Synthesis of Labeled DNA by PCR Using New Fluorescent Thymidine Nucleotide Analogue and Superthermophilic KOD Dash DNA Polymerase", Bioorganic & Medicinal Chemistry Letters, 12(8): 1167-1170, 2002. Compounds 1-4.

Pauly et al. "Template-Dependent Incorporation of Spin-Labeled Thymidine Analogs Into Viral DNA", Helvetica Chimica Acta, 72(1): 110-116, 1989. Scheme on p. 111.

Perrin et al. "Bridging the Gap Between Proteins and Nucleic Acids: A Metal-Independent RNAseA Mimic With Two Protein-Like Functionalities", Journal of the American Chemical Society, 123(8): 1556-1563, 2001. Fig. 1.

Pinkert et al. "An Albumin Enhancer Located 10 KB Upstream Functions Along With Its Promoter to Direct Efficient, Liver-Specific Expression in Transgenic Mice", Genes & Development, 1: 268-276, 1987.

Rodríguez-Tanty et al. "Synthesis of a New 5'-0-Triphosphate Analog of 5-Methyl 2'-0-Deoxycytidine. Preliminary In Vitro Labeling for Non-Radioactive Detection of DNA", Nucleosides, Nucleotides & Nucleic Acids, 20(8): 1449-1461, 2001. Scheme 1.

Roychowdhury et al. "2'-Deoxycytidines Carrying Amino and Thiol Functionality: Synthesis and Incorporation by Vent (Exo-) Polymerase", Organic Letters, 6(4): 489-492, 2004. Compounds 18 & 19.

Ruth "Chemical Synthesis of Non-Radioactively-Labeled DNA Hybridization Probes", Fourth Annual Congress for Recombinant DNA Research, 3: 123, 1984.

Safronov et al. "New Photoreactive N4-Substituted dCTP Analogues: Preparation, Photochemical Characteristics, and Substrate Properties in HIV-1 Reverse Transcriptase-Catalyzed DNA Synthesis", Russian Journal of Bioorganic Chemistry, 23(7): 531-539, 1997. Scheme on p. 532.

Sakthivel et al. "Expanding the Potential of DNA for Binding and Catalysis: Highly Functionalized dUTP Derivatives That Are Substrates for Thermostable DNA Polymerases", Angewandte Chemie, Internationale Edition, 37(20): 2872-2875, 1998. Scheme 2.

Sarfati et al. "New Fluorescent and Photoactivable Analogs Acting on Nucleotide Binding Enzymes", Tetrahedron Letters, 32(36): 4699-4702, 1991. Compounds 6 & 7.

Sarfati et al. "Synthesis of Fluoresceinylated 2'-Deoxyadenosine. Mono, Di and Triphosphate Derivatives", Tetrahedron Letters, 31(18): 2581-2584, 1990. p. 2583.

Sarfati et al. "Synthesis of Fluorescent of Biotinylated Nucleoside Compounds", Tetrahedron, 43(15): 3491-3498, 1987. Compounds 15 & 16.

Sarfati et al. "Synthesis of Uridine and 2'-Deoxyuridine Mono- and Tri-Phosphates Alkylated in Position 5 by Glycosides of α-D-Mannose and N-Acetyl-β-D-Glucosamine: DNA and RNA Monomers With Tethered Lectin Targets", Journal of the Chemical Society Perkin Transactions I, 4: 1065-1070, 1990. p. 1066, Compounds 19, 20, 21.

Smith et al. "The Challenges of Genome Sequence Annotation or 'The Devil is in the Details'", Nature Biotechnology, 15: 1222-1223, 1997.

Suto et al. "Synthesis of γ-Phosphate-Linked Nucleoside Affinity Chromatography Resins for Protein Purification, Including Ribonucleoside Triphosphate Reductase", Nucleosides & Nucleotides, 17(8): 1453-1471, 1998. Fig.3.

Toppin et al. "Three Novel Spin-Labeled Substrates for Enzymatic Incorporation Into Nucleic Acid Lattices", Helvetica Chimica Acta, 69(2): 345-349, 1986. Schemes 2 & 3.

Wagner et al. "Transferrin-Polycation Conjugates as Carriers for DNA Uptake Into Cells", Proc. Natl. Acad. Sci. USA, 87(9): 3410-3414, 1990.

Wender et al. "The Design, Synthesis, and Evaluation of Molecules That Enable or Enhance Cellular Uptake: Peptoid Molecular Transporters", Proc. Natl. Acad. Sci. USA, 97(24): 13003-13008, 2000. Scheme 1, in Particular.

Winoto et al. "A Novel, inducible and T Cell-Specific Enhancer Located at the 3' End of the T Cell Receptor α Locus", The EMBO Journal, 8(3): 729-733, 1989.

Wright et al. "Synthesis and Characterization of $N^2$-(p-n-Butylphenyl)-2'- Deoxyguanosine and Its 5'-Triphosphate and Their Inhibition of HeLa DNA Polymerase α", Journal of Medicinal Chemistry, 27(2): 175-181, 1984. p. 180, Compound 19.

* cited by examiner

SYSTEM FOR DELIVERING THERAPEUTIC AGENTS INTO LIVING CELLS AND CELLS NUCLEI

This application is a continuation-in-part of U.S. patent application Ser. No. 11/320,411 filed Dec. 29, 2005, which is a continuation-in-part of PCT Patent Application No. PCT/US2005/024443 filed Jul. 6, 2005, which claims the benefit of U.S. Provisional Patent Application No. 60/585,075 filed Jul. 6, 2004.

This application also claims the benefit of U.S. Provisional Patent Application No. 60/809,827 filed Jun. 1, 2006.

The teachings of all of the above Patent Applications are incorporated herein by reference in their entirety.

FIELD AND BACKGROUND OF THE INVENTION

The present invention relates to a novel delivery system for delivering therapeutic agents into living cells, and more particularly, to novel chemical moieties that are designed capable of targeting and/or penetrating cells or other targets of interest and further capable of binding therapeutic agents to be delivered to these cells, and to delivery systems containing same.

All known life forms and life processes are based on proteins which are essential to all biological functions. Consequently, all the illnesses and disorders associated with life involve proteins. Among many other functions, proteins play a key role in signaling pathways of immunological and/or neurological processes and are thus major players in many congenital, chronic and infectious diseases and disorders.

As such, proteins exhibit highly potent therapeutic efficacy. Indeed, proteins have already been used successfully in the treatment of diseases such as cancer, hemophilia, anemia and diabetes.

However, although proteins have enormous therapeutic potential, their widespread use has been limited by several restrictive technical factors. First, proteins remain difficult and expensive to manufacture compared to other pharmaceuticals. Large-scale purification of proteins in bioactive form can be a limiting step in the commercialization of these drugs. Second, many proteins are metabolized or otherwise eliminated rapidly in the body. This results in the need for frequent re-administration, which may also prove to be inefficient when the administered protein fails to reach its intended target due to many delivery related factors. Finally, protein drugs generally must be given by injection which increases the complexity and expense of the treatment, and the disagreeable nature of administration also limits potential clinical applications.

The identification of defective genes responsible for disease states, either through defective control of gene expression which leads to overproduction or underproduction of key proteins, or the production of defective proteins, offers new possibilities for the treatment of disease. By controlling the defect at the genetic level, a range of diseases could potentially be treated effectively rather than by merely treating the symptoms of these diseases.

The use of genetic material to deliver genes for therapeutic purposes has been practiced for many years. Experiments outlining the transfer of DNA into cells of living animals were reported as early as 1950. Later experiments using purified genetic material only further confirmed that the direct DNA gene injection, even in the absence of viral vectors results in the expression of the inoculated genes in the host. There have been additional experiments that extend these findings to recombinant DNA molecules, further illustrating the idea that purified nucleic acids could be directly delivered into a host and proteins would be produced.

Generation of therapeutic gene products (such as polypeptides, proteins, mRNA and RNAi) by expression of therapeutic gene product-encoding DNA in transformed cells has attracted wide attention as a method to treat various mammalian diseases and enhance production of specific proteins or other cellular products. This promising technology, often referred to as gene therapy (Crystal et al., Science 1995, 270, 404 and Rhang et al., *Human Gene Therapy*, 1999, 10:1735-1737), is generally accomplished by introducing exogenous genetic material into a mammalian patient's cells. Transformed cells can be accomplished by either direct transformation of target cells within the mammalian subject (in vivo gene therapy) or transformation of cells in vitro and subsequent implantation of the transformed cells into the mammalian subject (ex vivo gene therapy) (for reviews, see Chang et al. 1994 *Gastroenterol*. 106:1076-84; Morsy et al. 1993 *JAMA* 270:2338-45; and Ledley 1992 *J. Pediatr. Gastroenterol. Nutr.* 14:328-37). The introduced genetic material can be designed to replace an abnormal (defective) gene of the mammalian patient ("gene replacement therapy"), or can be designed for expression of the encoded protein or other therapeutic product without replacement of any defective gene ("gene augmentation"). Because many congenital and acquired medical disorders result from inadequate production of various gene products, gene therapy provides means to treat these diseases through either transient or stable expression of exogenous nucleic acid encoding the therapeutic product.

Although the initial motivation for gene therapy was the treatment of genetic disorders, it is becoming increasingly apparent that gene therapy will be useful for the treatment of a broader range of acquired diseases such as cancer, infectious disorders (such as AIDS), heart disease, arthritis, and neurodegenerative disorders such as Parkinson's and Alzheimer's diseases.

In addition to gene therapy, other therapeutic approaches at the DNA level are known. These include, for example, gene vaccination and antisense oligonucleotide therapy.

In 1992, scientists Tang and DeVit [Tang, D. C., M. DeVit, et al., 1992, *Nature*, 356(6365): 152-4] reported that the delivery of human growth hormone in a gene expression cassette in vivo resulted in production of detectable levels of the growth hormone in host mice. They also found that these inoculated mice developed antibodies against the human growth hormone; they termed this immunization procedure "genetic immunization", which describes the ability of inoculated genes to be individual immunogens. From this seminal work stemmed the concept of gene vaccination, which is based on bacterial expression plasmids. Expression plasmids used in DNA-based vaccination normally contain the antigen expression unit composed of promoter/enhancer sequences, followed by antigen-encoding and polyadenylation sequences and the production unit composed of bacterial sequences necessary for plasmid amplification and selection [Schirmbeck, R. et al., 2001, *Biol. Chem.*, 382:543-552]. The construction of bacterial plasmids with vaccine inserts is accomplished using recombinant DNA technology. Once constructed, mass-produced in bacteria and purified, the DNA acts as the vaccine. More information regarding gene vaccination can be found in many publications such as, for example, by Koprowski, H. and Weiner, D. B., 1998, "DNA Vaccination and Genetic Vaccination", Spriner-Verlag, Heidelberg, p 198.

The emerging concept of "antisense therapy" focuses on defeating diseases before the proteins which cause them can even be formed. The production of these faulty proteins begins in the cellular DNA. In the nucleus the DNA forms pre-mRNA, which leaves the nucleus to enter the cytoplasm, interacts with the ribosome and translated into the protein. DNA is termed "antisense" when its base sequence is complementary to the gene's messenger RNA, for example a "sense-DNA" segment of 5'-AAGGTC-3' corresponds to the "antisense-DNA" segment 3'-TTCCAG-5'. While many traditional drugs attempt to defeat the diseases by focusing on the faulty proteins themselves, antisense therapy goes a step further, by preventing the production of these incorrect proteins. The prevention or attenuation of the disease-causing gene expression is accomplished by insertion of the antisense DNA of the disease-producing gene into the cell's cytoplasm, wherein instead of being translated by the ribosome, the disease-producing mRNA hybridizes with the strand of antisense DNA and instead of producing proteins, the faulty mRNA is negated by the antisense oligonucleotide.

DNA is inherently an unstable material in an active biological environment where many specific enzymes capable of degrading and metabolizing DNA are found (Ledoux et al., *Prog. Nucl. Acid. Res.*, 1965, 4, 231). In addition, natural protection against alien DNA exists in the body. Thus, the gene therapy, antisense oligonucleotide therapy and gene vaccination approaches described above require that the DNA and DNA analogues would survive in such a hostile biological environment and in addition, that the DNA and DNA analogs would penetrate biological barriers, be taken up into cells and be delivered to the correct subcellular compartment to exert their therapeutic effects. While some DNA is taken up naturally into cells, the amount taken up is typically small and inconsistent, and expression of added DNA is therefore poor and unpredictable.

A number of strategies have been proposed to achieve delivery of DNA into living cells. These include the use of liposomes (Fraley et al., *Proc. Natl. Acad. Sci. USA*, 1979, 76, 3348), cationic lipids (Felgner et al., *Proc. Natl. Acad. Sci USA*, 1987, 84, 7413), and the use of cationic polymers, or polycations, such as polylysine and polyornithine as DNA delivery agents (Farber et al., *Biochim. Biophys. Acta*, 1975, 390, 298 and Wagner et al., *Proc. Natl. Acad. Sci. USA*, 1990, 87, 3410).

Unfortunately cationic polymers which have been used for the purpose of DNA delivery were found deficient in a number of respects. Poly-L-lysine, the principal polymer presently used for this purpose, is known to be toxic above a small molecular weight (Clarenc et al., *Anticancer Drug Design*, 1993, 8, 81), and does not interact stoichiometrically with DNA, leading to an unstable and unreliable complex with DNA.

An alternative for genetic augmentation and therapy using DNA manipulation is the use of RNA molecules, a relatively new concept which has received increasing attention during the past decade. Most genes function by expressing a protein via an intermediate, termed messenger RNA (mRNA), or sense RNA. Therefore, the ability to specifically knock-down expression of a gene of interest, e.g., by complementary mRNA agents, is recognized as powerful tool for regulation of gene expression (Green & Pines, *Annu. Rev. Biochem.*, 1986, 55, 569-597). These complementary RNA molecules, termed antisense RNA molecules, or small interfering RNA (siRNA), specifically recognize their target transcripts (mRNA) by forming base-paired strands with the mRNA in a sequence-dependent manner. The formation of an RNA duplex interferes with the translation of the mRNA into a protein by the ribosome, and further leads to the degradation of the target mRNA by naturally occurring cellular enzymes which target duplex RNA molecules (Hamilton & Baulcombe, *Science*, 1999, 286:950-952). This phenomenon, also known as gene silencing or RNA interference (RNAi) has been reported to be accompanied by the accumulation of short fragments of double stranded siRNAs, 20-25 nucleotides long, which are reported to be synthesized from an RNA template (Fire et al., *Nature*, 1998, 391:806-811; Timmons & Fire, *Nature*, 1998, 395:854; WO99/32619; Kennerdell & Carthew, *Cell*, 1998, 95:1017-1026; Ngo et al., *Proc. Natl. Acad. Sci. USA*, 1998, 95:14687-14692; Waterhouse et al., *Proc. Natl. Acad. Sci. USA*, 1998, 95:13959-13964; WO99/53050; Cogoni & Macino, *Nature*, 1999, 399:166-169; Lohmann et al., *Dev. Biol.*, 1999, 214:211-214; Sanchez-Alvarado & Newmark, *Proc. Natl. Acad. Sci. USA*, 1999, 96:5049-5054; and Elbashir et al., *Nature*, 2001, 411:494-29).

Nevertheless, the use of siRNA for gene silencing also suffers from major drawbacks, which mainly stem from the inherent instability of RNA molecules in a biological environment, and which impede its delivery into cells. Thus, the delivery of intact siRNA molecules into a cell, and more so into the desired cells, is limited by the rapid breakdown of the RNA in the bloodstream, by poor absorption of RNA through the membranes of mammalian cells, and further by the breakdown of the RNA down inside the cell by RNAse enzymes and other scavenger proteins.

In a search for a genetic material delivery platform, researchers have turned their attention to one of nature's most efficient DNA/RNA delivery machines—the viruses. Viruses are known for their ability to be extremely efficient in delivering genes to the particular cells that are required for the survival and progression of the viral species (Smith, *Annual. Rev. Microbiol.*, 1995, 49:807-838). Indeed, studies aimed at understanding the molecular mechanisms in which the viral genetic code is integrated into the cell has paved the path for viral based gene delivery platforms (Wei et al., *J. Virol.*, 1981, 39: 935-944). Yet, an optimal synthetic virus which does not involve serious health-related side effect has not been designed yet.

In order to overcome the obstacle of the rapid and efficient DNA/RNA degradation by scavenging enzymes, one of the impedances on the path to genetic therapy, researches have attempted to generate DNA/RNA derivatives which will be less susceptible to degradation yet still active as a coding sequence, via the manipulation and modification of nucleotides (for example, Draper, *Nucleic Acids Res.*, 1984, 12(2): 989-1002 and Freier and Altmann, *Nucleic Acids Res.*, 1997, 25(22): 4429-43). Yet, these DNA/RNA analogs based on chemically modified nucleotides and nucleotide-mimicking compounds are typically found toxic or otherwise unpredictable and therefore therapeutically unusable, and are mostly used for in vitro research purposes.

Thus, although therapeutic approaches that involve intervention at the gene level are widely recognized as promising technologies, these methods are limited by the absence of an efficient and reliable method of delivering DNA and RNA.

There is thus a widely recognized need for, and it would be highly advantageous to have, a novel delivery system for delivering therapeutic agents such as DNA and RNA molecules into living cells, which would overcome the present limitations associated with gene therapy.

SUMMARY OF THE INVENTION

According to one aspect of the present invention there is provided an oligomeric compound having the general Formula I:

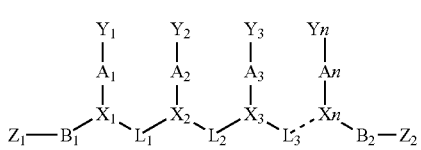

Formula I wherein:

n is an integer from 3 to 20, preferably from 6 to 12;

each of $X_1$-$X_n$ is independently a residue of a building block of the oligomer;

each of $L_1$-$L_n$ is independently a first linking group or absent;

each of $A_1$-$A_n$ is independently a second linking group or absent;

each of $Y_1$-$Y_n$ is independently a delivering group or absent, provided that at least one of $Y_1$-$Y_n$ is the delivering group;

each of $B_1$ and $B_2$ is independently a spacer or absent; and each of $Z_1$ and $Z_2$ is independently a reactive group capable of binding a biologically active moiety or absent, provided that at least one of $Z_1$ and $Z_2$ is the reactive group.

According to further features in preferred embodiments of the invention described below, the building blocks ($X_1$-$X_n$) and the linking moieties form together an oligomer of a polyether.

According to still further features in the described preferred embodiments at least one of said building blocks ($X_1$-$X_n$) comprises a -D-(CR'R'')mCR(CR'''R'''')l-F— group, whereas: D and F are each independently selected from the group consisting of nitrogen, oxygen, and sulfur; m and l are each independently an integer from 1 to 6; and R, R', R'', R''' and R'''' are each independently selected from the group consisting of hydrogen, alkyl, cycloalkyl and aryl. Preferably m and l are each 1. Further preferably R, R', R'', R''' and R'''' are each hydrogen.

According to still further features in the described preferred embodiments each of said building blocks ($X_1$-$X_n$) is said -D-(CR'R'')mCR(CR'''R'''')l-F— group.

According to still further features in the described preferred embodiments each of said first and said second linking moieties is independently selected from the group consisting of a substituted or unsubstituted hydrocarbon chain and a substituted or unsubstituted hydrocarbon chain interrupted by at least one heteroatom, said heteroatom being selected from the group consisting of oxygen, nitrogen and sulfur.

According to still further features in the described preferred embodiments each of said first linking moieties is independently a substituted or unsubstituted hydrocarbon chain.

Preferably, each of said first linking moieties is methylene ($CH_2$).

According to still further features in the described preferred embodiments each of said residues of said building block ($X_1$-$X_n$) is said -D-CR—(CR'R'')m-F— group; and each of said first and said second linking moieties is independently selected from the group consisting of a substituted or unsubstituted hydrocarbon chain and a substituted or unsubstituted hydrocarbon chain interrupted by at least one heteroatom, said heteroatom being selected from the group consisting of oxygen, nitrogen and sulfur.

According to still further features in the described preferred embodiments at least one, and preferably each, of the residues of the building block X1-Xn is selected from the group consisting of a -D-CR—(CR'R'')m-F— group, a -E-(CR'R'')m-C(=D)- and any combination thereof, wherein:

D, E and F are each independently selected from the group consisting of nitrogen, oxygen, and sulfur;

m is an integer from 1 to 6; and

R, R' and R'' are each independently selected from the group consisting of hydrogen, alkyl, cycloalkyl and aryl.

According to still further features in the described preferred embodiments at least one, and preferably each, each of the residues of the building block ($X_1$-$X_n$) independently comprises a phosphorous-containing residue.

According to still further features in the described preferred embodiments the phosphorous-containing residue is selected from the group consisting of a phosphate-containing residue and a phosphonate-containing residue.

According to still further features in the described preferred embodiments each of the residues of the building blocks is independently a -J-O—P(=O)(Ra)—O— group, whereas J is selected from the group consisting of alkyl, cycloalkyl, aryl, and ether and Ra is selected from the group consisting of hydrogen, hydroxy, alkoxy, aryloxy, alkyl, aryl and cycloalkyl. According to still further features in the described preferred embodiments the at least one delivering group is attached to the J.

According to still further features in the described preferred embodiments each of $X_1$-$X_n$ is a nucleotide.

According to still further features in the described preferred embodiments at least one of the nucleotides is a modified nucleotide having the delivering group attached thereto.

According to still further features in the described preferred embodiments each of the first and second linking moieties is independently selected from the group consisting of a substituted or unsubstituted hydrocarbon chain and a substituted or unsubstituted hydrocarbon chain interrupted by at least one heteroatom, the heteroatom being selected from the group consisting of oxygen, nitrogen and sulfur.

According to still further features in the described preferred embodiments the hydrocarbon chain comprises from 2 to 20 carbon atoms, preferably from 4 to 10 carbon atoms.

According to still further features in the described preferred embodiments each of $B_1$ and $B_2$ is independently selected from the group consisting of a substituted or unsubstituted hydrocarbon chain and a substituted or unsubstituted hydrocarbon chain interrupted by at least one heteroatom, the heteroatom being selected from the group consisting of oxygen, nitrogen and sulfur.

According to still further features in the described preferred embodiments the hydrocarbon chain comprises from 2 to 6 carbon atoms.

According to still further features in the described preferred embodiments the compound comprises at least four delivering groups.

According to still further features in the described preferred embodiments each of the delivering groups is independently selected from the group consisting of a membrane-permeable group, a ligand, an antibody, an antigen, a substrate, and an inhibitor.

According to still further features in the described preferred embodiments the membrane-permeable group comprises at least one positively charged group.

According to still further features in the described preferred embodiments the positively charged group is selected from the group consisting of amine, guanidine, and imidazole.

According to still further features in the described preferred embodiments each of $Z_1$ and $Z_2$ is independently selected from the group consisting of hydroxy, amine, halide, a phosphorous-containing group, amide, carboxy, thiol, thioamide, thiocarboxy, alkoxy, thioalkoxy, aryloxy, thioaryloxy, hydrazine, hydrazide, and phosphoramidite.

According to still further features in the described preferred embodiments at least one of the reactive groups is a protected reactive group.

According to still further features in the described preferred embodiments the biologically active moiety is selected from the group consisting of a therapeutically active agent, a labeling moiety, and any combination thereof.

According to still further features in the described preferred embodiments the therapeutically active agent is selected from the group consisting of an oligonucleotide, a nucleic acid construct, an antisense, a plasmid, a polynucleotide, an amino acid, a peptide, a polypeptide, a hormone, a steroid, an antibody, an antigen, a radioisotope, a chemotherapeutic agent, a toxin, an anti-inflammatory agent, a growth factor and any combination thereof.

According to still further features in the described preferred embodiments the labeling moiety is selected from the group consisting of a fluorescent moiety, a radiolabeled moiety, a phosphorescent moiety, a heavy metal cluster moiety and any combination thereof.

According to another aspect of the present invention there is provided a conjugate comprising at least one delivery moiety and at least one biologically active moiety being linked thereto, the delivery moiety being an oligomeric compound having the general Formula II:

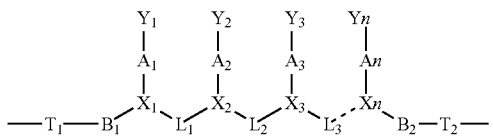

Formula II wherein:

n is an integer from 4 to 20;

each of X1-Xn is independently a residue of a building block of the oligomer;

each of L1-Ln is independently a first linking group or absent;

each of A1-An is independently a second linking group or absent;

each of Y1-Yn is independently a delivering group or absent, provided that at least one of Y1-Yn is the delivering group;

each of B1 and B2 is independently a spacer or absent; and each of T1 and T2 is independently a binding group binding the biologically active moiety or absent, at least one of the T1 and T2 being the binding group.

$X_1$-Xn, $Y_1$-Yn, $A_1$-An, $T_1$-Tn and $B_1$-Bn are as described hereinabove.

According to further features in preferred embodiments of the invention described below, the conjugate comprises at least one delivery moiety and at least two biologically active moieties being linked thereto via the binding groups.

According to still further features in the described preferred embodiments the conjugate comprises at least two delivery moieties and at least two biologically active moieties being linked thereto via the binding groups.

According to still further features in the described preferred embodiments each of the at least two biologically active moieties is attached to each of the at least two delivery moieties via the binding groups.

According to still further features in the described preferred embodiments at least one of the at least two biologically active moieties is an oligonucleotide.

According to still further features in the described preferred embodiments at least one of the at least two biologically active moieties is a second oligonucleotide being capable of hybridizing the oligonucleotide.

According to still further features in the described preferred embodiments the second oligonucleotide is hybridized to the oligonucleotide.

According to still further features in the described preferred embodiments the at least one biologically active moiety comprises at least one modified oligonucleotide, the modified oligonucleotide having at least one protecting group attached thereto.

According to still further features in the described preferred embodiments the at least one protecting group is a positively charged group.

According to still further features in the described preferred embodiments at least one of the biologically active moieties comprises a labeling moiety.

According to still another aspect of the present invention there is provided a method of delivering a biologically active moiety to a cell, comprising:

contacting the cell with the conjugate described herein, thereby delivering the biologically active moiety to the cell.

According to further features in preferred embodiments of the invention described below, contacting the cell is effected ex-vivo.

According to still further features in the described preferred embodiments contacting the cell is effected in-vivo.

According to still further features in the described preferred embodiments the delivering comprises delivering the biologically active moiety into the cell.

According to yet another aspect of the present invention there is provided a pharmaceutical composition comprising the conjugate described herein and a pharmaceutically acceptable carrier.

According to further features in preferred embodiments of the invention described below, the pharmaceutical composition is packaged in a packaging material and identified in print, in or on the packaging material, for use in the treatment and/or diagnosis of a condition in which delivering the biologically active moiety to a cell is beneficial.

According to an additional aspect of the present invention there is provided a use of the conjugate described herein for delivering a biologically active moiety into a cell.

According to still an additional aspect of the present invention there is provided use of the conjugate described herein for the preparation of a medicament for treating a condition in which delivering the biologically active moiety to a cell is beneficial.

According to still an additional aspect of the present invention there is provided use of the conjugate described herein for the preparation of a diagnostic agent for diagnosing a condition in which delivering the biologically active moiety to a cell is beneficial.

According to a further aspect of the present invention there is provided a process of preparing the conjugate described herein, which comprises:

providing at least one oligomeric compound having the general Formula III:

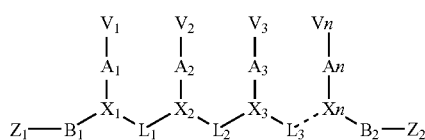

Formula III wherein:

n is an integer from 4 to 20;

each of $X_1$-Xn is independently a residue of a building block of the oligomer;

each of $L_1$-Ln is independently a first linking group or absent;

each of $A_1$-An is independently a second linking group or absent;

each of $V_1$-Vn is independently a delivering group, a group capable of being converted to a delivering group or absent, provided that at least one of the $V_1$-Vn is the delivering group or the group capable of being converted to the delivering group;

each of $B_1$ and $B_2$ is independently a spacer or absent; and each of $Z_1$ and $Z_2$ is independently a reactive group capable of binding the biologically active moiety, or absent, provided that at least one of $Z_1$ and $Z_2$ is the reactive group;

providing at least one biologically active compound having at least one functional group capable of reacting with the reactive group; and coupling the at least one biologically active compound and the compound having the Formula III, thereby obtaining the conjugate.

According to further features in preferred embodiments of the invention described below, the coupling is effected by reacting at least one of the reactive groups and at least one of the functional groups.

According to still further features in the described preferred embodiments the process further comprising, prior to the coupling:

protecting the delivering group and/or the group capable of being converted to the delivering group.

According to still further features in the described preferred embodiments the process further comprises, prior to the coupling, protecting at least one of the reactive groups.

According to still further features in the described preferred embodiments the process further comprises, subsequent to the coupling, deprotecting the delivering group and/or the group capable of being converted to the delivering group.

According to still further features in the described preferred embodiments the process further comprises, at least one of the $V_1$-Vn is a group capable of being converted to the delivering group, the process further comprising, prior to, during or subsequent to the coupling:

converting the group to a delivering group.

According to still further features in the described preferred embodiments at least one of said biologically active moiety and said oligomeric compound is attached to a solid support.

According to still further features in the described preferred embodiments the process further comprising, subsequent to said coupling, detaching the conjugate from said solid support.

According to still further features in the described preferred embodiments providing the oligomeric compound having the general formula III comprises:

providing an oligomeric compound having a plurality of the building blocks linked therebetween; and attaching at least one delivering group and/or a group capable of being converted to the delivering group to at least one of the building blocks.

According to still further features in the described preferred embodiments providing the oligomeric compound having the general formula III comprises:

providing a plurality of compounds having the general formula IV:

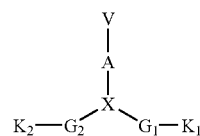

Formula IV wherein:

X is a residue of a building block of the oligomer;

A is a linking group or absent;

V is a delivering group, a group capable of being converted to the delivering group or absent;

each of $G_1$ and $G_2$ is independently a linking group or absent;

$K_1$ is a first reactive group; and $K_2$ is a second reactive being capable of reacting with the first reactive group, provided that in at least one of the compounds having the general Formula III Vn is the delivering group or the group capable of being converted to the delivering group; and reacting the first reactive group and the second reactive group, thereby obtaining the oligomeric compound.

According to still further features in the described preferred embodiments the residue of the building block comprises a -E-(CR'R'')mC(=D)- group, as described herein.

According to still further features in the described preferred embodiments the residue of the building block comprises a phosphorous-containing residue.

According to still further features in the described preferred embodiments the phosphorous-containing residue is selected from the group consisting of a phosphate-containing residue, a phosphonate-containing residue and a phosphorous-containing residue that is capable of being converted to a phosphate-containing or phosphonate-containing residue upon condensation.

According to still further features in the described preferred embodiments the residue of the building block and the first reactive group form together a phosphoramidite residue.

According to still further features in the described preferred embodiments the compound having the general Formula IV is a nucleotide.

According to still a further aspect of the present invention there is provided a compound having the general Formula V:

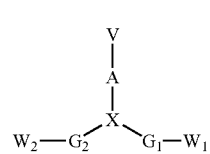

Formula V wherein:

X is a -E-(CR'R")mC(=D)- group, wherein:
E and D are each independently selected from the group consisting of nitrogen, oxygen, and sulfur;
m in an integer from 1-6; and
each of R and R' independently selected from the group consisting of hydrogen, alkyl, cycloalkyl and aryl;

A is a linking group;

V is a group capable of being converted to a delivering group;

each of $G_1$ and $G_2$ is independently a linking group or absent; and $W_1$ and $W_2$ are each independently selected from the group consisting of a reactive group, a protecting group or absent.

According to yet a further aspect of the present invention there is provided a compound having the general Formula VI:

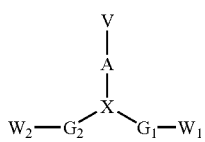

Formula VI wherein:

X is a phosphorous-containing residue;

A is a linking group;

V is a group capable of being converted to a delivering group;

each of $G_1$ and $G_2$ is independently a linking group or absent; and $W_1$ and $W_2$ are each independently selected from the group consisting of a reactive group, a protecting group or absent.

According to further features in preferred embodiments of the invention described below, the phosphorous-containing residue is capable of forming a phosphate-containing residue and/or a phosphonate-containing residue upon condensation.

According to still further features in the described preferred embodiments X and $W_1$ form together a phosphoramidite residue.

According to still further features in the described preferred embodiments the phosphorous-containing residue is a -J-O—P(U)(Ra)—O— group, where J is selected from the group consisting of alkyl, cycloalkyl, aryl, and ether; U is an oxo group or absent; and Ra is selected from the group consisting of hydrogen, hydroxy, alkoxy, aryloxy, alkyl, aryl and cycloalkyl.

According to still further features in the described preferred embodiments J is methylene.

According to still further features in the described preferred embodiments Ra is aryl.

According to still further features in the described preferred embodiments V is a group capable of being converted to an amine and/or to a guanidine.

According to still further features in the described preferred embodiments $W_1$ is a reactive group.

According to still further features in the described preferred embodiments $W_1$ dialkylamine.

According to still further features in the described preferred embodiments $G_2$ comprises a hydroxyalkyl residue.

According to still further features in the described preferred embodiments $W_2$ is a protecting group protecting the hydroxy.

According to still further features in the described preferred embodiments the protecting group is dimethoxytrityl.

According to still further features in the described preferred embodiments the compound according to this aspect of the present invention has the Formula:

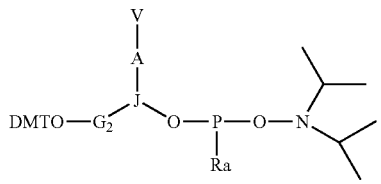

wherein:

$G_2$-ODMT form a protected hydroxyalkyl;

J is methylene;

V is a delivering group or a group capable of being converted to a delivering group; and Ra is selected from the group consisting of phenyl and —O—$CH_2CH_2CN$.

According to still further features in the described preferred embodiments the compounds is selected from the group consisting of 1-(4,4'-Dimethoxytrityl)-2-hydroxy, 10-Decyl[(N,N'-bis-CEOC-guanidinium) (Compound 66), 1-(4,4'-Dimethoxytrityl)-2-(N,N-diisopropylamino, phenyl)-phosphine, 10-Decyltrifluoroacetamide (Compound 60), 1-(4,4'-Dimethoxytrityl)-2-(N,N-diisopropylamino, cyanoethyl)-phosphoramidite, 10-Decyltrifluoroacetamide (Compound 61), and 1-(4,4'-Dimethoxytrityl)-2-(N,N-diisopropylamino, cyanoethyl)-phosphoramidite, 10-Decyl[(N,N'-bis-CEOC-guanidinium) (Compound 67).

According to a further aspect of the present invention there is provided a compound having the general Formula VII:

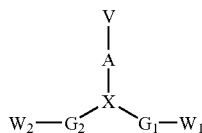

Formula VII wherein:

X is -D-(CR'R")mCR(CR'''R'''')l-F— group, whereas:

D and F are each independently selected from the group consisting of nitrogen, oxygen, and sulfur;

m and l are each independently is an integer from 1 to 6, as described herein;

R, R', R", R''' and R'''' are each independently selected from the group consisting of hydrogen, alkyl, cycloalkyl and aryl, as described herein;

A is a linking group, as described herein;

V is a group capable of being converted to a delivering group;

each of $G_1$ and $G_2$ is independently a linking group, as described herein or absent; and $W_1$ and $W_2$ are each independently selected from the group consisting of a reactive group, a protecting group or absent.

According to further features in preferred embodiments of the invention described below, each of said $G_1$ and $G_2$ is independently a substituted or unsubstituted hydrocarbon chain.

According to still further features in the described preferred embodiments each of said $G_1$ and $G_2$ is methylene ($CH_2$).

According to still further features in the described preferred embodiments each of said K1 and K2 is independently selected from the group consisting of —OR and —SR.

According to further aspects of the present invention there is provided a modified nucleotide comprising:

a triphosphate moiety or a phosphate-containing moiety attached to a ribose moiety; and a purine or pyrimidine base being attached to the ribose moiety and having at least one delivering group or a group capable of being converted to a delivering group being attached thereto, as well as an oligonucleotide comprising a plurality of nucleotides and at least one of the modified nucleotide described herein.

The present invention successfully addresses the shortcomings of the presently known configurations by providing novel chemical moieties, which are characterized by capability to penetrate cells and/or nuclei membranes, and/or as targeting moieties, and conjugates of such chemical moieties and biologically active agents, which can be beneficially used for efficient delivery of such agents into bodily targets such as living cells and/or cells nuclei.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic illustration of a delivery moiety according to an embodiment of the present invention, which is composed of an oligomer backbone having delivering groups attached thereto, a protected hydroxyl reactive group (DMTO—dimethoxytrityl) at one end thereof and a phosphoramidite reactive group at another end thereof;

Figure 2:
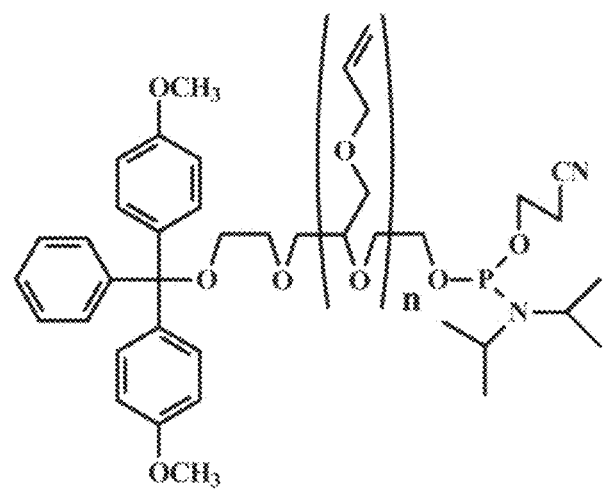
Figure 3:
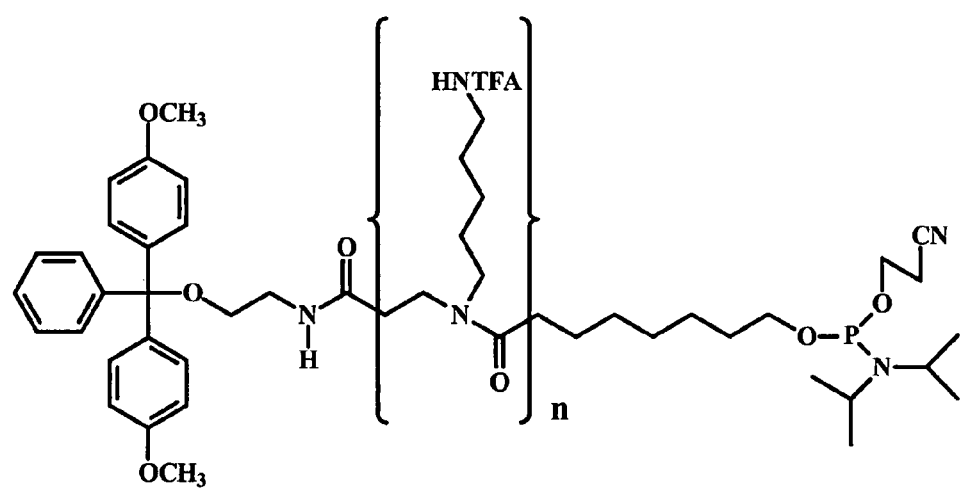
Figure 4:
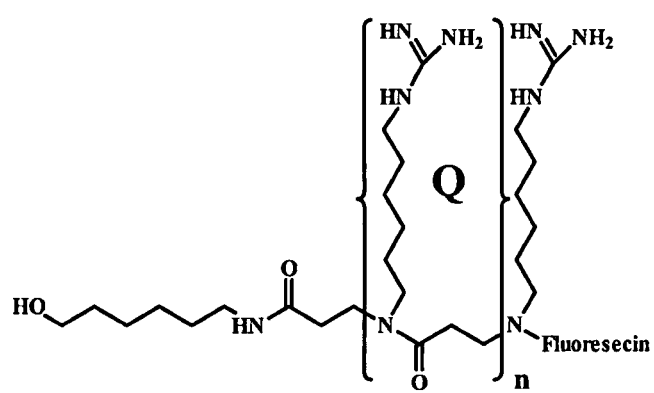
Figure 5:
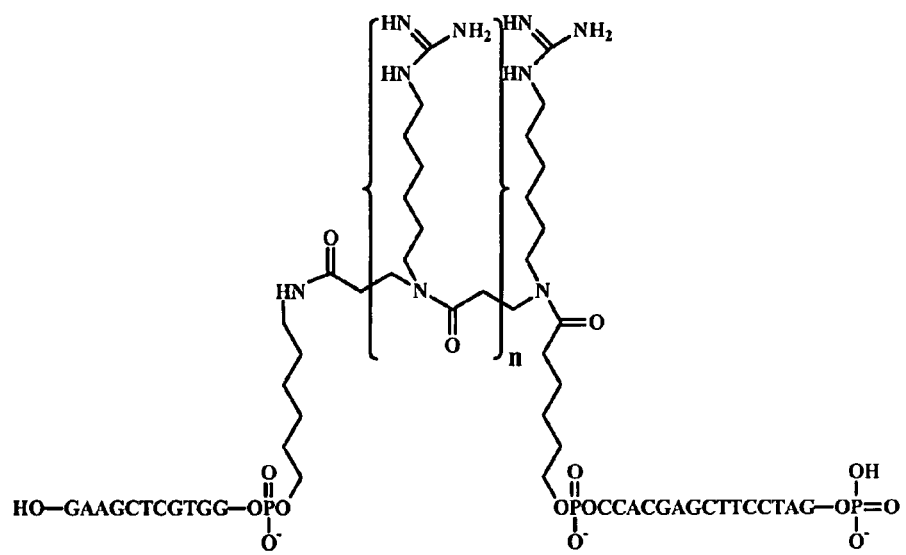
Figure 6:
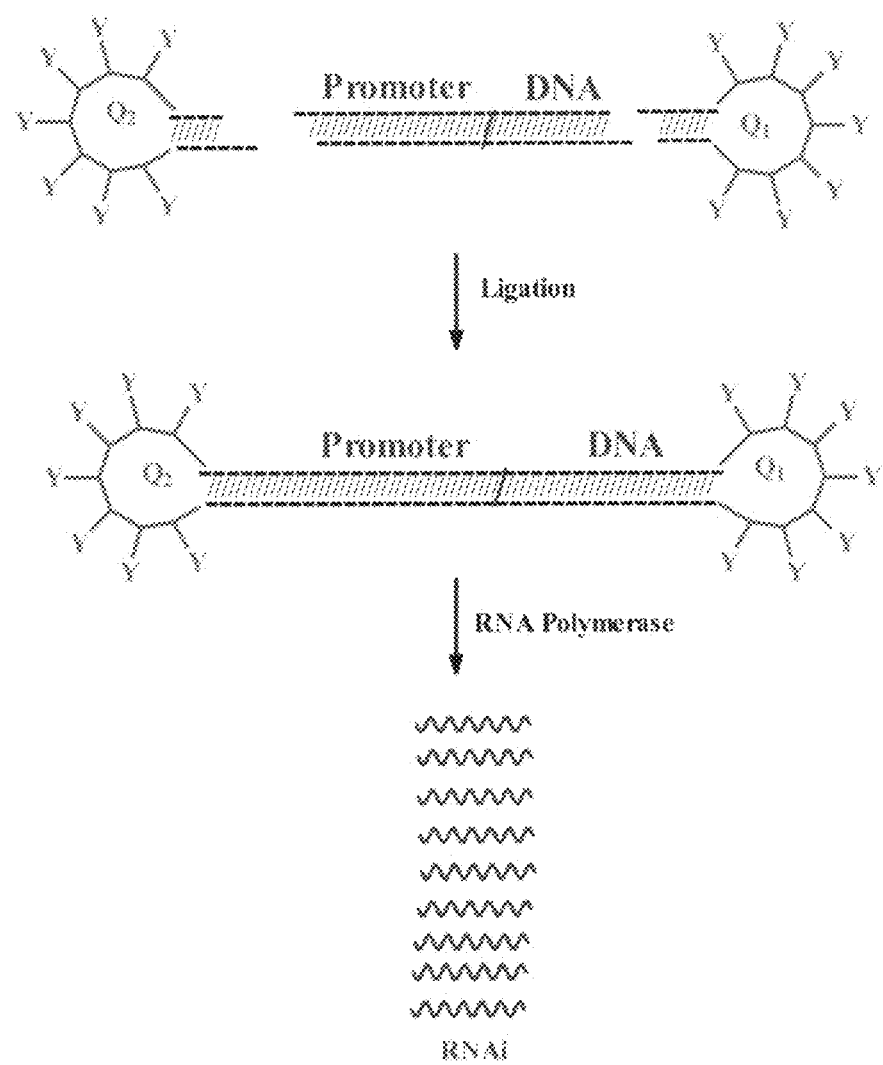
Figure 7:
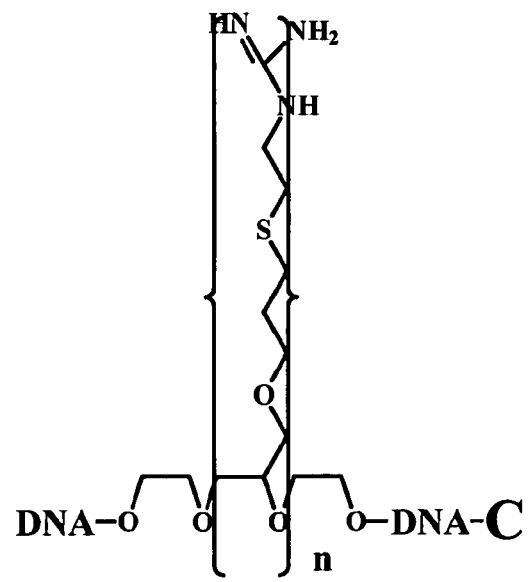
Figure 8:
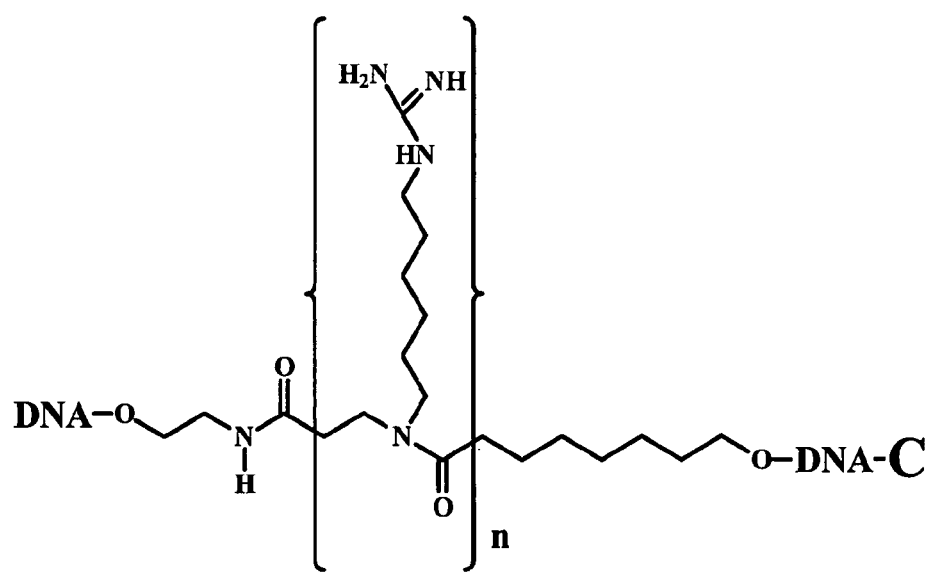
Figure 9:
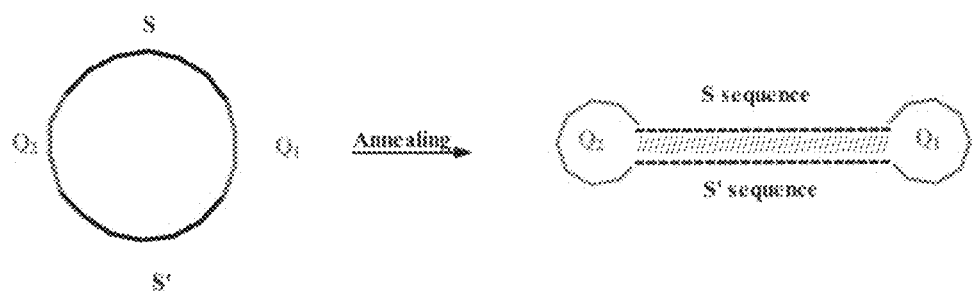
Figure 10:
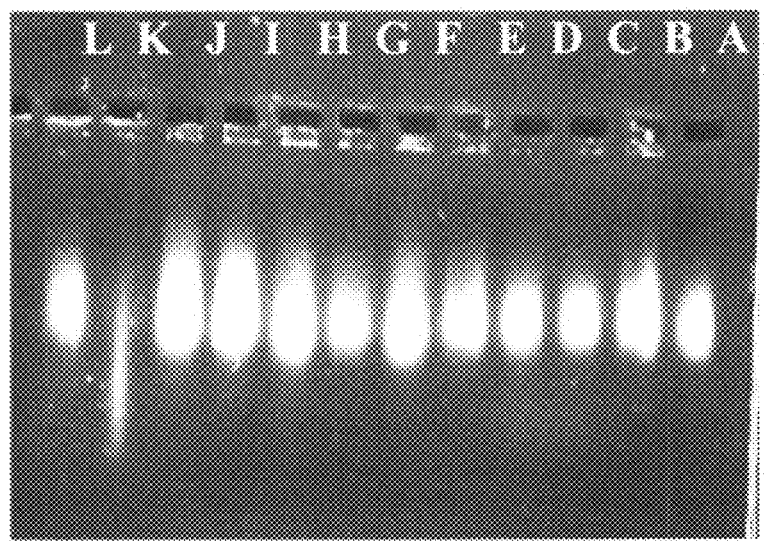
Figure 11:
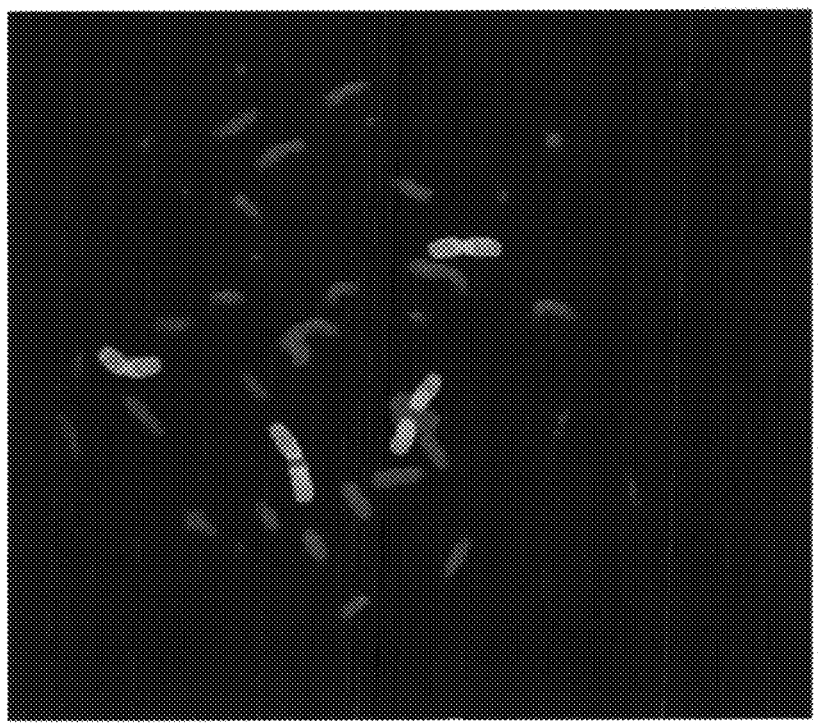
Figure 12:
Figure 13:
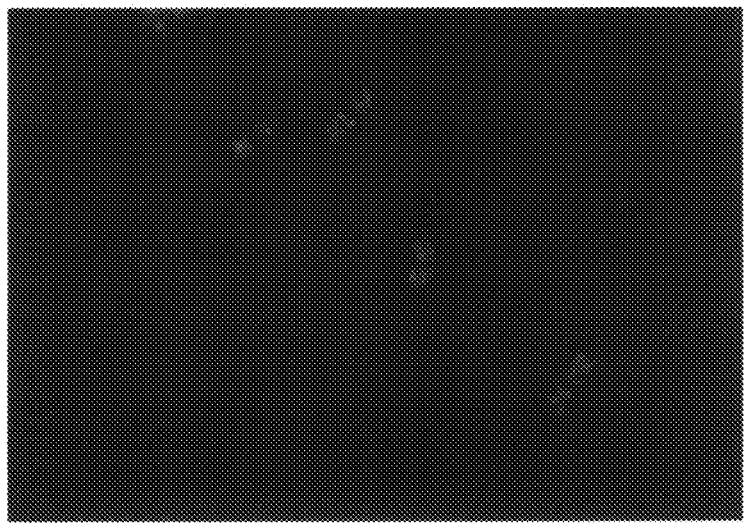
Figure 14A:
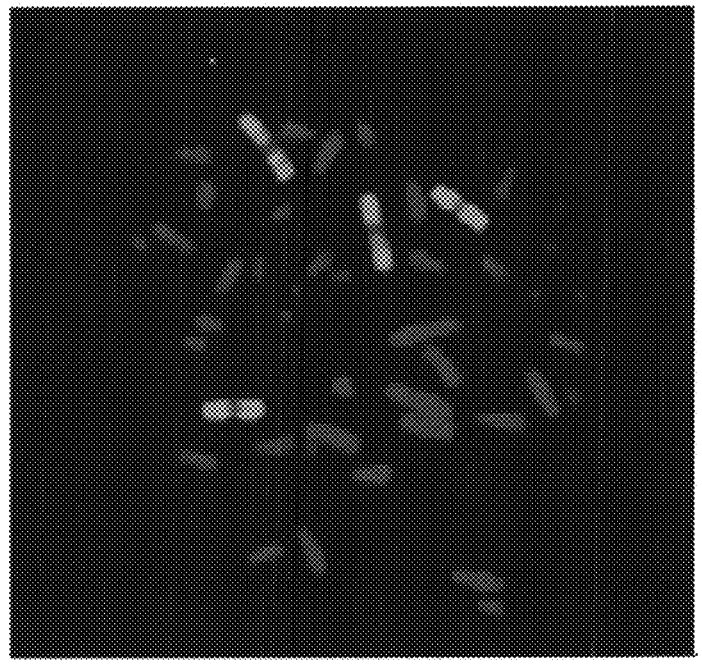
Figure 14B:
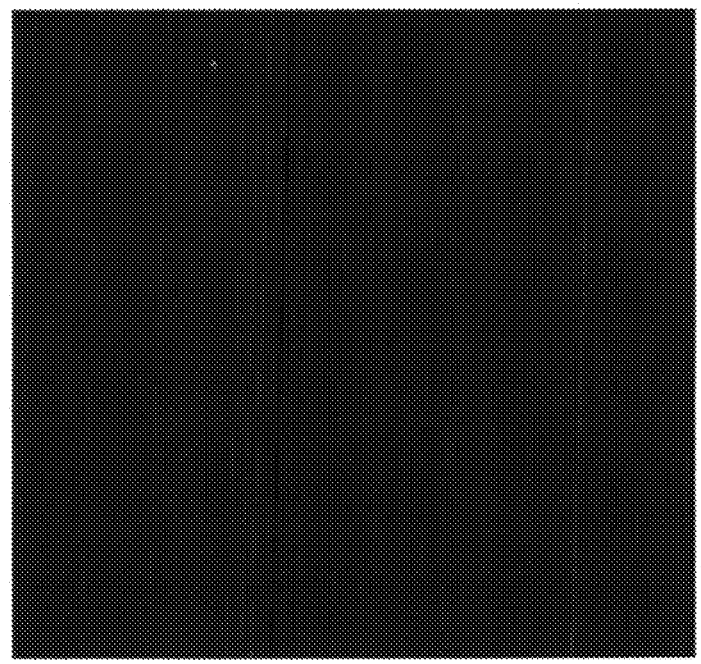
Figure 15:
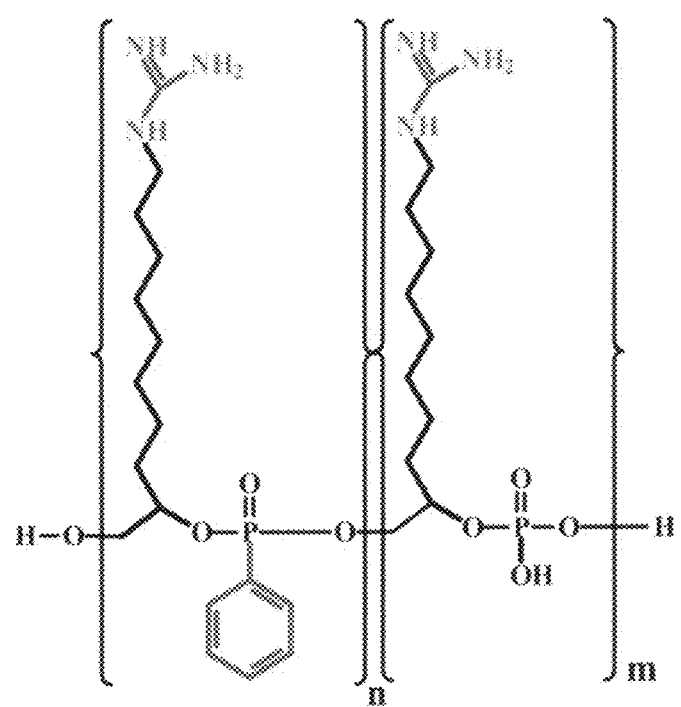
Figure 16:
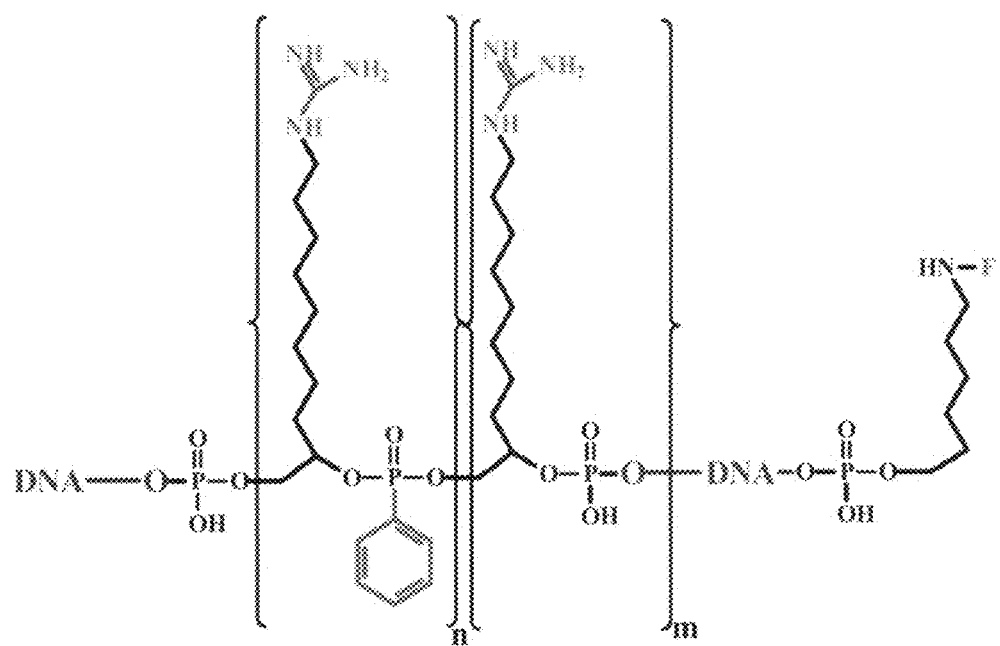

FIG. 2 presents the 2-D chemical structure of an exemplary delivery moiety according to an embodiment of the present invention, which includes a PEG backbone terminating with a protected reactive hydroxyl group at one end and a phosphoramidite at the other end, and which is substituted by a pro-delivering allyl group linked to the backbone via an ether group;

FIG. 3 presents the 2-D chemical structure of an exemplary delivery moiety according to an embodiment of the present invention, which includes a peptoid backbone terminating with a protected reactive hydroxyl group at one end and a reactive phosphoramidite attached to the backbone via an alkyl spacer at the other end, and in which the peptoidic nitrogen is substituted by a protected pro-delivering amine group (NHTFA) linked to the peptoid backbone via an alkyl group;

FIG. 4 presents the 2-D chemical structure of an exemplary conjugate according to an embodiment of the present invention, which includes a peptoid delivery moiety having Fluorescein, as a labeling moiety, attached thereto;

FIG. 5 presents the 2-D chemical structure of an exemplary conjugate according to an embodiment of the present invention, which includes a peptoid delivery moiety attached to two oligonucleotides;

FIG. 6 presents a schematic illustration of the use of an exemplary conjugate according to an embodiment of the present invention, in constructing a nucleic agent that can readily penetrate a cell and encode a genetic product such as RNAi;

FIG. 7 presents the 2-D chemical structure of an exemplary conjugate according to an embodiment of the present invention, which includes a PEG-based delivery moiety attached having a labeled oligonucleotide attached thereto;

FIG. 8 presents the 2-D chemical structure of an exemplary conjugate according to an embodiment of the present invention, which includes a peptoid delivery moiety having a labeled oligonucleotide attached thereto;

FIG. 9 presents a schematic illustration of a cyclic conjugate according to an embodiment of the present invention, which includes two complementary sequences, denoted as S and S' each being attached to two delivering moieties (denoted Q1 and Q2), which upon annealing produce a dsDNA terminating by the delivery moieties;

FIG. 10 presents a UV illuminated photograph of a DNA gel, showing the various incorporation levels of a modified, fluoresceinated nucleotide during PCR amplification of oligonucleotides derived from human chromosomes 1 and 3 in the presence of unlabeled primer and show the unrestricted incorporation of the modified nucleotide;

FIG. 11 presents an image showing the unrestricted hybridization of the amplified products obtained in the PCR synthesis described with regard to FIG. 10;

FIG. 12 presents a three-layer image (with red, green and DAPI filters), showing the unrestricted hybridization of the amplified products obtained in the PCR synthesis described with regard to FIG. 10, which incorporate a modified nucleotide, labeled with Spectrum Orange dUTP according to the present invention, dUTP, into the human chromosomes 1 and 3 which were labeled with Spectrum Orange dUTP;

FIG. 13 presents an image of the hybridization products described with regard to FIG. 12 above, using only a green filter;

FIGS. 14a-b present a three-layer image (FIG. 14a, with red, green and DAPI filters) and an image taken with a green filter only (FIG. 14b) of the hybridization products described with regard to FIG. 12 above, obtained with unmodified oligonucleotide from chromosomes 1 and 3;

FIG. 15 presents the 2-D chemical structure of an exemplary delivery moiety according to an embodiment of the present invention, which includes a phosphate- and/or phosphonate-containing backbone terminating with a reactive hydroxyl group at one end and a phosphate group (serving as a reactive group) at the other end, and in which the phosphate- and/or phosphonate-containing residue(s) in the backbone are substituted by a delivering guanidine group linked to the backbone via an alkylene group; and FIG. 16 presents the 2-D chemical structure of an exemplary conjugate according to an embodiment of the present invention, which includes a phosphate- and/or phosphonate-containing delivery moiety attached to a first oligonucleotide at one end and to a second oligonucleotide having a chromophore (denoted F), as a labeling moiety, attached thereto, at the other end.

DESCRIPTION OF THE PREFERRED EMBODIMENTS

The present invention is of a novel class of oligomeric compounds designed for forming conjugates with biologically active substances and delivering these substances to the desired target. The present invention is thus further of conjugates of biological moieties and such oligomeric compounds, of pharmaceutical compositions containing the conjugates, and of uses of these conjugates for delivering the biologically active substances to a desired target, and thus for treating a myriad of medical conditions. The present invention is further of processes of preparing the conjugates and the oligomeric compounds and of novel intermediates designed for and used in these processes.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, all diseases are related to proteins, either foreign proteins of foreign organisms, and those which are associated with self-proteins malfunctions caused by faulty somatic mechanisms, such as innate and acquired genetic defects, faulty gene expression, senescence processes and cancer. Therefore an ability to control diseases is the ability to control proteins.

While traditional pharmaceuticals based on small molecules are typically aimed at inhibiting the activity of a target protein, the emerging field of gene therapy is aimed at controlling the disease at the genetic level by modulating the expression of the target protein within the cell/organ of the subject. Modulating protein expression at the genetic level is well within the reach of researchers, when dealing with in vitro condition, test organisms and experimental studies. However, this objective is still not within the reach of presently known pharmaceutical technology due to the difficulties in delivering the genetically and/or pharmaceutically active moiety through cellular barriers and into the cells before it is metabolized and eliminated by the body's innate protection systems.

The rapid metabolism and elimination of active moieties before reaching the desired target is associated also with therapies other than gene therapy. Thus, for example, many therapies involve administration of high dosages of the drug, due to at least partial elimination thereof, which may cause adverse side effects. Such adverse side effects may be also caused by a non-targeted therapy, as in the case of chemotherapy, for example.

In addition, the rapid metabolism and elimination of active moieties before reaching the desired target further adversely affects in vivo diagnostic methods. Thus, for example, administration of large amounts of the diagnostic agent is oftentimes required, resulting in low resolution and inefficient diagnosis.

Rapid membrane penetration and/or efficient targeting are therefore known to be a crucial element in circumventing the limitations associated with the delivery of biologically active moieties into a desired target such as cells, in both therapy and diagnosis.

In a search for a novel delivery system for efficiently delivering biologically active moieties to a desired target, the present inventor has designed and successfully produced a novel delivery system, to which a myriad of biologically active moieties could be readily conjugated. Such a delivery system includes a delivery moiety that is based on biocompatible oligomeric compounds, which are designed so as to incorporate delivering groups such as cell-penetrative groups, recognition groups and/or other groups which may direct the conjugated moiety to the desired target, be it an organ, a tissue, a cell, a cellular compartment and the like, as is detailed herein. The delivery moiety is further designed to include reactive groups, optionally and preferably protected reactive groups, which are selected suitable to attach a desired biologically active moiety, and thus form the delivery system. The delivery system provided herein may therefore be efficiently used for therapy and/or diagnosis applications and particularly for cell therapy.

Figure 1:
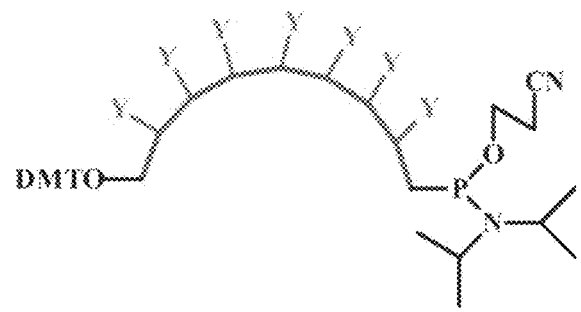

A schematic illustration of an exemplary delivery moiety is presented in FIG. 1.

As is demonstrated in the Examples section that follows, modified oligomeric compounds such as modified polyethylene glycol (PEG), other modified polyethers and modified oligonucleotides, all incorporating membrane-permeable groups, have been successfully prepared. As is further demonstrated in the Examples section that follows, labeling moieties, as well as biologically active moieties such as antisenses and plasmids, have been successfully conjugated to these modified oligomers, while maintaining their activity.

Thus, according to one aspect of the present invention, there is provided an oligomeric compound having the general Formula I:

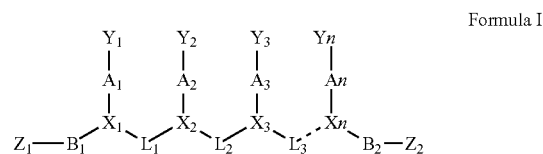

Formula I wherein:

n is an integer from 3 to 20;

each of $X_1$-$X_n$ is independently a residue of a building block of the oligomer;

each of $L_1$-$L_n$ is independently a first linking group or absent;

each of $A_1$-$A_n$ is independently a second linking group or absent;

each of $Y_1$-$Y_n$ is independently a delivering group or absent, provided that at least one of $Y_1$-$Y_n$ is a delivering group;

each of $B_1$ and $B_2$ is independently a spacer or absent; and each of $Z_1$ and $Z_2$ is independently a reactive group capable of binding a biologically active moiety or absent, provided that at least one of $Z_1$ and $Z_2$ is such a reactive group.

The term "oligomer" as used herein, describes a chemical substance, or a residue of a chemical substance, which is made up of two or more basic units which are chemically linked to one another in a sequential manner, thus forming a chain of repeating residues of these units, which constitutes the oligomer. An oligomer can be comprised of two or more chemically different basic units and typically includes from 2 to 50 units.

According to preferred embodiments of the present invention, the oligomer described herein comprises from 3 to 20 units, such that n in the general Formula I above ranges from 3 to 20. More preferably, n ranges from 4-18, more preferably from 4-16, more preferably from 4-12 and more preferably from 6-12. In certain cases, as is detailed hereinbelow, the oligomer comprises 9 units, such that n equals 9.

As used herein, the phrase "building block" describes a basic unit, which serves for assembling an oligomer, as this term is defined herein. Non-limiting examples of commonly used building blocks include amino acids in peptides, sugars in glycans, amino acids and sugars in glycoproteins, and nucleotides in a DNA molecule.

As is well known in the art, the term "residue" refers herein to a major portion of a molecule, which is chemically linked to another molecule, in analogy to the terminology used for amino acid residues in peptides.

The building blocks constructing the oligomers provided herein may be identical, similar (belonging to the same family of compounds) or different one from the other (belonging to a different family of compounds).

As is shown in the general Formula I above, at least some of the building block residues constructing the oligomeric compound have a delivering group linked thereto either directly or indirectly. The incorporation of the delivering groups can be performed by providing a corresponding unmodified oligomer and modifying the oligomer by attaching thereto a delivering group or a linking group to which a delivering group is attached. Alternatively, modified building blocks incorporating the delivering group can be first prepared and then assembled to form the oligomer. In any event, the building blocks are selected so as to allow the formation of such a delivering group-containing oligomer.

Since the oligomeric compounds described herein are aimed at delivering biological moieties to certain targets in the body, preferred building block for use within the oligomer are selected so as to provide a biocompatible oligomer.

Representative examples of such preferred building blocks therefore include, without limitation, ethylene glycols and derivatives thereof, which provide polyethylene glycol-type oligomers and derivatives thereof, respectively, other etherified monomers, which provide polyether-type oligomers, amino carboxylic acids and derivatives thereof, which may form peptoid backbone, nucleotides, which form polynucleotides, phosphorous-containing compounds, which may form phosphate- and/or phosphonate-containing backbone and any combination thereof. Other examples include natural and synthetic sugars, and naturally-occurring, synthetic and/or modified amino acids.

The presently most preferred oligomers according to the present embodiments are those forming, with or without linking moieties, a polyether backbone.

As used herein, the term "polyether backbone" describes a chain composed of repeating units, each including one or more hydrocarbon fragments, namely, short (e.g., 1-6 carbon atoms in length) alkylene, alkenylene and/or cycloalkyls, as these terms are defined herein, which are interrupted by one or more heteroatom such as oxygen, sulfur and/or nitrogen, preferably oxygen. Hence, this term describes a hydrocarbon chain, which is interrupted repeatedly by heteroatoms.

As is well known in the art, polyethers are typically biocompatible substances and therefore oligomers having such a backbone are highly suitable for use in the context of the present invention.

Thus, preferred residues of the building blocks that can compose the oligomeric compound described herein, which are denoted as $X_1$-Xn in the general Formula I above, include residues having the general structure:

-D-CR—(CR'R")m-F— wherein D and F are each independently selected from the group consisting of nitrogen, oxygen, and sulfur; m is an integer from 1 to 6; and R, R' and R" are each independently selected from the group consisting of hydrogen, alkyl, cycloalkyl and aryl, as these terms are defined hereinbelow.

Such residues can be substituted at the carbon adjacent to D (—CR—), by a delivering group or a linking group being attached to the delivering group. In residues that do not include a delivering group, namely, when Y is absent, the carbon adjacent to the variant D can be substituted by e.g., hydrogen, alkyl, cycloalkyl and aryl.

Thus, residues of building blocks in this category can be, for example, substituted or unsubstituted alkylene glycol residues, in which D and F are each oxygen. Exemplary alkylene glycol residues include, without limitation, ethylene glycol residues, in which D and F are each oxygen, R, R' and R'" are each hydrogen and m=1. Additional residues of building blocks in this category can be, for example, substituted or unsubstituted thioalkylene glycol residues (in which D and F are each sulfur), and substituted or unsubstituted 1,2-diaminalkylene residues (in which D and F are each nitrogen, being NRa, wherein Ra is as defined for R, R' or R").

The term "alkylene" as used herein describes a chain of 1-20, preferably 1-6, —CR'R"— groups, as defined herein, and thus includes, for example, substituted or unsubstituted methylene, ethylene, propylene, butylene and so on.

Additional residues in this category include sulfoxide $(S(=O)_2)$ derivatives of alkylene glycols, in which at least one of D and F is a $(S(=O)_2)$ group.

Oligomers formed from such residues are commonly available. As is detailed hereinbelow and is further exemplified in the Examples section that follows, such oligomers, which incorporate one or more delivering groups, can be readily prepared either by attaching a delivering group (or a pro-delivering group, as is detailed hereinunder) to some or all of the carbons in the oligomer chain, or by preparing a suitable reactive derivative of a compound that is used as the building block of the polymer, which is optionally and preferably substituted by the delivering (or pro-delivering) group, and reacting such compounds one with the other, so as to form the oligomer.

The presently most preferred residue in this category is an ethylene glycol residue, such that in the general structure above each of R, R' and R" is hydrogen, D and F are both oxygen and m equals 1. Oligomers including such building block residues are also referred to herein as PEG-based oligomers. As is well known in the art, polyethylene glycols are biocompatible substances and therefore oligomers built from ethylene glycol building blocks are highly suitable for use in the context of the present invention.

Additional preferred residues of the building blocks that can compose the oligomeric compound described herein, which are denoted as $X_1$-Xn in the general Formula I above, include residues having the general structure:

-D-(CR'R")m-CR—(CR'''R'''')l-F— wherein D and F are each independently selected from the group consisting of nitrogen, oxygen, and sulfur; m and l are each independently an integer from 1 to 6;

and R, R', R", R'" and R"" are each independently selected from the group consisting of hydrogen, alkyl, cycloalkyl and aryl, as these terms are defined herein.

Such residues can be substituted at the carbon denoted as (—CR—), by a delivering group or a linking group being attached to the delivering group. In residues that do not include a delivering group, namely, when Y is absent, this carbon can be substituted by e.g., hydrogen, alkyl, cycloalkyl and aryl.

Thus, residues of building blocks in this category can be, for example, substituted or unsubstituted alkylene glycol residues, in which D and F are each oxygen. Exemplary alkylene glycol residues include, without limitation, residues, in which D and F are each oxygen, R, R' and R'" are each hydrogen and each of m and l is 1. Additional residues of building blocks in this category can be, for example, substituted or unsubstituted thioalkylene glycol residues (in which D and F are each sulfur), substituted or unsubstituted thioalkylene glycol residues (in which one of D and F is sulfur and the other is oxygen) and substituted or unsubstituted 1,2-diaminalkylene residues (in which D and F are each nitrogen, being NRa, wherein Ra is as defined for R, R' or R").

The presently most preferred residue in this category is an alkylene glycol residue, such that in the general structure above each of R, R' and R" is hydrogen, D and F are both oxygen and m and l each equals 1. Preferred oligomers formed from such building block residues preferably further include linking groups, linking these residues to one another, which are preferably hydrocarbons.

Such linking groups are referred to herein as first linking groups and are denoted $L_1$-Ln in the general Formula I above.

The first linking group can be, for example, a substituted or unsubstituted, saturated or unsaturated hydrocarbon chain and a substituted or unsubstituted, saturated or unsaturated hydrocarbon chain interrupted by at least one heteroatom such as oxygen, nitrogen and sulfur, as detailed hereinbelow.

In a preferred embodiment, the linking groups are each a hydrocarbon chain and more preferably, the linking groups are each a short, saturated, unsubstituted hydrocarbon chain. The presently most preferred oligomers in this category include linking groups which are each a methylene group, which together with the residues described supra form a polyether-polyacetal backbone.

As is detailed hereinbelow and is further exemplified in the Examples section that follows, such oligomers, which incorporate one or more delivering groups, can be readily prepared either by attaching a delivering group (or a pro-delivering group, as is detailed hereinunder) to some or all of the carbons in the oligomer chain, or by preparing a suitable reactive derivative of a compound that is used as the building block of the polymer, which is optionally and preferably substituted by the delivering (or pro-delivering) group, and reacting such compounds one with the other, so as to form the oligomer.

Various building blocks and polyether-polyacetal-based oligomers formed therefrom and methodologies for preparing same have been designed and successfully practiced.

Thus, exemplary preferred oligomeric compounds according to the present embodiments is presented as Structures B and C in the Examples section that follows.

Other exemplary preferred oligomeric compounds having a polyether backbone are presented, for example, in Scheme 68 hereinbelow.

Additional residues of the building blocks that can be used within the oligomeric compound described herein, denoted as $X_1$-Xn in the general Formula I above, include residues having the general structure:

-E-(CR'R")m-C(=D)- wherein D, F, m, R' and R" are as defined hereinabove and E is as defined for D and F.

Preferably, E is nitrogen. In such residues, the nitrogen atom can be substituted by a delivering group or a linking group being attached to the delivering group, so as to form a stable tertiary nitrogen atom. In residues that do not include a delivering group, namely, when Y is absent, the nitrogen atom can be substituted by e.g., hydrogen, alkyl, cycloalkyl and aryl. Alternatively, when E is oxygen or sulfur, a carbon adjacent either to E or to the C(=D) group can be substituted by a delivering group or a linking group being attached to the delivering group.

Further preferably, D is oxygen, such that the building block residue is an aminocarboxy residue. Such aminocarboxy residues, when assembled into the oligomer, form a peptoid backbone, namely, a plurality of groups that are linked to one another by amide bonds. However, unlike peptides, the nitrogen in such amide bonds is preferably a tertiary nitrogen (being substituted by a delivering group or a linking group attached to the delivering group) and therefore such an oligomer is substantially less susceptible to hydrolysis of the amide bond as compared with common peptides.

Preferred residues in this category include residues in which E is nitrogen, D is oxygen and each of R' and R" is hydrogen. Oligomers comprised of such residues are also referred to herein as "peptoid" oligomers. As is detailed hereinbelow and is further exemplified in the Examples section that follows, oligomers comprising such residues are readily prepared.

Additional preferred residues of the building blocks that can be used within the oligomeric compound described herein, denoted as $X_1$-Xn in the general Formula I above, include phosphorous-containing residues. These residues are the presently most preferred building block residues in the backbone of the oligomers described herein.

The phrase "phosphorous-containing residue", as used herein, encompasses residues that comprise one or more organophosphorous group(s) such as, for example, one or more of a phosphate group, a phosphonate group, a phosphine group, a phosphite group and the like. The phosphorus-containing residues can further comprise, in addition to the organophosphorous group, one or more other organic groups, such as alkyl, cycloalkyl, aryl, ether and the like.

As used herein, the term "phosphate" describes an —O—P(=O)(OR')—O— group, with R' as defined herein.

The term "phosphonate" describes an —O—P(=O)(R')—O— group, with R' as defined herein.

The term "phosphite" describes an O—P(OR')—O— group, with R' as defined herein.

The term "phosphine" describes a —R'—PR'R" group, with R', R" and R'" as defined herein.

Preferred phosphorous-containing residues according to the present embodiments comprise a phosphate or phosphonate group. Further preferred phosphorous-containing residues have the general structure:

-J-O—P(=O)(Ra)—O— wherein J is selected from the group consisting of alkylene, cycloalkyl, aryl, and ether and Ra is selected from the group consisting of hydrogen, hydroxy, alkoxy, aryloxy, alkyl, aryl and cycloalkyl. Alternatively, J can be, for example, an amide or a carboxy, as defined herein. Further alternatively, Ra can be thiohydroxy, thioalkoxy, thioaryloxy and the like.

In cases where Ra is, for example, hydroxy, alkoxy or aryloxy, the phosphorous-containing residue is a phosphate-containing residue. In other cases, the phosphorus-containing residue is a phosphonate-containing residue.

According to preferred embodiments of the present invention, the phosphorous-containing residues composing the building blocks of the oligomer presented herein can be all phosphate-containing residues, all phosphonate-containing residues, or, can include a combination of both. By selecting phosphate-containing residues or phosphonate-containing residues as the building block residues, the hydrophilic/hydrophobic nature of the oligomer, and thus its solubility in aqueous or organic media, can be determined. Thus, for example, by selecting the majority or all of the building blocks as phosphate-containing residues, more hydrophilic and thus aqueous-soluble oligomers can be obtained. By selecting the majority or all of the building blocks as phosphonate-containing residues, more hydrophobic oligomers can be obtained.

Preferably, J is substituted by a delivering group or a linking group being attached to the delivering group. Thus, for example, in cases where J is an alkylene, being linked to one or more linking group(s), if present, or directly to another residue of a building block at one end, and to the phosphate at the other end, the alkylene can be further substituted by the delivering group or a linking group being attached to the delivering group. In cases where J is an ether, such as an alkylene-O-alkylene group (—$(CH_2)_m$—O—$(CH_2)_m$-), the delivering group can be attached, either directly or indirectly, via the linking group, to one of the carbon atoms in the alkylene residues composing the ether. In cases where J is amide, the delivering group can be attached, either directly or indirectly, to the nitrogen atom in the amide.

Preferably, J is an alkylene and more preferably it is a methylene.

The chemical structure of an exemplary oligomer according to these embodiments of the present invention is presented in FIG. 15. In this chemical structure, J is methylene, Ra is phenyl or hydroxy, such that m residues are phosphonate-containing residues (where Ra is phenyl) and n residues are phosphate-containing residues (where Ra is hydroxy). The first linking groups, $L_1$-Ln in this oligomer are each a methylene and the second linking groups are each a $C_8$-alkylene. The delivering groups are each a guanidine group.

As used herein, the term "alkyl", which is also referred to herein interchangeably as "alkylene" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 6 carbon atoms. The term "alkyl" is also used herein to describe an alkylene group, as defined herein, which is an alkyl group that is linked to two residues at its ends.

The term "cycloalkyl" describes an all-carbon monocyclic or fused ring (i.e., rings which share an adjacent pair of carbon atoms) group where one or more of the rings does not have a completely conjugated pi-electron system.

The term "aryl" describes an all-carbon monocyclic or fused-ring polycyclic (i.e., rings which share adjacent pairs of carbon atoms) groups having a completely conjugated pi-electron system.

The term "ether", as used herein, describes a —R'—O—R"— group, where R' and R" are as described herein, but are not hydrogen. The term "ether", as used herein, encompasses also a —R'—S—R"— group and a —R'—NR'''—R"— group, where R''' is as defined herein.

In one embodiment of the present invention, the building block residues forming the oligomer are nucleotides and/or modified nucleotides, and the oligomer is therefore an oligonucleotide.

The term "nucleotide" as used herein describes a substance composed of a purine or pyrimidine base, a sugar moiety and a phosphate moiety, which are typically used to form a nucleic acid (e.g., RNA or DNA). The purine or pyrimidine bases can include the naturally-occurring bases adenine, guanine, cytosine, thymine, and uracil and/or any synthetic analog thereof. The sugar moiety is typically a ribose or a deoxyribose such 2'-deoxyribose or 3'-deoxyribose and the phosphate moiety is typically a monophosphate, diphosphate or triphosphate. The oligonucleotide, in accordance with this embodiment of the present invention, typically comprises a plurality (i.e., 4-20) of nucleotides that are linked therebetween by covalent internucleoside linkages.

Preferably, the oligomer (oligonucleotide), according to this embodiment of the present invention, comprises at least one modified nucleotide, that is, a nucleotide that has a delivering group attached thereto, either directly or via a linking group, as is detailed hereinbelow. Preferably, the delivering group is attached to the purine or pyrimidine base and more preferably to the C-5 position of pyrimidine bases and to position 8 of purine bases.

As is detailed hereinbelow and is further exemplified in the Examples section that follows, oligonucleotides incorporating such modified nucleotides can be prepared by either chemical (e.g., solid phase synthesis) or enzymatic (e.g., PCR) methods. As is further exemplified in the Examples section that follows, to this end, modified nucleotides that have a delivering group or a pro-delivering group, as is detailed hereinbelow, and which are designed to be compatible with either chemical oligonucleotide synthesis or enzymatic nucleotide synthesis, have been designed and successfully prepared. Oligonucleotides incorporating such modified nucleotides were found to maintain their cellular intake and compatibility in cellular polymerization to form nucleic acids.

The use of such oligonucleotides in the context of the present invention is highly beneficial since (i) oligonucleotides are biocompatible substances; and (ii) such modified oligonucleotides can be readily incorporated in other oligonucleotides or polynucleotides, to thereby form a substance with improved characteristics, as is detailed hereinbelow.

The building block residues that form the oligomer backbone according to the present embodiments may be connected one to the other either directly or via a linking group. Such a linking group is referred to herein as the first linking group and is denoted $L_1$-Ln in the general Formula I above.

The first linking group can be, for example, a substituted or unsubstituted, saturated or unsaturated hydrocarbon chain and a substituted or unsubstituted, saturated or unsaturated hydrocarbon chain interrupted by at least one heteroatom such as oxygen, nitrogen and sulfur.

As used herein, the phrase "hydrocarbon chain" describes a substance that includes a plurality of carbon atoms having mostly hydrogen atoms attached thereto. The hydrocarbon chain can be aliphatic, alicyclic and/or aromatic and thus may be composed of, for example, alkyls, alkenyls, alkynyls, cycloalkyls, and aryls, as these terms are defined herein, and any combination thereof.

As used the term "alkenyl" describes a substance that includes at least two carbon atoms and at least one double bond.

The term "alkynyl" describes a substance that includes at least two carbon atoms and at least one triple bond.

The hydrocarbon chain that form the linking group preferably includes 2 to 20 carbon atoms, more preferably 2-10 carbon atoms, more preferably 2-6 carbon atoms and more preferably 4-6 carbon atoms.

The incorporation of such linking moieties within the backbone of the oligomer described herein can provide the oligomer with certain characteristics such as a hydrophobic nature, a hydrophilic nature, an amphiphilic nature and the like. In addition, the incorporation of such linking moieties can further serve for spacing the delivering groups from one another or for determining the space therebetween, in cases where such a space is desired.

The oligomers described herein include one or more delivering groups that are attached to one or more of the building block residues forming the oligomer backbone.

The term "delivering" or "delivery" as used in the context of the present invention refers to the act of enabling the transport of a substance to a specific location, and more specifically, to a desired bodily target, whereby the target can be, for example, an organ, a tissue, a cell, and a cellular compartment such as the nucleus, the mitochondria, the cytoplasm, etc.

The term "delivering group", as used herein, therefore describes a chemical or biological group which enables the transport of a substance that contains such a group to a desired bodily site.

Representative examples of delivering groups, denoted as $Y_1$-Yn in general Formula I delineated above, that can be beneficially utilized in the context of the present invention include, without limitation, membrane-permeable groups, recognition moieties and any combination thereof.

As used herein, the phrase "membrane-permeable groups" describes a group that is capable of penetrating a bodily membrane, e.g., a cell membrane, a nucleus membrane and the like. Membrane-permeable groups therefore provide membrane-penetrative or membrane-permeability characteristics to compounds that incorporate same and enable the penetration of such compounds into cells, nuclei and the like. Such delivering groups therefore serve for delivering substances into cells and/or cellular compartments.

Recent studies have shown that positively charged groups efficiently act as membrane-penetrating groups. It has been further shown that peptides substantially comprised of positively charged amino acids such as lysine, histidine and particularly arginine, are characterized by membrane permeability. It has been particularly shown that a polypeptide that includes 9 arginine residues has exceptional membrane permeability (see, for example, Wender et al., PNAS, 2000, 97, 13003).

Thus, preferred membrane-permeable groups according to the present embodiments are positively charged groups such as, but not limited to, amine, imidazole, histidine and guanidine. In view of the beneficial effect of arginine, a particularly preferred membrane-permeable group is guanidine.

As used herein, the term "amine" describes both a —NR'R" where R' and R" are each independently hydrogen, alkyl, cycloalkyl, aryl, as these terms are defined herein.

The term "guanidine" describes a —R'NC(=N)—NR"R'" group, where R' and R" are as defined herein and R'" is as defined for R' or R".

The term "imidazole" describes a substituted or unsubstituted five-membered heteroaromatic ring including two non-adjacent nitrogen atoms. When substituted, the substituent can be, for example, hydrogen, alkyl, cycloalkyl, aryl, as these terms are defined herein.

As used herein, the term "recognition moiety" describes a substance that interacts with a specific site by means of molecular recognition; a phenomenon also known as "host-guest chemistry", in which molecules are distinguished accurately from other molecules. Chemically, it indicates that certain molecules abnormally bond with other molecules (or the same species) with respect to other molecules found in the same environment. This phenomenon involves the three-dimensional positioning of various sub-molecular functionalities which can form interactions among molecules via such reciprocal actions as hydrogen bonds, hydrophobic interactions, ionic interaction, or other non-covalent bond interactions.

Specific examples of molecular recognition include systems in which hydrophobic molecules are included in cyclodextrin as well as the relatively simple interaction between crown ether and alkali metals, ligand-receptor systems to complex systems such as protein-protein interaction.

Molecular recognition consists of static molecular recognition and dynamic molecular recognition. Static molecular recognition is likened to the interaction between a key and a keyhole; it is a 1:1 type complexation reaction between a host molecule and a guest molecule. To achieve advanced static molecular recognition, it is necessary to make recognition sites that are suitable for guest molecules. Dynamic molecular recognition is a molecular recognition reaction that dynamically changes the equilibrium to an n:m type host-guest complex by a recognition guest molecule. There are some equivalents by the combination of host molecules. Dynamic molecular recognition appearing in supramolecules is essential for designing highly functional chemical sensors and molecular devices.

Thus, a recognition moiety is typically any substance that forms a part of a biological pair such as receptor-ligand, enzyme-substrate, antibody-antigen, biotin-avidin and the like.

Recognition moieties are used in the context of the present invention to selectively transport a biologically active moiety to a specific target, taking advantage of the high affinity of the recognition moiety to a biological moiety that is associated with or is present in the target.

Thus, the recognition moiety can be, for example, a ligand which in known to bind a receptor that is typically present in the desired target, a substrate or an inhibitor that can bind an enzyme that is typically present in the desired target, an antibody that an bind an antigen that is typically present in the desired target, and an antigen of an antibody that is typically present in the desired target. Optionally, the recognition moiety can be a biotinylated moiety that can form a complex with strepavidin or an avidin-containing moiety that can form a complex with mitochondrial biotin.

Depending on the nature of the delivering group, the number of delivering groups in the oligomer, namely, the number of the Y groups that are present within the oligomer, can range from 1 to 20.

Thus, for example, in cases where the delivering group is a membrane-permeable group, the oligomer preferably includes at least 4 delivering groups, more preferably at least 5 delivering groups and more preferably at least 6 delivering groups. In cases where the membrane-permeable group is guanidine, the most preferred number of guanidine groups in the oligomer is 9. As is discussed hereinabove, it was found that compounds including 9 arginine residues are characterized by exceptional membrane-permeability, whereby, as is well known in the art, an arginine residue comprises a guanidine group in its side-chain.

The oligomer described herein may include same or different delivering groups and thus can include several, same or different, membrane-permeability group, several, same or different, recognition moieties as described hereinabove and a combination of membrane-permeable groups and one or more recognition moieties.

Further, the oligomer may include one or more groups capable of being converted into delivering groups. Such groups, which are also referred to herein as "pro-delivering groups" include, for example, functional groups that can be chemically converted to the delivering groups and functional groups to which the delivering moiety can be attached. Representative examples include amines, which, for example, by a simple reaction with 1h-Pyrazole-1-carboxamide, can be converted to guanidine, or which, by an addition reaction, can be used to attach various recognition moieties. Additional examples include reactive groups, as this term is defined herein, which are selected chemically compatible with functional groups in the recognition moiety and can thus be used to attached such moieties.

Thus the phrase "delivering group", as used in this context of the present invention further includes a pro-delivering group.

The delivering and pro-delivering groups incorporated in the oligomer described herein are optionally and preferably protected, namely, have protecting groups attached thereto. Protecting groups that are suitable for use in this context are detailed hereinbelow.

The delivering group or the pro-delivering group can be attached to a building block residue in the oligomer either directly or via a linking group. A linking group linking the delivering group to the oligomer backbone is denoted as $A_1$-An in the general Formula I above and is also referred to herein as the second linking group.

The second linking group serves for chemically attaching the delivering moiety to the building block residue within the oligomer and may provide additional desired characteristics such a hydrophobic nature, a hydrophilic nature and an amphiphilic nature. The second linking group further enables to space the delivering group from the oligomer backbone. Such spacing is particularly advantageous in cases where the oligomer is an oligonucleotide since otherwise, the delivering group may affect the essential activity of the oligonucleotide in terms of hybridization (pairing) interactions, enzymatic reactions and the like.

Representative examples of the second linking groups include, without limitation, a substituted or unsubstituted, saturated or unsaturated hydrocarbon chain and a substituted or unsubstituted, saturated or unsaturated hydrocarbon chain interrupted by at least one heteroatom such as oxygen, nitrogen and sulfur, as is detailed hereinabove with respect to the first linking group. Preferably, the hydrocarbon chain comprises 2-20 carbon atoms, more preferably 2-10 carbon atoms and most preferably 4-10 carbon atoms.

While the oligomer described herein is aimed at forming a conjugate with various moieties, as is detailed hereinunder, so as to deliver these moieties to a desired target, the oligomer terminates by at least one reactive group, as is further detailed hereinunder, which is capable of reacting with a desired biologically active moiety.

The reactive group can be attached to the end of the oligomeric backbone either directly or indirectly, via a spacer, which is denoted as $B_1$ and $B_2$ in general Formula I above. The spacer spaces the reactive group from the oligomeric backbone and thus allows for reacting the oligomer with a biologically active moiety without affecting or being affected by the oligomeric backbone. Thus, for example, the presence of a spacer may reduce a stearic hindrance of the reactive group which may possibly be induced by the oligomer. The spacer can further be incorporated in the oligomer in the course of the oligomer preparation, such as in cases where the oligomer is prepared by solid phase synthesis. The spacer, in these cases, serves to bind the oligomer to a solid surface during its synthesis.

The spacer can be, for example, a substituted or unsubstituted, saturated or unsaturated hydrocarbon chain and a substituted or unsubstituted, saturated or unsaturated hydrocarbon chain interrupted by at least one heteroatom such as oxygen, nitrogen and sulfur, as is detailed hereinabove. Preferably, the hydrocarbon chain comprises 2-20 carbon atoms, more preferably 2-10 carbon atoms and most preferably 2-6 carbon atoms.

Thus, the spacer can be, for example, a substituted or unsubstituted alkylene chain, a substituted or unsubstituted ether, and a substituted or unsubstituted sulfone ether, as defined herein.

In embodiments of the present invention, the spacer terminates by a residue of a reactive group, as defined herein, whereby the reactive group serves to attach the spacer to the end building block of the oligomer and/or to attach additional moieties to the delivering moiety.

Non-limiting examples of spacers that have been used in the context of the present invention include an allylamine residue (see, for example, Compounds 8-10 in the Examples section that follows), a diaminoethane residue (see, for example Compounds 14-16 in the Examples section that follows), and a diaminohexane residue (see, for example, Compounds 17-19 in the Examples section that follows).

Additional examples are presented in the Examples section that follows (see, for example, phosphoramidite-containing spacers as presented in Schemes 66 and 67.

As used herein, the phrase "reactive group", describes a chemical moiety that is capable of undergoing a chemical reaction that typically leads to a bond formation. The bond, according to the present invention, is preferably a covalent bond. Chemical reactions that lead to a bond formation include, for example, nucleophilic and electrophilic substitutions, nucleophilic and electrophilic addition reactions, cycloaddition reactions, rearrangement reactions and any other known organic reactions that involve a reactive group. Hence, a reactive group is a group that is capable of participating in such reactions and can therefore be, for example, a nucleophilic group, an electrophilic group, a leaving group, a dienophilic group and the like.

The oligomer described herein therefore includes one or two reactive groups, depending on the desired number of biologically active moieties that would be attached thereto. Similarly, each of the reactive groups is selected depending on the chemical nature of the biologically active moiety, so as to be chemically compatible with functional groups present within the biological moiety.

The reactive groups can thus be selected, for example, from amine, hydroxy, halide, a phosphorous-containing group (such as a phosphoramidite), C-amide, N-amide, carboxy, thiol, thioamide, thiocarboxy, alkoxy, thioalkoxy, aryloxy, thioaryloxy, hydrazine, hydrazide, and any combination thereof, as these terms are defined herein.

As used herein, the term "halide" describes fluoride, chloride, bromide or iodide.

The term "hydroxy" describes a —OH group.

The term "thiol" describes a —SH group.

The term "C-amide" describes a —C(=O)—NR'R" group where R' and R" are as defined herein.

The term "N-amide" describes a R'C(=O)—NR"— group, where R' and R" are as defined herein.

The term "C-thioamide" describes a —C(=S)—NR'R" group where R' and R" are as defined herein.

The term "N-thioamide" describes a R'C(=S)—NR"— group, where R' and R" are as defined herein.

The term "carboxy" describes a —C(=O)—OR' group, where R' is as defined herein.

The term "thiocarboxy" describes a —C(=S)—OR' group, where R' is as defined herein.

The term "alkoxy" describes a —OR' group, where R' is as defined herein.

The term "thioalkoxy" describes a —SR' group, where R' is as defined herein.

The term "aryloxy" describes both an —O-aryl and an —O-heteroaryl group, as defined herein.

The term "thioaryloxy" describes both an —S-aryl and an —S-heteroaryl group, as defined herein.

The term "hydrazine" describes a —NR'—NR"R'" group where R', R" and R'" are as defined herein.

The term "hydrazide", as used herein, describes a —C(=O)—NR'—NR"R'" group wherein R', R" and R'" are each independently as defined herein.

The term "phosphorous-containing group" describes a group that has one or more phosphor atoms and includes, for example, phosphate, phosphonate, phosphine, and the like, as these terms are defined herein, and derivatives thereof. A preferred phosphorous-containing group for use in the context of the present invention is phosphoramidite.

The term "phosphoramidite" describes a —O—P(OW)—NR'R" group, where R' and R" are as described herein and W serves as an oxygen protecting group. Phosphoramidites are commonly used in the chemical synthesis of oligonucleotides, as a group that is converted to a phosphate bond during the elongation of the oligonucleotide. A representative example of such a commonly used phosphoramidite includes a N≡C-Et- group as W and isopropyl groups as R' and R".

The term "phosphoramidite", as used herein, further encompasses phosphoramidite derivatives, being, for example, a —O—P(Ra)—NR'R" group, where Ra, R' and R" are as described herein.

The reactive group(s), as well as the delivering groups and the pro-delivering groups, in the oligomer described herein, can be protected by a protecting group. The protecting groups are selected chemical compatible with the oligomerization process and the binding process to the biologically active moiety that follows. The protecting group is therefore selected such that it provides a selective stability to the protected group during or subsequent to the various synthetic and/or enzymatic processes undertaken on route to the final oligomer and may be further selected by the conditions required for its removal. Such conditions should not affect other desirable moieties that are present within the oligomer.

The phrase "protecting group" as used herein refers to a group that when attached to a reactive group in a molecule, selectively masks, reduces or prevents the reactivity of the reactive group. Examples of protecting groups can be found in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971-1996).

Representative amine protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like.

Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers, allyl ethers, monomethoxytrityl and dimethoxytrityl.

By incorporating one or more delivering groups, the oligomeric compounds described herein can efficiently serve as a delivery moiety for delivering desired moieties to desired bodily targets, upon conjugating thereto such a desired moiety. Thus, the oligomeric compounds described herein are also referred to herein as delivery moieties and are collectively denoted as Q in the schemes and figures accompanying the description.

The 2-D chemical structures of exemplary preferred oligomers according to the present invention, which can be efficiently utilized for conjugating thereto a biologically active moiety and thus form an efficient delivery system, as is detailed hereinunder, are presented in FIGS. 2, 3 and 15, and in the Examples section that follows.

In FIG. 2, the chemical structure of an exemplary PEG-based delivery moiety is presented. The delivery moiety includes a polyethylene glycol backbone (corresponding to $X_1$-Xn in general Formula I, wherein X is an ethylene residue) to which allyl pro-delivering groups (corresponding to $Y_1$-Yn in general Formula I) is attached via ether linking groups (corresponding to $A_1$-An in general Formula I), and which terminates by a reactive hydroxyl group (corresponding to $Z_1$ in general Formula I) protected by a dimethoxytrityl group (DMTO) at one end and by a reactive phosphoramidite group (corresponding to $Z_2$ in general Formula I) at another end thereof. The phosphoramidite reactive group can serve, for example, for attaching to the delivery moiety the 5' end of an oligonucleotide whereby the hydroxyl group can serve for attaching the 3' end of an oligonucleotide and further for attaching any biologically active moiety that can react with the hydroxyl group. The pro-delivering group in such an oligomer can be readily converted, for example, to a guanidine-containing delivering group by reacting the allyl ether with 2-aminoethanethiol followed by reaction with 1H-pyrazole-1-carboxamide. As discussed hereinabove, such a delivery moiety can be efficiently utilized for introducing a biologically active moiety that is attached thereto into a cell.

In FIG. 3, the chemical structure of an exemplary peptoid delivery moiety is presented. The delivery moiety includes a peptoid backbone (corresponding to $X_1$-Xn in general Formula I, wherein X is an aminocarboxy building block residue) to which trifluoroacetic acid-protected amine (NHTFA) pro-delivering groups (corresponding to $Y_1$-Yn in general Formula I) is attached via alkyl linking groups (corresponding to $A_1$-An in general Formula I), and which terminates by a reactive hydroxyl group (corresponding to $Z_1$ in general Formula I) protected by a dimethoxytrityl group (DMTO) at one end and by a reactive phosphoramidite group (corresponding to $Z_2$ in general Formula I) at another end thereof. The phosphoramidite reactive group can serve, for example, for attaching to the delivery moiety the 5' end of an oligonucleotide whereby the hydroxyl group can serve for attaching the 3' end of an oligonucleotide and further for attaching any biologically active moiety that can react with the hydroxyl group. The pro-delivering group in such an oligomer can be readily converted, for example, to a guanidine-containing delivering group by reacting the protected amine group with 1-H-Pyrazole-1-carboxamide. As discussed hereinabove, such a delivery moiety can be efficiently utilized for introducing a biologically active moiety that is attached thereto into a cell.

In FIG. 15, the chemical structure of an exemplary phosphorous-containing delivery moiety is presented. The delivery moiety includes a phosphorous-containing backbone composed of m phosphate-containing residues and n phosphonate-containing residues (corresponding to $X_1$-$Xn$ in general Formula I, wherein X is a residue that comprises a phosphate or phosphonate group) to which guanidine delivering groups (corresponding to $Y_1$-$Yn$ in general Formula I) are attached via alkylene linking groups (corresponding to $A_1$-$An$ in general Formula I), and which terminates by a reactive hydroxy group (corresponding to $Z_1$ in general Formula I) at one end and by a reactive phosphate group (corresponding to $Z_2$ in general Formula I) at another end thereof.

In preferred embodiments of the present invention, the hydroxy group is protected, by, for example, a dimethoxytrityl group, whereby the phosphate reactive group is a phosphoramidite reactive group. The phosphoramidite reactive group can serve, for example, for attaching to the delivery moiety the 5' end of an oligonucleotide whereby the hydroxyl group can serve for attaching the 3' end of an oligonucleotide and further for attaching any biologically active moiety that can react with the hydroxyl group. As discussed hereinabove, the ratio between the phosphate-containing and phosphonate-containing residues in the oligomer, represented by m and n in FIG. 15, can be selected so as to determine the hydrophilic/hydrophobic nature of the oligomer and its solubility characteristics. Thus, each of m and n can independently be, for example, an integer ranging from 0-20, preferably from 0-10.

Thus, according to another aspect of the present invention there is provided a conjugate comprising at least one delivery moiety and at least one biologically active moiety being linked thereto, whereby the delivery moiety is a residue of the oligomer described hereinabove. Thus, according to this aspect of the present invention, the delivery moiety in the conjugate is a residue, as this term is defined herein, of an oligomeric compound that has the general Formula II:

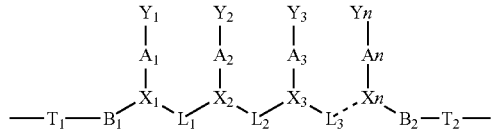

Formula II wherein:

n is an integer from 4 to 20;

each of $X_1$-$Xn$ is independently a residue of a building block of said oligomer;

each of $L_1$-$Ln$ is independently a first linking group or absent;

each of $A_1$-$An$ is independently a second linking group or absent;

each of $Y_1$-$Yn$ is independently a delivering group or absent, provided that at least one of $Y_1$-$Yn$ is said delivering group;

each of $B_1$ and $B_2$ is independently a spacer or absent; and each of $T_1$ and $T_2$ is independently a binding group binding said biologically active moiety or absent, at least one of $T_1$ and $T_2$ being a binding group.

Thus, the delivery moiety in the conjugate according to the present invention is a residue of the oligomer compound described in detail hereinabove, which is formed upon conjugating to the oligomer, via the $Z_1$ and $Z_2$ reactive groups (see, general Formula I above) one or more biologically active moieties, as is detailed hereinbelow. Following such a conjugation, binding groups, denoted as $T_1$ and $T_2$ in general Formula II above, binding the biologically active moiety to the delivery moiety, are formed.

Thus, the binding groups can be, for example, bonds, including covalent bond, an electrostatic bond, an organometallic bond, a hydrogen bond and the like, formed between a reactive group of the oligomer and a suitable functional group of the biologically active moiety.

Preferably, the binding groups are covalent bonds, such as sigma bonds, amide bonds, ester bonds, ether bonds, phosphodiester bonds and the like.

Alternatively, the binding groups can be a chemical moiety such as, for example, a cyclic moiety, an aromatic moiety, a heteroaromatic moiety and the like, formed, for example, upon addition reactions between the reactive group in the oligomer and a suitable functional group in the biologically active substance.

The nature of the binding groups can be determined by selecting the reactive groups incorporated in the oligomer described above, based on the functional group of the biologically active moiety which is attached to the oligomer.

By conjugating one or more biologically active moieties to one or more delivery moieties, a delivery system for efficiently delivering the biologically active moieties into a desired target is obtained. Hence, the conjugates described herein serve and are also referred to herein interchangeably, as a delivery system.

Biologically active moieties that can be beneficially delivered into various bodily targets by utilizing the delivery system described herein include, for example, therapeutically active agents, labeling agents (moieties) and combinations thereof, that is, labeled therapeutically active agents.

The phrase "biologically active moiety" as used herein describes a molecule, compound, complex, adduct and composite which has a biological function and/or exerts one or more pharmaceutical activities, either in vivo or in vitro, and is used to prevent, treat, diagnose or follow a medical condition of any sort at any stage and in any subject.

The phrase "therapeutically active agent" as used herein describes a molecule, compound, complex, adduct and composite which exerts one or more pharmaceutical activities, and is used to prevent, ameliorate or treat a medical condition.

Representative examples of therapeutically active agents that can be beneficially incorporated in the delivery system described herein include, without limitation agonists, amino acids, antagonists, anti histamines, antibiotics, antibodies, antigens, antidepressants, anti-hypertensive agents, anti-inflammatory agents, antioxidants, anti-proliferative agents, antisense, anti-viral agents, chemotherapeutic agents, co-factors, fatty acids, growth factors, haptens, hormones, inhibitors, ligands, oligonucleotides, labeled oligonucleotides, nucleic acid constructs peptides, polypeptides, polysaccharides, radioisotopes, steroids, toxins, vitamins and radioisotopes and any combination thereof.

Non-limiting examples of chemotherapeutic agents include amino containing chemotherapeutic agents such as daunorubicin, doxorubicin, N-(5,5-diacetoxypentyl)doxorubicin, anthracycline, mitomycin C, mitomycin A, 9-amino camptothecin, aminopertin, antinomycin, $N^8$-acetyl spermidine, 1-(2-chloroethyl)-1,2-dimethanesulfonyl hydrazine, bleomycin, tallysomucin, and derivatives thereof; hydroxy containing chemotherapeutic agents such as etoposide, camptothecin, irinotecaan, topotecan, 9-amino camptothecin, paclitaxel, docetaxel, esperamycin, 1,8-dihydroxy-bicyclo[7.3.1]trideca-4-ene-2,6-diyne-13-one, anguidine, morpholino-doxorubicin, vincristine and vinblastine, and derivatives thereof, sulfhydril containing chemotherapeutic agents and carboxyl containing chemotherapeutic agents, as well as platinum-containing agents such as cisplatin.

Examples of radio-isotopes include cytotoxic radio-isotopes such as β radiation emitters, γ emitters and α-radiation emitting materials. Examples of β radiation emitters which are useful as cytotoxic agents, include isotopes such as scandium-46, scandium-47, scandium-48, copper-67, gallium-72, gallium-73, yttrium-90, ruthenium-97, palladium-100, rhodium-101, palladium-109, samarium-153, rhenium-186, rhenium-188, rhenium-189, gold-198, radium-212 and lead-212. The most useful γ emitters are iodine-131 and indium-m 114. Other radio-isotope useful with the invention include α-radiation emitting materials such as bismuth-212, bismuth-213, and At-211 as well as positron emitters such as gallium-68 and zirconium-89.

Examples of enzymatically active toxins and fragments thereof which can be used as cytotoxic agents include diphtheria A chain toxin, non-binding active fragments of diphtheria A toxin, exotoxin A chain (from Pseudomonas aeruginosa), shiga toxin, verotoxin, ricin A chain, abrin A chain toxin, modeccin A chain toxin, α-sarcin toxin, Abrus precatorius toxin, amanitin, pokeweed antiviral protein, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes.

Non-limiting examples of antibiotics include octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids.

Non-limiting examples of non-steroidal anti-inflammatory agents include oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone.

Non-limiting examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, fluc-etonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Non-limiting examples of anti-oxidants include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of vitamins include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of hormones include androgenic compounds and progestin compounds such as methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, flurogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

Ligands, inhibitors, agonists, antagonists, co-factors and the like can be selected according to a specific indication.

The term "antibody" as used herein includes intact molecules as well as functional fragments thereof, such as Fab, F(ab')$_2$, and Fv that are capable of binding to macrophages. These functional antibody fragments are defined as follows:
(1) Fab, the fragment which contains a monovalent antigen-binding fragment of an antibody molecule, can be produced by digestion of whole antibody with the enzyme papain to yield an intact light chain and a portion of one heavy chain;
(2) Fab', the fragment of an antibody molecule that can be obtained by treating whole antibody with pepsin, followed by reduction, to yield an intact light chain and a portion of the heavy chain; two Fab' fragments are obtained per antibody molecule;
(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;
(4) Fv, defined as a genetically engineered fragment containing the variable region of the light chain and the variable region of the heavy chain expressed as two chains; and
(5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art (See for example, Harlow and Lane, Antibodies: A Laboratory Manual, Cold Spring Harbor Laboratory, New York, 1988, incorporated herein by reference).

As used herein, the term "epitope" means any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

According to a preferred embodiment of the present invention, the therapeutically active agent is a genetic material, namely, a nucleic acid agent, including oligonucleotides, polynucleotides (nucleic acids), antisense and antisense-producing oligonucleotides as these are defined herein, chromosomes and nucleic acid constructs such as plasmids. Such genetic substances are collectively referred to herein as nucleic acid agents or oligonulaotides.

The term "plasmid" refers to a circular, double-stranded unit of DNA that replicates within a cell independently of the chromosomal DNA. Plasmids are most often found in bacteria and are used in recombinant DNA research to transfer genes between cells, used as a vector for gene insertion or genetic engineering uses. Plasmids are often the site of genes that encode for resistance to antibiotics.

The term "chromosome" as used herein describes small bodies in the nucleus of a cell that carry the chemical "instructions" for reproduction of the cell and consist of double-stranded DNA wrapped in coils around a core of proteins. Each species of plant or animal has a characteristic number of chromosomes (46 in humans).

The term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly.

As used herein the phrase "an isolated polynucleotide" refers to a nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Alternatively, oligonucleotides may include small interfering duplex oligonucleotides [i.e., small interfering RNA (siRNA)], which direct sequence specific degradation of mRNA through the previously described mechanism of RNA interference (RNAi) [Hutvagner and Zamore (2002) Curr. Opin. Genetics and Development 12:225-232].

As used herein, the phrase "duplex oligonucleotide" refers to an oligonucleotide structure or mimetics thereof, which is formed by either a single self-complementary nucleic acid strand or by at least two complementary nucleic acid strands. The "duplex oligonucleotide" of the present invention can be composed of double-stranded RNA (dsRNA), a DNA-RNA hybrid, single-stranded RNA (ssRNA), isolated RNA (i.e., partially purified RNA, essentially pure RNA), synthetic RNA and recombinantly produced RNA.

A small interfering duplex oligonucleotide can be an oligoribonucleotide composed mainly of ribonucleic acids.

Instructions for generation of duplex oligonucleotides capable of mediating RNA interference are provided in www.ambion.com.

Nucleic acid constructs are substances that enable the cellular expression of polynucleotides and typically include a polynucleotide or an oligonucleotide and at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al.

(1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). The nucleic acid construct can further include an enhancer, which can be adjacent or distant to the promoter sequence and can function in up regulating the transcription therefrom.

The nucleic acid construct can further include an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to pcDNA3, pcDNA3.1 (±), pGL3, PzeoSV2 (±), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the trasgene is transcribed from CMV promoter. Vectors derived from Mo-MuLV are also included such as pBabe, where the transgene will be transcribed from the 5'LTR promoter.

The term "antisense" as used in the context of the present invention, is of or relating to a nucleotide sequence that is complementary to a sequence of messenger RNA. When antisense DNA or RNA is added to a cell, it binds to a specific messenger RNA molecule and inactivates it thus can be a useful tool for gene therapy.

Antisenses can also include antisense molecules, which are chimeric molecules. "Chimeric antisense molecules", are oligonucleotides, which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target polynucleotide. An additional region of the oligonucleotide may serve as a substrate for enzymes capable of cleaving RNA:DNA or RNA:RNA hybrids. An example for such include RNase H, which is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense molecules may be formed as composite structures of two or more oligonucleotides, modified oligonucleotides, as described above. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein fully incorporated by reference.

Finally, chimeric oligonucleotides can comprise a ribozyme sequence. Ribozymes are being increasingly used for the sequence-specific inhibition of gene expression by the cleavage of mRNAs. Several ribozyme sequences can be fused to the oligonucleotides of the present invention. These sequences include but are not limited ANGIOZYME specifically inhibiting formation of the VEGF-R (Vascular Endothelial Growth Factor receptor), a key component in the angiogenesis pathway, and HEPTAZYME, a ribozyme designed to selectively destroy Hepatitis C Virus (HCV) RNA, (Ribozyme Pharmaceuticals, Incorporated—WEB home page).

The incorporation of the genetic therapeutically active agents described above in the delivery systems according to the present invention is highly beneficial since (i) as is discussed in detail hereinabove, such agents may be beneficially used to treat medical conditions by interfering with the condition cause rather than symptoms; and (ii) the use of such agents in in vivo applications is limited by their poor resistance to biological environment. Thus, by incorporating such agents in the delivery systems described herein, efficient and rapid delivery thereof into cells and cell nuclei is achieved, thus overcoming the limitations associated with rapid elimination thereof.

Other preferable therapeutically active agents that can be efficiently used as biologically active moieties delivered by the delivery system according to the present invention include amino acids peptides, and polypeptides (proteins).

As used herein the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The term "peptide" and "polypeptide" as used herein encompasses native peptides (either degradation products, synthetically synthetic peptides or recombinant peptides) and peptidomimetics (typically, synthetic peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, $CH_2$—S, $CH_2$—S=O, O=C—NH, $CH_2$—O, $CH_2$—$CH_2$, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Proteins constitute a subgroup of polypeptides which are naturally occurring and are coded for by genes in organisms.

As is discussed in detail hereinabove, peptide therapy is oftentimes limited by poor biostability of the peptidic drugs. Thus, efficient delivery thereof using the delivery systems described herein is highly beneficial.

As used herein, the phrase "labeling moiety" refers to a detectable moiety, a tag or a probe which can be used in the diagnosis and following of medical conditions both in vitro and in vivo, and includes, for example, chromophores, phosphorescent and fluorescent compounds, heavy metal clusters, radioactive labeling (radiolabeled) compounds, as well as any other known detectable moieties.

As used herein, the term "chromophore" refers to a chemical moiety that, when attached to another molecule, renders the latter colored and thus visible when various spectrophotometric measurements are applied.

The phrase "fluorescent compound" refers to a compound that emits light at a specific wavelength during exposure to radiation from an external source.

The phrase "phosphorescent compound" refers to a compound emitting light without appreciable heat or external excitation as by slow oxidation of phosphorous.

A heavy metal cluster can be for example a cluster of gold atoms used, for example, for labeling in electron microscopy techniques.

Radiolabeled compounds can be almost any compound into which a radioactive isotope is incorporated. A radioactive isotope is an element which is an α-radiation emitters, a β-radiation emitters or a γ-radiation emitters.

An example of a therapeutically active agent which can also serve as a labeling moiety is a radiolabeled oligonucleotide into which, for example, an isotope of phosphorous is incorporated. Another example of a therapeutically active agent which can also serve as a labeling moiety is an oligonucleotide to which a chromophore, a fluorescent compound or a fluorescence compound is attached. An exemplary chromophore is Fluorescein (also referred to herein as a fluorophore).

Any of the biologically active moieties used in the context of the present invention can be incorporated into or onto a variety of carriers such as, but not limited to, liposomes, nanoparticles, microparticles and polymers, which are attached to the delivery moiety.

Liposomes are artificial microscopic vesicles consisting of an aqueous core enclosed in one or more phospholipid layers, used to convey vaccines, drugs, enzymes, or other substances to target cells or organs.

A nanoparticle or a microparticle is a microscopic particle whose size is measured in nanometers or micrometers which can be used in biomedical applications acting as drug carriers or imaging agents.

The conjugates described herein can comprise one delivery moiety as is described in detail hereinabove and one biologically active moiety, as is detailed hereinabove, for efficiently delivering the biologically active moiety into a desired bodily site.

As is demonstrated in the Examples section that follows, an exemplary conjugate of a peptoid delivery moiety having arginine moieties attached to its backbone, as described herein, and Fluorescein as a labeling moiety has been successfully prepared (see, Compound 54 in the Examples section that follows). The chemical structure of such a conjugate is presented in FIG. 4. In experiments conducted for evaluating the ability of such a compound to cross cells membranes, it was found that the cellular intake of such a compound is high, thus demonstrating the capability of the conjugates described herein to deliver biological moieties into the cell.

As further demonstrated in the Examples section that follows, another exemplary conjugate of a polyether-based delivery moiety having arginine moieties attached to its backbone, as described herein, and Fluorescein as a labeling moiety has been successfully prepared (see, Scheme 52 in the Examples section that follows).

While, as is shown in general Formula I and II, the delivery moiety can have two reactive groups or binding groups to which the biologically active moiety is attached, the conjugates described herein can also comprise one delivery moiety and two biologically active moieties linked to the same delivery moiety. The two biologically active moieties can be the same (identical), similar (of the same family of substances) or different.

Thus, for example, the two biologically active moieties can include a therapeutically active agent and a labeling moiety, which would enable detection of the active agents in the body.

In a preferred embodiment of the present invention, the two biologically active moieties conjugated to the delivery moiety are oligonucleotides.

Such conjugates can be formed by designing a delivery moiety to which the 5' end and/or the 3' end of an oligonucleotide can be attached.

As is exemplified in the Examples section that follows, such delivery moieties have been designed and successfully used for providing such conjugates, by appropriately selecting the building blocks, the reactive groups and the protecting groups used for constructing such a conjugate by convenient solid phase syntheses and/or enzymatic syntheses.

Exemplary delivery moieties to which two oligonucleotides can be efficiently attached are presented in FIGS. 2, 3 and 15 and are further described in detail hereinabove, as well as in the Examples section that follows.

The chemical structure of an exemplary conjugate according to this embodiment of the present invention, which incorporates a peptoid delivery moiety as presented in FIG. 3, and which has been successfully prepared, is presented in FIG. 5. In FIG. 5, a conjugate of a short peptoid delivery moiety having guanidine delivering groups attached thereto via an alkyl linking group, and to which two oligonucleotides are attached is shown.

The chemical structure of another exemplary conjugate according to this embodiment of the present invention, which incorporates a phosphorous-containing delivery moiety as presented in FIG. 15, and which has been successfully prepared, is presented in FIG. 16. In FIG. 16, a conjugate of a delivery moiety composed of phosphate- and/or phosphonate-containing residues and having guanidine delivering groups attached thereto via an alkylene linking group, and to which two oligonucleotides are attached is shown. This conjugate further comprises a fluorescence moiety as a labeling moiety, attached to one of the oligonucleotides.

The chemical structure of another exemplary conjugate according to this embodiment of the present invention, which incorporates a polyether-based delivery moiety is presented in Schemes 77 and 79. In Scheme 79, a conjugate of a polyether-based delivery moiety having guanidine delivering groups attached thereto via an alkylene linking group, and to which two oligonucleotides are attached is shown.

A conjugate according to this embodiment of the present invention can be beneficially utilized for delivering various oligonucleotides, including plasmids, nucleic acid constructs, antisenses and nucleic acids, as described hereinabove, into cells.

Thus, such a conjugate can be further conjugated to a nucleic acid agent such as a linear nucleic acid, as shown for example in FIG. 6. Alternatively, the nucleic acid agent can be a nucleic acid construct (e.g., a plasmid), as is described hereinabove and is further exemplified in the Examples section that follows. For example, the nucleic acid agent may encode an oligonucleotide drug such as for example, a double stranded RNA for RNA interference (RNAi) or an antisense molecule. To facilitate transcription of the nucleic acid agent in the cell, a promoter element (as well as other cis acting regulatory elements), as defined hereinabove, may be operably linked to the nucleic acid sequence.

Conjugates that include an oligonucleotide as the biologically active moiety, whereby the oligonucleotide is labeled by e.g., a chromophore, can also be beneficially used in the context of the present invention. Such conjugates allow detecting and following the delivered biological moiety upon penetration into the cell. Such labeled conjugates can be conjugated to nucleic acid agents such as described hereinabove or to any other biologically active moiety.

Representative examples of such conjugates, which include the delivering moieties depicted in FIGS. 2, 3 and 15, whereby the pro-delivering groups have been converted into guanidine-containing delivering groups, to which two oligonucleotides are attached, whereby one oligonucleotide has a labeling moiety such as chromophore denoted as (C) attached thereto, are presented in FIGS. 7, 8 and 16, respectively.

The syntheses of such exemplary conjugates, which include a flourescienated oligonucleotide, are described in the Examples section that follows.

According to another embodiment of this aspect of the present invention, the conjugate comprises two delivery moieties and two biologically active moieties being linked thereamongst. Such conjugates may enable to combine various therapies and various oligomers that form the delivery moiety, according to the desired characteristics thereof.

According to a preferred embodiment of this aspect of the present invention, each of the two biologically active moieties is attached to each of the two delivery moieties, such that a cyclic structure is formed. Preferably, such a cyclic structure includes at least one oligonucleotide as the biologically active moiety. More preferably, such a cyclic structure can include two oligonucleotides as the biologically active moiety.

In a preferred embodiment, the two oligonucleotides are selected such that a first nucleotide is a nucleic acid agent, as described hereinabove, including for example a promoter and a DNA sequence encoding a desirable transcript, whereby a second oligonucleotide includes a complementary sequence, which can hybridize, upon annealing, with the first oligonucleotide, as is shown for example, in FIG. 9, where S and S' are the first and the second oligonucleotides and Q1 and Q2 are the delivery moieties. Q1 and Q2 can be the same or different delivery moieties.

As is further shown in FIG. 9, upon annealing, a double stranded nucleic acid which has two delivery moieties at both ends thereof is obtained and can be efficiently delivered into a cell.

While Q1 and Q2 can be any of the delivery moieties described hereinabove, in an embodiment of this aspect of the present invention, the delivery moieties forming such a cyclic structure are oligonucleotides having delivering groups attached thereto, as is detailed hereinabove. Such oligonucleotides may be of any sequence, either relevant or random, as long as they incorporate one or more nucleotides that have been modified to include a delivering moiety.

An exemplary cyclic structure of such a conjugate, as well as its preparation, are depicted in the Examples section that follows (see, for example, Schemes 30-34 and the description relating to Dcirc-1).

The oligonucleotides described herein as biologically active moieties that are attached to delivery moieties so as to form a conjugate, can be modified or unmodified oligonucleotides. In a preferred embodiment of the present invention, the oligonucleotides are modified oligonucleotides, incorporating nucleotides that have been modified so as to improve the biological resistance of the oligonucleotide. Preferably, the oligonucleotides include one or more protecting groups that are attached thereto, so as to protect the oligonucleotide from degradation.

As is described in detail hereinafter and is further exemplified in the Examples section that follows, the present inventor has designed modified nucleotides, which have a protecting group, preferably a positively charged group, attached thereto. Such modified oligonucleotides were designed to be compatible either in chemical DNA syntheses such as solid phase syntheses or in enzymatic DNA syntheses such as those employing PCR. Exemplary modified nucleotides have been successfully prepared, incorporated in oligonucleotides and were found suitable to polymerization reactions with a DNA polymerase. Thus, as is demonstrated in FIGS. 10-14 and is further detailed in the Examples section that follows, incorporation of such modified oligonucleotides during the amplification of labeled chromosomes was demonstrated.

The conjugates described herein, by containing delivering groups, can therefore be efficiently used for delivering various biologically active moieties into a desired bodily site. These conjugates are particularly useful for delivering various biologically active moieties to cells.

Hence, according to another aspect of the present invention there is provided a method of delivering a biologically active moiety to a cell. The method is effected by contacting cells with a conjugate as described hereinabove, and preferably with conjugates including oligonucleotides and/or nucleic acid agents, as described hereinabove.

Contacting the cells with the conjugate can be effected either in-vivo or ex-vivo. When performed ex-vivo, the cells can be contacted with the conjugate by incubating the cells with a solution containing the conjugate and a buffer, at a temperature that ranges from 4° C. to 37° C.

In a preferred embodiment, the cell can be an animal cell that is maintained in tissue culture such as cell lines that are immortalized or transformed. These include a number of cell lines that can be obtained from American Type Culture Collection (Bethesda) such as, but not limited to: 3T3 (mouse fibroblast) cells, Rat1 (rat fibroblast) cells, CHO (Chinese hamster ovary) cells, CV-1 (monkey kidney) cells, COS (monkey kidney) cells, 293 (human embryonic kidney) cells, HeLa (human cervical carcinoma) cells, HepG2 (human hepatocytes) cells, Sf9 (insect ovarian epithelial) cells and the like.

In another preferred embodiment, the cell can be a primary or secondary cell which means that the cell has been maintained in culture for a relatively short time after being obtained from an animal. These include, but are not limited to, primary liver cells and primary muscle cells and the like. The cells within the tissue are separated by mincing and digestion with enzymes such as trypsin or collagenases which destroy the extracellular matrix. Tissues consist of several different cell types and purification methods such as gradient centrifugation or antibody sorting can be used to obtain purified amounts of the preferred cell type. For example, primary myoblasts are separated from contaminating fibroblasts using Percoll (Sigma) gradient centrifugation.

In another preferred embodiment, the cell can be an animal cell that is within the tissue in situ or in vivo meaning that the cell has not been removed from the tissue or the animal. When performed in-vivo, contacting the cells with the conjugate can be effected by administering the compound to a subject in need thereof.

The conjugates described herein can be administered or otherwise utilized according to the various aspects of the present inventions either per se or as a part of a pharmaceutical composition.

Thus, according to another aspect of the present invention there is provided a pharmaceutical composition, which comprises the conjugate, as described herein, and a pharmaceutically acceptable carrier.

As used herein a "pharmaceutical composition" refers to a preparation of one or more of the conjugates described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the conjugates into preparations which, can be used pharmaceutically. Proper formulation is dependent upon the route of administration chosen.

For injection, the conjugates described herein may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the conjugates described herein can be formulated readily by combining the conjugates with pharmaceutically acceptable carriers well known in the art. Such carriers enable the conjugates of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active doses of the conjugates.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the conjugates may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

The conjugates described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the conjugates preparation in water-soluble form. Additionally, suspensions of the conjugates may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the conjugates to allow for the preparation of highly concentrated solutions.

Alternatively, the conjugates may be in powder form for constitution with a suitable vehicle, e.g., sterile, pyrogen-free water, before use.

The conjugates described herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of conjugates effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any conjugates used in the context of the invention, the therapeutically effective amount or dose can be estimated initially from activity assays in animals. For example, a dose can be formulated in animal models to achieve a circulating concentration range that includes the $IC_{50}$ as determined by activity assays. Such information can be used to more accurately determine useful doses in humans.

Toxicity and therapeutic efficacy of the conjugates described herein can be determined by standard pharmaceutical procedures in experimental animals, e.g., by determining the $EC_{50}$, the $IC_{50}$ and the $LD_{50}$ (lethal dose causing death in 50% of the tested animals) for a subject conjugates. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects, termed the minimal effective concentration (MEC). The MEC will vary for each preparation, but can be estimated from in vitro data; e.g., the concentration necessary to achieve 50-90% vasorelaxation of contracted arteries. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a conjugates as described herein formulated in a compatible pharmaceutical carrier may also be prepared, placed in an appropriate container, and labeled for treatment of an indicated condition or diagnosis, depending on the biological moiety used.

Thus, according to an embodiment of the present invention, depending on the selected components of the conjugates, the pharmaceutical compositions of the present invention are packaged in a packaging material and identified in print, in or on the packaging material, for use in the treatment of a condition in which delivering of the biological moiety to a certain bodily target is beneficial.

Such conditions include, for example, any medical conditions in which intracellular administration of the active moiety is therapeutically or diagnostically beneficial.

As mentioned hereinabove, the design of the conjugates described herein was done while taking into consideration the conditions at which such conjugates can be assembled, in view of the relative high reactivity and instability of at least some of the components thereof. Thus, special synthetic methods have been developed to that end, as follows.

According to further aspects of the present invention, there are provided processes of preparing the conjugates, the delivery moieties and the building blocks described herein. The building blocks, and hence the oligomers and the conjugates incorporating same, were designed by the present inventor such that they furnish, by virtue of their functionalities, the following attributes:

(i) the ability to form an oligomer by conventional chemical processes which may be, in some cases, carried out by manual or automatic solid phase methods, or by enzymatic oligomerization processes;

(ii) the ability to form a conjugate with a biologically active moiety by conventional chemical processes which may be, in some cases, carried out by manual or automatic solid phase methods, or by enzymatic oligomerization processes;

(iii) the ability to have the functional groups be selectively protected and therefore selectively deprotected so as to allow various chemical processes to take place without jeopardizing any of their desired attributes;

(iv) the ability to be modified prior to the oligomerization process and/or the conjugation process, or thereafter, so as to have delivering groups attached thereto; and (v) a wide range of versatile alteration, substitutions and modifications which can be performed on the individual building block either before or after the oligomerization process, or on the entire group of building block residues once oligomerized, so as to allow the attachment of any moiety thereto such as a labeling moiety, a probe, a therapeutically active moiety, a reporter group and the like.

A process of preparing a conjugate of one or more of the oligomeric compounds described herein and one or more of a biologically active moiety, according to the present embodiments therefore involves:

providing one or more oligomeric compound, having the general Formula III:

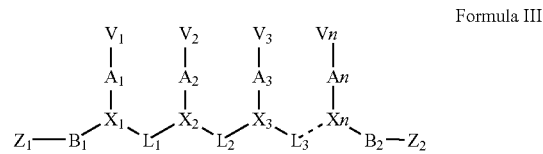

Formula III wherein n is an integer from 4 to 20; each of $X_1$-Xn is independently a residue of a building block of the oligomer as these are defined and discussed hereinabove; each of $L_1$-Ln is independently a first linking group as these are defined and discussed hereinabove or absent; each of $A_1$-An is independently a second linking group as these are defined and discussed hereinabove or absent; each of $B_1$ and $B_2$ is independently a spacer as these are defined and discussed hereinabove or absent; each of $Z_1$ and $Z_2$ is independently a reactive group, as these are defined and discussed hereinabove, capable of binding a biologically active moiety; and each of $V_1$-Vn is independently a delivering group, a group capable of being converted to a delivering group (also referred to herein as a pro-delivering group) or absent, and provided that the oligomer has at least one such delivering or pro-delivering group attached thereto;

providing one or more biologically active compound having at least one functional group capable of reacting with the reactive group of the oligomer; and coupling the biologically active compound and the oligomer compound, so as to provide the conjugate.

Thus, coupling the oligomer and the biologically active compound is effected by reacting at least one of the reactive groups of the oligomer and at least one of the functional groups of the biologically active compound. The oligomer is therefore designed, inter alia, to include at least one reactive group that is chemically compatible with a functional group of the biologically active compound to be delivered by the conjugate.

The coupling can be effected either by directly reacting the oligomer and the biologically active compound or by reacting the biologically active compound, consecutively, with the building blocks forming the oligomer. Thus, for example, in cases where the conjugate includes a delivery moiety and two oligonucleotides attached thereto, the first oligonucleotide can be formed first and the building blocks of the oligomer are sequentially attached to the oligonucleotide and to one another. Once the desired delivery moiety is formed, a second oligonucleotide moiety is similarly attached thereto.

The oligomer that is used in the process according to this aspect of the present invention, having the general Formula III, can be either the same as the oligomeric compounds described herein (see, general Formula I), or a derivative of such oligomer. The oligomer of choice is determined by the nature of the delivering group and the reaction conditions of the coupling. In cases where the delivering group is unstable under the coupling conditions, an oligomer including one or more pro-delivering group is used in the coupling reaction and the pro-delivering group is thereafter converted to the desired delivering group.

However, while the pro-delivering group can also be susceptible to the coupling process, protecting of the pro-delivering group, and/or the delivering group, prior to the coupling, is desirable. In such cases, deprotecting of the delivering or pro-delivering group is effected subsequent to the coupling. Since in some cases the required chemistry of the coupling may affect other functionalities of the oligomer, such as the delivering group or the pro-delivering group, the oligomer is constructed as, or converted to a protected form of the same, i.e., having a protecting group on each delivering group and/or pro-delivering group. Other functionalities which may require protection may be the reactive group of the oligomer which is not participating in the reaction, as, for example, is the case when the conjugate comprises two biologically active moieties and one delivery moiety, and reacting each biological moiety with a reactive group of the oligomer is performed sequentially.

Since current protecting-group technology offers a wide range of alternatives particularly suitable for specific functional groups and protection/deprotection conditions, each group requiring protection may be selectively protected to allow selective deprotection, under controlled conditions, of each group at the appropriate stage of the coupling.

Once the coupling between the oligomer and the biologically active compound is completed, the protecting group attached to the delivering group(s) and/or pro-delivering group(s) may be removed, rendering the delivery group(s) available or the pro-delivering group(s) ready for being converted into delivering group(s).

An exemplary protecting group which has been designed and efficiently used in the context of the present invention is 1-(4,4'-Dimethoxytrityl)-2-hydroxy, 10-Decyl (N,N'-bis-CEOC-guanidinium) (Compound 64). As is demonstrated in the Examples section that follows, such a compound efficiently served as a protecting group of a guanidine delivering group (see, for example, Compounds 65-67 in Schemes 40-42 in the Examples section that follows), which was removed subsequent to the coupling of the delivery moiety to oligonucleotides.

Thus, in the case where the oligomer contains pro-delivering group(s), the process of preparing the conjugate of the present invention further includes the conversion of the pro-delivering group to a delivering group. A non-limiting example of a pro-delivering group is an amine, such as in Compound 49, presented in the Example section that follows, which is protected by an Fmoc protecting group during the in situ construction of the oligomer and prior to the coupling with the second biologically active compound, on route to forming the desired intermediate Compound 51. The amine group in the case of Compound 51 is a pro-delivering group with respect to the final conjugate, Compound 52, having a guanidine group serving as a delivering group after a conversion of the deprotected amine to guanidine by treatment with pyrazole carboxamidine and ammonium hydroxide.

Another non-limiting example of a pro-delivering group is an amine, as in Compounds 60 and 61, presented in the Examples section that follows, which is protected by a TFA protecting group during the in situ construction of the oligomer and its conjugation to the biologically active moieties (e.g., oligonucleotides). The amine group in the case of Compounds 60 and 61 is a pro-delivering group with respect to the final conjugate, represented by Structure A, having a guanidine group serving as a delivering group after a conversion of the deprotected amine to guanidine by treatment with pyrazole carboxamidine and sodium carbonate.

Providing the oligomer having the general Formula III can be alternatively effected, according to an embodiment of the present invention, by providing an oligomer devoid of delivering or pro-delivering groups and thereafter attaching thereto these groups. In this case, the oligomer is designed so as to have reactive groups to which delivering or pro-delivering groups can be attached.

Further alternatively, according to another embodiment of this aspect of the present invention, providing the oligomer is effected by sequentially building the oligomer from a plurality of building clocks, whereby at least a portion of the building blocks includes a delivering or pro-delivering moiety.

According to this embodiment, the oligomer is therefore obtained by providing two or more compounds, also referred to herein as a residue of a building block, having the general Formula IV:

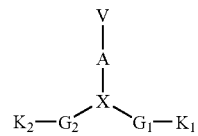

Formula IV wherein:

X is a residue of a building block of the oligomer;

A is a linking group or absent;

V is a delivering group, a group capable of being converted to a delivering group or absent;

each of $G_1$ and $G_2$ is independently a linking group or absent;

$K_1$ is a first reactive group;

K2 is a second reactive group being capable of reacting with the first reactive group, provided that in one or more of the compounds having the general Formula III Vn is the delivering group or the pro-delivering group; and reacting the first reactive group and the second reactive group, thereby obtaining the oligomeric compound.

In one embodiment of the present invention, the building block is a nucleotide or a modified nucleotide. In this embodiment, the reactive groups $K_1$ and $K_2$ form a part of the building block. More specifically, the reactive group denoted $K_1$ in Formula IV is the terminal phosphate in the triphosphate group of the nucleotide, and the reactive group denoted $K_2$ in Formula IV is the 3' hydroxyl group on the ribose residue of the nucleotide.

In another embodiment of the present invention the residue of the building block comprises a phosphorous-containing residue, whereby the phosphorous-containing residue can be a phosphate-containing residue, a phosphonate-containing residue, or, preferably, a phosphorous-containing residue that is capable of being converted to a phosphate-containing or phosphonate-containing residue upon condensation.

A representative example of such a phosphorous-containing residue that is capable of being converted to a phosphate-containing or phosphonate-containing residue upon condensation is a phosphoramidite residue or a derivative thereof, as described hereinabove.

As discussed hereinabove, phosphoramidite residues are reactive groups that form a phosphate group upon condensation thereof with a hydroxy group and are therefore widely used in the synthesis of oligonucleotides. As is further discussed hereinabove, a phosphoramidite can serve as a preferred reactive group in the oligomers described herein, for coupling to the oligomer a biologically active moiety such as an oligonucleotide.

Thus, in a preferred embodiment of this aspect of the present invention, in cases where the oligomer comprises phosphate-containing or phosphonate-containing residues, the building block used for constructing the oligomer comprises a phosphoramidite residue. This phosphoramidite residue serves as both the residue of the building block and the reactive group in the building block.

The phosphoramidite residue in such building blocks is selected according to the desired nature of the resulting oligomer. Thus, for example, a phosphoramidite having the general structure —O—P(OW)—NR'R", as presented hereinabove, where R' and R" are as described above and W serves as an oxygen protecting group, can be used for providing a phosphate-containing building block residue in the oligomer. A phosphoramidite derivative having the general structure —O—P(Ra)—NR'R", where Ra, R' and R" are as described above, can be used for providing a phosphonate-containing building block residue in the oligomer.

In another example of this aspect of the present invention, the coupling is effected by using solid phase synthetic methods, while having the oligomeric compound or the biologically active agent attached to a solid support. Thus, for example, the oligomeric compound can be prepared via solid phase synthesis, by modifying the solid support, attaching thereto a building block as described herein and then sequentially forming the oligomer, to thereby obtain an oligomer attached to the solid support, as depicted for example in Schemes 58-68 (see, the Examples section that follows). In this embodiment, the biologically active moiety can be attached to the oligomer while being bound to the solid support, or, alternatively, upon detaching the oligomer from the solid support.

Optionally, in cases where the biologically active moiety can be prepared by being bound to a solid support, as in the case of a DNA or an RNA, the oligonucleotide can be prepared by solid phase synthesis, and then be coupled to the delivery moiety while being bound to the solid support.

As discussed herein and demonstrated in the Example section that follows, a building block may be a naturally occurring compound, a modified naturally occurring compound or a synthetically prepared compound and the oligomer may contain a mixture of modified and unmodified building blocks from various sources and families in any combination thereof. Furthermore, the building block may naturally contain one or both of the first and second reactive groups, denoted $K_1$ and $K_2$ in general Formula IV. In any event, the building block is designed to be chemically compatible and efficient, when utilized in both the formation of the oligomer and the coupling thereof with the biologically active compound.

Exemplary such compatible building blocks have been designed and successfully prepared. These building blocks where designed to include reactive groups that allow an efficient oligomerization thereof and further provide a biocompatible oligomer. In addition, the reactive groups are designed to form such an oligomeric backbone that would not be susceptible to degradation during any of the reactions that follow its formation.

Such meticulously designed building blocks are therefore highly efficient and furthermore, have not been prepared or practiced for the purpose of assembling such oligomers and conjugates of the same.

Thus, according to a further aspect of the present invention, there are provided novel compounds, having the general Formula VII:

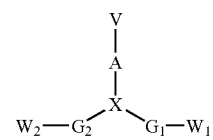

Formula VII wherein:

X is -D-(CR'R")mCR(CR'''R'''')l-F— group, whereas:

D and F are each independently selected from the group consisting of nitrogen, oxygen, and sulfur;

m and l are each independently an integer from 1 to 6;

R, R', R", R''' and R'''' are each independently selected from the group consisting of hydrogen, alkyl, cycloalkyl and aryl;

A is a linking group, as described herein, and is preferably a hydrocarbon such as alkyl or alkenyl, as defined herein;

V is a group capable of being converted to a delivering group;

each of $G_1$ and $G_2$ is independently a linking group or absent; and $W_1$ and $W_2$ are each independently selected from the group consisting of a reactive group, a protecting group or absent.

In one example, the novel building blocks according to this embodiment of the present invention are based on an alkylene glycol, preferably propylene glycol and an acetal moiety, which are aimed at forming a polyether oligomer. In a specific example demonstrated in the Examples section that follows, the building block is prepared by condensing a reactive derivative of a propylene glycol with a reactive diacetal derivative of a propylene glycol, each having attached thereto a protected aminohexane, to form a repeating unit of 3 building block residues. The building blocks used for preparing the repeating unit and the repeating unit itself are referred to hereinbelow as Compounds 72, 73 and 75.

49

Additional advantages of such a building block and of oligomers formed thereby are delineated hereinabove.

Thus, preferably, in Formula VII above, m and l are each 1.

R, R', R", R'" and R"" are preferably each hydrogen.

Further preferably, each of $G_1$ and $G_2$ is independently a substituted or unsubstituted hydrocarbon chain, more preferably, a methylene ($CH_2$) group.

Further preferably, each of K1 and K2 is independently a derivatized hydroxy (—OR) or derivatized thiol (—SR), preferably selected as reactive groups that are capable of undergoing a condensation reaction. For example, a hydroxy can be derivatized to a carboxylate or by a methylthioalkyl.

Additional exemplary preferred building blocks in this category include Compound 78, as depicted hereinbelow.

Thus, according to another aspect of the present invention, there are provided novel compounds, having the general Formula V:

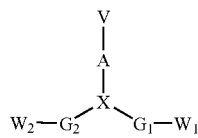

Formula V wherein:

X is a -E-(CR'R")mC(=D)- group, wherein:

E and D are each independently selected from the group consisting of nitrogen, oxygen, and sulfur;

m in an integer from 1-6; and each of R and R' independently selected from the group consisting of hydrogen, alkyl, cycloalkyl and aryl;

A is a linking group;

V is a group capable of being converted to a delivering group;

each of $G_1$ and $G_2$ is independently a linking group or absent; and $W_1$ and $W_2$ are each independently selected from the group consisting of a reactive group, a protecting group or absent.

In one example, the novel building blocks according to this embodiment of the present invention is based on an amine and a carboxyl which are aimed at forming a peptoid oligomer resembling a polypeptide chain but offers advantages over the latter being more stable and versatile for alterations. In a specific example demonstrated in the Examples section that follows, the building block is prepared by reacting 1,6-diaminehexane N'-protected by a trifluoroacetate group with methyl acrylate to form the repeating unit, which can be viewed as a 3-aminopropanoic acid having a "side chain" stemming from the terminal amine thus rendering it more stable during the oligomerization and conjugation process, and also less susceptible to metabolic degradation once within the biological system. The so-called side-chain consists of a six-carbon long linking group and an amine at the end, resembling a lysine residue, and offering a wide range of alternatives for modification, such as the conversion, by a guanidine group, to a arginine-like residue.

50

Such a building block is referred to herein as Compound 44 and has the following structure:

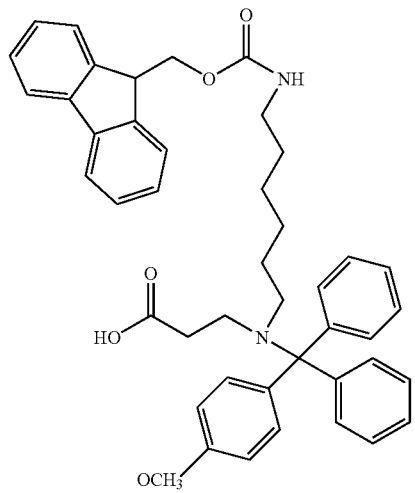 [SMILES: COc1ccc(C(c2ccccc2)(c2ccccc2)N(CCCCCCNC(=O)OCC2c3ccccc3-c3ccccc32)CCC(=O)O)cc1]

Using such a building block, solid phase synthesis of the oligomer can be performed.

Additional advantages of such a building block and of oligomers formed thereby are delineated hereinabove.

According to another aspect of the present invention, there are provided novel compounds, having the general Formula VI:

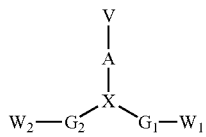

Formula VI wherein:

X is a phosphorous-containing residue;

A is a linking group;

V is a delivering group or a group capable of being converted to a delivering group;

each of $G_1$ and $G_2$ is independently a linking group or absent; and $W_1$ and $W_2$ are each independently selected from the group consisting of a reactive group, a protecting group or absent.

Preferred compounds according to this aspect of the present invention are compounds having a phosphorous-containing residue that is capable of forming a phosphate-containing and/or a phosphonate-containing residue upon condensation.

As discussed hereinabove, such compounds preferably include a phosphoramidite residue, preferably formed by X and $W_1$ in Formula VI above. The presence of a phosphoramidite residue enables to use these compounds in the preparation of an oligomer, according to the present embodiments, while using solid-phase syntheses methods that can be applied also for sequentially attached to the oligomer an oligonucleotide.

Further preferred compounds according to this aspect of the present invention are compounds having a -J-O—P(U)(Ra)—O— group as the phosphorous-containing residue, where J is selected from the group consisting of alkyl, cycloalkyl, aryl, ether and amide; U is an oxo group or absent;

and Ra is selected from the group consisting of hydrogen, hydroxy, alkoxy, aryloxy, alkyl, aryl and cycloalkyl.

As used herein, the term "oxo" describes a =O group.

Preferably, in such compounds, $W_1$ is a reactive group and further preferably it is a dialkylamine, such that the phosphorous-containing residue is a phosphoramidite or a derivative thereof.

Particularly preferred compounds according to this aspect of the present invention are compounds in which J is methylene; Ra is aryl, preferably phenyl; V is a delivering group, preferably guanidine, or a group capable of being converted to an amine and/or to a guanidine, as described hereinabove; $W_1$ is a reactive group, preferably a dialkylamine; $G_1$ is absent and $G_2$ is a hydroxyalkyl residue, preferably protected by a protecting group represented by $W_2$ in Formula VI above. Preferably, the hydroxy-protecting group is dimethoxytrityl.

Such preferred compounds can be collectively represented by the following Formula:

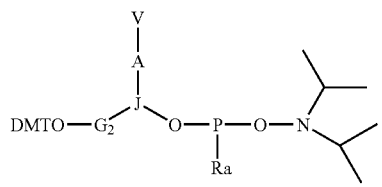

wherein:

$G_2$-ODMT form a protected hydroxyalkyl;

J is alkylene;

V is a delivering group (e.g., guanidine) or a group capable of being converted to a delivering group (e.g., a protected amine or a protected guanidine); and Ra is selected from the group consisting of phenyl and O—$CH_2CH_2CN$.

Exemplary compounds in this category include, for example, 1-(4,4'-Dimethoxytrityl)-2-hydroxy, 10-Decyl[(N, N'-bis-CEOC-guanidinium) (Compound 66), 1-(4,4'-Dimethoxytrityl)-2-(N,N-diisopropylamino, phenyl)-phosphine, 10-Decyltrifluoroacetamide (Compound 60), 1-(4,4'-Dimethoxytrityl)-2-(N,N-diisopropylamino, cyanoethyl)-phosphoramidite, 10-Decyltrifluoroacetamide (Compound 61), and 1-(4,4'-Dimethoxytrityl)-2-(N,N-diisopropylamino, cyanoethyl)-phosphoramidite, 10-Decyl[(N,N'-bis-CEOC-guanidinium) (Compound 67).

The chemical structures, preparation and characterization of these compounds are presented in the Examples section that follows.

Using such a building block, solid phase synthesis of the oligomer can be performed.

In another example, modified naturally occurring building blocks are designed.

Such modified building blocks, may be prepared according to a variety of processes, some of which are presented and demonstrated in the Examples section that follows. The present inventor, however, has designed and successfully prepared a variety of modified nucleotides, which can serve either as building blocks of the oligomeric compound described herein or for providing protected nucleotides that form a protected oligonucleotide, as described in detail hereinabove. Such modified nucleotides have been particularly designed so as to be compatible for both chemical syntheses and enzymatic syntheses with a polymerase. The modification were performed so as to maintain the recognition of the modified base by a polymerase, as is demonstrated in the Examples section that follows.

An exemplary process of preparing such modified building block is the preparation of a series of modified nucleotidic building blocks, which starts with the substitution of the pyrimidine base at the 5-position with 3-aminoallyl to form 5-(3-aminoallyl) derivative of the nucleotide, followed by the reaction of the amine group of the 3-aminoallyl with a series of N-hydroxysuccinimide esters (NHS-esters) of three exemplary delivering group residues namely urocanic acid, imidazole and histidine. Using this process, various modified oligonucleotides having a positively charged group have been prepared (see, for example, Tables 1-5 in the Example section that follows). Such modified nucleotides were designed suitable for use in manual or automated enzymatic synthesis of nucleotides.

Another exemplary process of preparing such modified nucleotides according to the present embodiments is directed at providing modified nucleotides having positively charged groups attached thereto, which are suitable for use in common solid phase syntheses. Such a process and the modified nucleotides formed thereby is described in detail in the Examples section that follows (see, for example, Schemes 1-5).

Thus, according to a further aspect of the present invention there is provided a modified nucleotide that comprises: a triphosphate moiety or a phosphate-containing moiety attached to a ribose moiety; and a purine or pyrimidine base being attached to the ribose moiety and having at least one delivering group or a group capable of being converted to a delivering group being attached thereto.

According to another aspect of the present invention there is provided an oligonucleotide comprising a plurality of nucleotides and at least one of the novel modified nucleotides described herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

All reagents and solvents were purchased from commercial sources unless otherwise indicated.

2-Cyanoethanol, N,N'-disuccinimidyl carbonate (DSC), N-(2-hydroxy)-phthalimide, 2-cyanoethyl-N,N,N',N'-tetraisopropylphosphoro-diamidite, 6-amino-hexanol and 2-methyl-2-thiopseudourea-sulfate were obtained from Aldrich Chemical Co., Inc. (Milwaukee, Wis.).

Reagents for the DNA synthesizer were purchased from PerSeptive Biosystems, Inc. (Framingham, Mass.).

2,2'-Anhydro-5-methyluridine was purchased from Ajinomoto (Tokyo, Japan). Flash chromatography was performed on silica gel (Baker, 40 mm).

Thin-layer chromatography was performed on Kieselgel glass plates from E. Merck and visualized with UV light and p-anisaldehyde/sulfuric acid/acetic acid spray followed by charring.

Other experimental methods and instrumental data are cited hereinbelow.

Syntheses of Nucleotide Building Blocks for the Preparation of Oligonucleotide-Based Delivery Systems Preparation of Modified Nucleotides for Chemical Syntheses of Oligonucleotides Preparation of Trifluoroacetyl Allylamine (Compound 1)

Ethyltrifluoroacetate (14.2 grams, 100 mmol) was added to a solution of allylamine (4.05 grams, 6 ml, 80 mmol) and N,N-diisopropylethyl amine (10.32 grams 7.3 ml, 80 mmol) in methanol (30 ml). The reaction mixture was stirred at room temperature for 15 hours. The solvent was thereafter removed under reduced pressure and the product (see, Compound 1 in Scheme 1 below) was extracted with ethyl acetate.

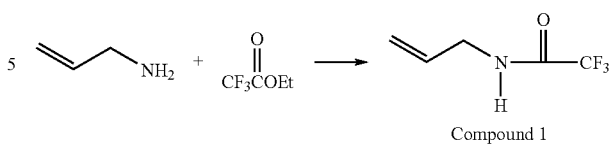

Scheme 1

Compound 1

Preparation of 5-(3-trifluoracetylaminopropenyl)-2'-deoxyuridine (Compound 2)

Uridine was reacted with diacetoxymercury to afford 5-Chloromercuri-2'-deoxyuridine [Ruth, J. L., 1984, *DNA* 3. 123]

5-Chloromercuri-2'-deoxyuridine (3.6 grams, 7.8 mmol) was suspended in 200 ml methanol. N-allyltrifluoroacetamide (Compound 1, 6.8 ml, 55 mmol) was added to the resulting mixture, followed by addition of 41 ml of 0.2 N lithium tetrachloropalladate in methanol. The obtained mixture was stirred at room temperature for 18 hours, and was thereafter filtered to remove the palladium (obtained as a black solid). The yellow methanolic filtrate was treated with five 200 mg portions of sodium borohydride and was thereafter concentrated under reduced pressure to give a solid residue. The residue was purified by flash column chromatography on silica gel using a mixture of 15:85 (v/v) methanol:chloroform as eluent. Adequately pure fractions of the eluted product were combined and concentrated under reduced pressure to afford 2.4 grams of crystalline 5-(3-trifluoroacetylamino-propenyl)-2'-deoxyuridine (see, Compound 2 in Scheme 2 below). Silica TLC of the product using a mixture of 15:85 (v/v) methanol:chloroform as eluent gave an Rf of 0.4.

Scheme 2

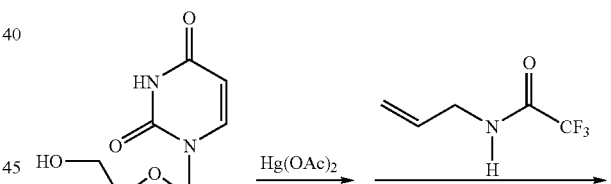

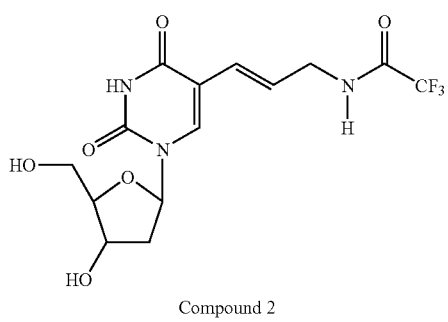

Compound 2

Preparation of 5'-(4,4'-Dimethoxytrityl)-5-(3-trifluoracetylaminopropenyl)-2'-deoxyuridine (Compound 3)

5-(3-trifluoroacetylamino-propenyl)-2'-deoxyuridine (Compound 2, 3.93 grams, 10 mmols) was dissolved in anhydrous pyridine (50 ml) and the pyridine was evaporated to dryness under reduced pressure. The residue was redissolved in anhydrous pyridine (50 ml) and cooled to 0° C. under argon. A solution of 4,4'-dimethoxytrityl-chloride (DMTCl, 3.75 grams, 11 mmols) in anhydrous pyridine (30 ml) was added dropwise to the cooled solution while stirring over a period of 1 hour. The reaction mixture was allowed to warm to room temperature, and was stirred for additional 4 hours. The reaction mixture was thereafter evaporated to dryness under reduced pressure, the residue was extracted with ethyl acetate (250 ml), brine (200 ml), and the organic layer was dried over anhydrous sodium sulfate, and concentrated by rotary evaporator to a foam. The product (see, Compound 3 in Scheme 3 below) was purified by column chromatography on a 3×30 cm neutralized silica gel column, using a linear gradient of 2 liters chloroform containing 0.2% triethylamine to 2 liters of a mixture of 1:9 (v/v) methanol:chloroform as eluent, yielding 5.1 grams of a white powder at 74% yield. Silica TLC of the product using a mixture of 1:9 (v/v) methanol:chloroform as eluent gave an Rf of 0.3.

Scheme 3

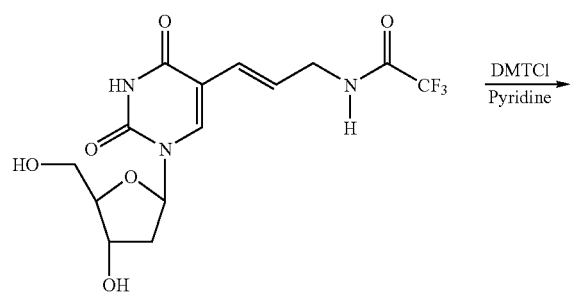

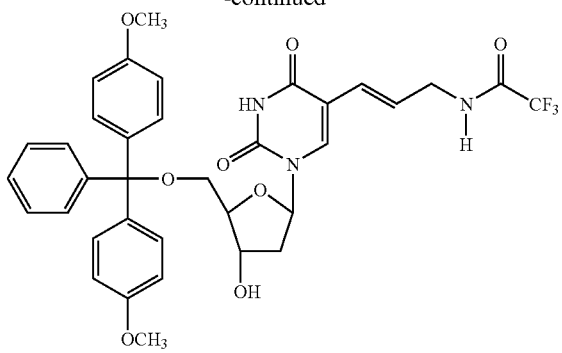

Compound 3

Preparation of 3'-β-cyanoethyl-N,N-diisopropylphosphoramidite-5'-(4,4'-dimethoxytrityl)-5-(3-trifluoracetylaminopropenyl)-2'-deoxyuridine (Compound 4)

5'-(4,4'-Dimethoxytrityl)-5-(3-trifluoracetylaminopropenyl)-2'-deoxyuridine (Compound 3, 4.31 grams, 6.2 mmols) was dissolved in anhydrous tetrahydrofuran (30 ml) and the solution was cooled to 0° C. under argon atmosphere. Diisopropylethylamine (2.1 ml) was then added to the cooled solution, while maintaining argon atmosphere, followed by dropwise addition of chloro-β-cyanoethyl N,N-diisopropylphosphoramidite (1.5 ml). The reaction mixture was stirred at 4° C. for 20 minutes, while being monitored by TLC (eluent: a mixture of 2:1 (v/v) ethyl acetate:cyclohexane, Rf of the starting material=0.30; Rf of the product=0.45). Upon reaction completion, the mixture was evaporated to dryness under reduced pressure, the residue was extracted with ethyl acetate (250 ml), brine (200 ml) and the organic layer was dried over anhydrous sodium sulfate, and concentrated under reduced pressure to give the product (see, Compound 4 in Scheme 4 below) as a foam. The product was purified by column chromatography on a 3×30 cm neutralized silica gel column using a linear gradient of 500 ml mixture of 2:3 (v/v) ethyl acetate:cyclohexane containing 0.2% triethylamine to 500 ml a mixture of 9:1 (v/v) ethyl acetate:cyclohexane. The fractions containing the purified product were collected, combined and were evaporated to dryness under reduced pressure. The obtained residue was dissolved in anhydrous benzene (20 ml) and was lyophilized to afford 4.9 grams of a white powder (49.7% yield).

Scheme 4

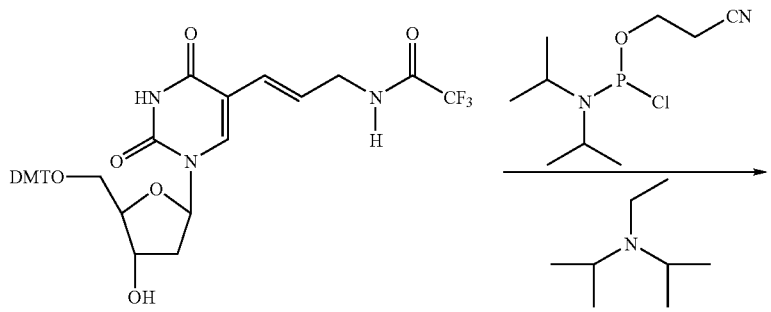

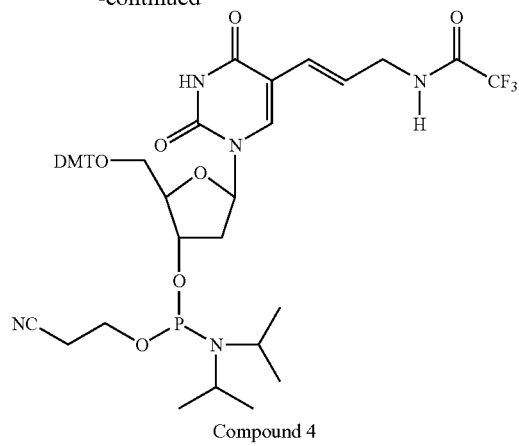

Compound 4

Preparation of 3'-β-cyanoethyl-N,N-diisopropylphosphoramidite-5'-(4,4'-dimethoxytrityl)-5-(3-trifluoracetylaminopropenyl)-2'-deoxycytidine (Compound 5)

3'-β-cyanoethyl-N,N-diisopropylphosphoramidite-5'-(4,4'-dimethoxytrityl)-5-(3-trifluoracetylaminopropenyl)-2'-deoxycytidine (Compound 5) was prepared from cytosine as described above for the preparation of 3'-β-cyanoethyl-N,N-diisopropylphosphoramidite-5'-(4,4'-dimethoxytrityl)-5-(3-trifluoracetylamino propenyl)-2'-deoxyuridine (Compound 4).

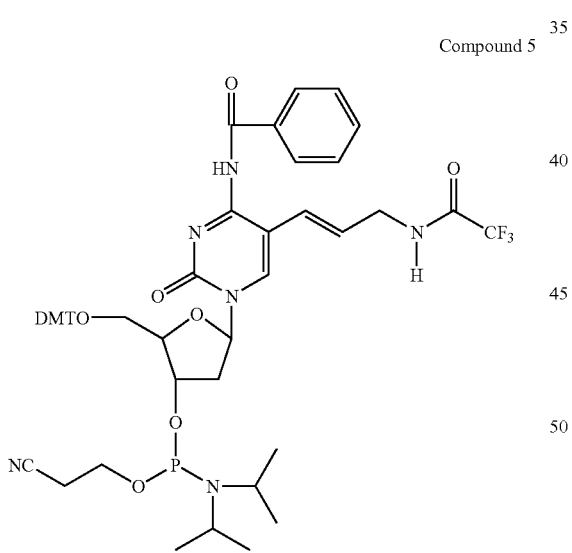

Compound 5

Preparation of 5'-O-DMT-N⁴-(ethyltrifluoroacetamido),3'-β-cyanoethyl-N,N-diisopropylphosphoramidite, 2'-deoxycytidine (Compound 6)

5'-O-DMT-N⁴-(ethyltrifluoroacetamido),3'-β-cyanoethyl-N,N-diisopropyl phosphoramidite-2'-deoxycytidine (see, Compound 6 in Scheme 5 below) was prepared according to Jerry L. Ruth, Oligonucleotides and Analogues IRL PRESS (1991).

Scheme 5

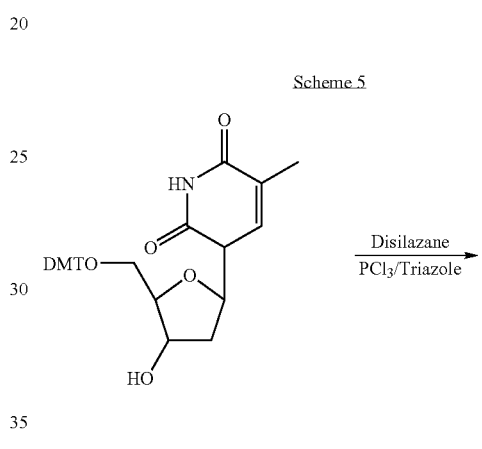

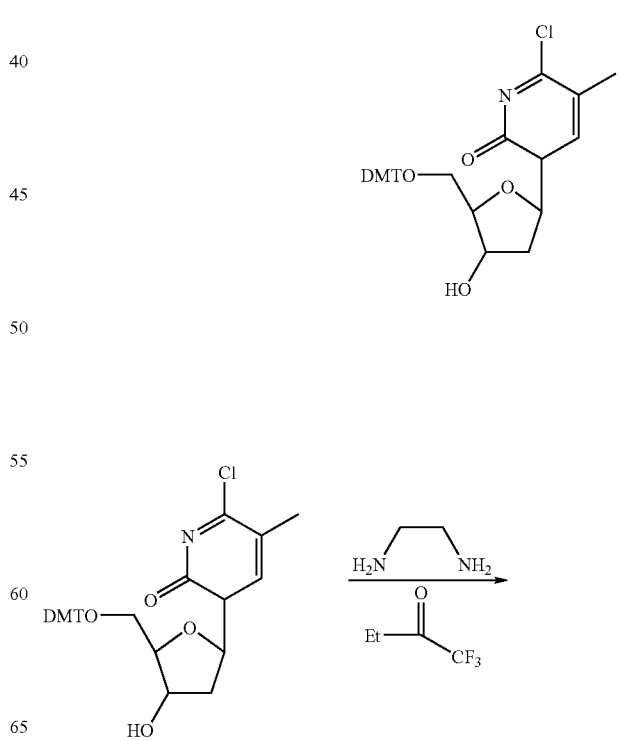

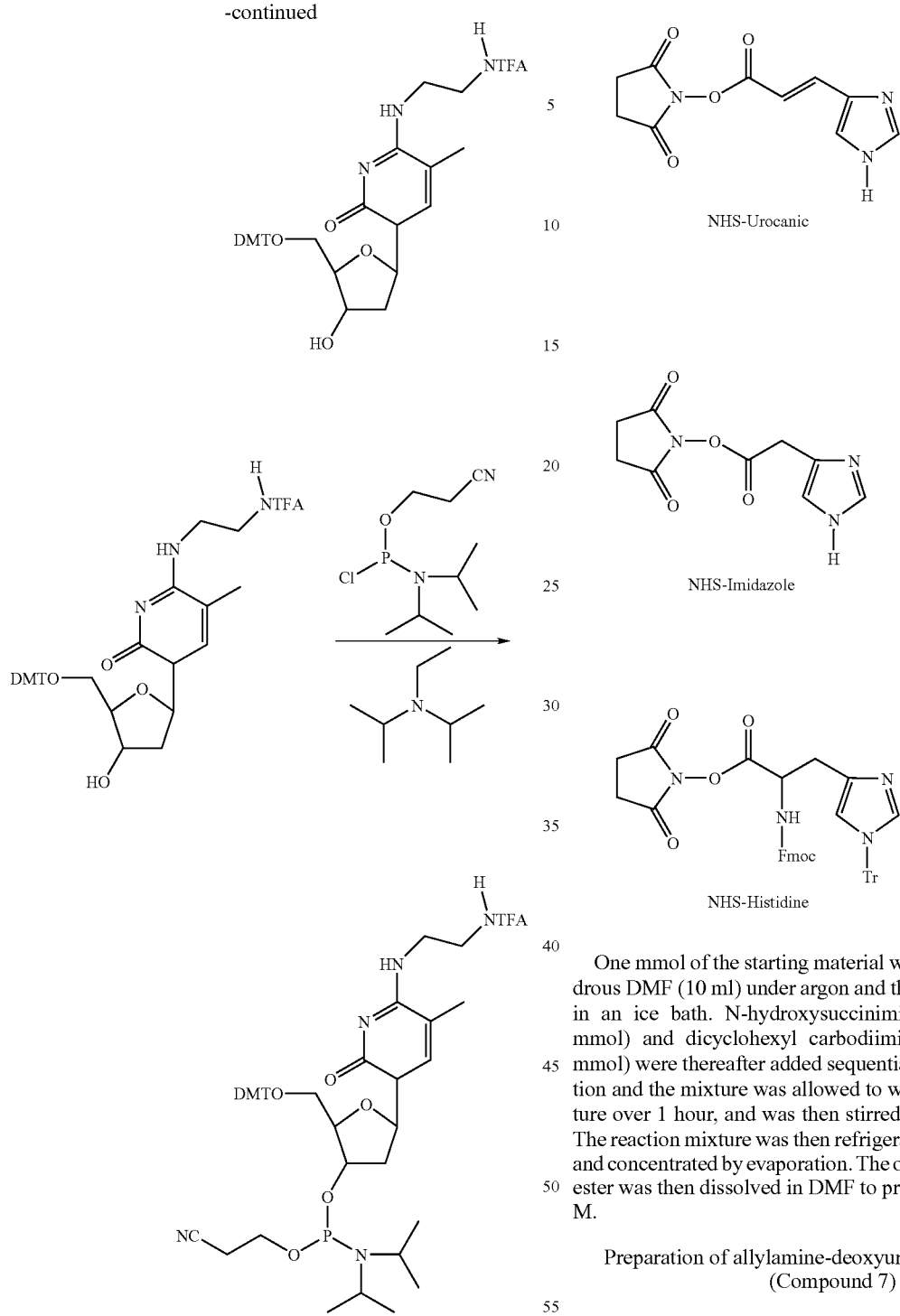

Preparation of Modified Nucleotides for Enzymatic Syntheses of Oligonucleotides

Preparation of Reactive NHS-Esters—General Procedure

Exemplary reactive NHS-esters were prepared based on a procedure by Lee et al., 2001, *Nucleic Acids Res.* 29: 1565-1573, using urocanic acid, imidazole 4-acetic acid and histidine as starting materials, as presented in Scheme 6 below.

One mmol of the starting material were dissolved in anhydrous DMF (10 ml) under argon and the solution was cooled in an ice bath. N-hydroxysuccinimide (0.126 gram, 1.1 mmol) and dicyclohexyl carbodiimide (0.226 gram, 1.1 mmol) were thereafter added sequentially to the stirred solution and the mixture was allowed to warm to room temperature over 1 hour, and was then stirred for additional 1 hour. The reaction mixture was then refrigerated overnight, filtered and concentrated by evaporation. The obtained reactive NHS-ester was then dissolved in DMF to provide a solution of 0.5 M.

Preparation of allylamine-deoxyuridinetriphosphates (Compound 7)

Deoxyuridinetriphosphate (dUTP, 554 mg, 1.0 mmol, Sigma) was dissolved in 100 ml of 0.1 M sodium acetate buffer pH 6.0, and mercuric acetate (1.59 grams, 5.0 mmols) was added thereto. The solution was heated at 50° C. for 4 hours, and cooled to 0° C. Lithium chloride (392 mg, 9.0 mmols) was added and the solution was extracted six times with equal volumes of ethyl acetate to remove excess $HgCl_2$. Completion of the extraction process was monitored by determining the mercuric ion concentration in the organic layer using 4,4'-bis(dimethylamino)-thiobenzophenone according to Christoper, A. N., 1969, *Analyst,* 94, 392. The efficiency of the nucleotide mercuration process was monitored spectrophotometrically, by following the iodination of the aqueous solution according to Dale, R. M. K. et al., 1975, *Nucleic Acid Res.* 2, 915, and was found to remain between 90% and 100% efficiency. The mercurated nucleotide product in the aqueous layer was precipitated by the addition of three volumes of ice cold ethanol and collected by centrifugation. The precipitate was washed twice with cold anhydrous ethanol, once with ethyl ether, and then air dried.

The resulting mercurated nucleotide were dissolved without further purification in 0.1M sodium acetate buffer at pH 5.0, and adjusted to a concentration of 20 mM. An absorbance measurement of the mercurated nucleotide solution gave a reading of 200 OD/ml at 267 nm. A fresh 2.0 M solution of allylamine acetate in aqueous acetic acid was prepared by slowly adding 1.5 ml of allylamine (13.3 mmols) to 8.5 ml of ice-cold 4 M acetic acid. Three ml (6.0 mmols) of the neutralized allylamine stock was added to 25 ml (0.5 mmol) of nucleotide solution. A molar equivalent (with respect to the nucleotide) of 1 M $Li_2PdCl_4$ (0.5 ml, 0.5 mmol) was then added to initiate the reaction. Upon addition of the palladium salt the solution gradually turned black with metal deposits appearing on the walls of the reaction vessel. The reaction mixture was allowed to rest at room temperature for 24 hours, and was thereafter filtered through a 0.45 mm membrane (Nalgene) to remove most of the remaining metal precipitate.

The yellow filtrate was diluted five-fold with the solvent and applied onto a 100 ml HPLC column of DEAE-Sephadex TM A-25 (Pharmacia). The loaded column was washed with 0.1 M sodium acetate buffer at pH 5.0 and a one liter of linear gradient (0.1 M to 0.6 M) of either sodium acetate at pH 8-9, or triethylammonium bicarbonate (TEAB) at pH 7.5 was used as the mobile phase. The major product was eluted at a 0.30-0.35 M salt concentration. Spectral analysis of the eluted fraction showed that it contained several products. Final purification of the product, 5'-triphosphate-5-(3-aminopropen-1-yl)deoxyuridine or allylamine-dUTP (see, Scheme 7 below), was achieved by reverse phase HPLC chromatography on columns of Partisil-ODS2, using either 0.5 M $NH_4/NH_4$—$H_2PO_4$ buffer at pH 3.3 (analytical separations), or 0.5 M triethylammonium acetate at pH 4.3 (preparative separations) as the mobile phase.

Scheme 7

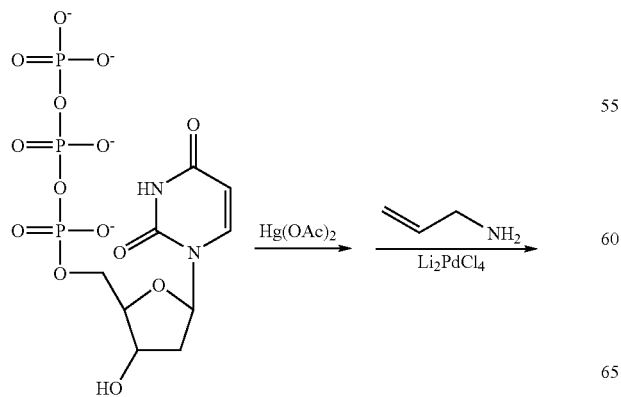

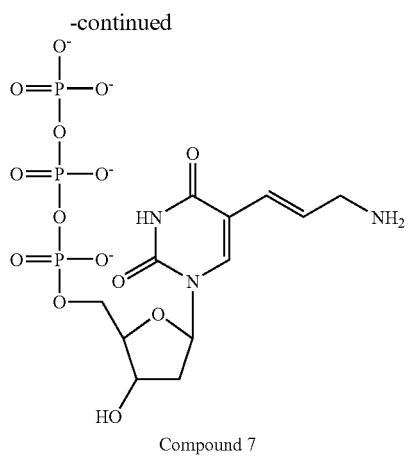

Compound 7

Preparation of a Modified Deoxyuridinetiphosphate (dUTP)—General Procedure

5'-Triphosphate-5-(3-aminopropen-1-yl)deoxyuridine (allylamine-dUTP, Compound 7) was dissolved in 0.5 ml of a 1:1 solution of 0.1 M sodium borate buffer, pH 9 and DMF at room temperature. An active NHS-ester, prepared as described above, (3 equivalents) was then added and the pH of the reaction mixture was adjusted with triethylamine to pH 9. The reaction mixture was stirred overnight at room temperature and was thereafter evaporated to dryness.

The crude residue was dissolved in 2 ml of 50 mM aqueous TEAB buffer set at pH 7.5, and was then filtered and purified by reversed phase HPLC.

Further purification of the modified dUTP was performed on a micropore Bondapak 3.9×300 mm C18 column (Waters) using 0.1 M TEAB set at pH 7.5 and a flow rate of 1 ml/minute.

All modified dUTPs were ion-exchanged from triethylammonium to sodium ion using standard procedures and the final modified dUTP products were lyophilized to dryness.

Scheme 8

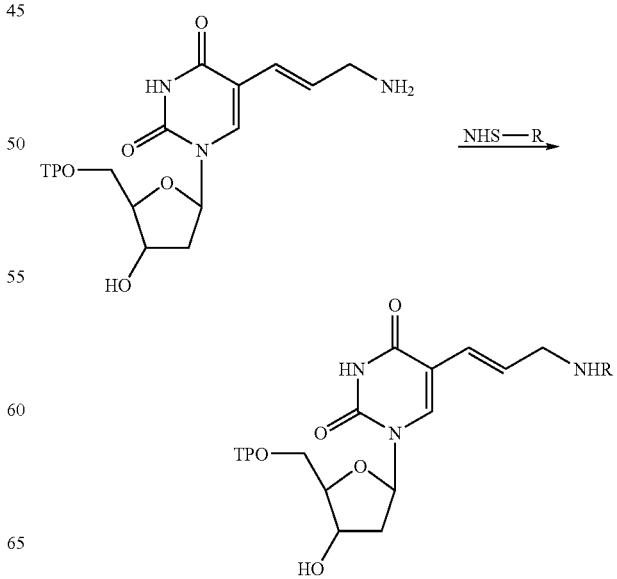

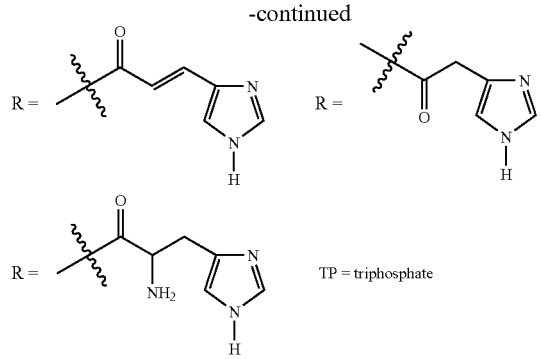

TP = triphosphate

Table 1 presents the modified dUTP prepared according to the general procedure described above, alongside with their Compound numbers as these are referred to herein throughout.

Preparation of Modified Deoxycytidinetiphosphate (dCTP)—General Procedure 5-aminoallyl-dCTP was purchased from Trilink Biotechnologies. $N^4$-(2-aminoethyl)dCTP and $N^4$-(6-aminohexyl)dCTP, commonly referred to as $N^4$-(6-aminoalkyl)dCTP, were prepared according to Draper D. E., 1984, *Nucleic Acid Res.*, 12, 989, by treatment of the dCTP with diaminoethane or diaminohexane in the presence of bisulfite at pH 5.5, followed by adjustment of the pH to 8.5, to afford $N^4$-(2-aminoalkyl)dCTP at a yield of less than 50%.

The aminoalkylated-dCTP products were treated with the active NHS-esters described above as illustrated in Scheme 9 below.

TABLE 1

| Compound Number | Structure |
|---|---|
| Compound 8 | 8 |
| Compound 9 | 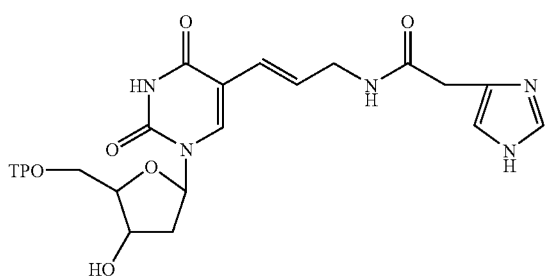 |
| Compound 10 | 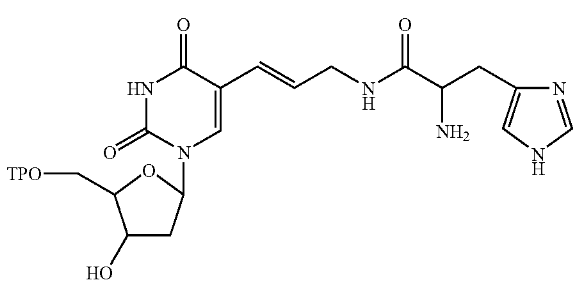 |

Scheme 9
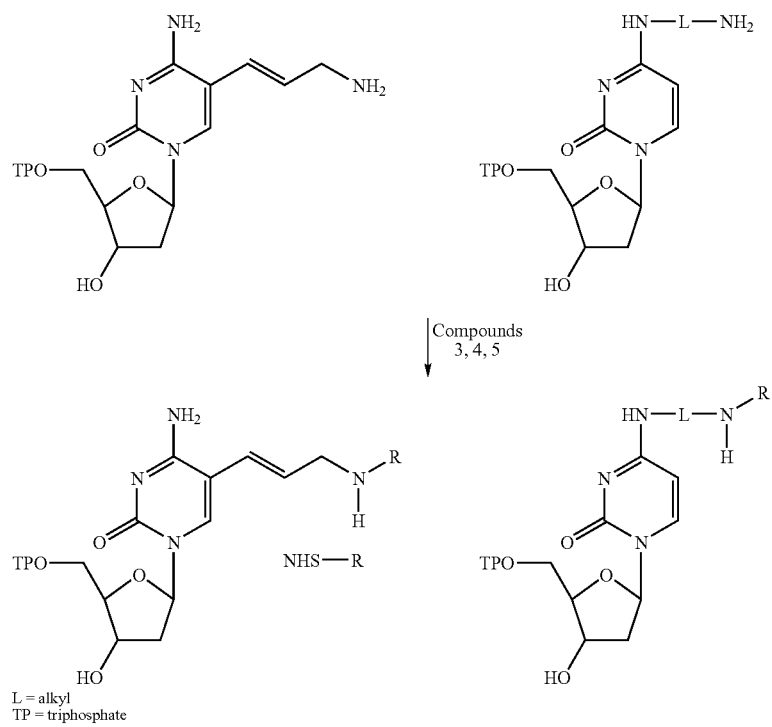
L = alkyl
TP = triphosphate
Table 2 presents the modified dCTP prepared according to the general procedure described above, alongside with their Compound numbers as these are referred to herein throughout.
TABLE 2
| Compound Number | Structure |
| --- | --- |
| Compound 11 | 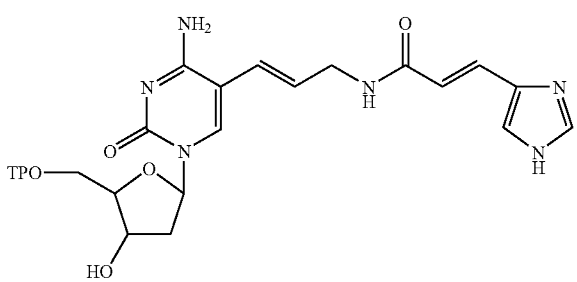 |
| Compound 12 | 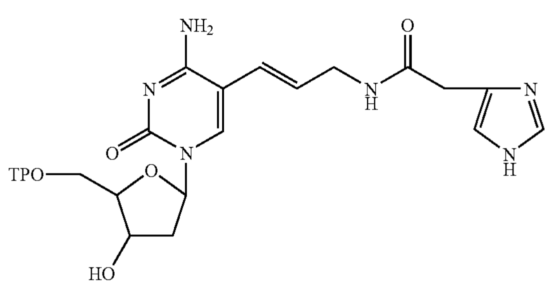 |

TABLE 2-continued

| Compound Number | Structure |
| --- | --- |
| Compound 13 | 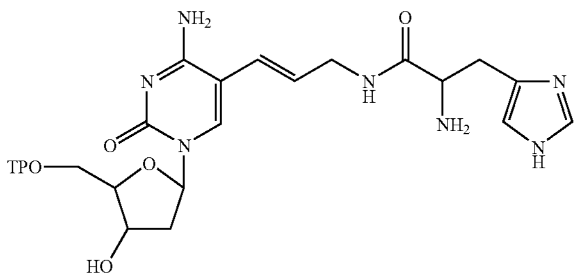 |
| Compound 14 | 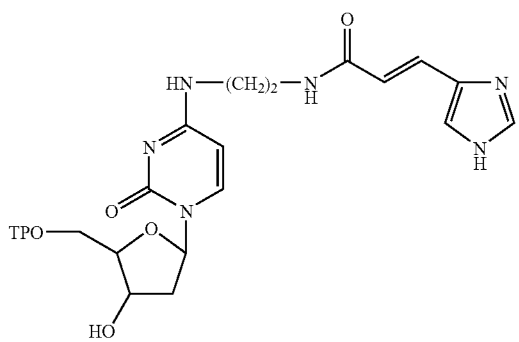 |
| Compound 15 | 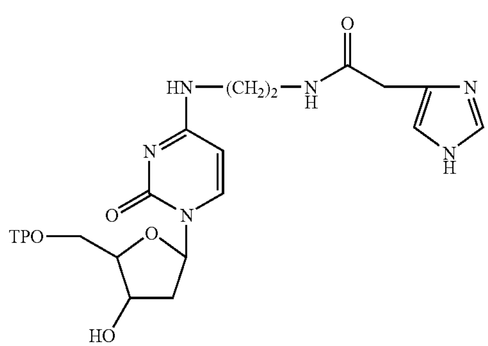 |
| Compound 16 | 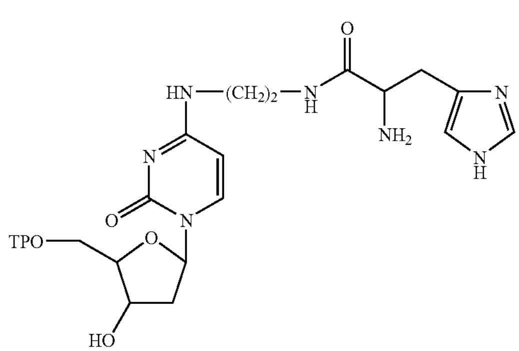 |

TABLE 2-continued

| Compound Number | Structure |
|---|---|
| Compound 17 | *[structure: cytidine with TPO-5', 3'-OH, N4-(CH2)6-NH-C(=O)-CH=CH-(imidazole)]* |
| Compound 18 | *[structure: cytidine with TPO-5', 3'-OH, N4-(CH2)6-NH-C(=O)-CH2-(imidazole)]* |
| Compound 19 | *[structure: cytidine with TPO-5', 3'-OH, N4-(CH2)6-NH-C(=O)-CH(NH2)-CH2-(imidazole)]* |

Preparation of Modified Deoxyguaninetiphosphate (dGTP)—General Procedure

The synthesis of modified deoxyguaninetiphosphate (dGTP) was performed according to Yoshikawa et al., 1967, *Tetrahedron Letters* 5095, by phosphorylation of 2-chloro-2'-deoxyinosine, followed by treatment with diaminoalkane, to afford the corresponding N²(n-aminoalkyl)dGTP as illustrated in Scheme 10 below.

Scheme 10

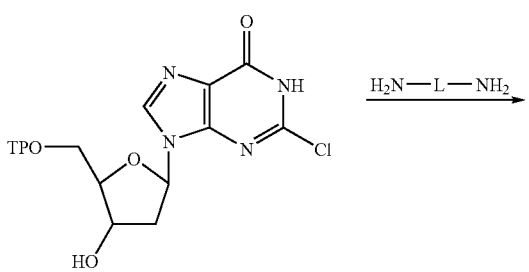

-continued

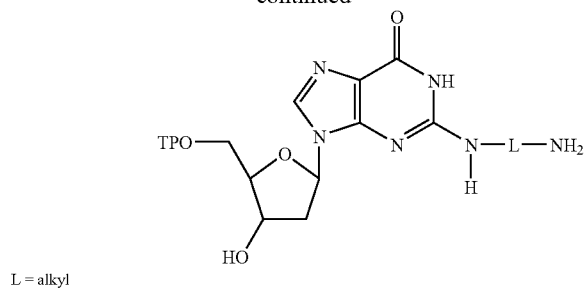

L = alkyl
TP = triphosphate

The aminoalkylated-dGTP products were treated with the active NHS-esters described above as illustrated in Scheme 11 below.

Scheme 11

-continued

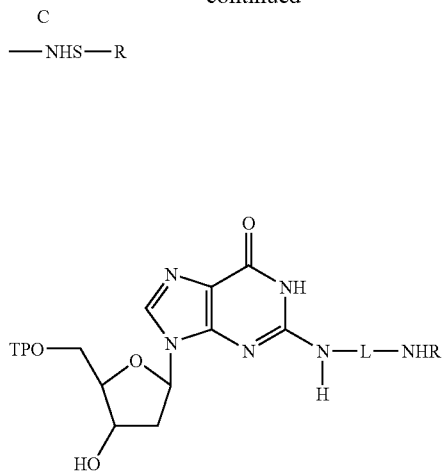

L = alkyl
TP = triphosphate

Table 3 presents the modified dGTP prepared according to the general procedure described above, alongside with their Compound numbers as these are referred to herein throughout.

TABLE 3

| Compound Number | Structure |
|---|---|
| Compound 20 | 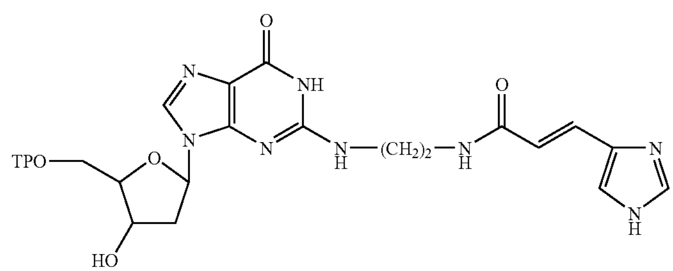 |
| Compound 21 | 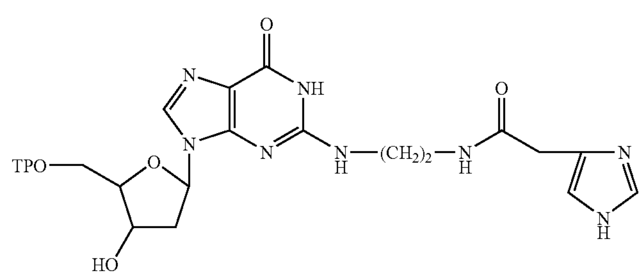 |

TABLE 3-continued

| Compound Number | Structure |
|---|---|
| Compound 22 | 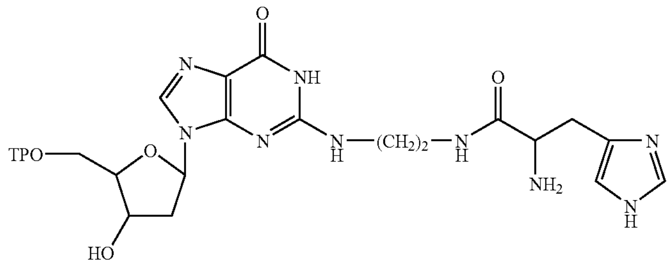 |
| Compound 23 | 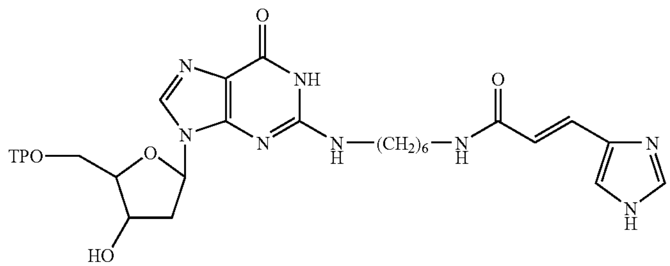 |
| Compound 24 | 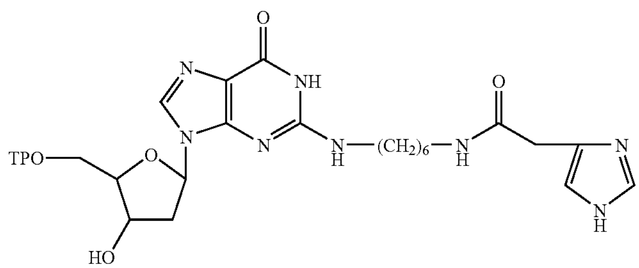 |
| Compound 25 | 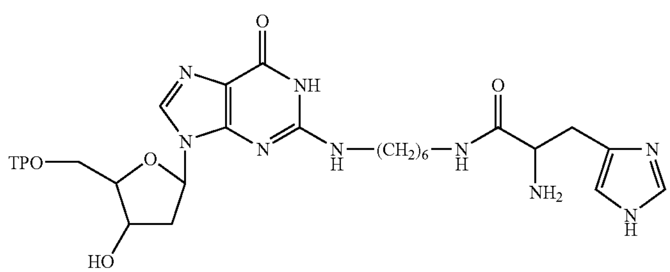 |

Preparation of Modified Deoxyadeninetiphosphate (dATP)—General Procedure

Modified deoxyadeninetiphosphate (dATP) were prepared according to U.S. Pat. No. 4,828,979, as shown in Scheme 12 below. 6-Chloropurine-2'-deoxyriboside was prepared from 2'-deoxyinosine according to a procedure by Robins M. J. and Basom G. L., 1978, *Nucleic Acid Chemistry, p.* 602, at about 70% yield, and was thereafter phosphorylated using $POCl_3$/$(EtO)_3PO$ according to a procedure by Yoshikawa M., Kato T. and Takenishi T., 1967, *Tetrahedron Lett.* 5095 in the presence of 4 Å molecular sieves. The resulting monophosphate was then treated with diaminoalkane to give the desired $N^6$-(n-aminoalkyl)dAMP.

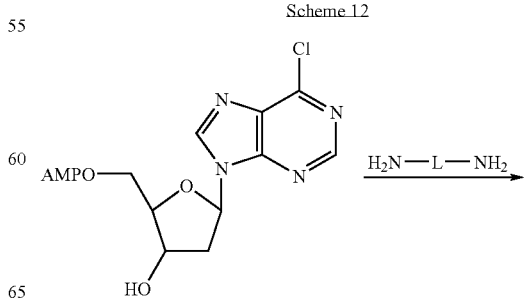

Scheme 12

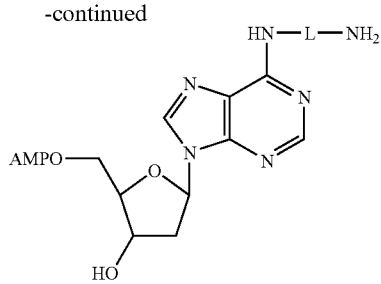

This method was used to afford N⁶-(n-aminohexyl)dAMP and N⁶-(n-aminoethyl)dAMP.

The aminoalkylated-dAMP products were treated with the active NHS-esters described above as illustrated in Scheme 13 below. Thereafter the triphosphates were prepared according to a procedure by Hoard D. E. and Otts D. G., 1965, *J. Am. Chem. Soc.* 87, 1785, by treating the monophosphates dicyclohexyl carbodiimide followed by tributylammonium pyrophosphate (see, Scheme 20 below) to afford N⁶-(n-aminohexyl)dATP and N⁶-(n-aminoethyl)dATP, at a yield varying between 60% and 80%.

Scheme 13

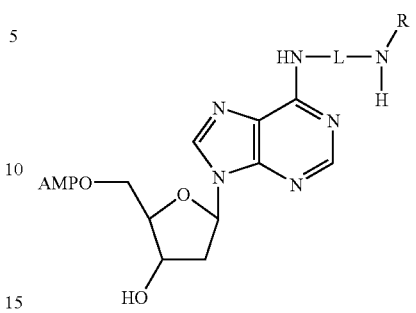

AMP = monophosphate
TP = triphosphate

Table 4 presents the modified dATP prepared according to the general procedure described above, alongside with their Compound numbers as these are referred to herein throughout.

TABLE 4

| Compound Number | Structure |
|---|---|
| Compound 26 | 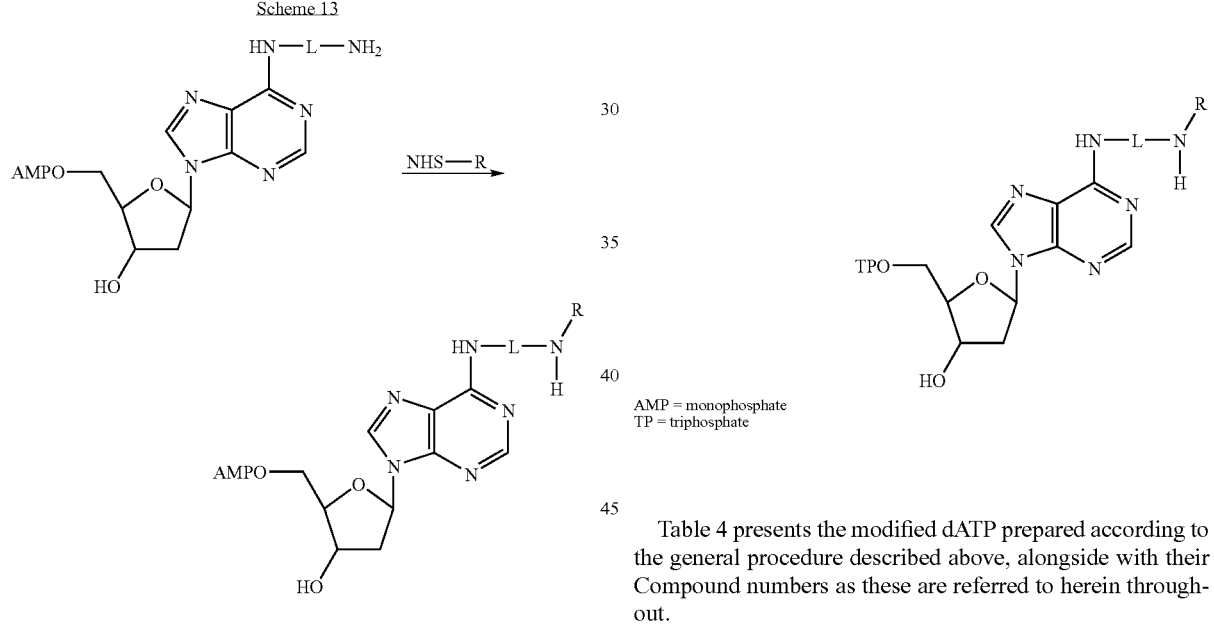 |

TABLE 4-continued
| Compound Number | Structure |
|---|---|
| Compound 27 | 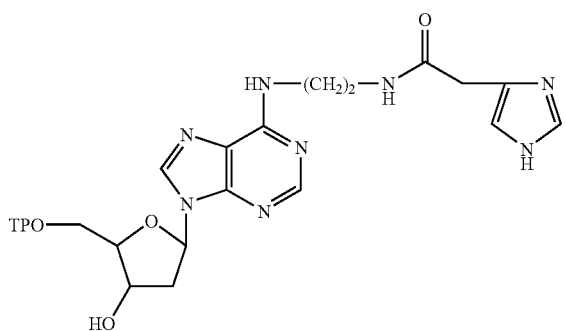 |
| Compound 28 | 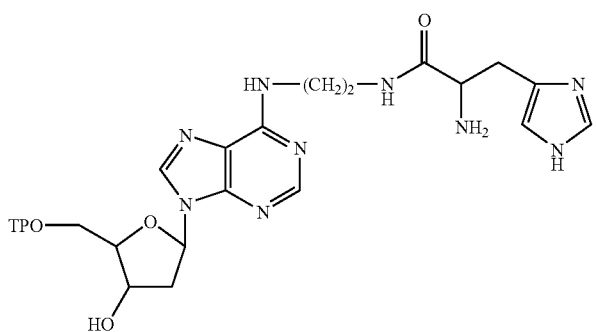 |
| Compound 29 | 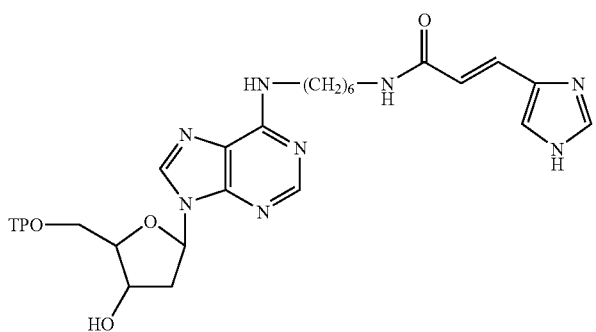 |

TABLE 4-continued

| Compound Number | Structure |
|---|---|
| Compound 30 | 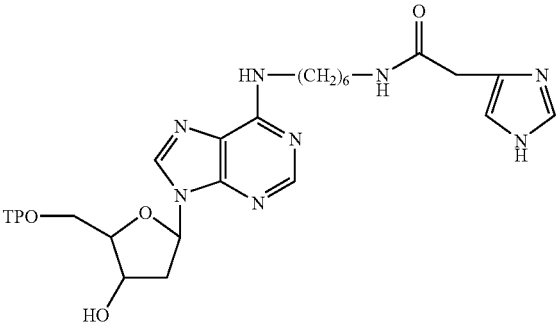 |
| Compound 31 | 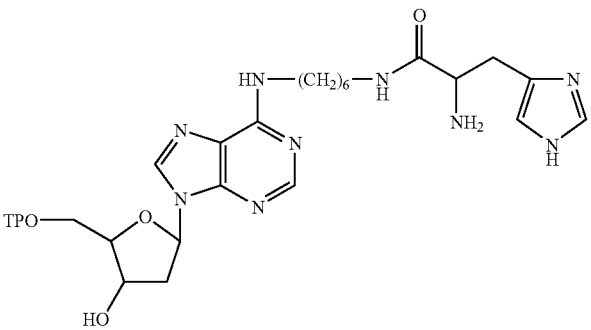 |

Similarly, deoxyadenosinetriphosphate was modified at the 8-position as described by Perrin et al., 1991, *J. Am. Chem. Soc.* 123: 1556-1563, using the NHS-esters described above to afford the modified nucleotides presented in Table 5 below.

TABLE 5

| Compound Number | Structure |
|---|---|
| Compound 32 | 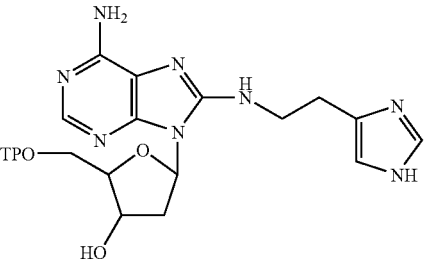 |
| Compound 33 | 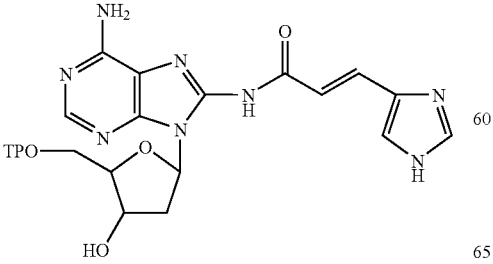 |

TABLE 5-continued

| Compound Number | Structure |
|---|---|
| Compound 34 | 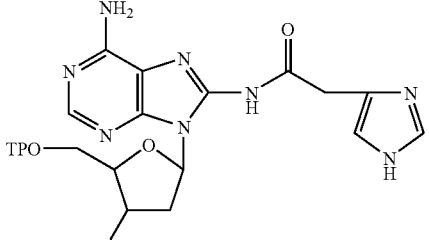 |
| Compound 35 | 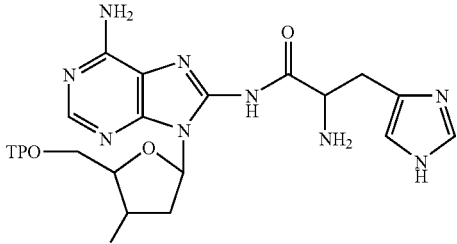 |

Preparation of a Modified Amphiphilic Deoxyuridinetriphosphate (dUTP)

Allylamine-dUTP, (30 mg, 50 mol) was prepared as described hereinabove, and was reacted with 3-trifluroacetylamiomethyl-trans-cinnamic acid-N-hydroxysuccinimideester (100 mg, 250 mol) in 0.1 M sodium borate buffer and DMF (1:1) at room temperature for 24 hours. The resulting reaction mixture was evaporated to dryness and the residue was added to concentrated ammonia (1 ml). The reaction mixture was evaporated to dryness again and the residue (see, Scheme 14 below) was purified by reverse phase HPLC.

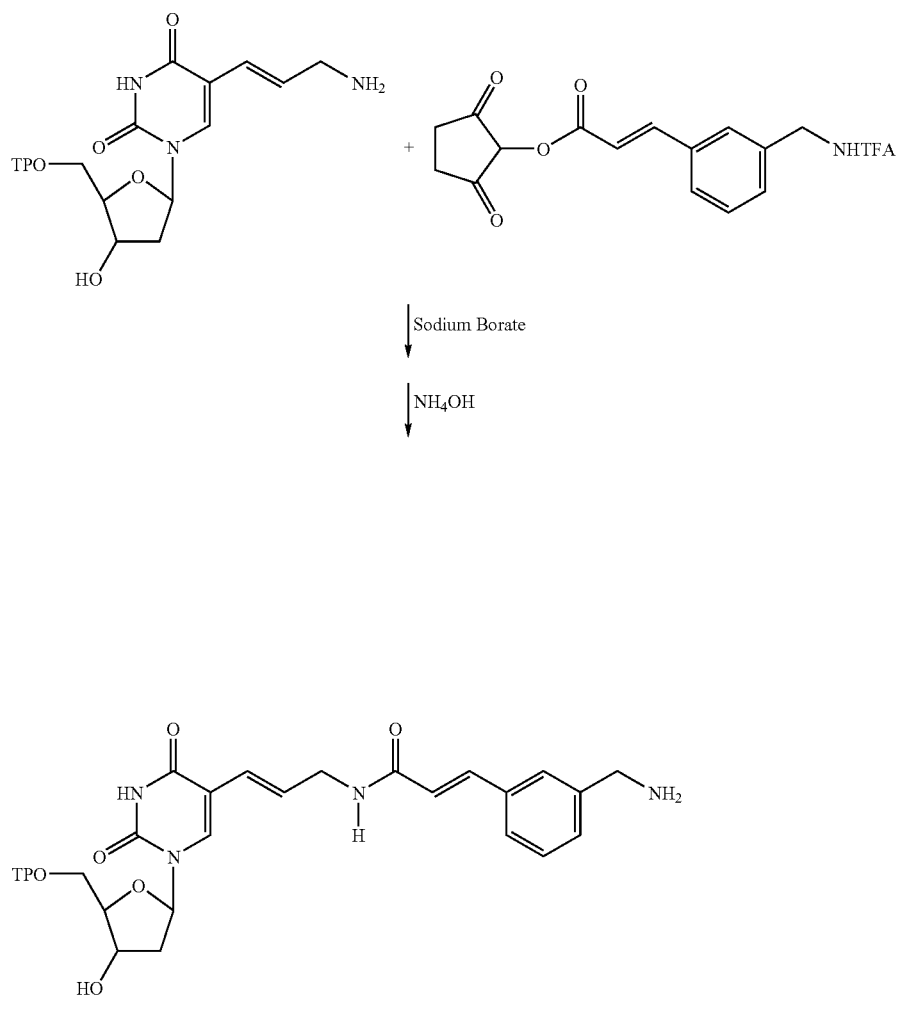

TFA = trifluroacetyl
TP = triphosphate

N-(Fmoc)-N-(Tritylimidazole) histidine (1.86 gram, 0.30 mmol) was reacted with N-hydroxysuccinimide (368 mg, 0.32 mmol) and 1,3-dicyclohexycarbodiimide (494 mg, 0.24 mmol) in DMF (3 ml) at room temperature for 12 hours. The reaction mixture was filtered thereafter and the filtrate was added to a solution of allylamine-dUTP (1.8 grams, 0.35 mmol) in sodium borate and DMF (1:1) and stirred for 10 hours at room temperature. The reaction mixture was thereafter evaporated to dryness and the modified nucleotide (See Scheme 15 below) was purified on reverse phase HPLC.

Scheme 15

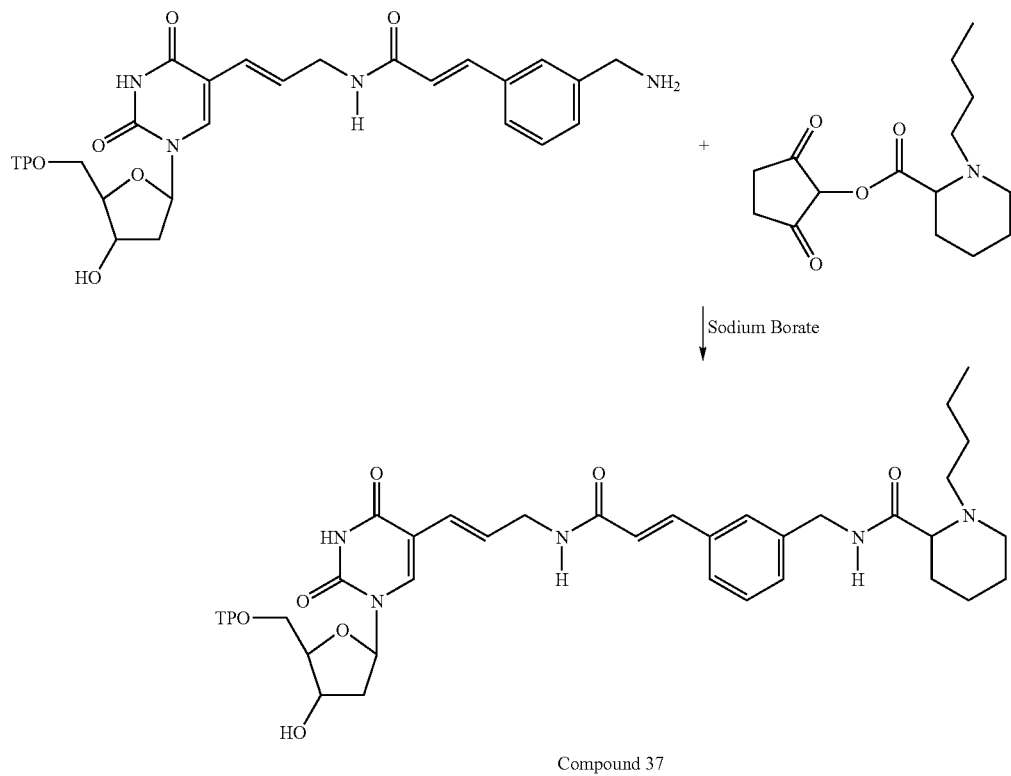

Compound 37

TP = triphosphate

Compatibility of the Modified Nucleotides in Polymerase Enzymatic Syntheses

The modified nucleotides described above were tasted in polymerase assays to determine their compatibility as substrates for polymerase reactions. The modified nucleotide Compound 7 (modified dUTP), served as a substrate in place of deoxythymidinetriphosphate, dTTP, for thermostable DNA polymerases using typical PCR conditions. Commercially available thermostable DNA polymerases from five organisms were used in the assays: Taq from *Thermus aquaticus*, Vent from *Thermococcus litoralis*, Pfu from *Pyrococcus furiosus*, and rTh from *Thennus thennophilus*.

PCR assays with Compound 7 demonstrated its incorporation into a 561 base pair product only with rTh polymerase. Several derivatives of Compound 7 have been shown to be substrates for *E. coli* DNA polymerase and useful in nick translation and random primed synthesis when use instead of dTTP.

In similar assays Compound 32 was found to be a suitable substrate for the polymerase from *Thermus aquaticus*.

Preparation of Non-Nucleotide Delivery Moieties and Delivery Systems Containing Same

Preparation of a PEG-Based Delivery Moiety

Preparation of DMTO-hexaethylene glycol (Compound 38)

A solution of 4,4'-dimethoxytrityl chloride (3.38 grams, 10 mmols) in pyridine (30 ml) was added dropwise over a period of 1 hour to a solution of hexaethylene glycol (28.2 grams, 100 mmols) in anhydrous pyridine (100 ml) while maintaining the solution at 0° C. under argon atmosphere. The reaction mixture was allowed to warm to room temperature, and was stirred for additional 4 hours. The reaction mixture was thereafter evaporated to dryness under reduced pressure. The obtained residue was extracted with ethyl acetate (250 ml), and brine (200 ml) and the organic layer was dried over anhydrous sodium sulfate, and concentrated under reduced pressure to an oil. The product (see, Compound 38 in Scheme 15 below) was purified by column chromatography on a 3×30 cm neutralized silica gel column, using a mixture of 1:9 (v/v) methanol:dichloromethane, containing 0.2% triethylamine, to afford 5.1 grams of Compound 38 as an oil (82% yield). Silica TLC of the product using a mixture of 1:9 (v/v) methanol:chloroform as eluent migrated with an Rf of 0.3.

Scheme 15

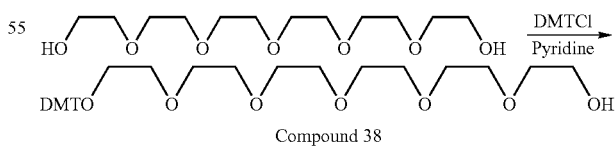

Compound 38

Preparation of 1-O-DMT-6-β-cyanoethyl-N,N-diisopropylphosphoramidite-hexaethylene glycol (Compound 39)

Diisopropylethylamine (3.4 ml) was added dropwise a solution of DMTO-hexaethylene glycol (Compound 38, 5.8 grams, 10 mmols) in anhydrous tetrahydrofuran (50 ml) while maintaining the solution at 0° C. under argon atmosphere. Chloro-β-cyanoethyl N,N-diisopropylphosphoramidite (2.4 ml) was then added dropwise, and the mixture was stirred at 4° C. for 20 minutes. The reaction progress was monitored by TLC, using a mixture of 2:1 (v/v) ethyl acetate: cyclohexane (Rf of starting material is 0.25 and Rf of the product is 0.40). The reaction mixture was evaporated to dryness. The residue was extracted with ethyl acetate (250 ml) and brine (200 ml) and the organic layer was dried over anhydrous sodium sulfate, and concentrated under educed pressure. The product (see, Compound 39 in Scheme 16 below), obtained as a foam, was purified by column chromatography on a 3×30 cm neutralized silica gel column, using a gradient starting from a mixture of 2:3 (v/v) ethyl acetate: cyclohexane containing 0.2% triethylamine and ending with a mixture of 9:1 (v/v) ethyl acetate:cyclohexane, as eluent. Fractions which contained the product were combined and evaporated to dryness to afford 4.1 grams of Compound 39 as yellowish oil (52.2% yield).

Scheme 16

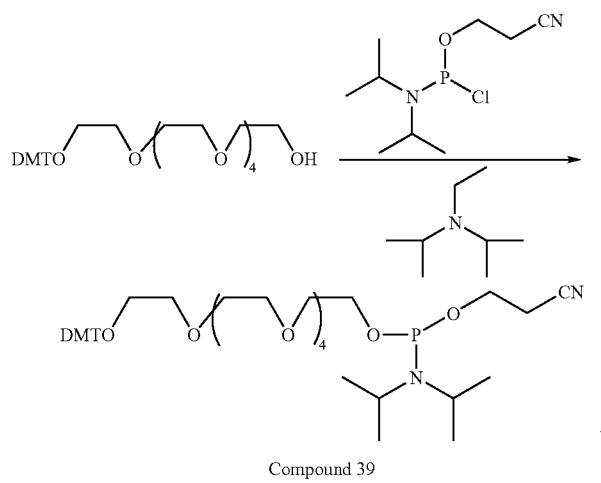

Compound 39

Preparation of a Peptoid Delivery Moiety

Preparation of $N^1$-trifluoroamidohexane-1,6-diamine (Compound 40)

Ethyltrifluoro acetate (9.19 grams, 64.73 mmol) was added dropwise over one hour to a stirred solution of 1,6-diaminohexane (7.52 grams, 64.73 mmol) and triethylamine (6.47 ml, 45.3 mmol) in methanol (100 ml) and the mixture was stirred for 4 hours at 20° C. The reaction progress was monitored by TLC, using a mixture of 2:3:4 (v/v/v) methanol:dichloromethane:triethyl amine as eluent (following the product at Rf=0.25).

Once the reaction was completed, the reaction mixture was evaporated to dryness and was extracted with ethyl acetate (250 ml) and brine (200 ml). The organic layer was dried over anhydrous sodium sulfate, and was concentrated under reduced pressure.

$N^1$-trifluoroamidohexane-1,6-diamine (Compound 40, see Scheme 17 below), obtained as a foam, was purified by column chromatography on a 3×30 cm neutralized silica gel column, using a 500 ml of dichloromethane followed by with a mixture of 2:3:4 (v/v/v) methanol:dichloromethane:triethyl amine, as eluents. The fractions containing the product were combined and evaporated to dryness to afford 2.73 grams of (Compound 40) as yellowish oil (32% yield).

Scheme 17

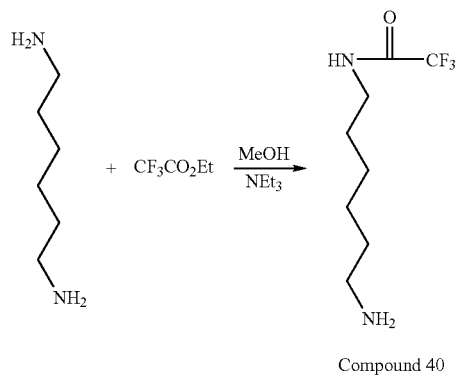

Compound 40

Preparation of methyl 3-(6$N^1$-trifluoroacetmidohexane-(hexylamino) propanoate (Compound 41)

$N^1$-trifluoroamidohexane-1,6-diamine (Compound 40, 2.12 grams, 10 mmol) was added to a stirred solution of LiCl (70 mg) in methanol (50 ml) and THF (50 ml) which was cooled in an ice/water vessel. Methyl acrylate (0.95 grams, 11 mmol) was added dropwise to the resulting solution over a time period of 10 minutes. The reaction mixture was allowed to warm to room temperature gradually and was stirred overnight. Thereafter, the reaction mixture was evaporated under reduced pressure to dryness and was extracted with ethyl acetate (250 ml), and brine (200 ml). The organic layer was dried over anhydrous sodium sulfate, and evaporated under reduced pressure to dryness.

Methyl 3-(6-(trifluoroacetamido)hexylamino) propanoate (Compound 41, see Scheme 18 below) was purified by column chromatography on a 3×30 cm neutralized silica gel column, using 500 ml of chloroform followed by with a mixture of 3:2:4 (v/v/v) dichloromethane:methanol:triethyl amine as eluents (TLC Rf=0.77). The fractions containing the product were combined and evaporated to dryness to afford 3.72 grams of Compound 41 as yellowish oil (83% yield).

Scheme 18

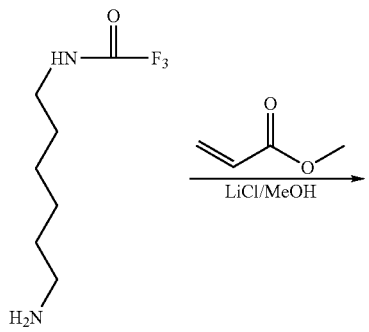

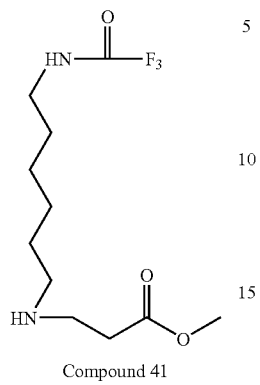

Compound 41

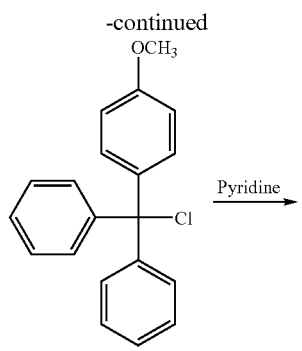

Preparation of methyl 3-(6-(trifluoroacetamido),1-monomethoxytritylhexylamino) propanoate (Compound 42)

A solution of 4-methoxytriphenylmethyl chloride (33.96 grams, 103 mmol) in dry pyridine (150 ml) was added dropwise to a solution of methyl 3-(6-(trifluoroacetamido)hexylamino) propanoate (Compound 41, 29.83 grams, 100 mmol) in dry pyridine (200 ml). The reaction mixture was stirred at room temperature for 18 hours. The reaction mixture was evaporated under reduced pressure to dryness and was extracted with ethyl acetate (250 ml), and brine (200 ml). The organic layer was dried over anhydrous sodium sulfate, and evaporated under reduced pressure to dryness.

Methyl 3-(6-(trifluoroacetamido),1-monomethoxytritylhexylamino) propanoate (Compound 42, see Scheme 19 below) was purified by column chromatography on a 3×30 cm neutralized silica gel column, using 500 ml of dichloromethane followed by with a mixture of 19:1 (v/v) dichloromethane:methanol as eluents (TLC Rf=0.65). The fractions containing the product were combined and evaporated to dryness to afford Compound 42 as yellowish oil (80% yield).

Scheme 19

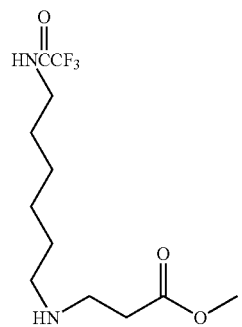

+

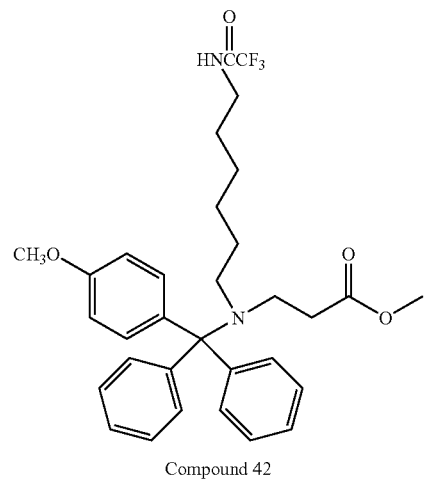

Compound 42

Preparation of 3-(((6-aminohexyl)((4-methoxyphenyl)diphenylmethyl) amino)propanoic acid (Compound 43)

Compound 42 (5.70 grams, 10 mmol) was dissolved in a mixture of concentrated ammonium hydroxide (50 ml) and of dioxane (20 ml). The reaction mixture was stirred at room temperature for 18 hours.). The reaction mixture is stirred at room temperature for 18 hours. Thereafter, the reaction mixture was evaporated under reduced pressure to dryness and the hydrolyzed form of Compound 43 (see, Scheme 20 below) was used without further purification.

Scheme 20

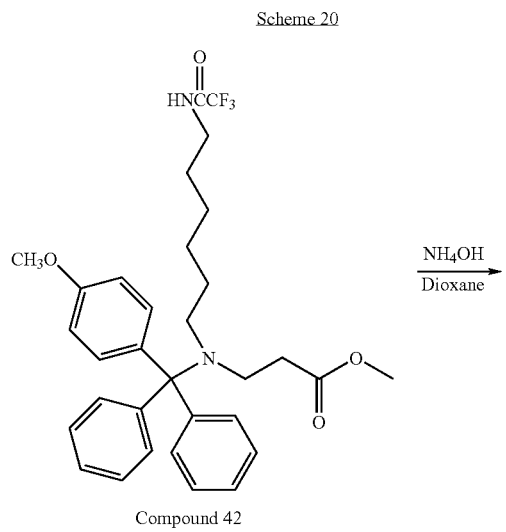

Compound 42

↓ NH₄OH / Dioxane

Compound 43

Scheme 21

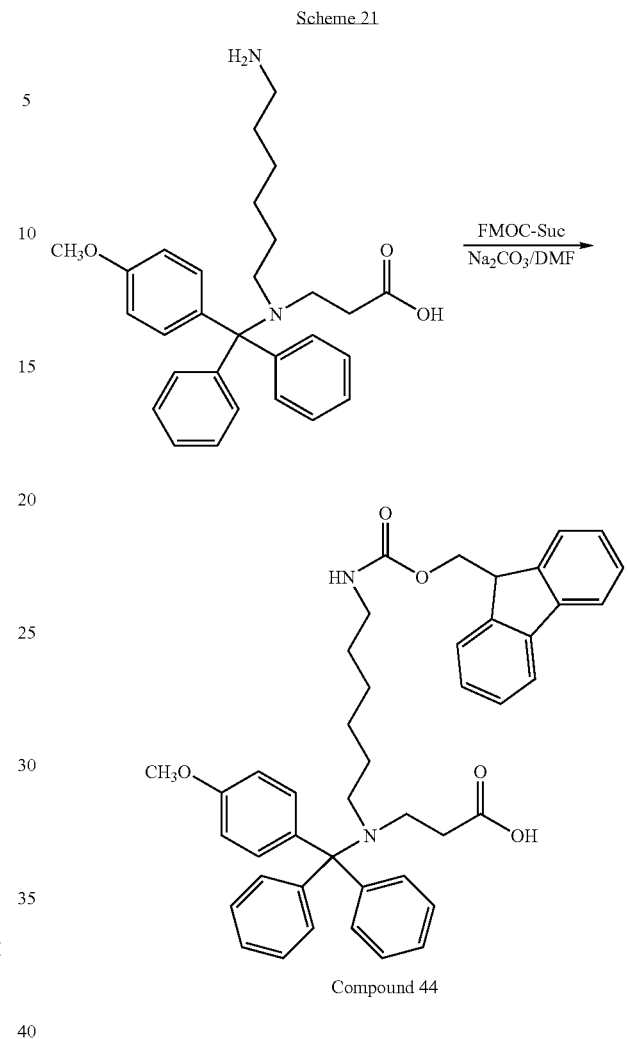

Preparation of 3-(6-(((9H-fluoren-9-yl)methoxy) carbonylamino) hexylamino)propanoic acid (Compound 44)

3-(6-Aminohexyl), 1-monomethoxytrityl amino)propanoic acid (Compound 43, 4.6 grams, 10 mmol) was dissolved in a mixture of 9% $Na_2CO_3$ (18.9 ml) and DMF (10 ml). The solution was cooled in an ice bath and a solution of Fmoc-OSu (3.72 grams, 10 mmol) in DMF (20 ml) was slowly added using a dropping funnel over a time period of 30 minutes. The mixture was warmed to room temperature and was stirred for additional 4 hours.

The DMF and water were removed by evaporation under reduced pressure and the obtained crude methyl 3-(6-(((9H-fluoren-9-yl)methoxy)carbonylamino)hexylamino) propanoate (Compound 44, see Scheme 21 below) was dissolved in cold water and was extracted with ethylacetate. The extract was washed twice with brine, dried over $MgSO_4$ and concentrated to afford a yellow solid. The crude solid was washed with cold methanol to afford 4.12 grams of Compound 44 as a white solid (99% yield).

Preparation 2,5-dioxopyrrolidin-1-yl 3-((6-(((9H-fluoren-9-yl)methoxy) carbonylamino)hexyl)((4-methoxyphenyl)diphenylmethyl)amino)propaneperoxoate (Compound 45)

A solution of 1,3-dicyclohextlcarbodiimide (2.26 grams, 11 mmol) in dry dichloromethane (20 ml) was added dropwise to a solution of Compound 44 (6.83 grams, 10 mmol) and N-hydroxysuccinimide (1.265 grams, 11 mmol) in dry dichloromethane (100 ml) cooled to 0° C. in an ice/water bath.

The reaction mixture was stirred at room temperature for 3 hours, and was thereafter evaporated to dryness under reduced pressure and extracted with ethyl acetate (250 ml), and brine (200 ml). The organic layer was dried over anhydrous sodium sulfate, and evaporated to dryness under reduced pressure.

Compound 45 (see, Scheme 22 below) was purified by column chromatography on a 3×30 cm neutralized silica gel column, using 500 ml of dichloromethane followed by with a mixture of 1:1 (v/v) ethyl acetate:hexane as eluents. The fractions containing the product were combined and evaporated to dryness under reduced pressure to afford 7.40 grams of Compound 45 as a yellowish powder (94% yield).

Scheme 22

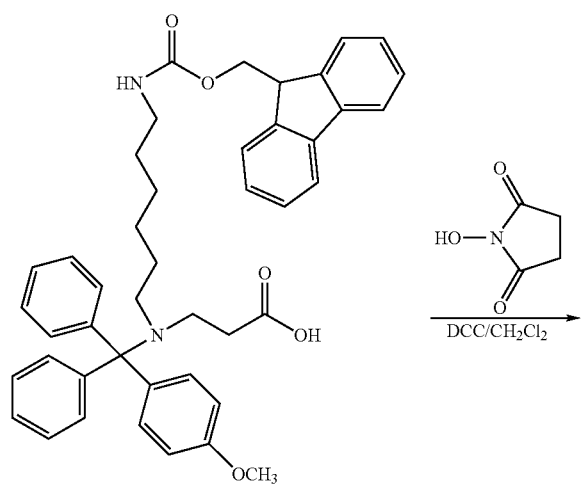

Scheme 23

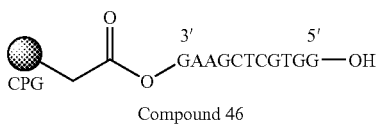

Compound 46

Preparation of a DNA-6-aminohexyl phosphoramidite conjugate (Compound 47)

N-monomethoxytrityl-6-aminohexyl phosphoramidite (Glen Research) was reacted with Compound 46 using the phosphoramidite cycle to afford the DNA-N-monomethoxytrityl-6-aminohexyl phosphoramidite conjugate (see, Scheme 24 below), an amino conjugate at the 5' end of the oligodeoxyribonucleotide of Compound 46.

The polymeric support containing Compound 46 was treated with a solution of 2% dichloroacetic acid in dichloromethane (3×1 ml) for 30 seconds followed by washings with methanol (10 ml) and with dichloromethane (10 ml) to afford the deprotection product Compound 47 (see, Scheme 24 below).

Scheme 24

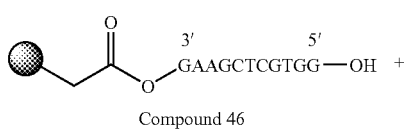

Compound 46

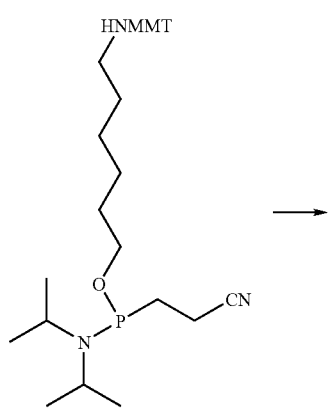

Compound 45

Preparation of a Peptoid Delivery Moiety Having Oligonucleotide Fragments Attached Thereto

Preparation of an Oligodeoxynucleotide of Sequence 3'-GAAGCTCGTGG-OH-5' (Compound 46)

The synthesis of Compound 46 (see, Scheme 23 below) was carried out using a controlled pore glass (CPG) support of 1000 Å pore size, loaded at 35 mmol per gram with 3'-succinylthymidine. The 1-mer oligodeoxynucleotide of sequence 3'-GAAGCTCGTGG-OH-5' (SEQ ID NO:1, a restriction site sequence for BamH1 restriction enzyme) is prepared at the 0.35 mmol scale on an Applied Biosystems 381A DNA Synthesizer using standard deoxynucleoside phosphoramidites, as described by Beaucage et al., 1981, *Tetrahedron Letters* 22, 5843-5846.

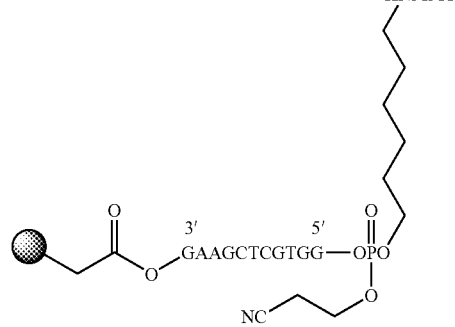

-continued

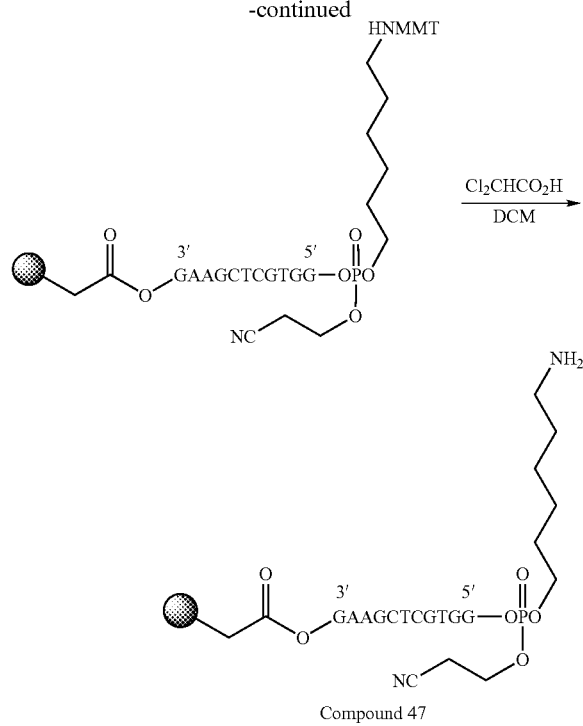

MMT = monomethoxytrityl

Elongation of Compound 47 with Compound 44:

A solution of Compound 45 (20 mole equivalents with respect to Compound 47) was dissolved in dry dichloromethane (1 ml) and added through the ABI DNA synthesizer to the column containing Compound 47, followed by addition of a solution of diisopropyl carbodiimide (20 equivalents) in dichloromethane (1 ml). The mixture was allowed to react for 30 minutes and then the polymeric support was washed with methanol (5 ml) and dichloromethane (5 ml), treated with a solution of 2% dichloroacetic acid in didhloromethane (3×1 ml) for 30 seconds each time, followed by washings with methanol (10 ml) and dichloromethane (10 ml).

The addition reaction of Compound 44 was repeated to afford Compound 48, in which the number of repeating residues of Compound 44 corresponds to the number of times the addition reaction was carried out and is denoted n in the general formula in Scheme 25below). Typically, n equals 1-12, preferably 9.

Scheme 25

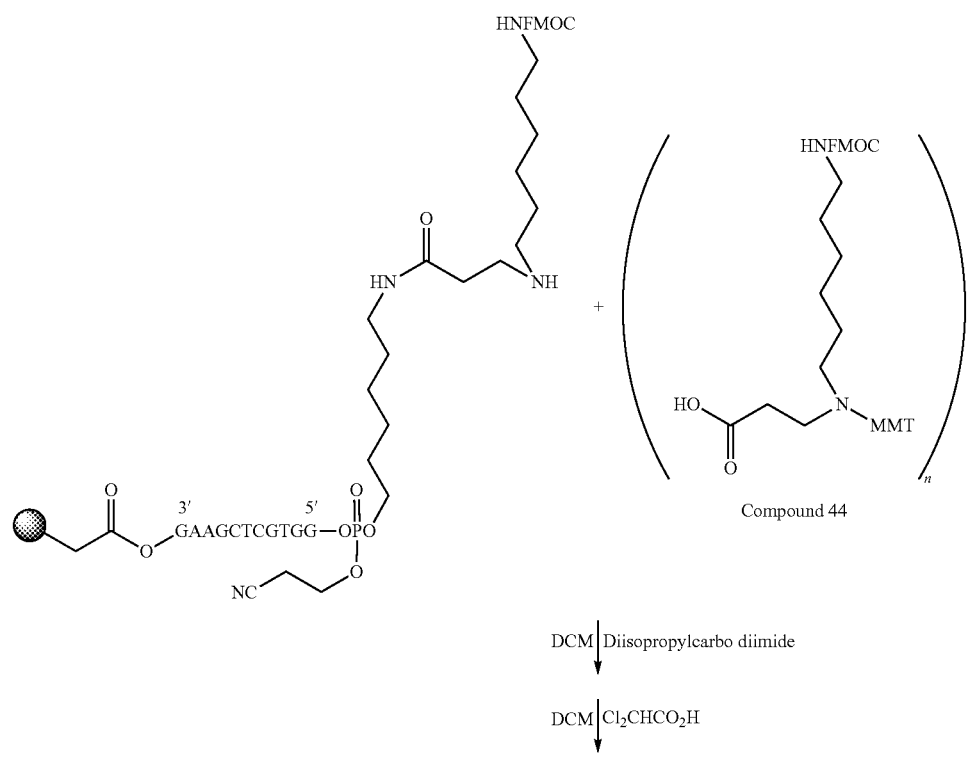

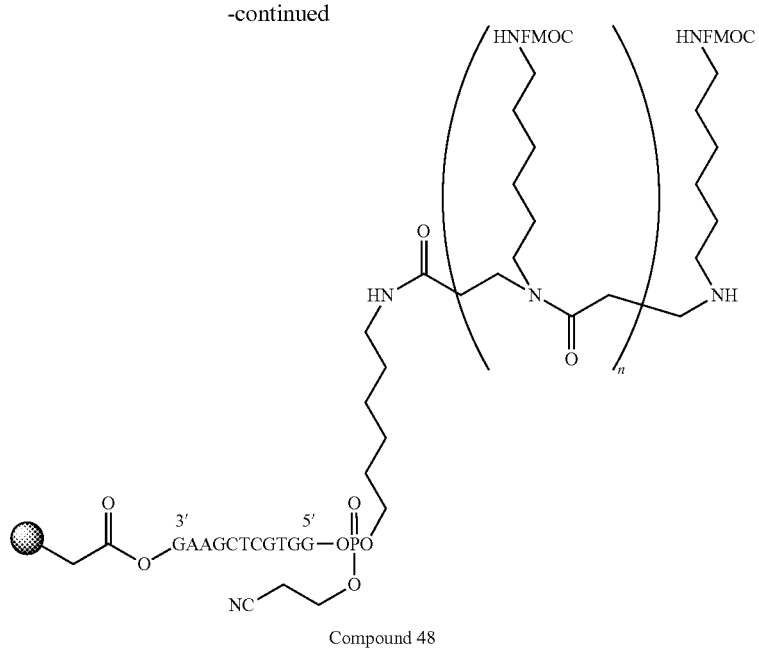

Compound 48

Preparation of a 6-DMT-hexanoic acid derivative of Compound 48

A solution of 6-DMT-hexanoic acid (20 equivalents) in dichloromethane (2 ml) was added to the polymeric support-bound Compound 48, followed by addition of a solution of diisopropyl carbodiimide (20 equivalents) in dichloromethane (1 ml). The mixture was allowed to react for 30 minutes, and then the polymeric support was washed with methanol (5 ml) and with dichloromethane (5 ml). The polymeric support was treated three time with a solution of 2% dichloroacetic acid in didhloromethane (1 ml) for 30 seconds each time, followed by washings with methanol (10 ml) and with didhloromethane (10 ml) to afford Compound 49 (see, Scheme 26 below).

Scheme 26

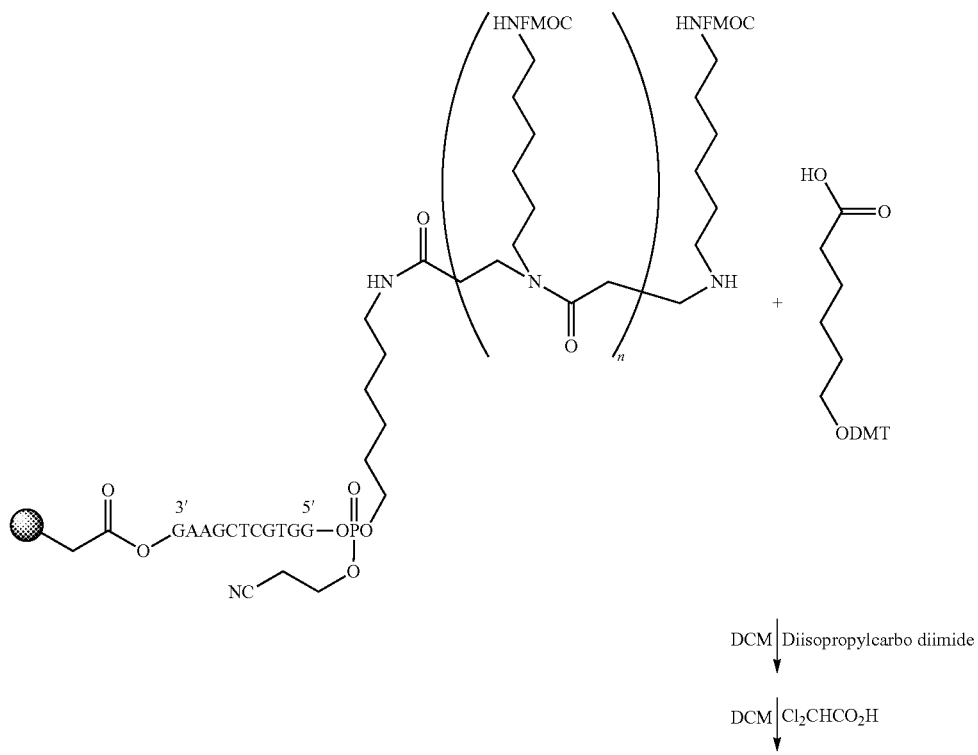

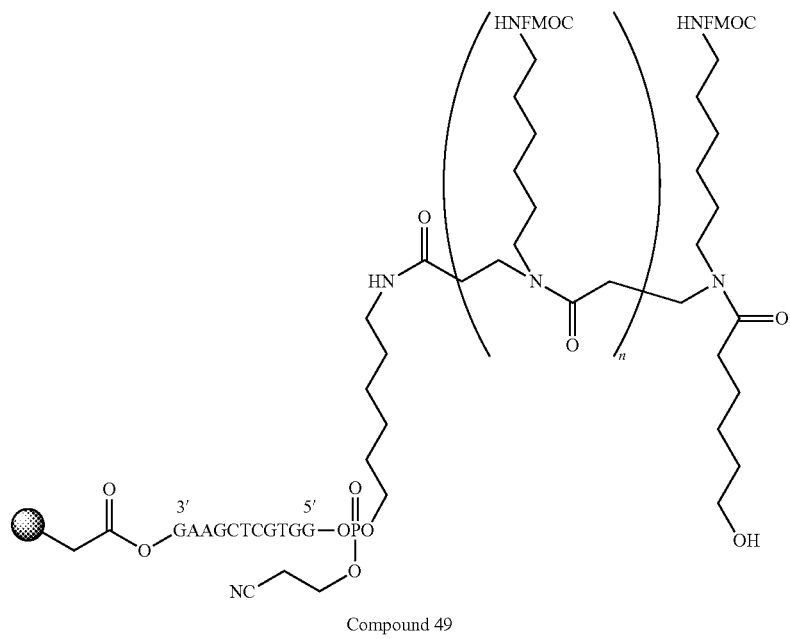

Compound 49

Addition of a Complementary Sequence to Compound 49

Compound 49 was reacted with phosphoramidites on an Applied Biosystems 381A DNA Synthesizer using standard deoxynucleoside phosphoramidites, essentially as described by Beaucage et al., 1981, *Tetrahedron Letters* 22, 5843-5846, and for Compound 46 hereinabove. The sequence 3'-CCAC-GAGCTTCCTAG-5' (SEQ ID NO:2), which includes a complementary sequence for the BamH1 restriction site sequence attached to the polymeric, was added to Compound 49 so as to afford Compound 50 (see, Scheme 27 below).

Scheme 27

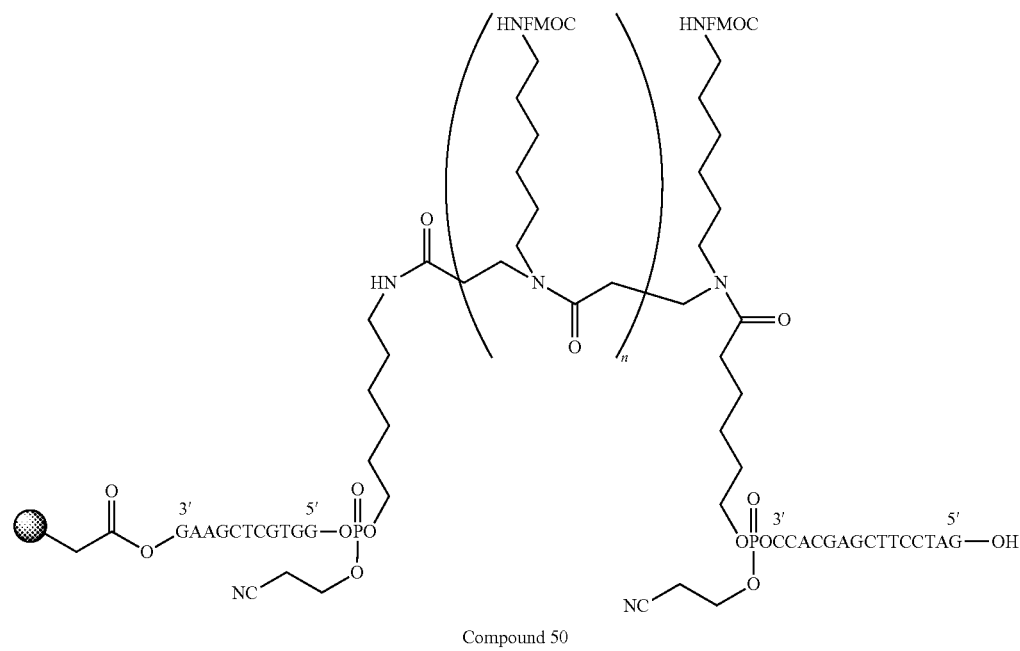

Compound 50

Labeling of Compound 50 with fluorescein-(di-t-butylate)-hexamethylene-phosphoramidite

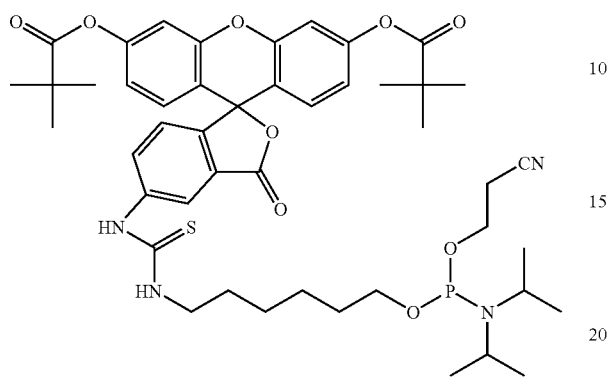

Fluorescein-(di-t-butylate)-hexamethylene-phosphoramidite (FAM-HPA

Fluorescein-(di-t-butylate)-hexamethylene-phosphoramidite (FAM-HPA, Glen Research) was added to the 5'-hydroxyl group of Compound 50 (see, Scheme 28 below) essentially as described by Beaucage et al., 1981, *Tetrahedron Letters* 22, 5843-5846.

Scheme 28

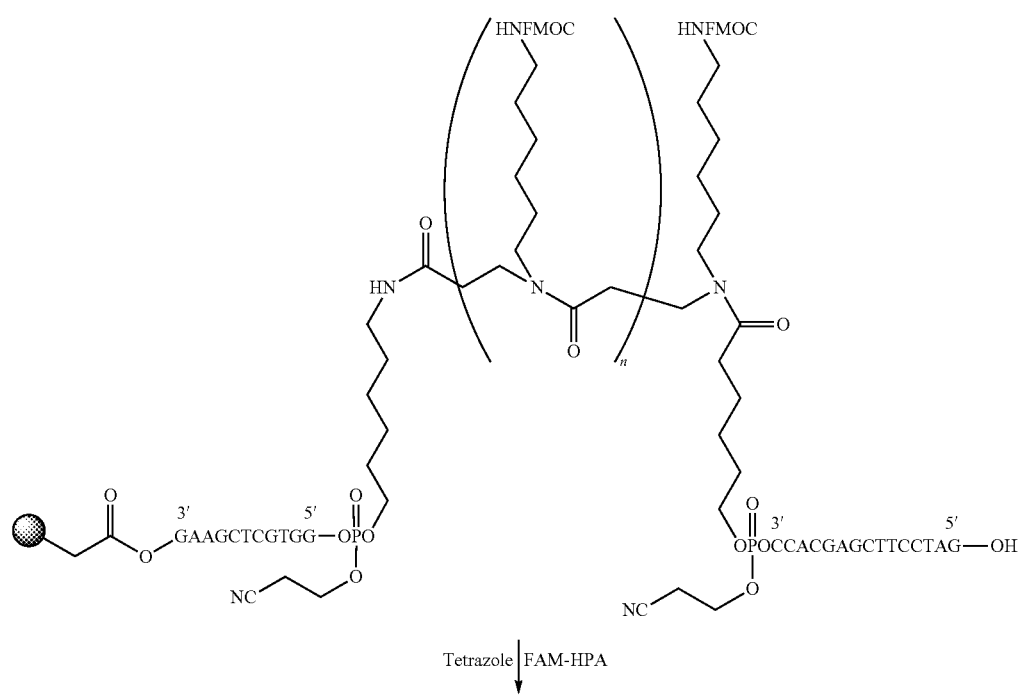

Tetrazole | FAM-HPA

-continued

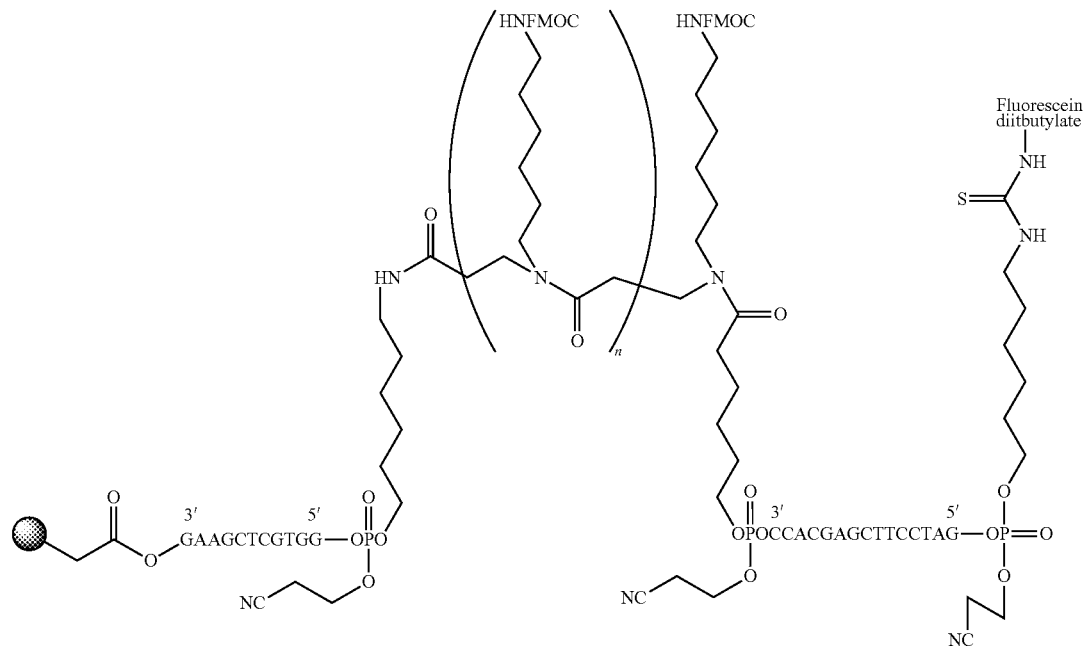

Compound 51

Preparation of a Guanidino-Substituted Peptoid Delivery Moiety Having Oligonucleotides and a Labeling Moiety Attached Thereto Polymeric support-bound Compound 51 was treated with a solution of 10% piperidine in DMF (5 ml) for 10 minutes at room temperature so as to remove the Fmoc protecting groups on the amine groups and the propionylnitrile protecting groups on the phosphate groups. The polymeric support was washed with DMF (10 ml), methanol (10 ml) and ether (10 ml)

The deprotected polymeric support was delivered from the ABI machine into a 20 ml vial and was treated with a solution of 1H-Pyrazole-1-carboxamidine hydrochloride (Aldrich) (50 equivalents) in 5% sodium carbonate (5 ml). The heterogenic solution was heated to 50° C. for 24 hours.

The reaction mixture was cooled to room temperature, a solution of concentrated ammonia was added thereto and the resulting mixture was heated to 60° C. for 18 hours. The reaction mixture was then cooled, filtered and the filtrate was concentrated to dryness under reduced pressure. The crude product (see, Compound 52 in Scheme 29 below) was dissolved in deionized doubly distilled water (1 ml) and was purified by HPLC.

Scheme 29
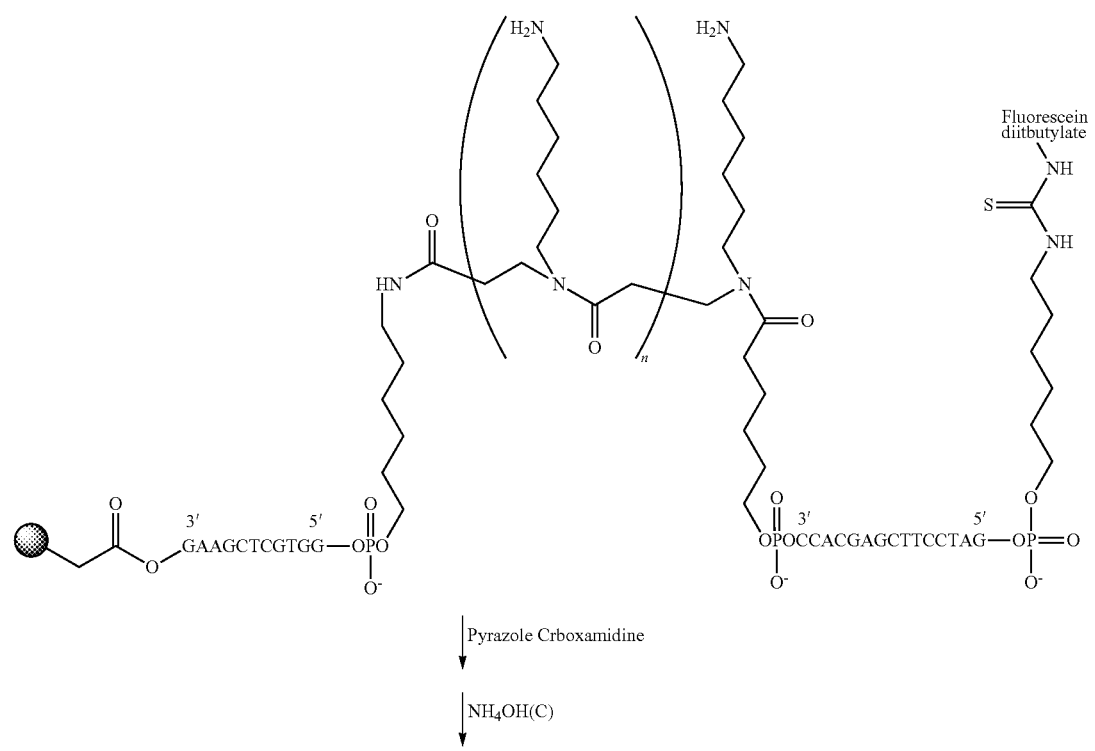
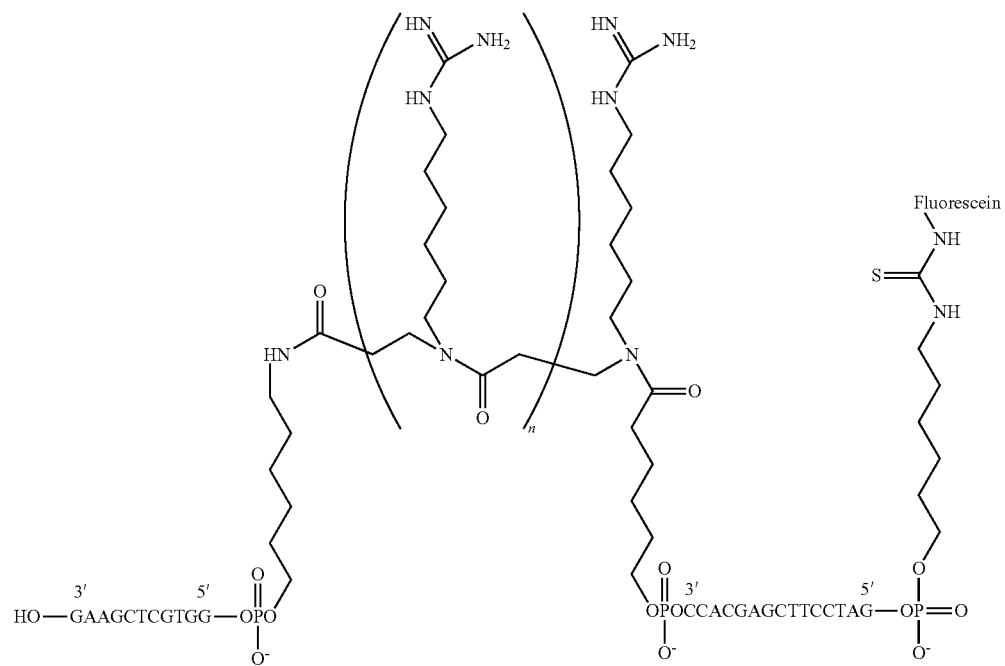
Compound 52

The following DNA-Peptoid pro-conjugate (Compound 52a) was prepared for producing a specific RNAi sequence:

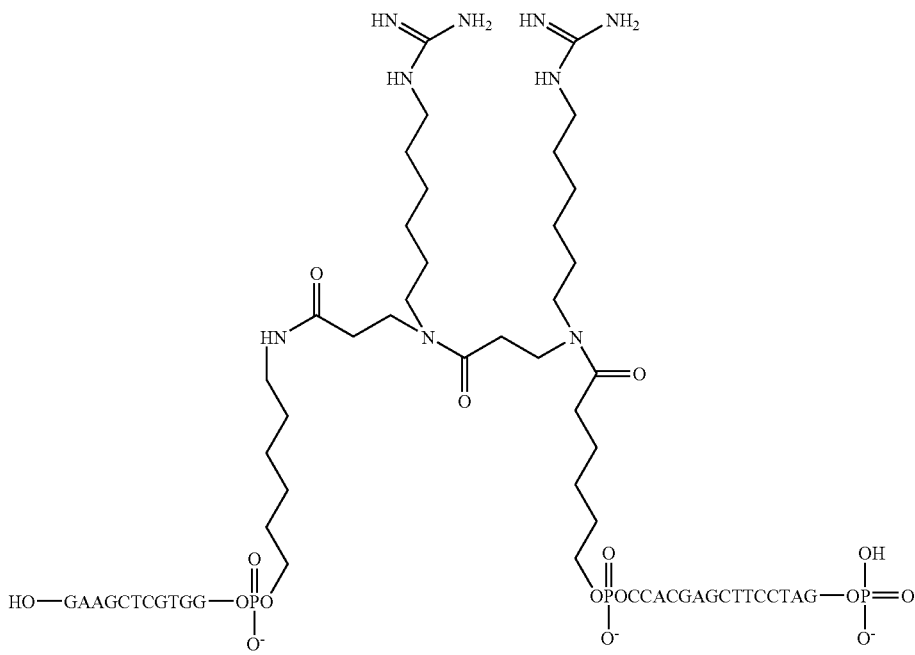

Compound 52a

Preparation of a Phosphate- and/or Phosphonate-Containing Delivery Moiety

Preparation of Undecene-10-enoyl Chloride (Compound 55)

Thionyl chloride (25.6 ml, 0.36 mole) was added to undec-10-enoic acid (62.6 grams, 0.34 mole) over a period of 45 minutes, while stirring and the resulting mixture was thereafter refluxed for 2 hours. The acyl chloride was then removed under reduced pressure (102° C./2 mm Hg), to give Compound 55 (see, Scheme 30 below) in 88% yield.

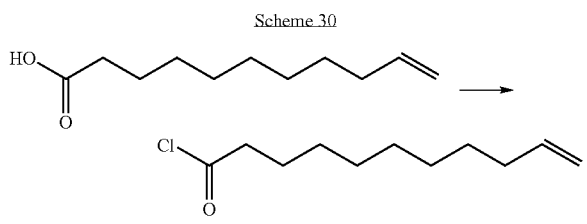

Compound 55

Preparation of Dec-9-enyltrifluoroacetamide (Compound 56)

A solution of 10-undecenoyl chloride (Compound 55, 15 grams, 75 mmol) and TBAB (600 mg, 1.86 mmol) in dichloromethane (180 ml) was cooled to 0° C. Sodium azide (5.79 grams, 90 mmol) was dissolved in water (30 ml) and the resulting solution was added to the cooled solution of 10-undecenoyl chloride. The mixture was thereafter stirred at 0° C. for 4 hours, and was then extracted with water (3×120 ml), and washed with brine (2×100 ml). The organic layer was separated and dried over anhydrous MgSO$_4$ for 24 hours. Continuous evolution of N$_2$ was observed during this period.

The reaction mixture was thereafter filtered and trifluoroacetic acid (TFA, 8.25 ml, 111 mmol) was added dropwise to the filtrate. The resulting mixture was refluxed overnight. Upon cooling, the mixture c was washed with saturated NaHCO$_3$, dried over anhydrous Na$_2$SO$_4$, filtered and concentrated, to give Compound 56 (see, Scheme 31 below) in 65% yield. TLC of the product using a 1:1 chloroform:hexane mixture as eluent showed one major spot at Rf=0.5.

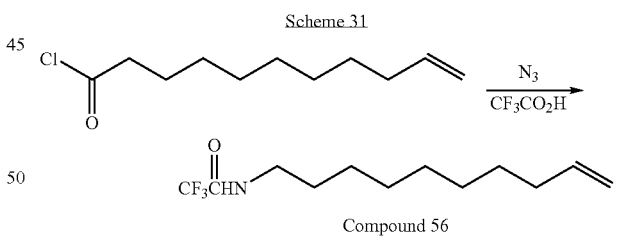

Compound 56

Preparation of 1,2-dihydroxy, 10-Decyltrifluoroacetamide (Compound 57)

To a solution of Compound 56 (10 grams, 39.8 mmol) in THF (200 ml), N-methylmorpholine-N-oxide (Aldrich, 10.30 grams, 88.3 mmol) was added, followed by addition of 4% aqueous solution of osmium tetroxide (Aldrich, 1.2 ml, 4.71 mmol). The reaction mixture was stirred at room temperature for 8 hours. The solvent was thereafter evaporated to dryness and the residue was dissolved in ethyl acetate (250 ml). The solution and washed with water (2×250 ml) and with brine (2×200 ml), the organic layer was separated and dried over sodium sulfate and the solvent was removed under reduced pressure, to give Compound 57 (see, Scheme 32 below). TLC of the product, using ethyl acetate as eluent, showed that the compound migrated with Rf=0.5.

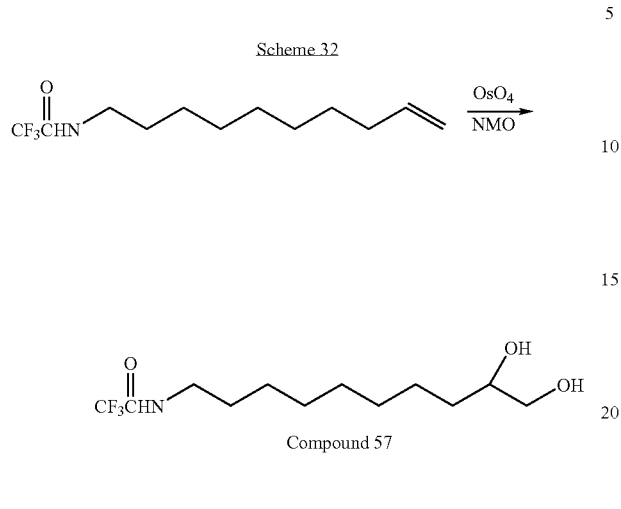

Compound 57

Preparation of 1-(4,4'-Dimethoxytrityl)-2-hydroxy,10-Decyl trifluoroacetamide (Compound 58)

To a solution of Compound 57 (2.50 grams, 8.77 mmol) in dry pyridine (100 ml), cooled to 0° C., a solution of dimethoxytrityl chloride (3.26 grams, 9.64 mmol) in dry pyridine (50 ml) was added dropwise, while stirring. The reaction mixture was thereafter allowed to warm gradually to room temperature and was stirred for additional 18 hours. The solvent was then evaporated to dryness and the residue was dissolved with ethyl acetate (250 ml). The solution was washed with water (2×250 ml) and with brine (2×200 ml), the organic layer was separated and dried over sodium sulfate and the solvent was removed under reduced pressure to give Compound 58 (see, Scheme 33 below). TLC of the product, using a 1:2 ethyl acetate:hexane mixture as eluent, showed that the compound migrated with Rf=0.49.

$^1$H-NMR (CDCl$_3$): δ=1.29 (m, 10H), 1.44 (m, 2H), 1.55 (m, 2H), 2.94, (m, 1H), 3.10 (m, 1H), 3.73 (s, 6H), 6.70-7.60 (aromatics, 13H).

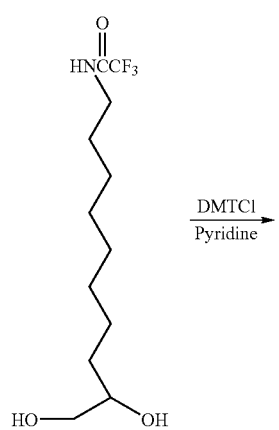

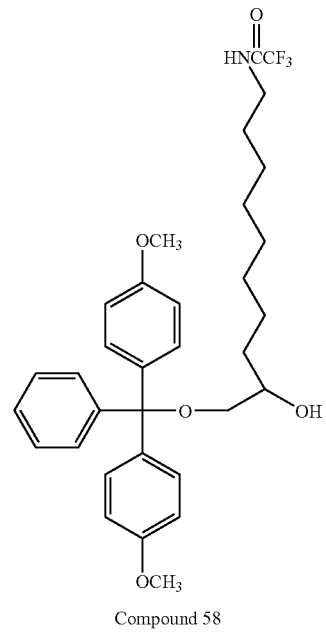

Compound 58

Preparation of chloro-(N,N-diisopropylamino)phenylphosphine (Compound 59)

A solution of diisopropylamine (8.90 grams, 88.3 mmol) in dry hexane (100 ml) was added dropwise to a stirred solution of phenyldichlorophosphine (7.91 grams, 44.2 mmol) in hexane (100 ml) cooled to 0° C., during 45 minutes. The resulting mixture was allowed to warm to room temperature and was then stirred for additional 18 hours and thereafter filtered. The precipitate was washed with hexane, and the product was further purified by distillation under reduced pressure, to give 8.62 grams (80% yield) of Compound 59 (see, Scheme 34 below) as a colorless oil.

b.p: 105° C. (0.3 mm Hg);

$^1$H-NMR (CDCl$_3$): δ=1.03 (m, 12H); 3.39 (m, 2H), 7.43 (m, 3H); 7.70 (m, 2H).

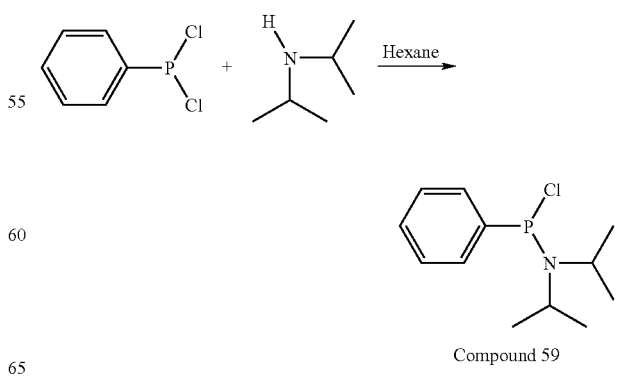

Preparation of 1-(4,4'-Dimethoxytrityl)-2-(N,N-diisopropylamino, phenyl)-phosphine, 10-Decyltrifluoroacetamide (Compound 60)

To a solution of Compound 58 (5.05 grams, 8.5 mmol) in dry dichloromethane (70 ml), diisopropylethylamine (11.1 ml, 63.7 mmol) was added, followed by addition of Compound 59 (5.7 grams, 23.4 mmol) under argon atmosphere. The resulting mixture was stirred at room temperature for 72 hours, and was thereafter refluxed for additional 24 hours. The mixture was then cooled to 0° C. and quenched with water (2 ml). After 20 minutes, ethyl acetate (300 ml) was added and the solution was washed with NaHCO$_3$ (2×75 ml). The organic phase was then dried over NaSO$_4$, evaporated under reduced pressure and the residue was purified by flash chromatography on silica gel using a 1:2 ethylacetate:hexane mixture containing 0.5% triethylamine as eluent TO GIVE Compound 60 (see, Scheme 35 below). TLC of the purified product using a 1:2 ethylacetate:hexane mixture as eluent showed that the compound migrated at Rf=0.7.

$^1$H-NMR (CDCl$_3$): δ=1.05 (2s, 12H); 1.29 (m, 10H); 1.44 (m, 2H); 1.55 (m, 2H); 2.94 (m, 2H); 3.20 (m, 2H); 3.54 (m, 1H); 3.73 (s, 6H); 6.7-7.3 (aromatics, 18H).

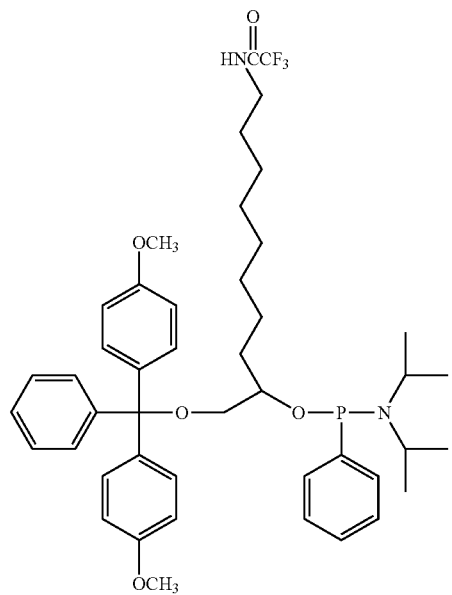

Compound 60

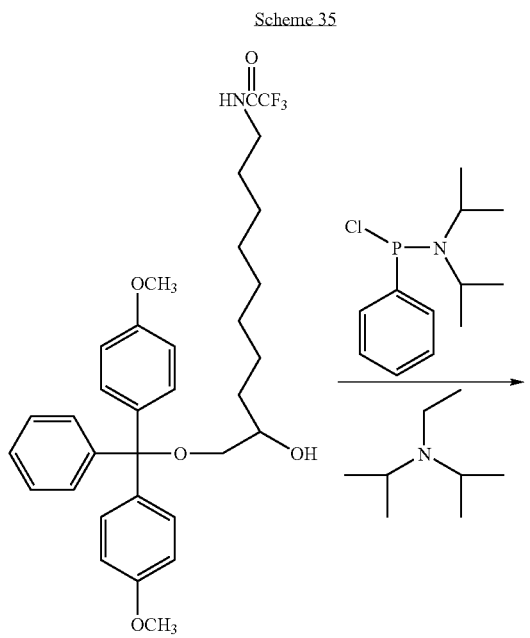

Scheme 35

Preparation of 1-(4,4'-Dimethoxytrityl)-2-(N,N-diisopropylamino, cyanoethyl)-phosphoramidite, 10-Decyltrifluoroacetamide (Compound 61): To a solution of Compound 58 (5.05 grams, 8.5 mmol) in dry dichloromethane (50 ml), diisopropylethyl amine (11.1 ml, 63.7 mmol) was added, followed by dropwise addition of 2-cyanoethyl tetraisopropylphosphorodiamidite (3 grams, 12.75 mmol, Aldrich) under argon atmosphere. After stirring at room temperature for 25 minutes, the mixture was diluted with ethyl acetate (300 ml) and washed with NaHCO$_3$ (2×75 ml) and with brine (300 ml). The organic layer was then dried over sodium sulfate and the solvent was removed under reduced pressure. The residue was purified by flash chromatography on silica gel using a 1:2 ethylacetate:hexane mixture containing 0.5 5 triethylamine, to give Compound 61 (see, Scheme 36 below). TLC of the product using a 1:2 ethylacetate:hexane mixture as eluent shoed that the compound migrated at Rf=0.62.

$^1$H-NMR (CDCl$_3$): δ=1.05 (2s, 12H), 1.29 (m, 10H), 1.44 (m, 2H), 1.55 (m, 2H), 2.60 (t, 2H), 2.97 (m, 2H), 3.20 (m, 2H), 3.39-3.46 (m, 2H), 3.54 (m, 1H), 3.73 (s, 6H), 3.90 (t, 2H), 6.7-7.19 (aromatics, 13H).

Scheme 36

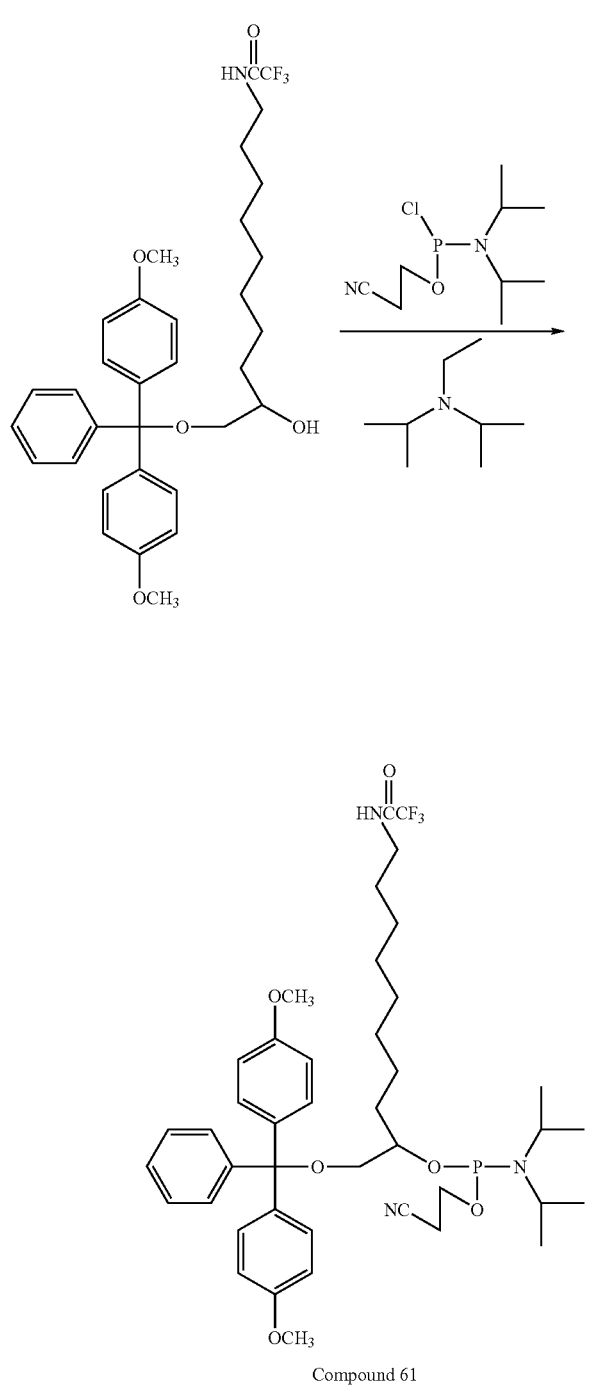

Compound 61

Preparation of a Phosphate- and/or
Phosphonate-Containing Delivery Moiety Having
Oligonucleotidefragments Attached Thereto—Route
I General Procedure for Incorporating Compound 60
or 61 in an Oligonucleotide Oligonucleotides incorporating Compound 60 or 61 were synthesized at one micromolar scale on Expedite Nucleic Acid Synthesis system (Millipore 8909), using the following synthesis cycles (see, Table 6 below): For compound 61, introducing the cyanoethyl phosphoramidite-containing moiety and a cyanoethyl phosphoramidite of the nucleotide bases, was effected using Cycle 1; For Compound 60, condensation was effected using cycle 2.

TABLE 6

| Reagent | Function | Cycle 1 | Cycle 2 |
|---|---|---|---|
| 3% TCA/DCM | Detritylation | 30 sec. | 30 sec. |
| Amidite + tetrazole | Condensation | 25 sec | 300 sec |
| Ac$_2$O/pyridine | Capping | 10 sec | 10 sec |
| I$_2$/water/pyridine | Oxidation | 30 sec | 30 sec |

Using the above procedure, oligonucleotides incorporating an oligonucleotide having SEQ ID NO:1 above, followed by 9 units of Compound 60 and then by an oligonucleotide having SEQ ID NO:2, were prepared. Similarly, oligonucleotides incorporating 9 units of Compound 61, or 9 units that include both Compounds 60 and 61, can be prepared.

The obtained oligonucleotides were labeled with fluoresceindipivalate (see above) after the last condensation, by condensation with 6-FAM (fluoresceindipivalate-aminohexyl phosphoramidite, obtained from Glen Research) using cycle 1 above.

Removal of nucleotide-protecting groups (e.g., iso-butanoyl groups from guanosines) and cleavage of the oligonucleotide from the solid support was accomplished by a one-hour treatment with concentrated ammonia at the DNA synthesizer (standard end procedure). The obtained mixture was evaporated to dryness and the residue was treated with one ml of a nethlenediamine:ethanol:cyanomethyl:H$_2$O (50.0:23.5:23.5:3.0 v:v:v:v) mixture to remove other nucleotide-protecting groups and the amine-protecting groups at the delivery moiety. After 6 hours at room temperature, the solution was diluted to a volume 15 ml with water and neutralized (to pH=7.5) with acetic acid. The obtained solution was directly loaded onto a C18 reversed-phase HPLC column and was eluted using a mixture of acetonitrile in 50 mM triethylammonium acetate as a mobile phase. From each fraction, one A2$_{60}$-unit was removed, detritylated and analyzed on a 16% polyacrylamide/7M urea gel. Fractions containing a homogeneous product were collected and lyophilized to give powdered products in a yield ranging from 25 to 45 A$_{260}$-units per µmol synthesis.

Introduction of guanidine groups to the delivery moiety incorporated in the oligonucleotide was performed as follows:

To a 100 O.D. sample of the labeled delivery moiety-oligonucleotide conjugate prepared as above, a solution of 5% sodium carbonate (2 ml) was added, followed by the addition of 1H-Pyrazole-1-carboxamidine hydrochloride (Aldrich, 50 equivalents). The resulting mixture was kept at 50° C. for 24 hours and was thereafter concentrated to a volume of 0.5 ml. The residue was purified on Sephadex G-25 column (Pharmacia). The fluorescinated fractions were collected and lyophilized to dryness.

The structure of an exemplary compound that was prepared as described hereinabove is presented hereinbelow as Structure A (F denotes Fluorescein):

Structure A

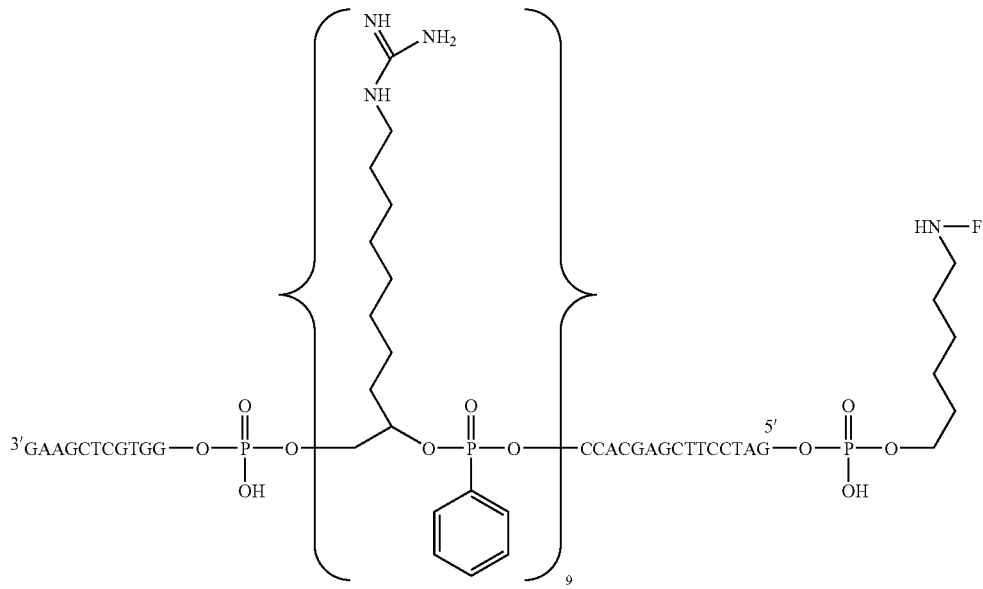

Preparation of a Phosphate- and/or Phosphonate-Containing Delivery Moiety Having Oligonucleotide Fragments Attached Thereto—Route II In this alternative route, conjugates of the phosphate-containing delivery moiety and oligonucleotides (as represented, for example, by Structure A above) were prepared by first providing a guanidine-substituted Compound 61 and then using this phosphoramidite reactant in the preparation of the oligonucleotide, as follows.

Hydrolysis of Compound 61 to Compound 62

To a solution of Compound 58 (5.87 grams, 10 mmol) in tetrahydrofuran (50 ml), cooled to 0° C., concentrated ammonium hydroxide (50 ml) was added in one portion. The resulting mixture was then allowed to warm gradually to room temperature and was stirred for additional 18 hours. The solvent was thereafter evaporated to dryness and the residue was dissolved in ethyl acetate (250 ml) and washed with water (2×250 ml) and brine (2×200 ml). The organic layer was dried over sodium sulfate and the solvent was removed under reduced pressure, to give Compound 62 (see, Scheme 37 below).

Scheme 37

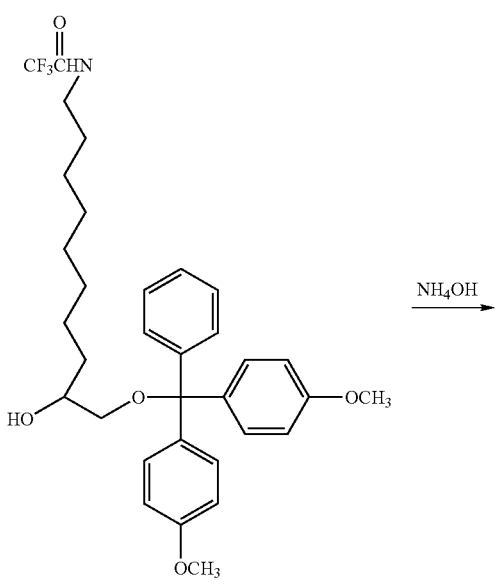

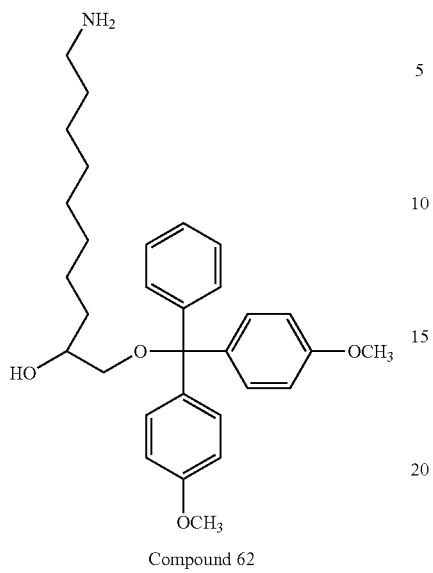

Compound 62

Preparation of N-(2-cyanoethoxycarbonyloxy)succinimide (CEOC-O-Succinimide, Compound 63)

To a stirred solution of 2-cyanoethanol (7.23 grams, 102 mmol) in anhydrous $CH_3CN$ (300 ml), under argon atmosphere, N,N'-disuccinimidyl carbonate (34.0 grams, 133 mmol) was added, followed by the addition of pyridine (11.3 ml, 140 mmol). The resulting suspension was stirred and became a clear solution after about 1 hour. The solution was stirred for additional 6 hours and was then concentrated under reduced pressure. The residue was re-dissolved in dichloromethane (200 ml), and was washed with a saturated $NaHCO_3$ solution (3×50 ml) and a saturated NaCl solution (3×50 ml). The organic layer was then dried over anhydrous $Na_2SO_4$ and concentrated to afford the crude product as a white solid. Traces of pyridine were removed from the crude product by co-evaporation with dry acetonitrile. The obtained white solid was dried overnight under reduced pressure and was then triturated with ether (150 ml) to yield 20.23 grams (94% yield) of partially purified Compound 63 (see, Scheme 38 below) as a colorless amorphous powder. The partially purified product was stable at room temperature, when stored in a desiccator for an extended period (1-2 years). Proton and carbon NMR spectra showed that the partially purified compound is homogeneous. Further purification of the product was performed by chromatography on silica gel using a 50:50 $CH_2Cl_2$:EtOAc mixture as eluent, to give pure Compound 63 a white crystalline compound (18.72 grams, 87% yield).

TLC: $R_f$=0.21;

m.p.=105.5° C.;

$^1$H-NMR ($CDCl_3$): δ=2.85 (t, J=6.62 Hz, 2H), 2.86 (s, 4H), 4.45 (t, J=5.96 Hz).

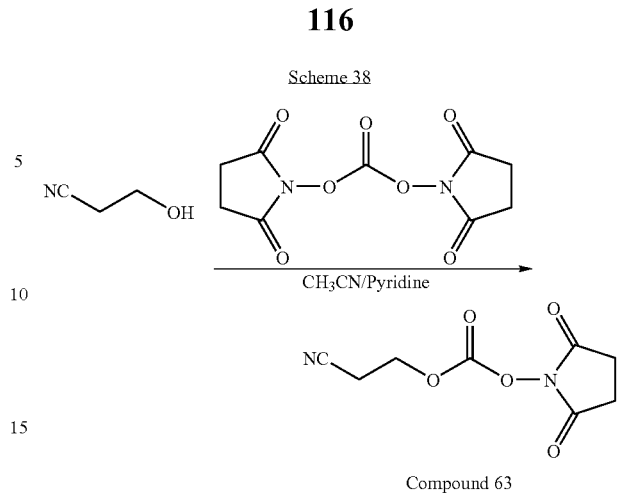

Compound 63

Preparation of N,N'-bis-CEOC-2-methyl-2-thiopseudourea 2-Methyl-2-thiopseudourea (Compound 64)

$H_2SO_4$ (5.29 grams, 38.0 mmol) was suspended in $CH_2Cl_2$ (250 ml) and a saturated $NaHCO_3$ solution (250 ml). Cyanoethoxycarbonyloxysuccinimide (Compound 63, 20.2 grams, 95.3 mmol) was added and the resulting mixture was stirred for 2 hours. The organic phase was then separated, the aqueous phase was extracted with DCM (2×200 ml) and the combined organic phase was dried over $Na_2SO_4$), filtered and evaporated. The crude product was purified by flash chromatography using a 95:5 AcOEt/DCM as eluent, to afford Compound 64 (3.78 grams, 35% yield) as a white solid (see, Scheme 39 below).

$^1$H-NMR ($CDCl_3$): δ=11.80 (br s, 1H), 4.39 (q, 4H), 2.80 (t, 4H), 2.45 (s, 3H).

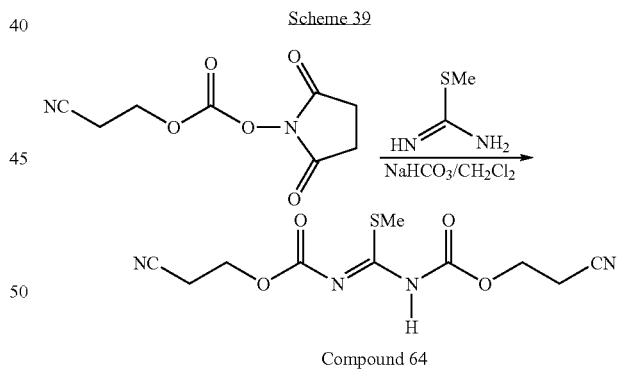

Compound 64

Preparation of 1-(4,4'-Dimethoxytrityl)-2-hydroxy, 10-Decyl (N,N'-bis-CEOC-guanidinium, Compound 65)

Compound 64 (0.27 gram, 0.95 mmol) was dissolved in anhydrous DMF (3 ml) at room temperature. To the resulting solution, compound 62 (0.42 gram, 0.86 mmol) was added, followed by the addition of then triethylamine (0.12 ml, 0.86 mmol). The resulting mixture was stirred at room temperature for 4 hours and was thereafter quenched by the addition of a 5% $NaHCO_3$ solution (40 ml). The mixture was then extracted with EtOAc (2×60 ml) and the combined organic layers were dried over Na$_2$SO$_4$, filtered and evaporated. The crude product was purified by flash column chromatography, using ethyl acetate (EtOAc) as eluent, to afford 0.480 gram (66% yield) of Compound 65 (see, Scheme 40 below).

$^1$H-NMR (CDCl$_3$): δ=1.29 (m, 10H), 1.37 (s, 3H), 1.44 (m, 2H), 1.55 (m, 2H); 2.80 (t, 4H), 2.94, (m, 1H), 3.10 (m, 1H), 3.73 (s, 6H), 4.39 (q, 4H), 6.70-7.60 (aromatics, 13H).

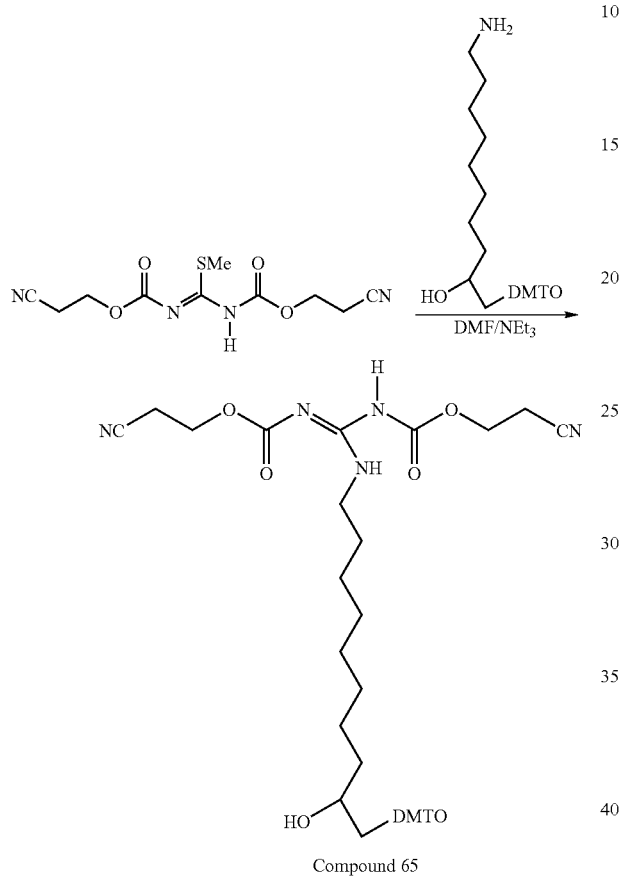

Compound 65

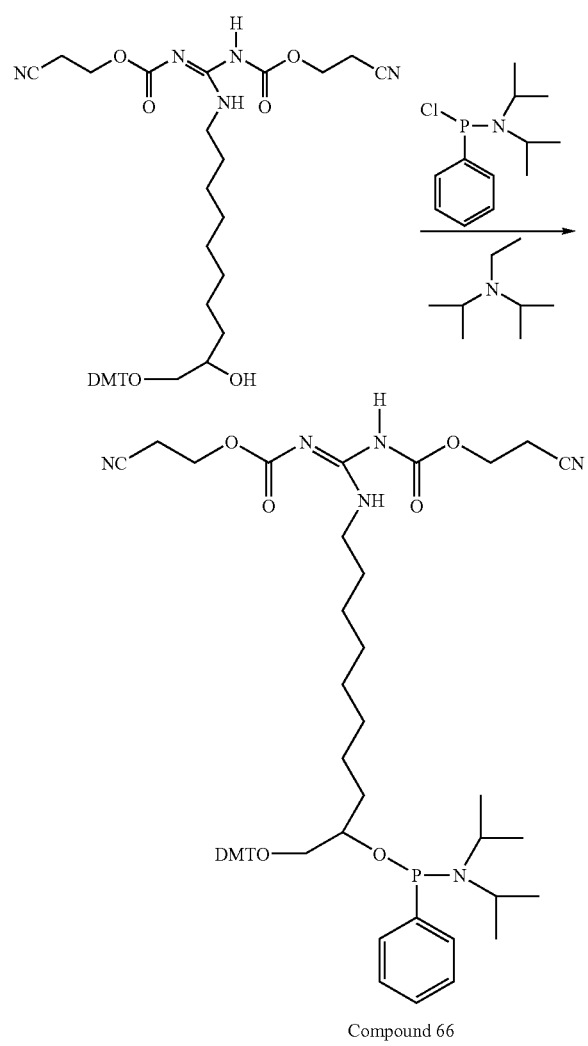

Compound 66

Preparation of 1-(4,4'-Dimethoxytrityl)-2-(N,N-di-isopropylamino, phenyl)-phosphine, 10-Decyl (N,N'-bis-CEOC-guanidinium) (Compound 66)

To a solution of Compound 65 (6.17 grams, 8.5 mmol) in dry dichloromethane (70 ml), diisopropylethylamine (11.1 ml, 63.7 mmol) was added followed by the addition of Compound 59 (5.7 grams, 23.4 mmol) under argon atmosphere. The resulting mixture was stirred at room temperature for 72 hours, and was thereafter refluxed for additional 24 hours. The mixture was then cooled to 0° C. and quenched with water (2 ml). After 20 minutes, the obtained solution was diluted with ethyl acetate (300 ml), washed with NaHCO$_3$ (2×75 ml), dried over Na$_2$SO$_4$, and evaporated under reduced pressure. The residue was purified by flash chromatography on silica gel using a 1:2 ethylacetate:hexane mixture containing 0.5% triethylamine as eluent, to give Compound 66 (see, Scheme 41 below). TLC of the product in a 1:2 ethyl acetate:hexane mixture showed that the product migrated at Rf of 0.52.

$^1$H-NMR (CDCl$_3$): δ=1.05 (2s, 12H), 1.29 (m, 10H), 1.44 (m, 2H), 1.55 (m, 2H), 2.80 (t, 4H), 2.94 (m, 2H), 3.20 (m, 2H), 3.54 (m, 1H), 3.73 (s, 6H), 4.39 (q, 4H), 6.7-7.3 (aromatics, 18H).

Preparation of 1-(4,4'-Dimethoxytrityl)-2-(N,N-di-isopropylamino, cyanoethyl)-phosphoramidite, 10-Decyl (N,N'-bis-CEOC-guanidinium) (Compound 67)

To a solution of Compound 65 (6.17 grams, 8.5 mmol) in dry dichloromethane (50 ml), diisopropylethyl amine (7.4 ml, 42.5 mmol) was added, followed by a dropwise addition of 2-cyanoethyl tetraisopropylphosphorodiamidite (3 grams, 12.75 mmol, Aldrich) under argon atmosphere. The resulting mixture was stirred at room temperature for 25 minutes, and was thereafter diluted with ethyl acetate (300 ml) and washed with NaHCO$_3$ (2×75 ml) and brine (300 ml). The organic layer was dried over sodium sulfate and the solvent was removed under reduced pressure. The residue was purified by flash chromatography on silica gel using a 1:2 ethylacetate:hexane mixture containing 0.5% triethylamine as eluent, to give Compound 67 (see, Scheme 42 below). TLC of the product in a 1:2 ethyl acetate:hexane mixture showed that the product migrated at Rf of 0.43.

$^1$H-NMR (CDCl$_3$): δ=1.05 (2s, 12H), 1.29 (m, 10H), 1.44 (m, 2H), 1.55 (m, 2H), 2.60 (t, 2H), 2.80 (t, 4H), 2.97 (m, 2H), 3.20 (m, 2H), (3.39-3.46) (m, 2H), 3.54 (m, 1H), 3.73 (s, 6H), 3.90 (t, 2H), 4.39 (q, 4H), 6.7-7.19 (aromatics, 13H).

Scheme 42

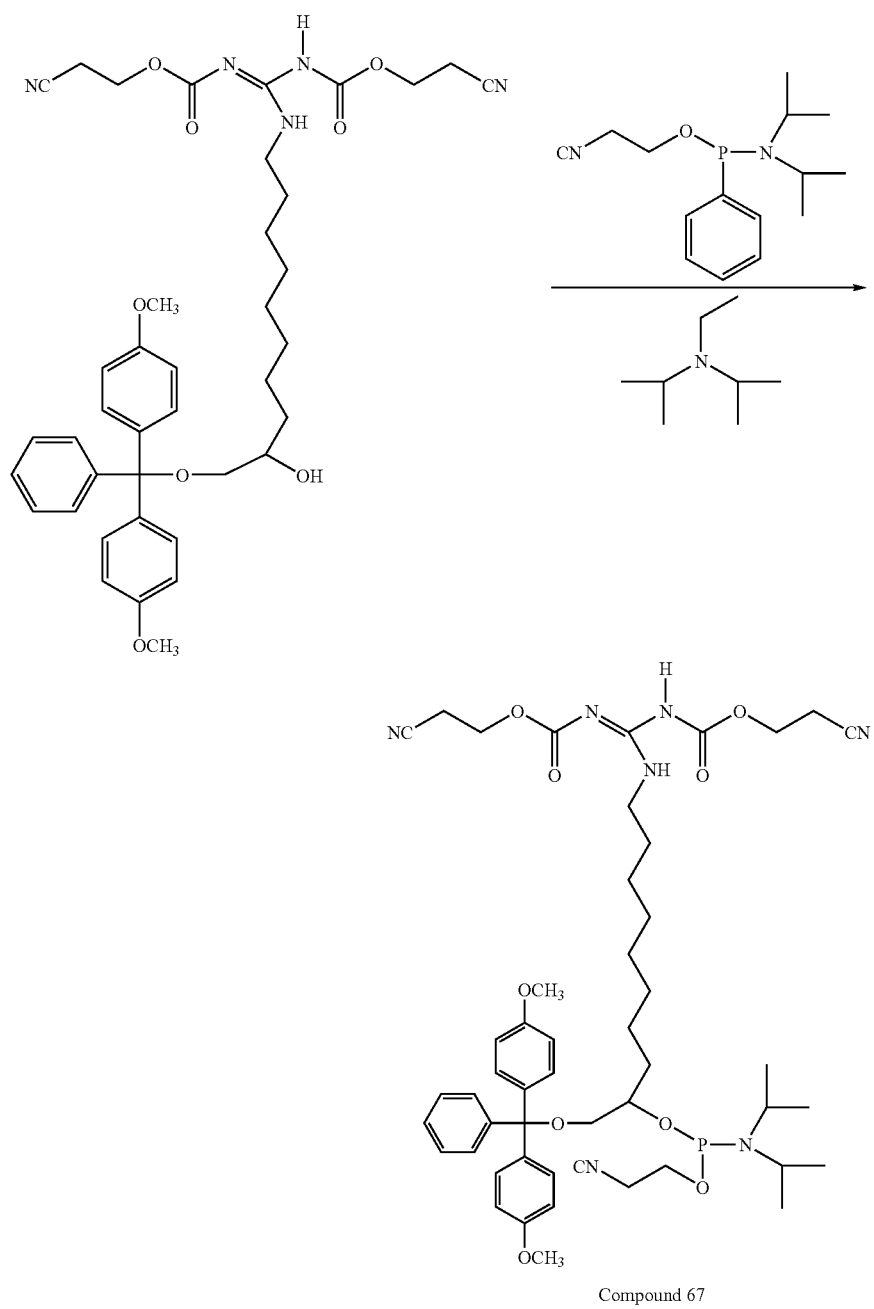

Compound 67

Compounds 66 and 67 were thereafter incorporated into the oligonucleotide syntheses and were labeled by Fluorescein, as described in Route I hereinabove, to afford compounds such as represented by Structure A hereinabove.

Preparation of Polyether-Based Delivery Moieties and Delivery Systems Containing Same Preparation of Polyether-Polyacetal Delivery Moieties The following describes compounds collectively represented by the following Structure B:

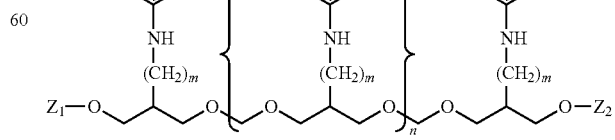

Structure B wherein m is an integer number from 2-12, and n is an integer number from 3-22.

Preparation of 1-N-Tritylamino-1,6-hexanol (Compound 68)

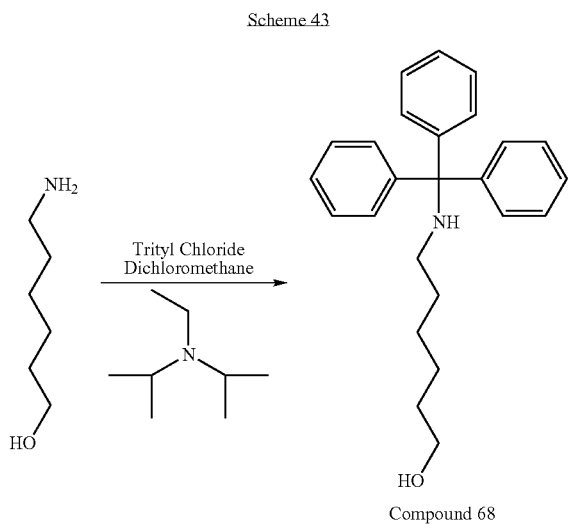

Scheme 43

Compound 68

To a solution of 6-amino hexanol (29.51 grams, 251.8 mmols) in dry dichloromethane (300 ml), and diisopropylethyl amine (65.47 grams, 506.6 mmols, 88.24 ml) was added dropwise a solution of trityl chloride (70.21 grams, 251.8 mmols) in dry dichloromethane (300 ml) at room temperature. The reaction mixture was stirred for 18 hours, while being monitored by TLC, and was thereafter quenched by adding methanol (30 ml) and stirring for additional 1 hour.

The obtained mixture was then evaporated to dryness and the residue was extracted with ethyl acetate (500 ml) and brine (2×200 ml) and the organic phase was dried over anhydrous sodium sulfate, and concentrated by rotary evaporator to a foam. The product was purified by column chromatography on a 3×30 cm neutralized silica gel column, using 500 ml of hexane, followed by a 2:1 mixture of hexane:ethyl acetate, as eluents. The appropriate fractions were combined and evaporated to dryness, yielding 87.8 grams (97% yield) of the desired product as yellowish oil.

TLC (a 2:1 mixture of hexane:ethyl acetate): Rf=0.36.

Preparation of 1-N-Tritylamino,6-p-toluenesulfonyl hexanol (Compound 69)

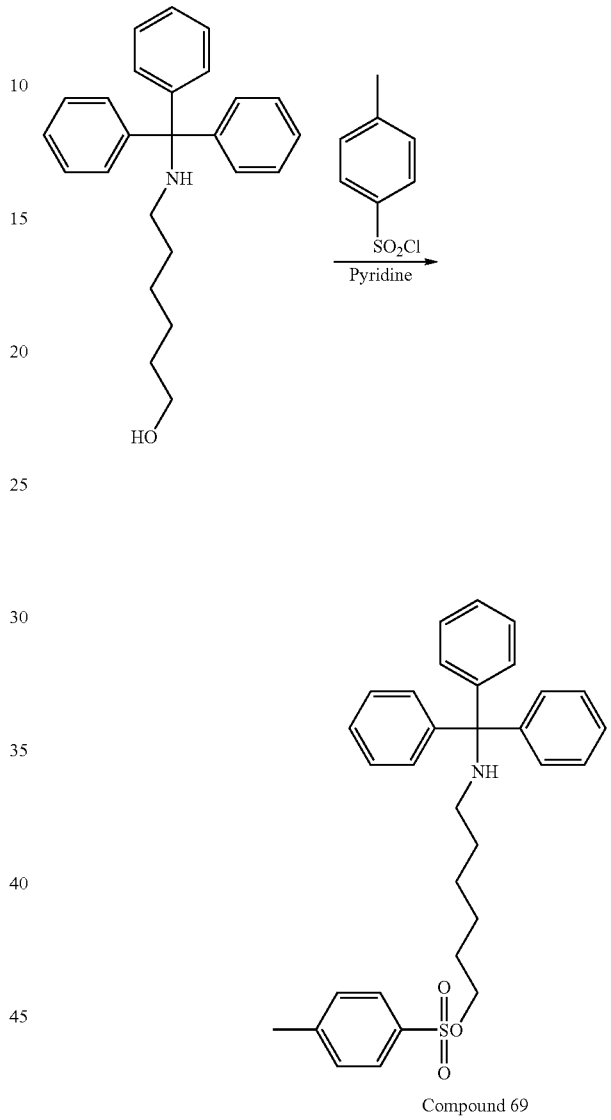

Scheme 44

Compound 69

To a cooled (0° C.) solution of Compound 68 (12 grams, 33.34 mmols) in dry pyridine (100 ml) under argon atmosphere, was added dropwise a solution of p-toluene sulfonyl chloride (9.6 grams, 50.4 mmols). The resulting pink mixture was stirred at room temperature for 2 hours, while being r monitored by TLC, and was thereafter quenched by adding methanol (30 ml) and stirring for an additional 1 hour.

The reaction mixture was then evaporated to dryness, extracted with ethyl acetate (500 ml) and brine (2×200 ml), and the organic layer was dried over anhydrous sodium sulfate, and concentrated by rotary evaporator to a foam. The product was purified by column chromatography on a 3×30 cm neutralized silica gel column, using 500 ml of hexane, followed by a 2:1 mixture of hexane:ethyl acetate, as eluents. The appropriate fractions were combined and evaporated to dryness, yielding 12.5 grams (85.6% yield) of the desired product as yellowish oil.

TLC (a 2:1 mixture of hexane:ethyl acetate): Rf=0.46;
$^1$H-NMR (CDCl$_3$): δ=1.45 (m, 4H), 1.48 (m, 2H), 1.63 (m, 2H), 2.15 (m, 2H), 2.46 (s, 3H), 4.02 (t, 2H), 7.17-7.82 (Aromatics, 19H).

Preparation of Compound 70 (Product of Reacting Compound 69 with Diethyl Malonate)

Scheme 45

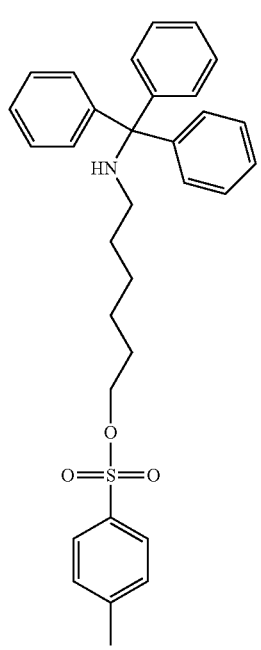

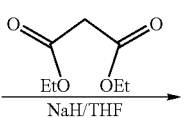

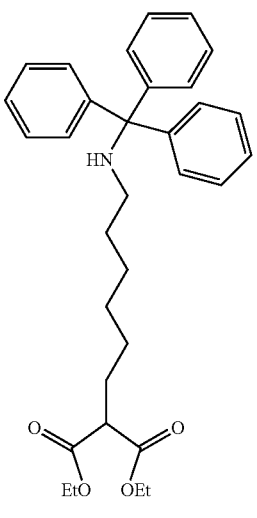

Compound 70 ethyl acetate (500 ml), brine (2×200 ml) and the organic layer was dried over anhydrous sodium sulfate, and concentrated by rotary evaporator to a foam. The product was purified by column chromatography on a 3×30 cm neutralized silica gel column, using 500 ml of hexane, followed by a 5:1 mixture of hexane:ethyl acetate, as eluents. The appropriate fractions were combined and evaporated to dryness, yielding 52 grams (90.7%) of the desired product as yellowish oil.

TLC (5:1 mixture of hexane:ethyl acetate): Rf=0.42.

Preparation of Compound 71 (Reduction of Compound 70 with Lithium Aluminum Hydride)

Scheme 46

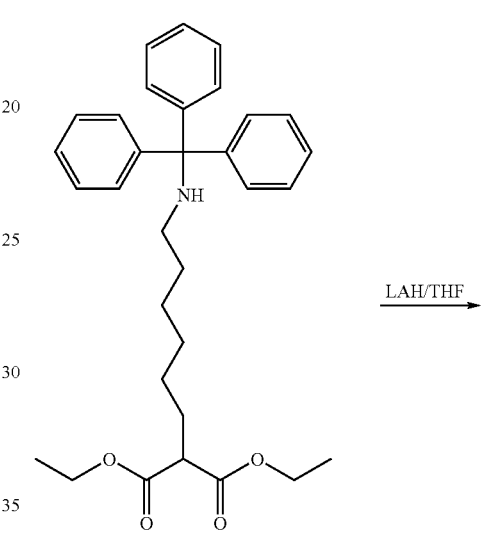

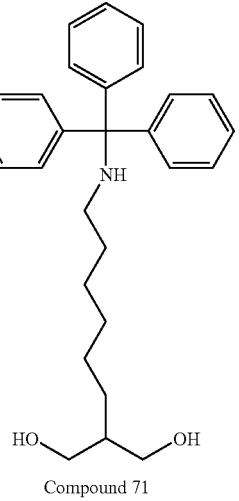

Compound 71

A mixture of sodium hydride (60% dispersion in mineral oil, 8.33 grams, 208 mmols) in dry tetrahydrofuran (300 ml) was cooled to 0° C. under argon atmosphere, and a solution of diethyl malonate (28.42 grams, 177.4 mmols) was added thereto. The reaction mixture was stirred for 30 minutes at 0° C., and thereafter at room temperature for 1 hour. A solution of Compound 69 (58.66 grams, 114.2 mmols) in dry THF (200 ml) was thereafter added dropwise and the resulting mixture was refluxed for 18 hours. The reaction mixture was then evaporated to dryness, the residue was extracted with To a cooled (0° C.) solution of Compound 70 (40 grams, 79.7 mmols) in dry THF (1000 ml) under argon atmosphere, was added dropwise a solution of lithium aluminum hydride (1M solution in THF, 120 ml, 0.12 mole). The reaction mixture was allowed to warm to room temperature, and was then refluxed for 4 hours. The reaction mixture was then cooled to 0° C., and methanol (20 ml) was added dropwise thereto, followed by addition of a 30% solution of NaOH (50 ml).

The obtained white mixture was filtered through Celite, evaporated to dryness, and extracted with ethyl acetate (500 ml) and brine (2×200 ml). The organic layer was dried over anhydrous sodium sulfate, and concentrated by rotary evaporator to a foam. The product was purified by column chromatography on a 3×30 cm neutralized silica gel column, using 500 ml of hexane, followed by a 2:1 mixture of hexane:ethyl acetate, as eluents. The appropriate fractions were combined and evaporated to dryness yielding 22.5 grams (78.5% yield) of the desired product as colorless oil.

TLC (a 2:1 mixture of hexane:ethyl acetate): Rf=0.39.

Preparation of Compound 72 (Reaction of Compound 71 with Chloromethyl Methyl Sulfide)

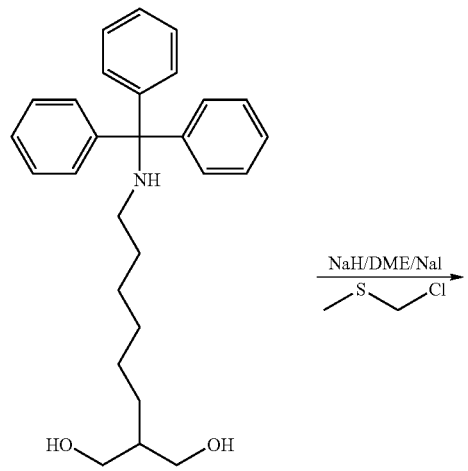

Scheme 47

To a cooled (0° C.) mixture of 60% NaH in mineral oil (1.8 grams, 45 mmols) in dry dimethoxyethane (40 ml) under argon atmosphere, was added dropwise a solution of Compound 71 (4.73 grams, 11.32 mmols), followed by addition of NaI (3.4 grams, 27 mmols) and then chloromethyl methyl sulfide (2.18 grams, 1.9 ml, 22.64 mmols). The reaction mixture was stirred at 0° C. 1 hour and was then allowed to warm to room temperature and stirred for 6 hours. The reaction mixture was poured into water (50 ml), extracted with ethyl acetate (200 ml), brine (2×200 ml) and the organic layer was dried over anhydrous sodium sulfate, and concentrated by rotary evaporator to a foam. The product was purified by column chromatography on a 3×30 cm neutralized silica gel column, using 500 ml of hexane, followed by a 2:1 mixture of hexane:ethyl acetate, as eluents. The appropriate fractions were combined and evaporated to dryness, yielding 4.85 grams (79.6% yield) of the desired product as colorless oil.

TLC (a 2:1 mixture of hexane:ethyl acetate): Rf=0.57

$^1$H-NMR (CDCl$_3$): δ=1.25-1.45 (m, 10H), 2.09 (s, 6H), 2.13 (m, 1H), 2.55 (t, 2H), 3.33 (s, 4H), 4.52 (s, 4H), 7.06-7.21 (Aromatic, 15H) ppm.

Preparation of Compound 73 (Reaction of Compound 72 with Benzoyl Chloride)

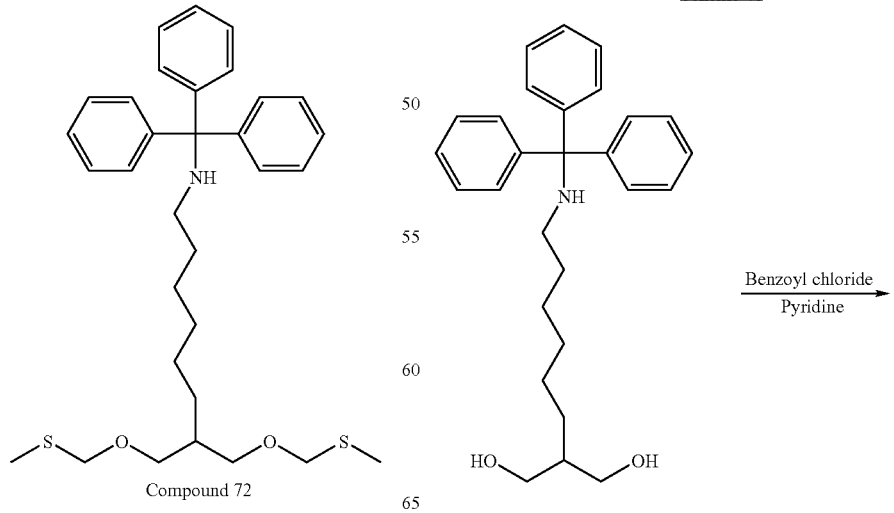

Scheme 48

Preparation of Compound 74 (Reaction of Compound 73 with Chloromethyl Methyl Sulfide)

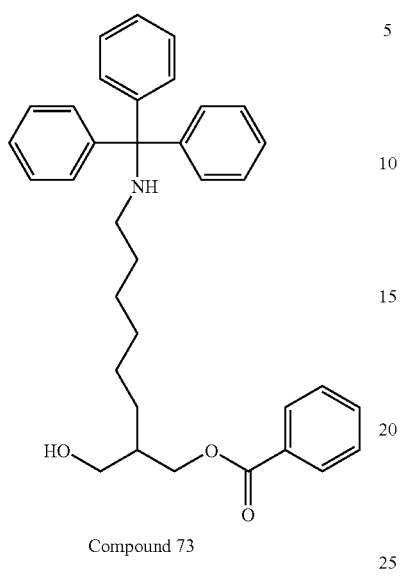

Compound 73

To a cooled (0° C.) solution of Compound 72 (4.17 grams, 10 mmols) in dry pyridine (50 ml), was added dropwise, under argon atmosphere, a solution of benzoyl chloride (1.4 grams, 10 mmols) in dry dichloromethane (30 ml).

The reaction mixture was stirred at 0° C. for one hour, was thereafter left to warm to room temperature gradually, and then stirred at room temperature for additional 2 hours. The solvent was thereafter evaporated to dryness, the residue was extracted with ethyl acetate (200 ml) and brine (2×200 ml) and the organic layer was dried over anhydrous sodium sulfate, and concentrated by rotary evaporator to a foam. The product was purified by column chromatography on neutralized silica gel column, using 200 ml of hexane, followed by a 5:2 mixture of hexane:ethyl acetate, as eluents. The appropriate fractions were combined and evaporated to dryness, yielding 4.12 grams (79%) of the desired product as colorless oil.

TLC (a 5:2 mixture of hexane:ethyl acetate): Rf=0.33;

$^1$H-NMR (CDCl$_3$): δ=1.25-1.45 (m, 10H), 2.16 (m, 1H), 2.55 (t, 2H), (3.37, 3.62) (AB, 2H), (4.09, 4.34) (AB, 2H), 7.06-7.97 (Aromatic, 20H) ppm.

Scheme 49

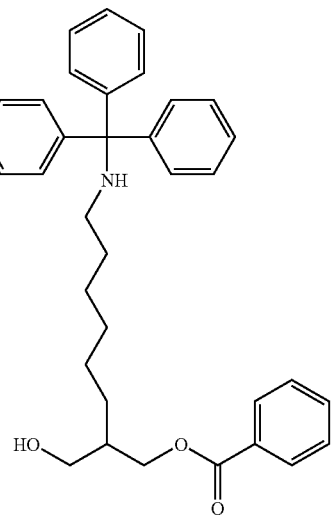

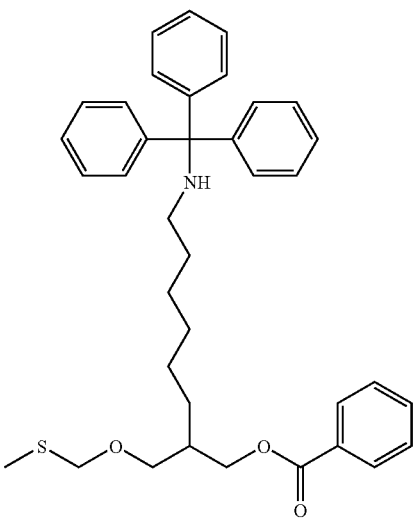

Compound 74

To a cooled (0° C.) mixture of 60% NaH in mineral oil (1.8 grams, 45 mmols) in dry dimethoxyethane (40 ml), under argon atmosphere, was added dropwise a solution of Compound 73 (11.60 grams, 22.25 mmols), followed by the addition of NaI (3.3 grams, 22.25 mmols) and then chloromethyl methyl sulfide (2.18 grams, 1.9 ml, 22.64 mmols). The reaction mixture was stirred at 0° C. for one hour and was thereafter allowed to warm gradually to room temperature and was stirred at room temperature for 5 hours. The mixture was then poured into water (50 ml), extracted with ethyl acetate (200 ml), brine (2×200 ml) and the organic layer was dried over anhydrous sodium sulfate, and concentrated by rotary evaporator to a foam. The product was purified by column chromatography on a 3×30 cm neutralized silica gel column, using 500 ml of hexane, followed by a 1:2 mixture of hexane:ethyl acetate, as eluents. The appropriate fractions were combined and evaporated to dryness, yielding 11.2 grams (86.6% yield) of the desired product as colorless oil.

TLC (a 3:1 mixture of hexane:ethyl acetate): Rf=0.57

$^1$H-NMR (CDCl$_3$): δ=1.25-1.45 (m, 10H), 2.09 (s, 3H), 2.40 (m, 1H), 2.55 (t, 2H), (3.20, 3.45) (AB, 2H), (4.09, 4.34) (AB, 2H), 4.55 (s, 2H), 7.06-7.22 (Aromatic, 15H) ppm.

Preparation of Compound 75 (Condensation of Compound 73 with Compound 74)

Scheme 50

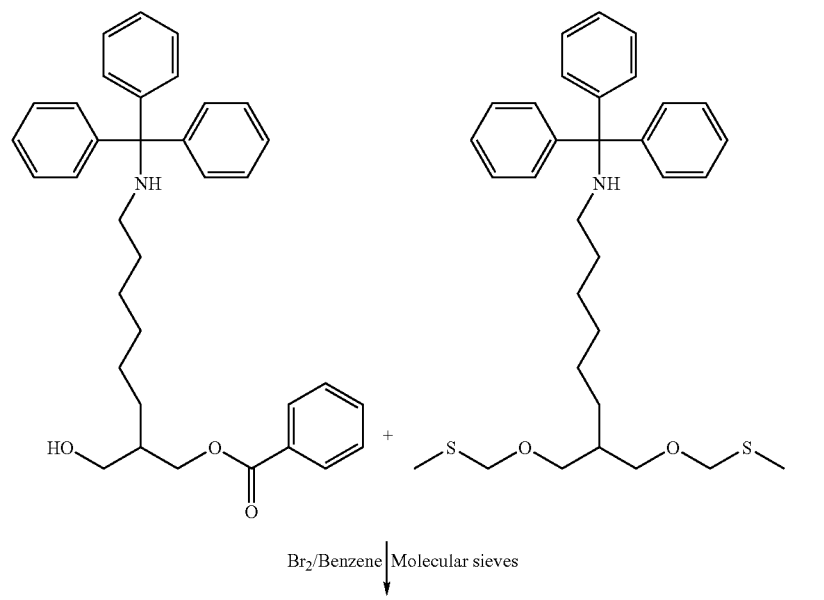

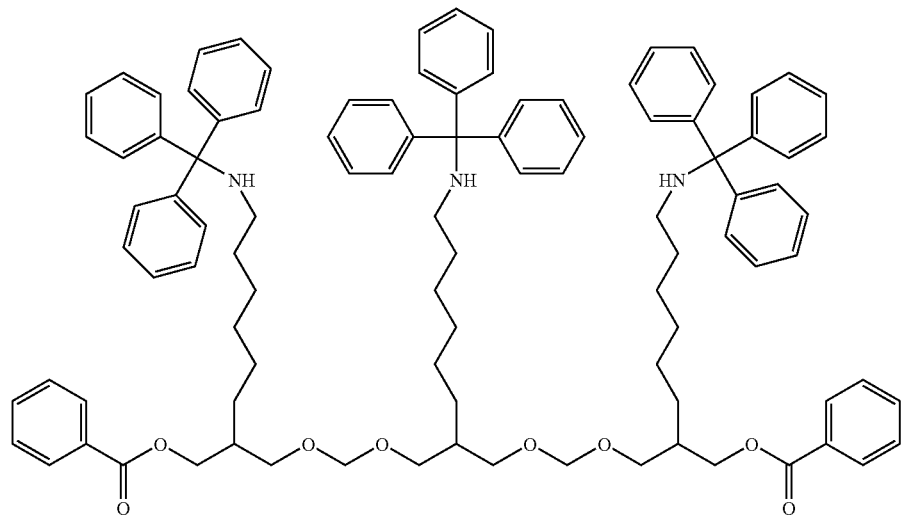

Compound 75

A mixture of Compound 73 (5.37 grams, 10 mmols), Compound 74 (15.65 grams, 30 mmols), 2,6-lutidine (7.5 grams, 70 mmols), and molecular sieves (4 Å, 5 grams) in dry toluene (100 ml) was stirred at room temperature for 2 hours, and bromine (1.0 M in benzene, 10 mmols) was thereafter added thereto. The resulting solution was stirred at room temperature for 2 hours and was thereafter washed with saturated aqueous sodium bicarbonate solution. The organic layer was separated, dried (Na$_2$SO$_4$) and evaporated to dryness. The residual oil was purified by column chromatography on neutralized silica gel column, using 500 ml of hexane, followed by a 1:2 mixture of hexane:ethyl acetate, as eluents. The appropriate fractions were combined and evaporated to dryness, yielding 10.54 grams (71% yield) of the desired product as colorless oil.

TLC (a 5:1 mixture of hexane:ethyl acetate): Rf=0.57;

$^1$H-NMR (CDCl$_3$): δ=1.25-1.45 (m, 30H), 2.13-2.40 (m, 3H), 2.55 (t, 6H) (3.20, 3.45) (AB, 4H), 3.33 (s, 4H), (4.09, 4.34) (AB, 4H), 5.45 (s, 4H), 7.06-8.02 (Aromatic, 55H) ppm.

Preparation of Compound 76 (Hydrolysis of Compound 75)

A mixture of Compound 75 (14.85 grams, 10 mmols), ammonium hydroxide (35%, 50 ml) and methanol (50 ml) was stirred at 50° C. for 3 hours. The solvent was evaporated to dryness and the residue was extracted with ethyl acetate (200 ml), sodium bicarbonate (5%, 200 ml) and brine (2×200 ml), and the organic layer was dried over anhydrous sodium sulfate, and concentrated by rotary evaporator to a foam. The product was used for the next step without further purification.

Preparation of Compound 77

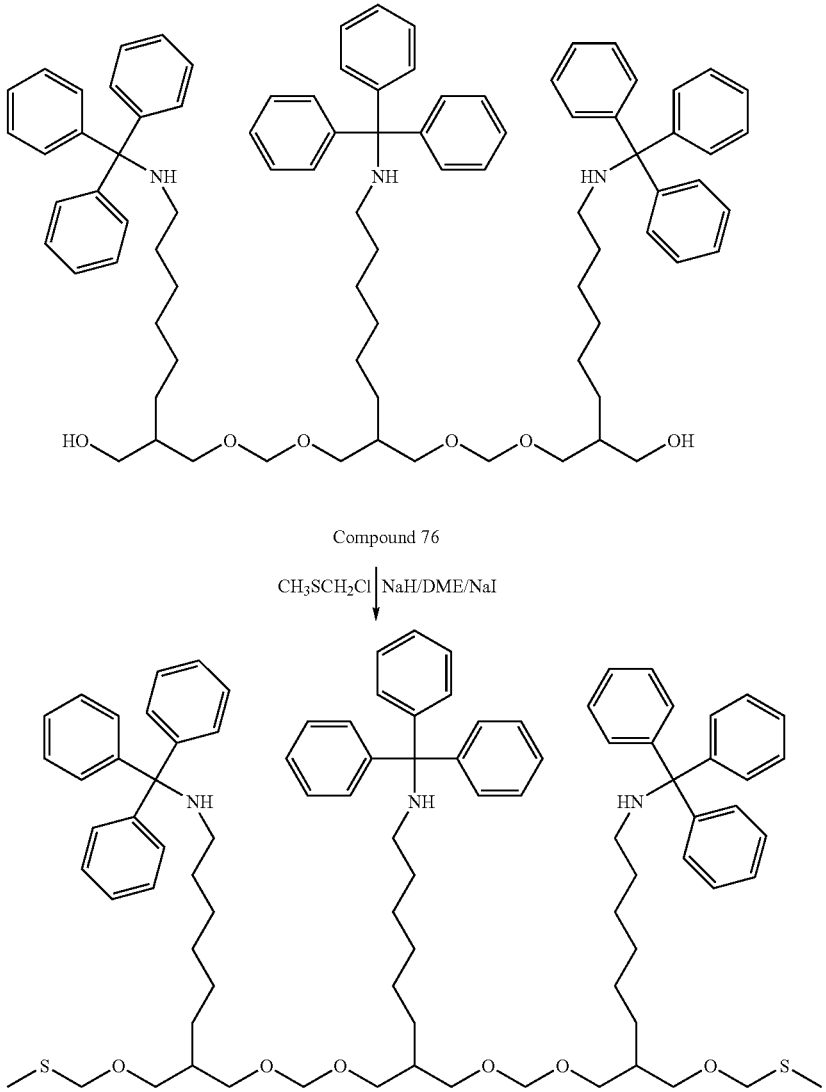

Scheme 51

Compound 76

Compound 77

The oily Compound 76 was reacted with chloromethyl methyl sulfide as described above in the preparation of Compound 74.

To a cooled (0° C.) mixture of 60% NaH in mineral oil (1.6 grams, 40 mmols) in dry dimethoxyethane (70 ml) under argon atmosphere, was added dropwise a solution of Compound 76 (12.76 grams, 10 mmols), followed by addition of NaI (2.96 grams, 20 mmols) and then chloromethyl methyl sulfide (1.92 grams, 1.7 ml, 20 mmols). The reaction mixture was stirred at 0° C. for one hour and then allowed to warm gradually to room temperature and stirred at room temperature for 5 hours. The resulting mixture was then poured into water (50 ml), extracted with ethyl acetate (200 ml) and brine (2×200 ml) and the organic layer was dried over anhydrous sodium sulfate, and concentrated by rotary evaporator to a foam. The product was purified by column chromatography on neutralized silica gel column, using 500 ml of hexane, followed by a 1:2 mixture of hexane:ethyl acetate, as eluents. The appropriate fractions were combined and evaporated to dryness, yielding 11.85 grams (85.12% yield) of the desired product as colorless oil.

$^1$H-NMR (CDCl$_3$): δ=1.25-1.45 (m, 30H), 2.09 (s, 6H), 2.13-2.40 (m, 3H), 2.55 (t, 6H), 3.20-3.45 (m, 4H), 3.33 (s, 4H), 4.20-4.34 (m, 4H), 4.52 (m, 4H), 5.45 (s, 4H), 7.06-7.21 (Aromatic, 45H) ppm.

Preparation of Structure B (Elongation of Compound 77)

Compound 77 is reacted with Compound 74, in a condensation reaction as described hereinabove (for preparing Compound 76), followed by basic hydrolysis as and reaction with chloromethyl methyl sulfide as described hereinabove.

This sequence of reactions is repeated as desired, so as to obtain the following structure B:

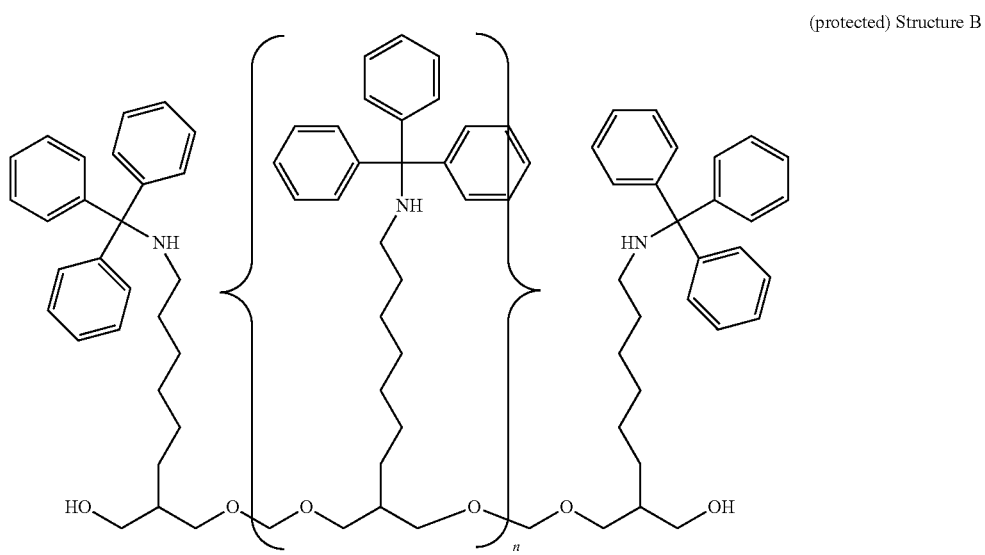

(protected) Structure B

Preparation of Fluorescein-Labeled Structure B (Condensation with Fluorescein (Di-t-Butylate)-Hexamethylene-Phosphoramidite (FAM-HPA))

Structure B is reacted with FAM-HPA (Glen Research), using the phosphoramidite cycle to form a difluoresceinated adduct as depicted in Scheme 52 below, according to known procedures for condensation between a hydroxyl group and FAM-HAP (see, e.g. Beaucage et al. in Tetrahedron Letters 22, 5843-5846 (1981)).

Scheme 52
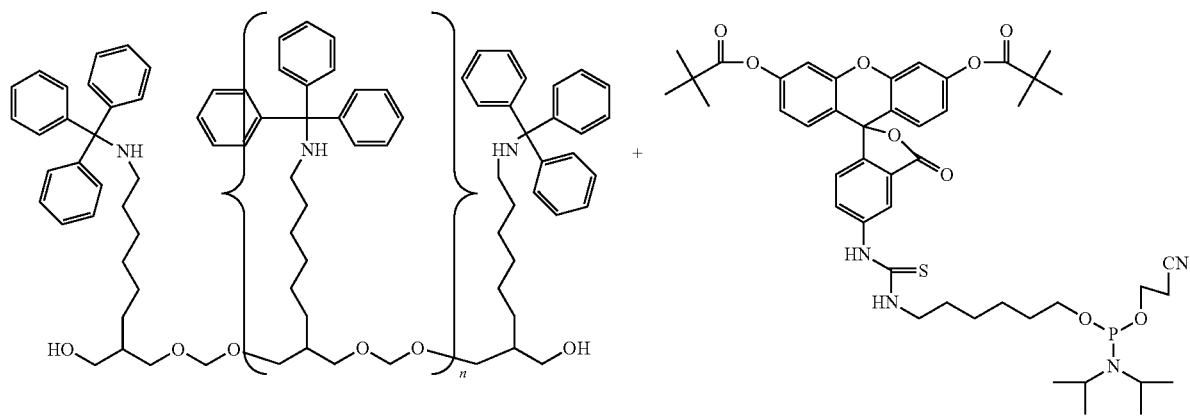
1. Tetrazole
2. I$_2$/Lutidine/THF/H$_2$O
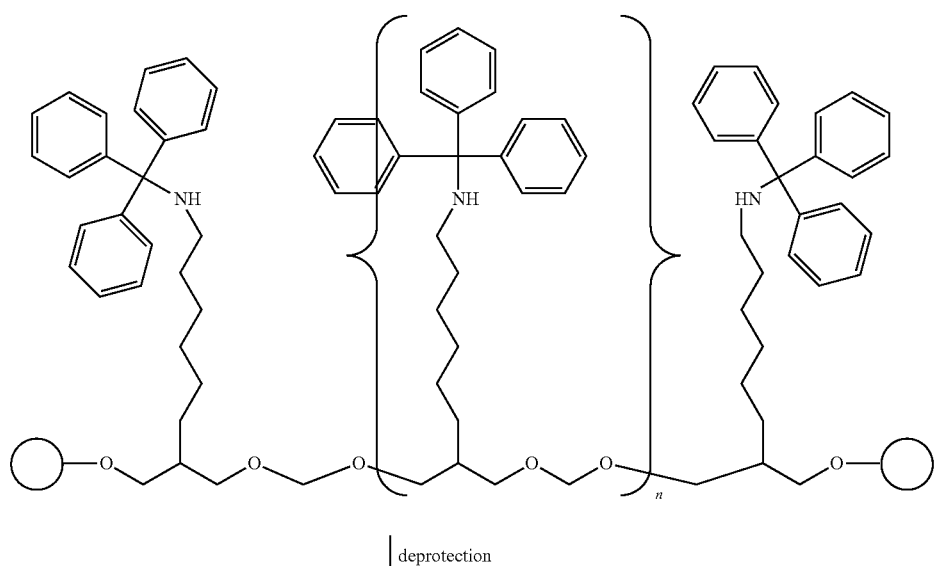
deprotection
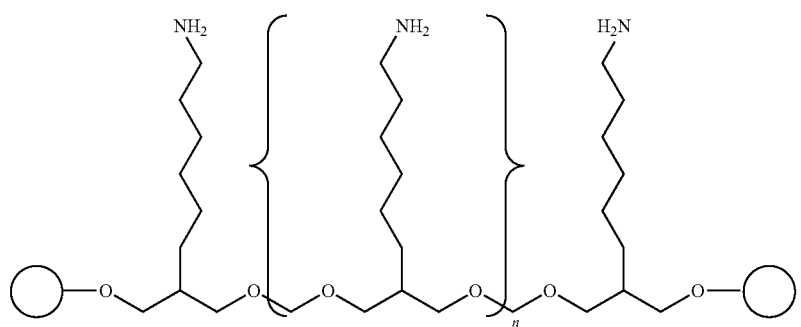
Fluorophore-labeled Structure B wherein

is fluorescein or other fluorophore.

Deprotection of the trityl groups and the pivaloate groups of the resulting product is then effected as follows: the condensation product (1 gram) is evaporated to dryness and the obtained residue is treated with 80% acetic acid (30 ml), while stirring at 60° C. for 2 hours. The solvent is evaporated to dryness and the residue is treated with concentrated ammonium hydroxide (30 ml) in a sealed tube and the mixture is kept at 60° C. for 4 hours. The solvent is then evaporated to dryness and the product is purified on Sephadex G25, using water as eluent. The fluoreseinated fractions are collected and lyophilized to obtain a pellet.

Preparation of guanidine-containing Structure B
(Reaction with 1H-Pyrazole-1-carboxamidine hydrochloride)

Structure B is treated with a solution of 1H-Pyrazole-1-carboxamidine hydrochloride (Aldrich) (50 equivalents) in 5% sodium carbonate (5 ml) and the solution is heated to 50° C. for 24-48 hours, as depicted in Scheme 53. The crude mixture is then neutralized to pH 7 with 3N HCl, evaporated to dryness and purified by RP-HPLC (using a mixture of $H_2O/CH_3CN$ as gradient mobile phase). The obtained products are characterized by electrospray mass spectrometry, isolated by lyophilization and further purified by RP-HPLC.

Scheme 53

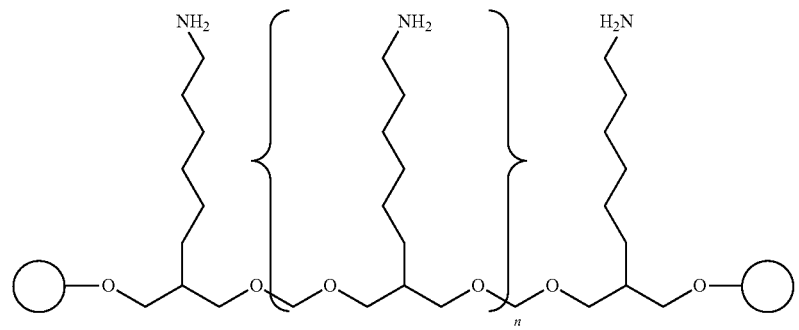

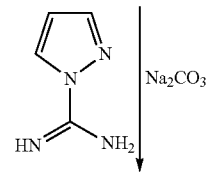

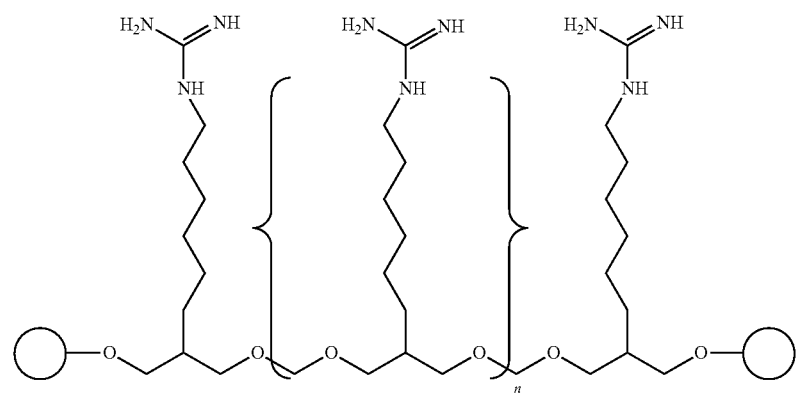

139
Preparation of Compound 78

As another exemplary building block for preparing polyether-polyacetal-based delivery moiety, Compound 78 is prepared according to the pathway depicted in Scheme 54 below.

Scheme 54

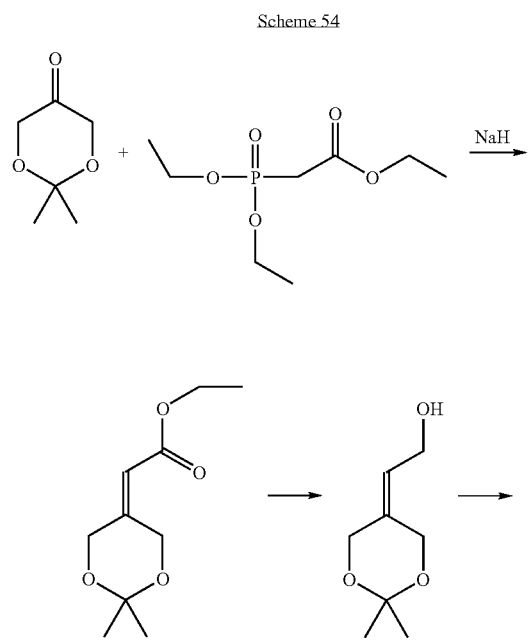

140
-continued

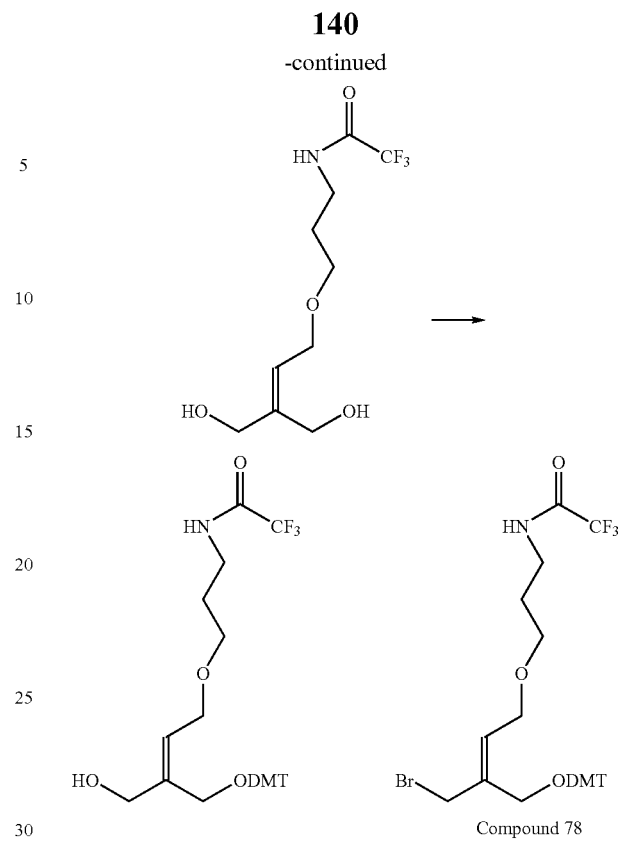

Preparation of Polyether-Polyacetal-Based Delivery Moieties Using a Polymeric (Solid) Support—Route I Various monomers can be attached sequentially to a polymeric support, as exemplified below.

Preparation of Compound 90 (Deprotection of Compound 71)

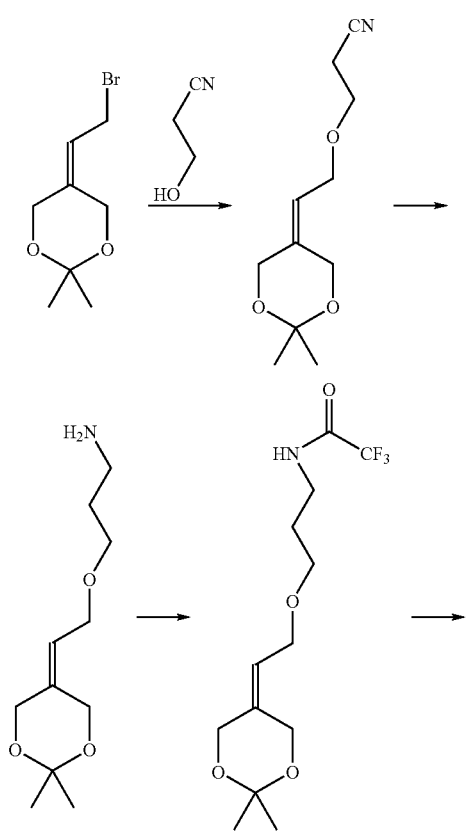

Scheme 55

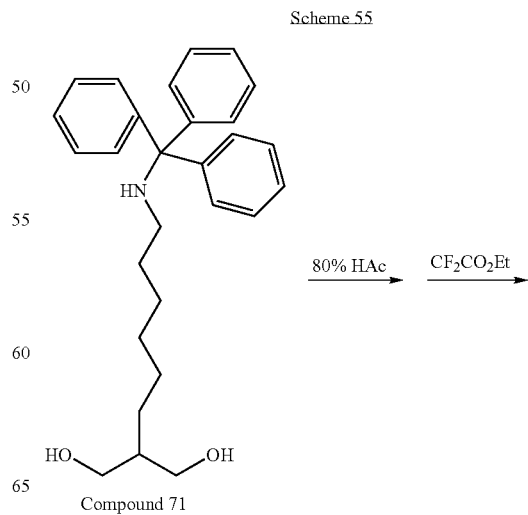

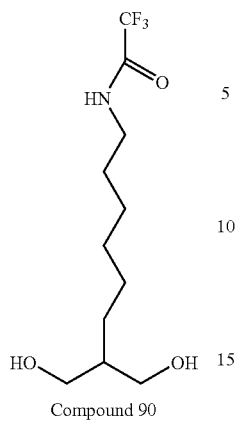

Compound 90

Compound 71 (4.15 grams, 10 mmols) was dissolved in 80% acetic acid and the solution was kept at 80° C. for 8 hours. After cooling to room temperature, the solvent was evaporated to dryness, the residue was dissolved in methanol (50 ml) and triethylamine (1 gram, 10 mmols) was added. The reaction mixture was cooled to 0° C., and a solution ethyl trifluoroacetate (2.1 grams, 15 mmols) in methanol (20 ml) was added thereto. The reaction mixture was allowed to warm gradually to room temperature and was stirred for additional 2 hours at room temperature. The solvents were thereafter evaporated to dryness, the residue was extracted with ethyl acetate (200 ml) and brine (2×200 ml) and the organic layer was dried over anhydrous sodium sulfate, and concentrated by rotary evaporator to a foam. The product was purified by column chromatography on neutralized silica gel column, using 500 ml of dichloromethane followed by a mixture of 95:5 dichloromethane:methanol, as eluents. The appropriate fractions were combined and evaporated to dryness, yielding 2.51 grams (92% yield) of the desired product as colorless oil.

TLC (a mixture of 95:5 dichloromethane:methanol): Rf=0.51;

$^1$H-NMR (CDCl$_3$): δ=1.25-1.31 (m, 8H), 1.55 (m, 2H), 1.75 (m, 1H), 3.20 (m, 2H), 3.63 (m, 4H), 8.0 (m, 1H) ppm.

Preparation of Compound 91 (Reaction of Compound 90 with (4,4')-Dimethoxytrityl chloride)

Scheme 56

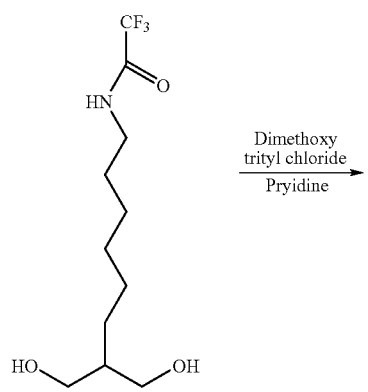

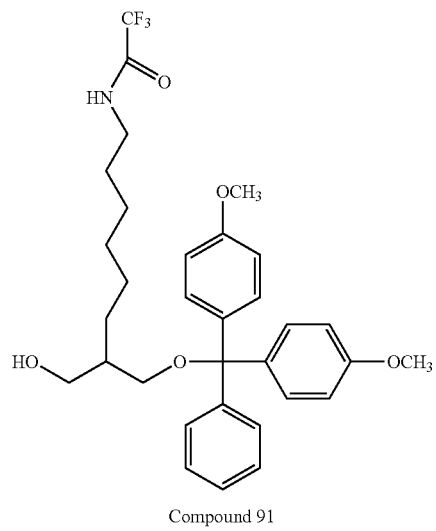

Compound 91

To a cooled (0° C.) solution of Compound 90 (2.71 grams, 10 mmols) in dry pyridine (50 ml), was added dropwise during 30 minutes under argon atmosphere a solution of (4,4')-dimethoxytrityl chloride (3.38 grams, 10 mmols) in dry pyridine (20 ml). The reaction mixture was allowed to warm gradually to room temperature and was stirred at room temperature for 18 hours. The solvent was then evaporated to dryness, the residue was extracted with ethyl acetate (200 ml) and brine (2×200 ml) and the organic layer was dried over anhydrous sodium sulfate, and concentrated by rotary evaporator to a foam. The product was purified by column chromatography on neutralized silica gel column, using 500 ml hexane, followed by a 3:1 mixture of hexane:ethyl acetate, as eluents. The appropriate fractions were combined and evaporated to dryness, yielding 2.51 grams (92% yield) of the desired product as colorless oil.

TLC (a mixture of 99:1 dichloromethane:methanol): Rf=0.51;

$^1$H-NMR(CDCl$_3$): δ=1.25-1.31 (m, 8H), 1.55 (m, 2H), 1.89 (m, 1H), 3.20 (m, 2H), 3.30-3.62 (m, 4H), 3.73 (s, 6H), 8.0 (m, 1H), Aromatics (m, 13H) ppm.

Preparation of Compound 92 (Reaction of Compound 91 with chloromethyl methyl sulfide)

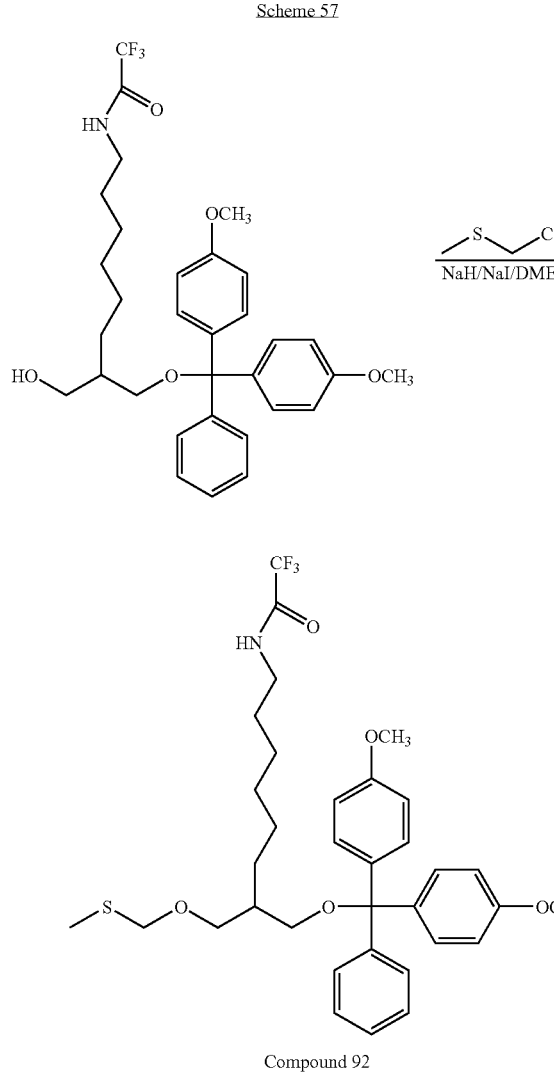

Scheme 57

Compound 92

To a cooled (0° C.) mixture of 60% NaH in mineral oil (1.8 grams, 45 mmols) in dry dimethoxyethane (40 ml) under argon atmosphere, was added dropwise a solution of Compound 91 (12.76 grams, 22.25 mmols), followed by the addition of NaI (3.3 grams, 22.25 mmols) and then chloromethyl methyl sulfide (2.18 grams, 1.9 ml, 22.64 mmols). The reaction mixture was stirred at 0° C. for one hour, was allowed to warm gradually to room temperature and stirred at room temperature for 5 hours. The obtained mixture was then poured into water (50 ml), extracted with ethyl acetate (200 ml) and brine (2×200 ml) and the organic layer was dried over anhydrous sodium sulfate, and concentrated by rotary evaporator to a foam. The product was purified by column chromatography on a 3×30 cm neutralized silica gel column, using 500 ml hexane followed by a 1:2 mixture of hexane:ethyl acetate, as eluents. The appropriate fractions were combined and evaporated to dryness, yielding 28 grams (84% yield) of the desired product as colorless oil. Compound 92 serves as a monomer building block.

$^1$H-NMR (CDCl$_3$): δ=1.25-1.31 (m, 8H), 1.55 (m, 2H), 2.09 (s, 3H), 2.13 (m, 1H), 3.20 (m, 2H), 3.20-3.45 (m, 4H), 3.73 (s, 6H), 4.52 (s, 2H), 8.0 (m, 1H), Aromatics (m, 13H) ppm.

Preparation of Compound 94 (a Polymeric Support)

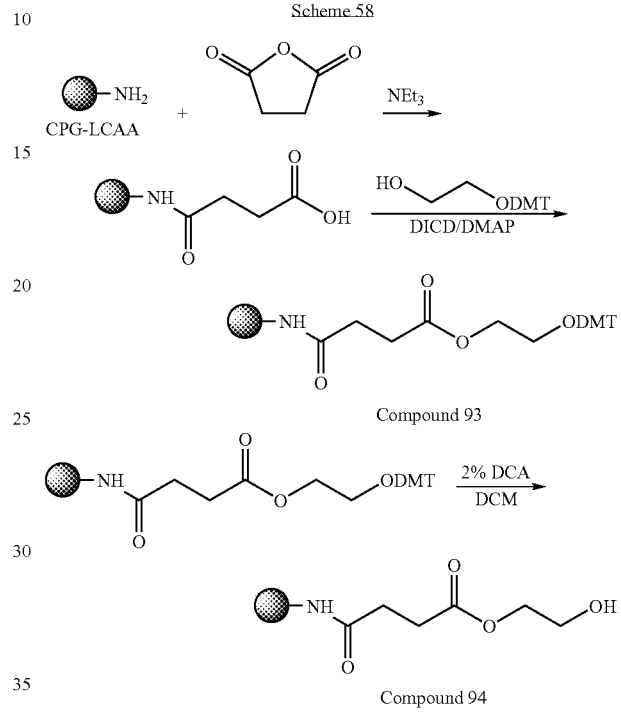

Scheme 58

Compound 93

Compound 94

Controlled pore glass-long chain alkyl amine (1 gram) (CPG Inc.) having a capacity of 73.8 μm/g is suspended with a solution of dry dichloromethane (20 ml) and triethylamine (0.5 ml), and succinic anhydride (3 grams) (Aldrich) is added thereto. The heterogenic mixture is agitated for 3 hours, and the polymeric support is washed successively with methanol (50 ml), dichloromethane (50 ml), and ether (50 ml). The support is treated with a solution of 2-(4,4'-dimethoxy trityl)-ethanol (DMTO-Ethanol, 3.64 grams, 10 mmols) in dry dichloromethane (20 ml), and with 1,3-diisopropylcarbodiimide (DICD, 1.38 grams, 11 mmols) and with 4-dimethylamino pyridine (120 mg, 1 mmol). The heterogenic mixture is agitated for 18 hours at room temperature, followed by successive washings with methanol (50 ml), dichloromethane (50 ml), and ether (50 ml).

The dried support is quantitated for loading as described, for example, by Gait in "Oligonucleotide synthesis" Oxford University Press (1984), page 48.

Compound 93 is deprotected (detritylated) by treatment with 2% dichloroacetic acid (DCA) in dichloromethane (2×1 minute), followed by successive washings with methanol (50 ml), dichloromethane (50 ml), and ether (50 ml).

Preparation of Polymeric Structure C (Cycling Procedure Using Monomers of Compound 92)

Condensation of Compound 92 with Compound 94

A mixture of Compound 94 (100 mg), Compound 92 (1.5 gram, 3 mmols), 2,6-lutidine (0.75 gram, 7 mmols), and grounded molecular sieves (4 Å, 0.2 gram) in dry toluene (100 ml) was agitated at room temperature for 2 hours, followed by addition of bromine (1.0 M in benzene, 1 mmol). The resulting solution was then agitated at room temperature for 2 hours and washed successively with methanol (50 ml), dichloromethane (50 ml), and ether (50 m), so as to obtain Compound 95.

The resulting dried polymeric support was treated with a solution of 1:1 acetic anhydride:pyridine (5 ml) during 1 minute followed by successive washings with methanol (50 ml), dichloromethane (50 ml), and ether (50 ml).

The dried polymeric support is then treated with 2% dichloroacetic acid (DCA) in dichloromethane (2×1 minute), followed by successive washings with methanol (50 ml), dichloromethane (50 ml), and ether (50 ml).

The above procedures are repeated as desire, so as to obtain the solid-support bound polymeric structure C, as depicted in Scheme 59.

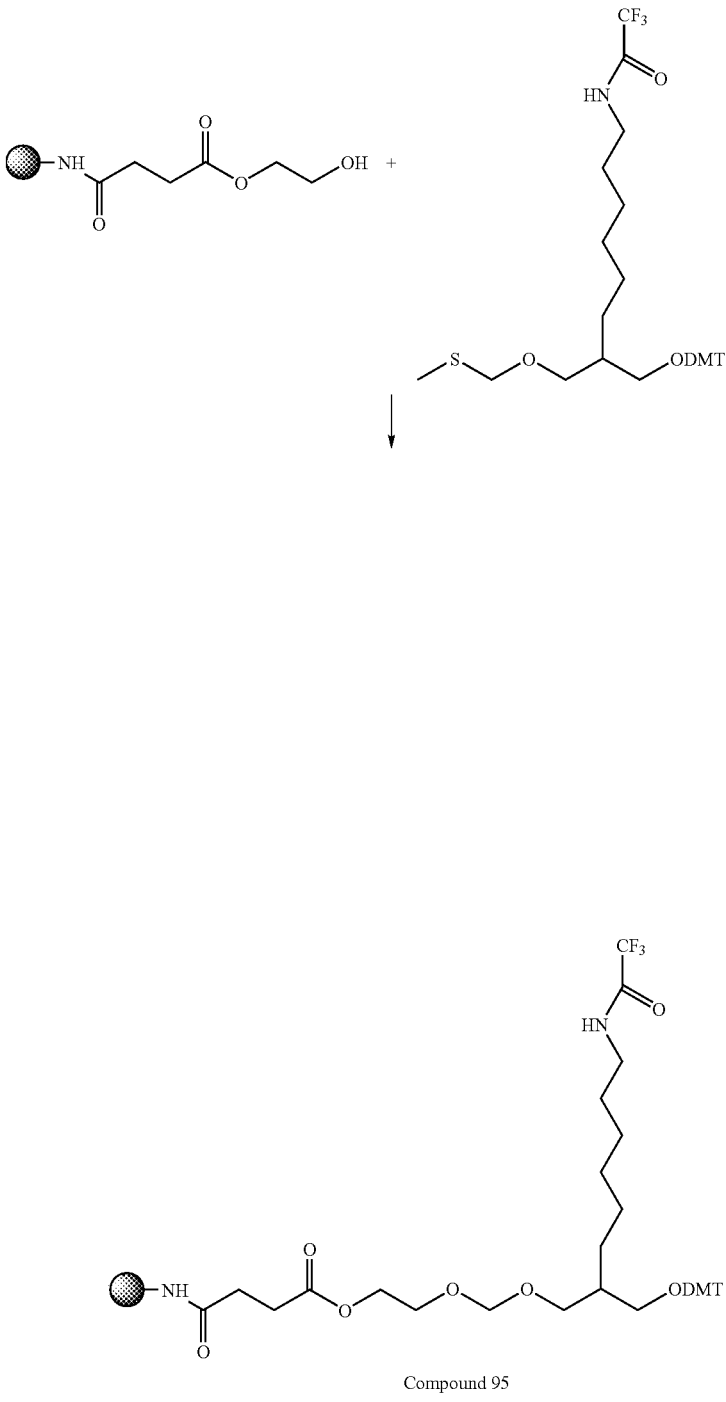

Compound 95

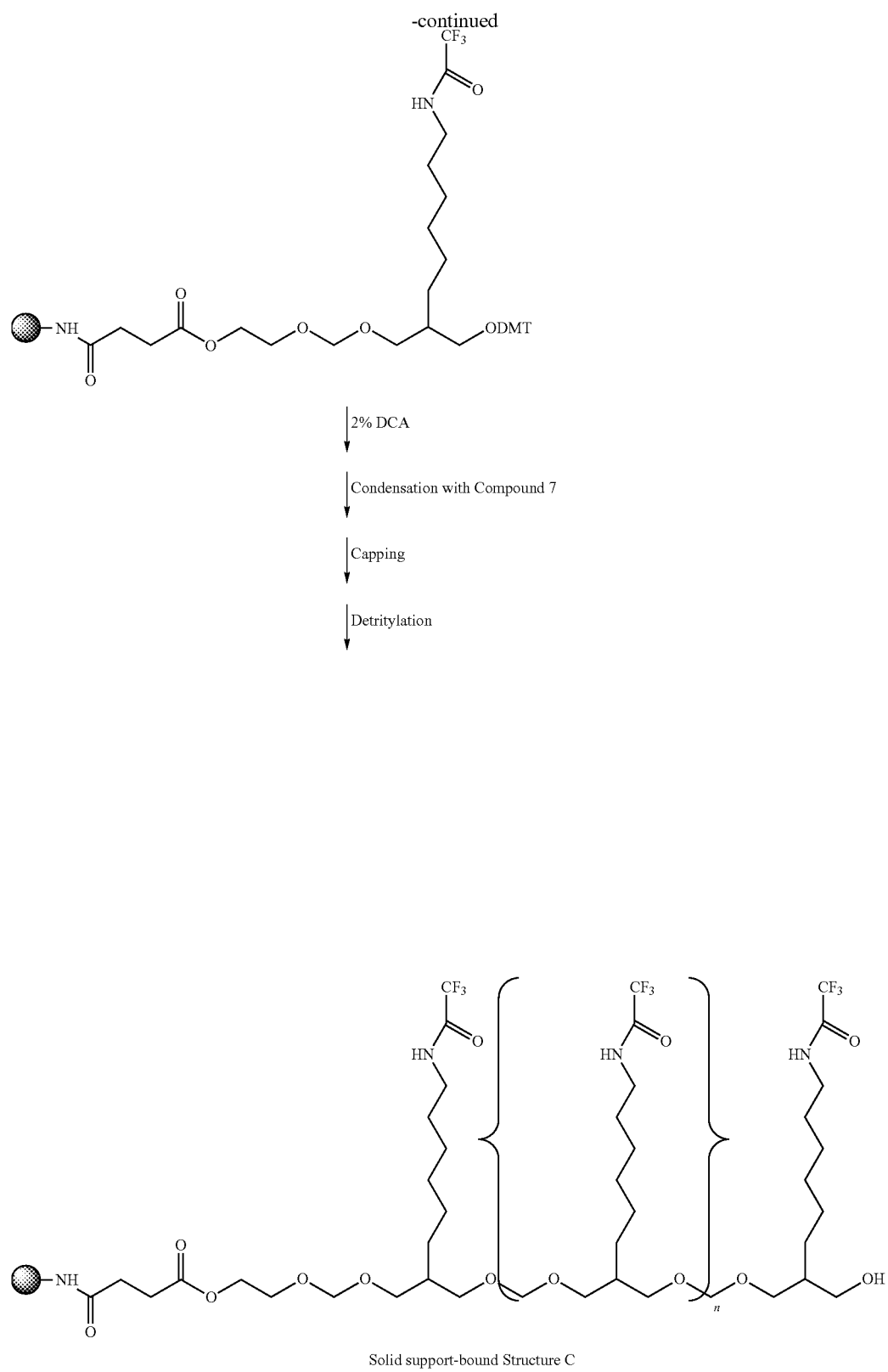
Solid support-bound Structure C
Solid support-bound Structure C can be reacted with FAM-HPA (Glen Research), using the phosphoramidite cycle described hereinabove, so as to obtain the corresponding fluoresceinated adduct, as depicted in Scheme 60.

Scheme 60
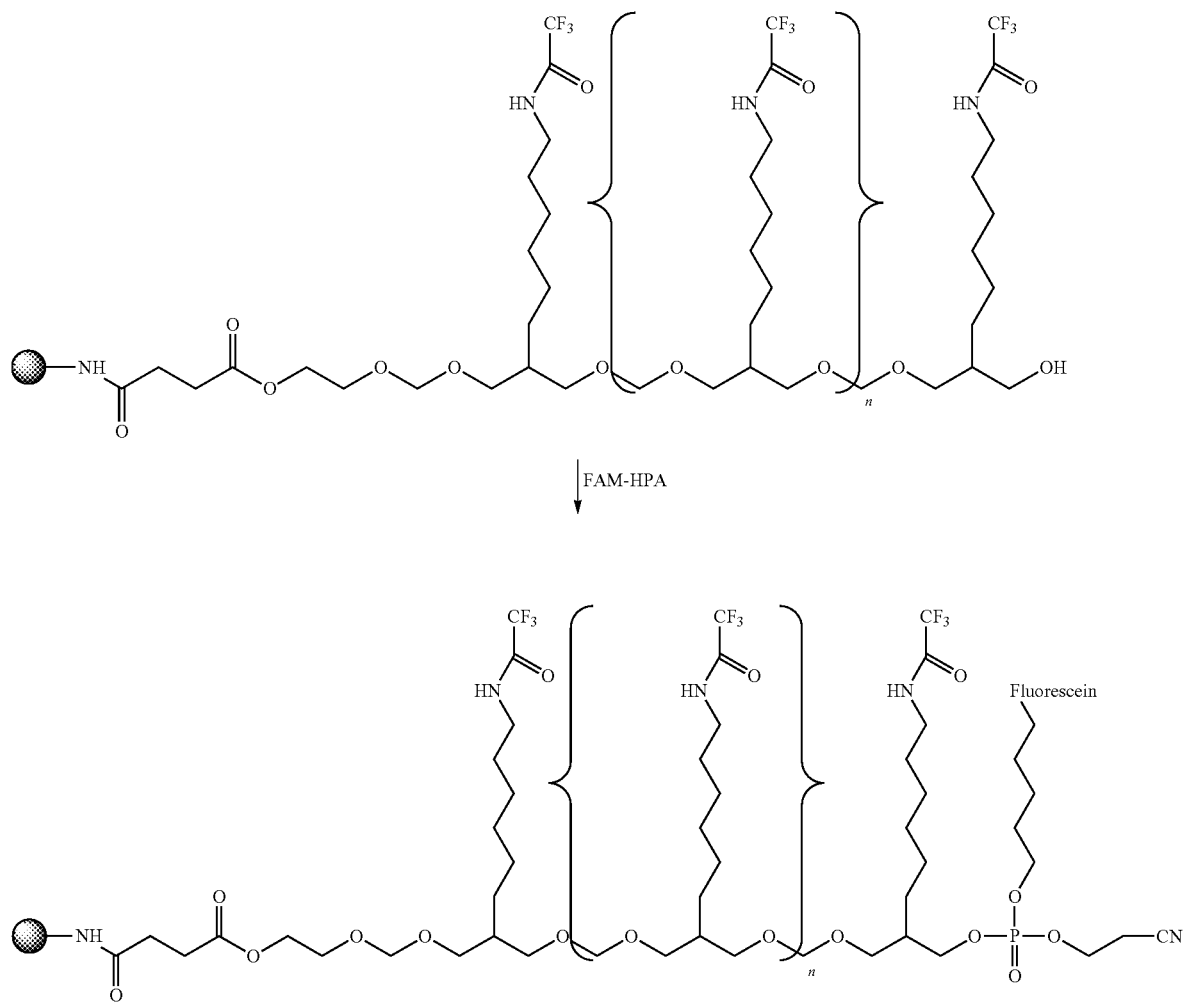
Alternatively, a drug, such as DNA/RNA, is attached to the solid support-bound structure C, using the procedures described herein.
Preparation of Polyether-Polyacetal-Based Delivery Moieties Using a Polymeric Support—Route II
Herein, attachment of a polymeric structure to a modified solid support is exemplified, as illustrated in Scheme 61.
Scheme 61
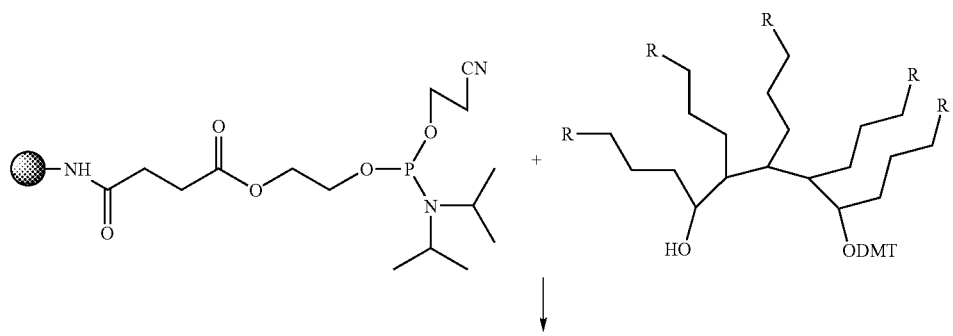

-continued

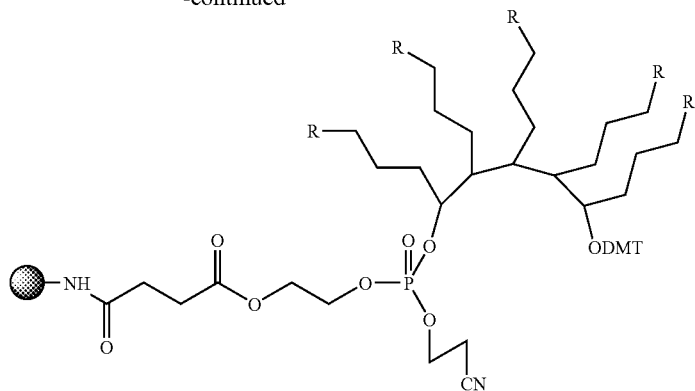

Preparation of derivatized (protected) Structure B (Reaction of protected Structure B with (4,4')-dimethoxytrityl chloride (DMTCl))

To a cooled (0° C.) solution of protected Structure B (10 mmols) (see, Scheme 51) in dry pyridine (50 ml), under argon atmosphere, a solution of (4,4')-dimethoxytrityl chloride (10 mmols) in dry pyridine (20 ml) is added dropwise during 30 minutes. The reaction mixture is allowed to warm gradually to room temperature and stirred at room temperature for 18 hours. The solvent is evaporated to dryness, the residue is extracted with ethyl acetate (200 ml), brine (2×200 ml) and the organic layer is dried over anhydrous sodium sulfate, and concentrated by rotary evaporator to a foam. The product is purified by column chromatography on neutralized silica gel column, using 500 ml hexane, followed by a 3:1 mixture of hexane:ethyl acetate as eluents. The appropriate fractions are combined and evaporated to dryness, yielding colorless oil.

Scheme 62

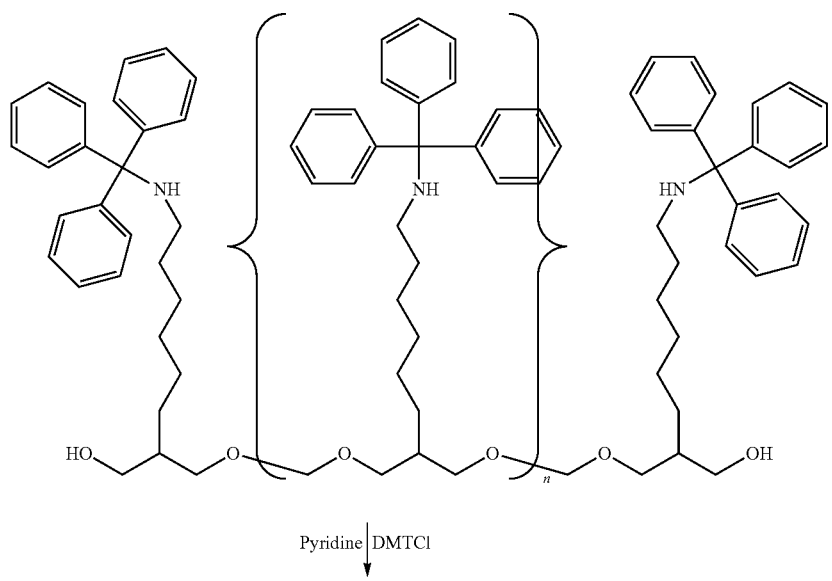

-continued

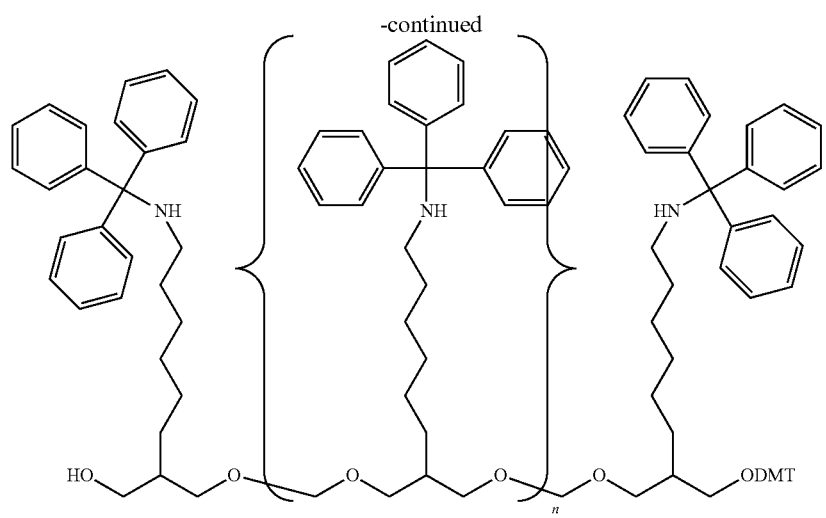

Preparation of Compound 96 (a Phosphoramidite-Derivatized Solid Support)

Scheme 63

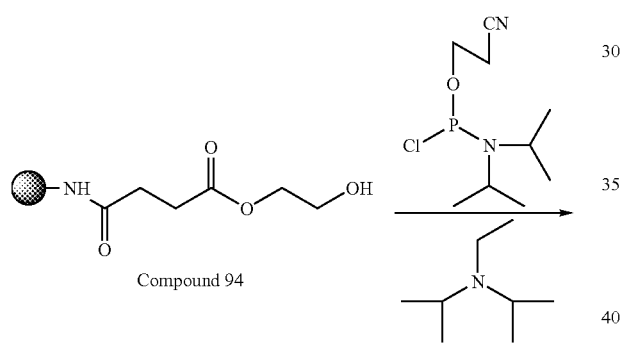

Compound 94

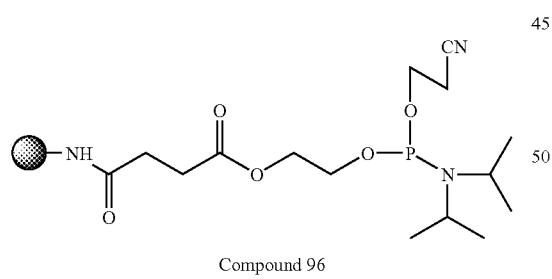

Compound 96

Compound 94 (100 mg, having a loading of 42 μmol/gram) is placed in an appropriate sinter glass, attached to a vacuum pump and equipped with serum cap, and washed with dry pyridine (3×20 ml) and dry dichloromethane (DCM, 3×20 ml). The resulting dry support is thereafter reacted, under argon atmosphere, with a solution of N,N-diisoprpylethylamine (0.5 ml) in DCM (3 ml), followed by addition through a syringe of 2-cyanoethyl N,N-diisopropylphosphoramidochloride (0.3 ml). The sinter glass is agitated for 1 hour at room temperature and the obtained solid support is thereafter washed with dry DCM (2×20 ml) and dry ether (2×20 ml).

Attachment of Derivatized (Protected) Structure B to the Modified Solid Support 96

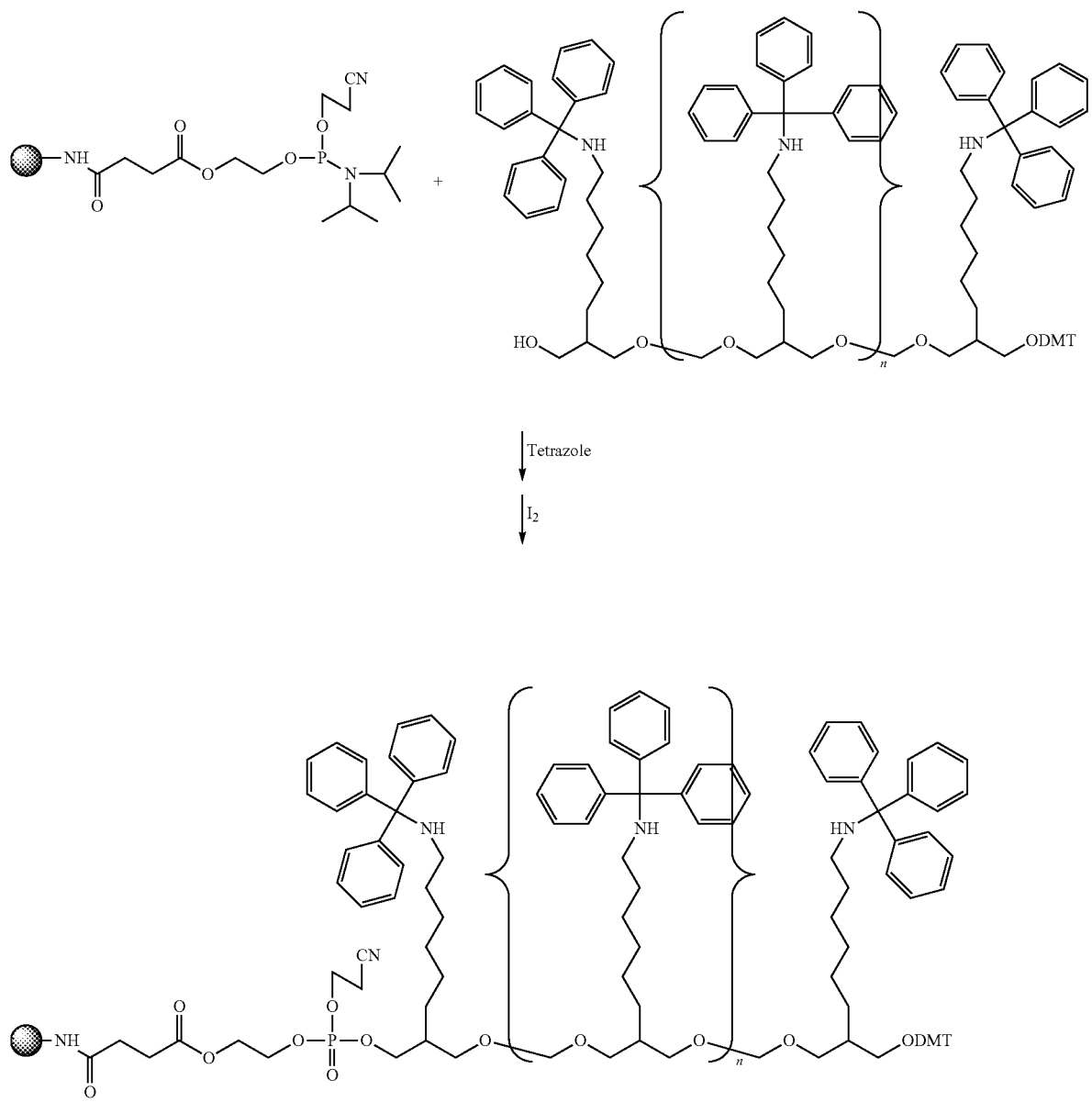

Scheme 64

Compound 96 (100 mg, with loading of 42 μmole/gram) is treated with a solution of the derivatized (protected) Structure B prepared as described hereinabove (0.5 gram, in dry acetonitrile, 1 ml, see Scheme 62), and the with tetrazole (0.5 M in dry acetonitrile, 0.8 ml, Bio-Lab Israel). The reaction mixture is agitated gently during 10 minutes, and then washed with methanol (30 ml), DCM (30 ml) and ether (30 ml). The resulting solid support is thereafter covered with iodine solution (0.1M in THF, 2,6-lutidine and water, Bio-Lab Israel) and the resulting support is washed successively with acetonitrile (30 ml), methanol (30 ml), DCM (30 ml) and ether (30 ml).

The obtained solid support-bound protected polymeric structure is then deprotected as depicted in Scheme 65.

Scheme 65

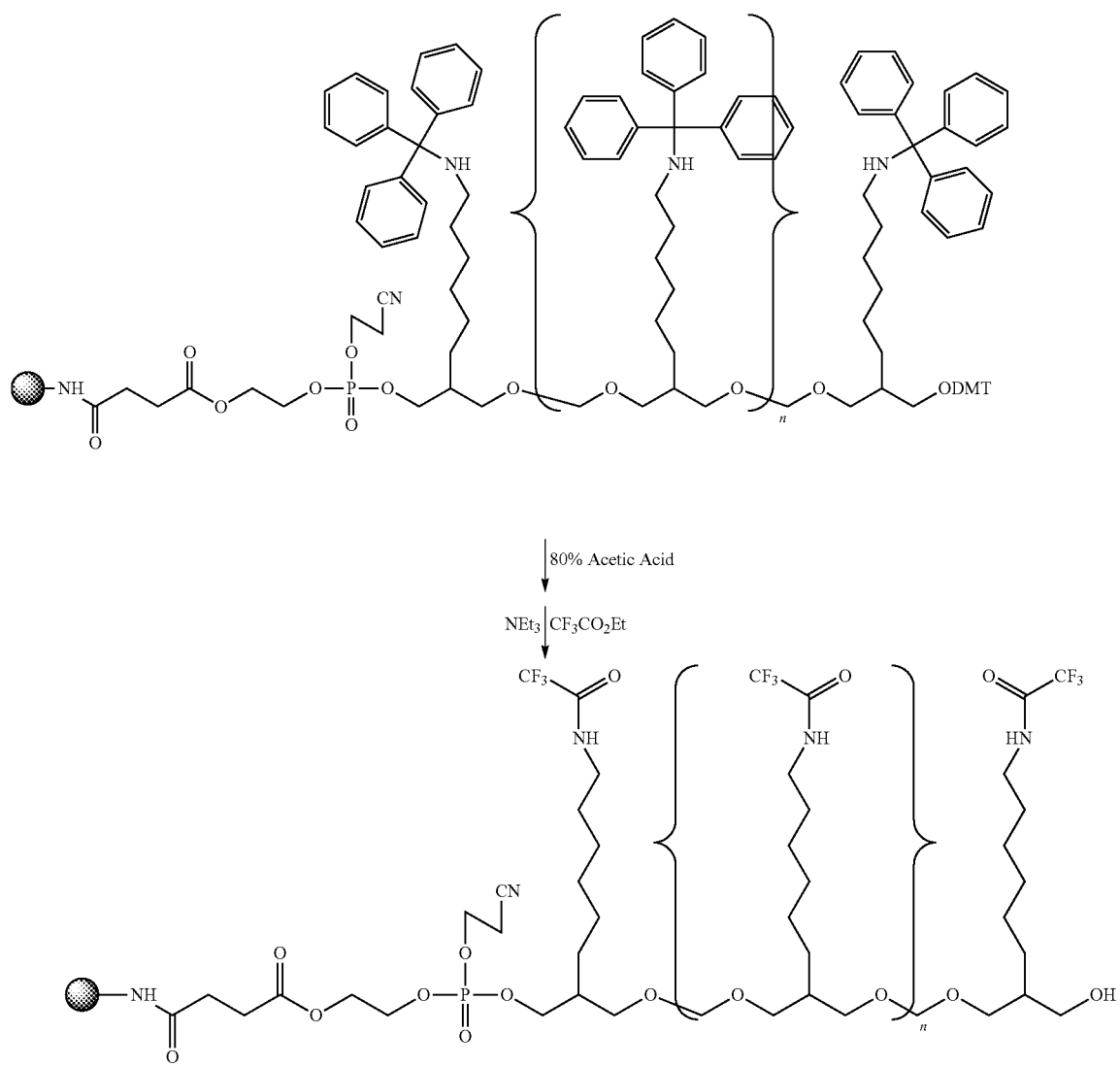

The protected solid support-bound polymeric structure B (100 mg) is placed in a vile, a solution of 80% acetic acid is added, and the vile is kept at 50° C. for 3 hours. The solid support is then placed in an appropriate sinter glass, attached to a vacuum pump, and washed successively with methanol (30 ml), DCM (30 ml) and ether (30 ml). To the dry support is added a solution of triethylamine (0.5 ml) in DCM followed by addition of ethyl trifluoroacetate (3 ml). The sinter is agitated gently at room temperature for 4 hours, the solution is thereafter drained by vacuum, and the support is washed successively with methanol (30 ml), DCM (30 ml) and ether (30 ml).

Attachment of a Linker Arm to a Solid Support-Bound Polymeric Structure B

Any of the solid support-bound polymeric structures described herein can be extended using phosphoramidite molecules such as:

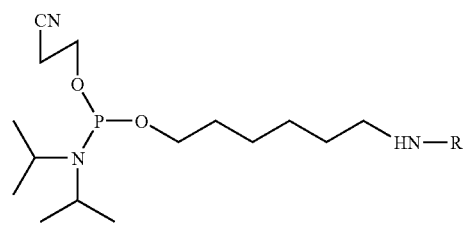
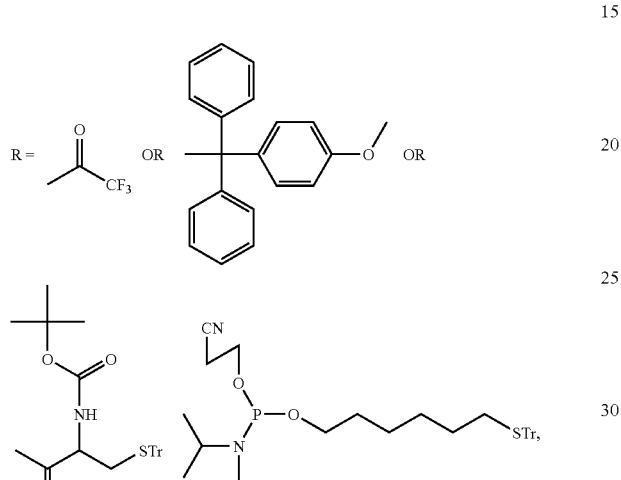
to thereby form a solid support-bound extended polymeric structure, which terminates with a reactive group (the phosphoramidite), as depicted in Scheme 66.
Scheme 66
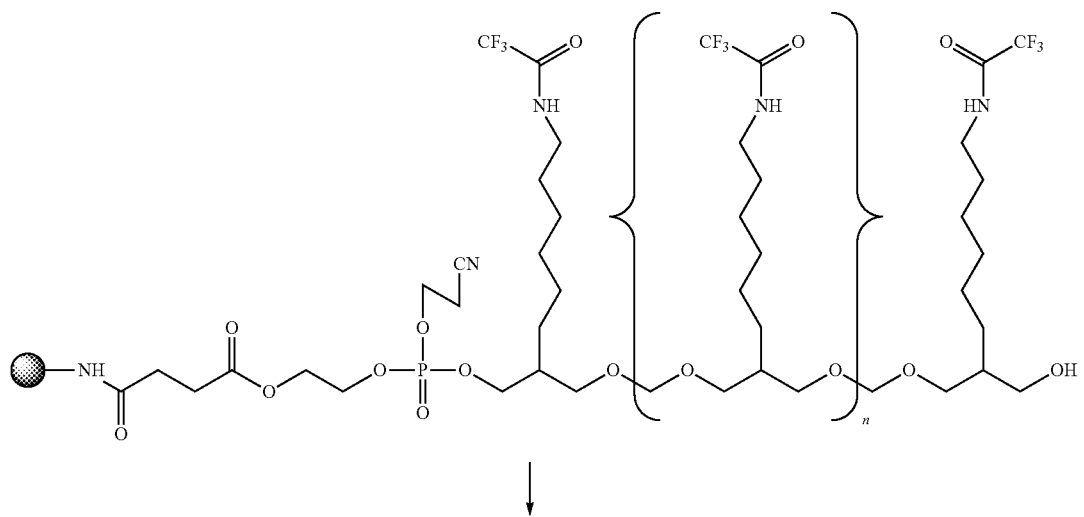

-continued
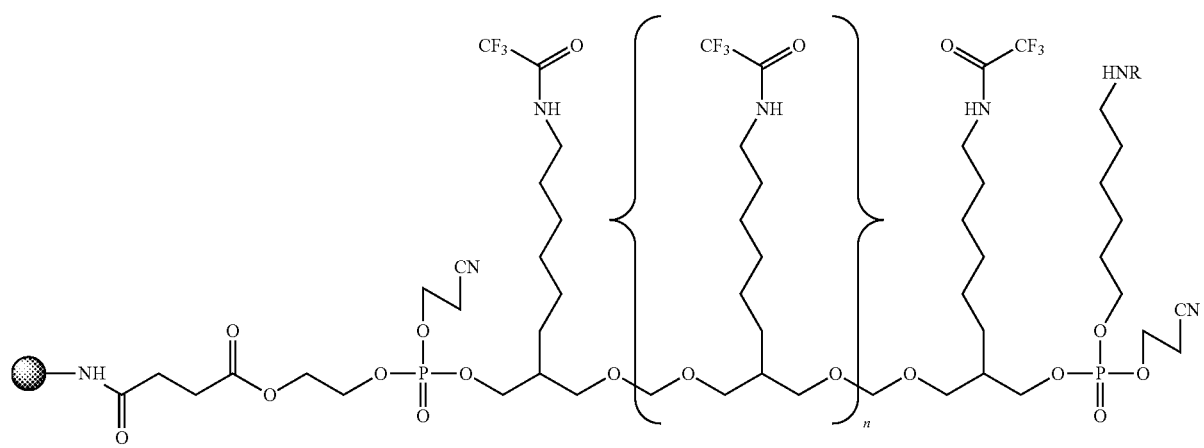
Further, any of the solid support-bound polymeric structures described herein is detached from the support, and the protected amino groups can thereafter be either deprotected or further reacted with 1H-Pyrazole-1-carboxamidine hydrochloride as described hereinabove, so as to produce guanidine delivering groups, as depicted in Scheme 67.
Scheme 67
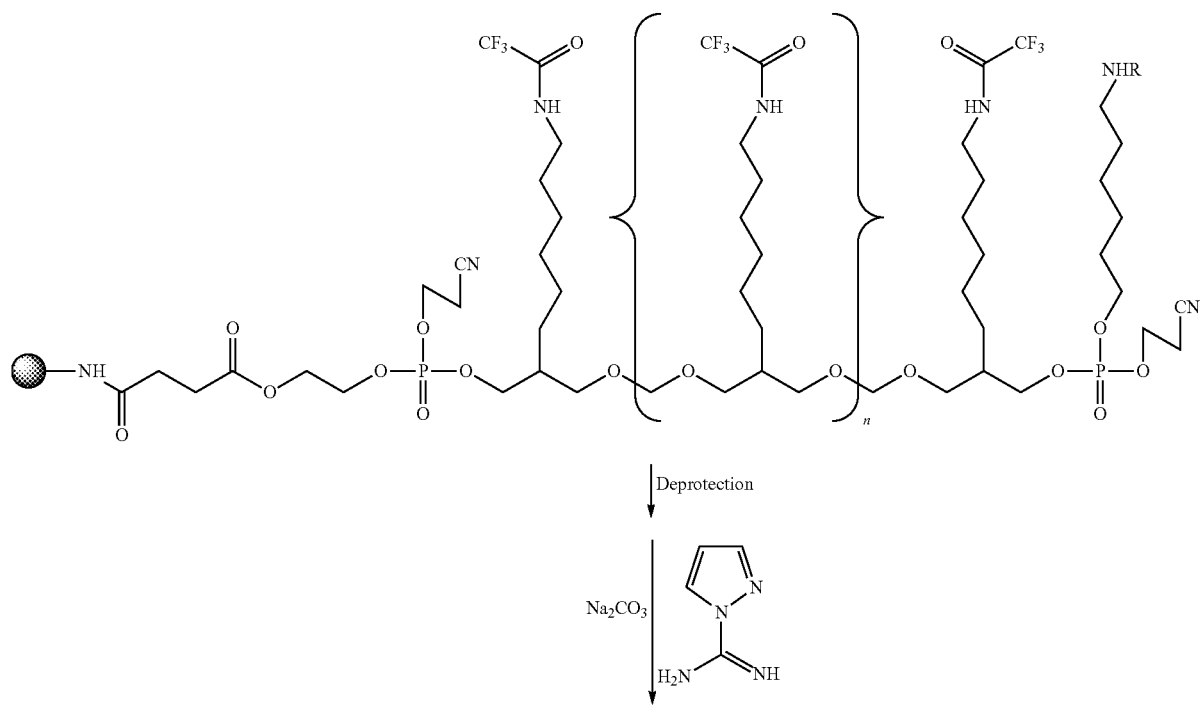

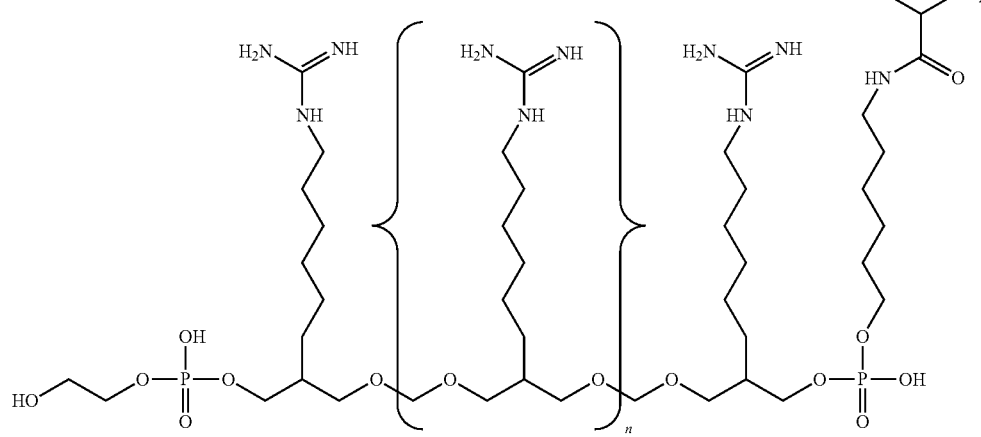

As exemplified in Scheme 67, additional modification of the obtained oligomeric delivery moiety can include attachment of a cysteine moiety, which can be effected by utilizing a compound in which R in Scheme 67 is

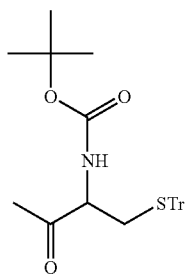

Otherwise, a thiol-protected phosphoramidite can be used as the attached moiety. Such a moiety can be obtained by utilizing the commercially available (Glen Research) compound:

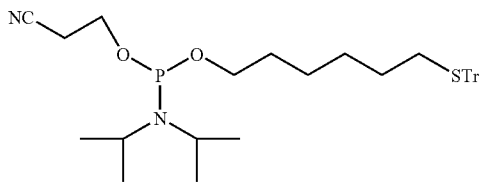

These phosphoramidite-containing moieties can be used to further attached to the obtained oligomer an oligonucleotide, via well-known DNA modification protocols.

Preparation of Polyether-Polyacetal-Based Delivery Moieties Using a Polymeric Support—Route III Using the procedures described hereinabove, and while utilizing Compound 78 as a monomeric building block, oligomeric structures containing guanidine delivering groups and fluorescein as a labeling moiety are obtained as depicted in Scheme 68.

Scheme 68

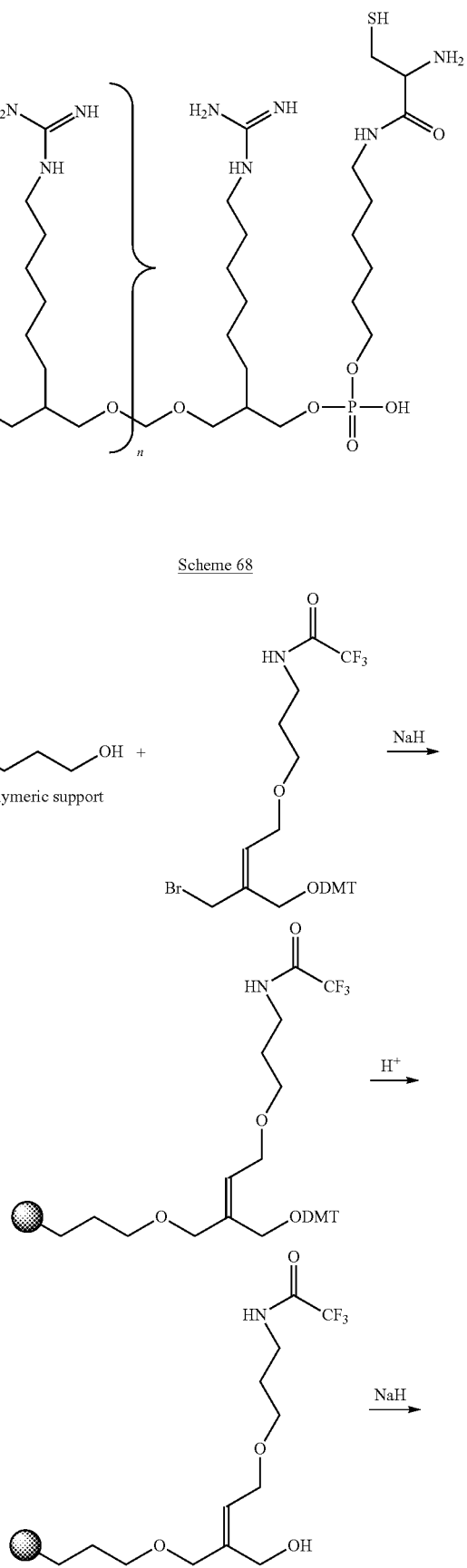

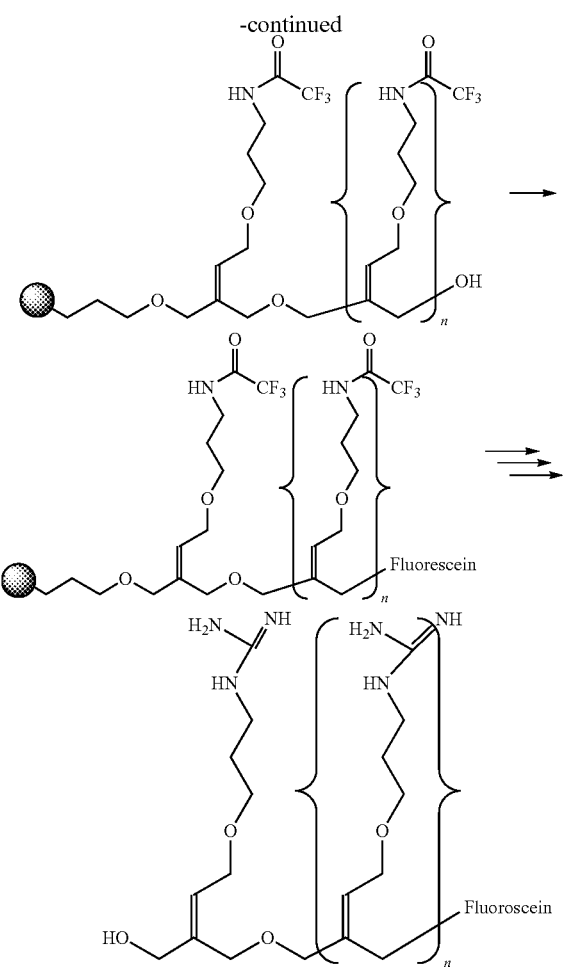

Preparation of a Polyether-Polyacetal-RNA Conjugate (Polyether-Based Delivery Moieties Conjugated to Oligonucleotides)

The solid support-bound polymeric Structure B described hereinabove (see, Schemes 61 and 64-68) can be utilized for conjugating RNA or DNA thereto, so as to obtain a delivery system. Thus, for example, an RNA strand is synthesized along the delivery moiety, according to the following general procedure:

General Procedures for Oligonucleotide Synthesis, Purification, and Analysis Synthesis RNA molecules are synthesized on a 394 ABI machine using the standard 93 step cycle written by the manufacturer with modifications to a few wait steps as described below. The monomers include, for example, RNA phosphoramidites with fast protecting groups such as (5'-O-dimethoxytrityl N6-phenoxyacetyl-2'-O-t-butyldimethylsilyladenosine)-3'-O—N,N'-diisopropyl-cyanoethylphosphoramidite, 5'-O-dimethoxytrityl-N-4-acetyl-2'-O-t-butyldimethylsilylcytidine-3'-O—N,N'-diisopropyl-2-cyanoethylphosphoramidite, 5'-O-dimethoxytrityl-N-2-p-isopropylphenoxyacetyl-2'-O-t-butyldimethylsilylguanosine-3'-O—N,N'-diisopropyl-2-cyanoethylphosphoramidite, and 5'-O-dimethoxytrityl-2'-O-t-butyldimethylsilyluridine-3'-O—N,N'-diisopropyl-2-cyanoethylphosphoramidite from Pierce Nucleic Acids Technologies. Amidites are used at a concentration of 0.15 M in acetonitrile and a coupling time of 12-15 minutes. The activator is 5-(ethylthio)-1H-tetrazole (0.25 M); for the PO-oxidation Iodine/Water/Pyridine can be used.

Deprotection-I (Nucleobase Deprotection)

After completion of synthesis the support is transferred to a screw cap vial (VWR Cat No. 20170-229) or screw caps RNase free microfuge tube. The oligonucleotide is cleaved from the support with simultaneous deprotection of base and phosphate groups with 1.0 ml of a mixture of ethanolic ammonia (3:1 ammonia:ethanol) for 15 hours at 55° C. The vial is cooled briefly on ice and then the ethanolic ammonia mixture is transferred to a new microfuge tube. The CPG is washed with 2×0.1 ml portions of RNase free deionized water. The washings are combined, cooled over a dry ice bath for 10 minutes and subsequently dried in speed vacuum.

Deprotection-II (Removal of 2' TBDMS Group)

The white residue obtained is re-suspended in 400 µL of triethylamine, triethylamine trihydrofluoride (TEA3HF) and NMP (4:3:7) and heated at 50° C. for overnight to remove the tert-butyldimethylsilyl (TBDMS) groups at the 2' position (Wincott et al., Nucleic Acids Res., 1995, 23, 2677). The reaction is then quenched with 400 µL of isopropoxytrimethylsilane (purchased from Aldrich) and further incubated on the heating block leaving the caps open for 10 minutes; (This causes the volatile isopropxytrimethylsilylfluoride adduct to vaporize). The residual quenching reagent is removed by drying in a speed vacuum. 1.5 ml of 3% triethylamine in diethyl ether is added and the mixture pelleted by centrifuging. The supernatant is pipetted out without disturbing the pellet and the pellet is dried in speed vacuum.

The crude transporter-RNA is obtained as a white fluffy material in the microfuge tube. Converting of the amino groups to guanido groups is performed by re-suspending the pellet with a solution containing 1H-Pyrazole-1-carboxamidine hydrochloride (Aldrich) (50 equivalents) in 5% sodium carbonate (3 ml), as described hereinabove. The solution is heated to 50° C. for 24-48 hours. The crude mixture is then neutralized to pH 7 with 3N HCl and evaporated to dryness.

Quantitation of Crude Oligomer or Raw Analysis

Samples are dissolved in RNase free deionized water (1.0 ml) and quantitated as follows: Blanking is first performed with water alone (1 ml). 20 µL of sample and 980 µL of water are mixed well in a microfuge tube, transferred to cuvette and absorbance reading obtained at 260 nm. The crude material is dried down and stored at −20° C.

Desalting of Purified Oligomer

The purified dry oligomer is then desalted using Sephadex G-25 M (Amersham Biosciences). The cartridge is conditioned with 10 ml of RNase free deionized water thrice. Finally, the purified oligomer is dissolved in 2.5 ml RNase free water and passed through the cartridge with very slow dropwise elution. The salt free oligomer is eluted with 3.5 ml of RNase free water directly into a screw cap vial.

The synthesis of oligonucleotides (RNA or DNA segments) can be performed using regular (naturally occurring)

nucleotides or derivatized nucleotides, such as, for example, those commercially available from e.g., Glen Research or from Oligo.

Exemplary derivatized nucleotides suitable for use in the synthesis of RNA oligonucleotides include:

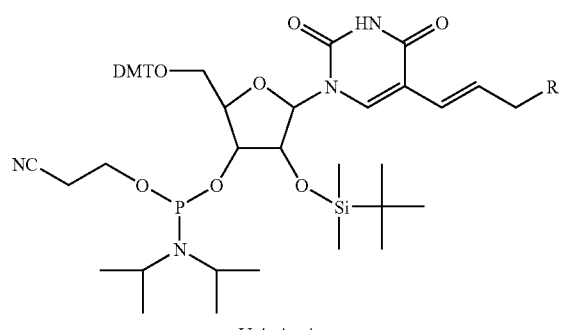

U derivative

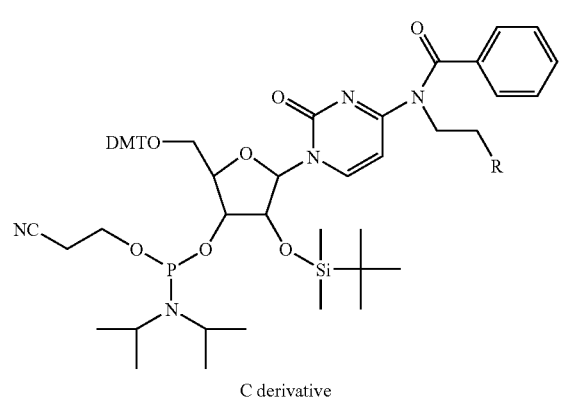

C derivative

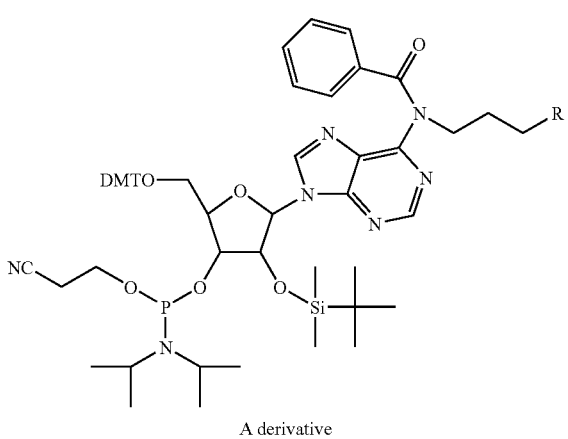

A derivative

Exemplary derivatized nucleotides suitable for use in the synthesis of DNA oligonucleotides include:

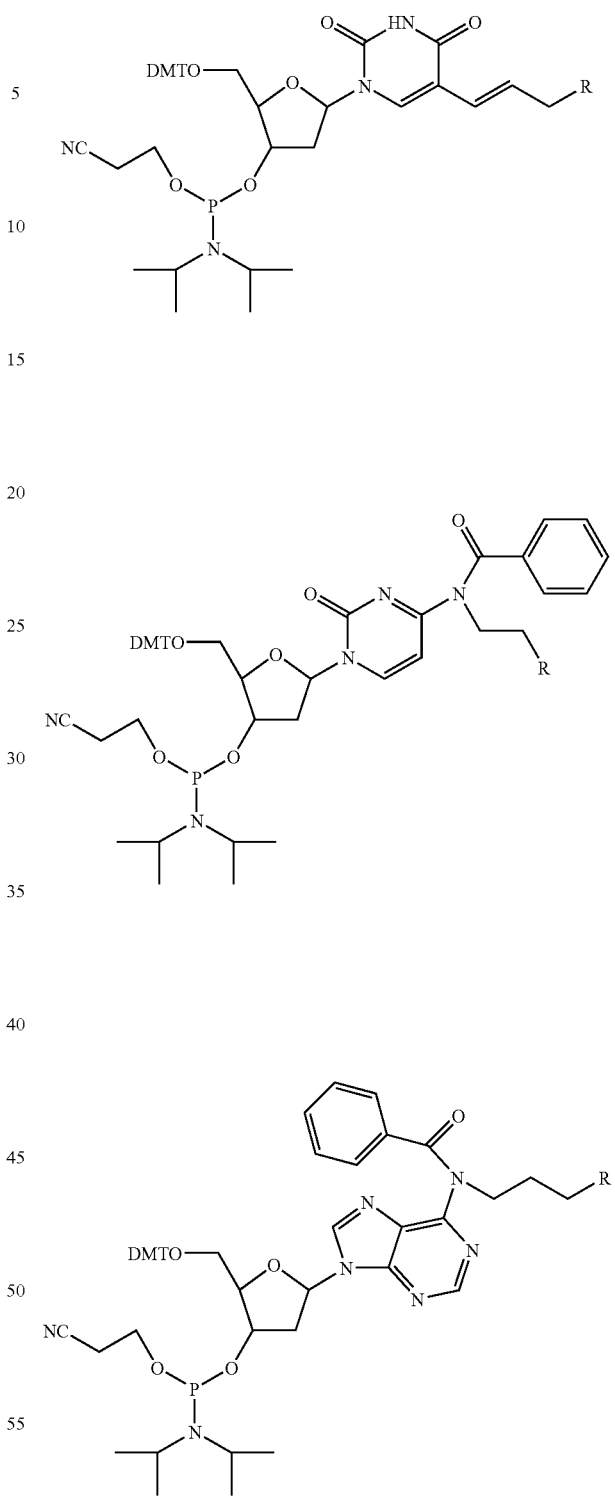

wherein R is an amino group protected with trifluoroacetamide, a protected carboxylic group, or from the groups a histidine or any of the delivering groups described herein.

Scheme 69 below describes the preparation of an exemplary polyether-polyacetal-RNA conjugate, in which the RNA segment has SEQ ID NO: 12.

Scheme 69
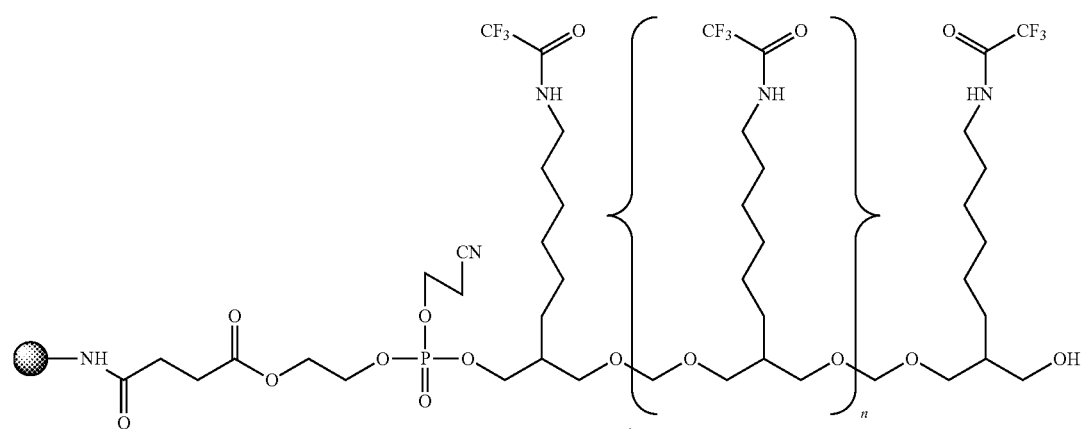
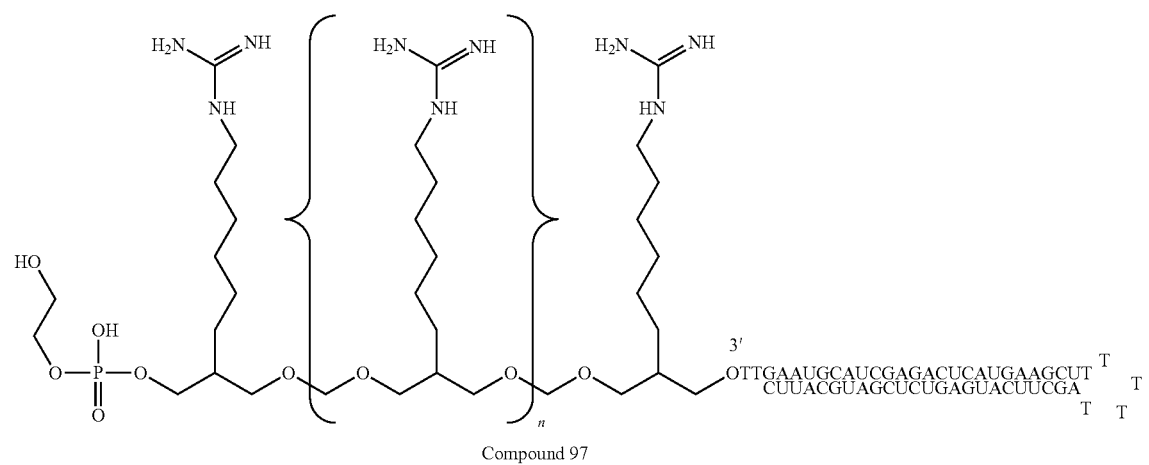
Compound 97
The synthesis of oligonucleotides (RNA or DNA segments) can be performed using regular (naturally occurring) nucleotides (as shown in Scheme 69) or derivatized nucleotides, such as, for example, those commercially available from e.g., Glen Research or from Oligo.

Exemplary derivatized nucleotides suitable for use in the synthesis of RNA oligonucleotides include:

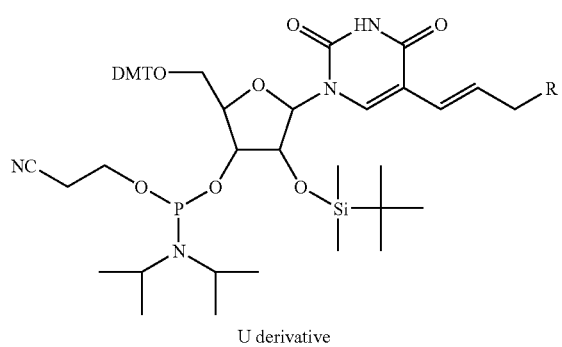

U derivative

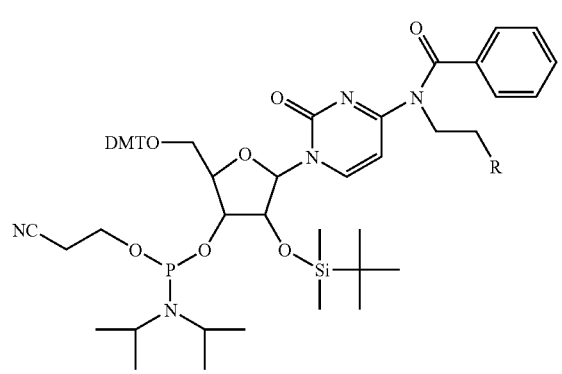

C derivative

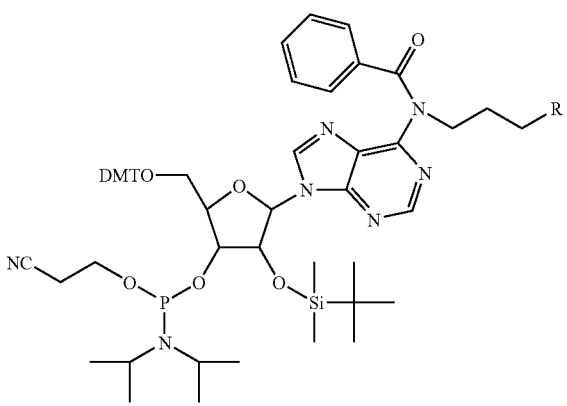

A derivative

Exemplary derivatized nucleotides suitable for use in the synthesis of DNA oligonucleotides include:

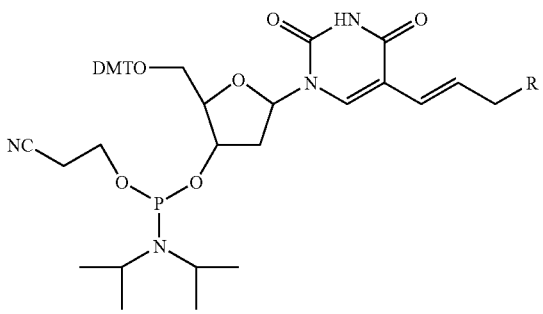

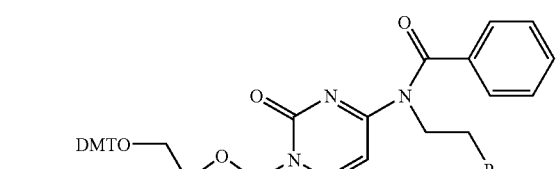

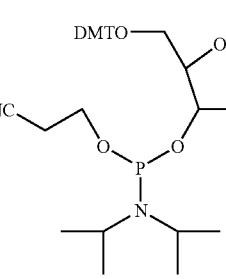

wherein R is an amino group protected with trifluoroacetamide, a protected carboxylic group, or from the groups a histidine or any of the delivering groups described herein. The use of derivatized nucleotides provides protection of the RNA segment and facilitate its cellular uptake. An example is depicted below (SEQ ID NO:17):

Compound 98

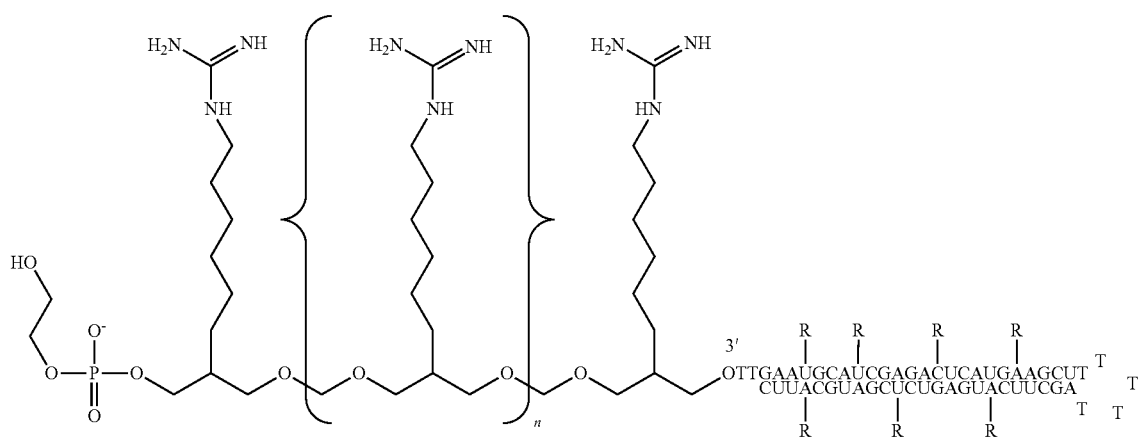

Similarly, delivery systems containing other types of modified nucleobases are prepared. Thus, a sequence similar to the above, in which a uracyl base is replaced by an alkyl guanido group, is utilized (SEQ ID NO:13), as depicted in Scheme 70. As shown in Scheme 70, a synthesis of siRNA duplexes with complementary mismatch to adenine at selected position is performed.

Scheme 70

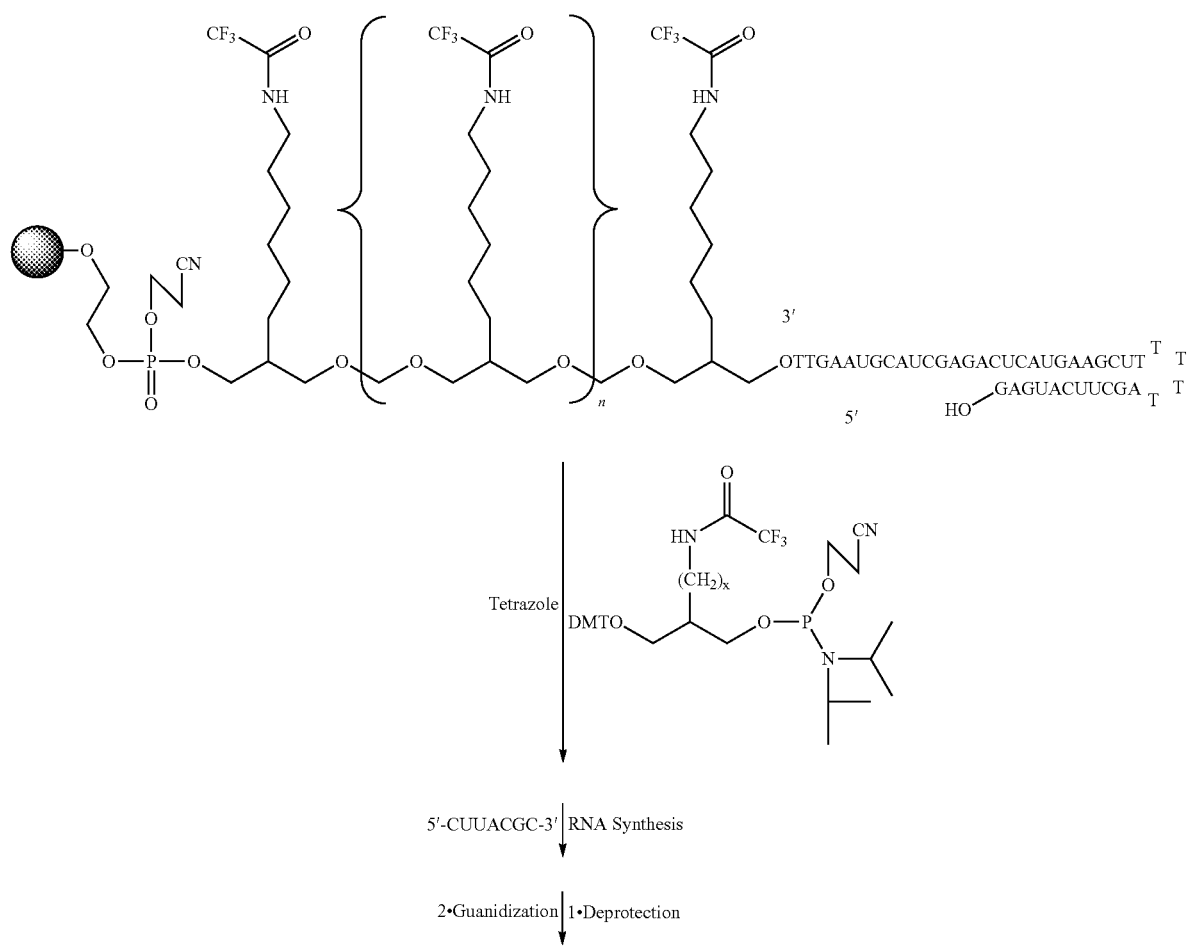

-continued

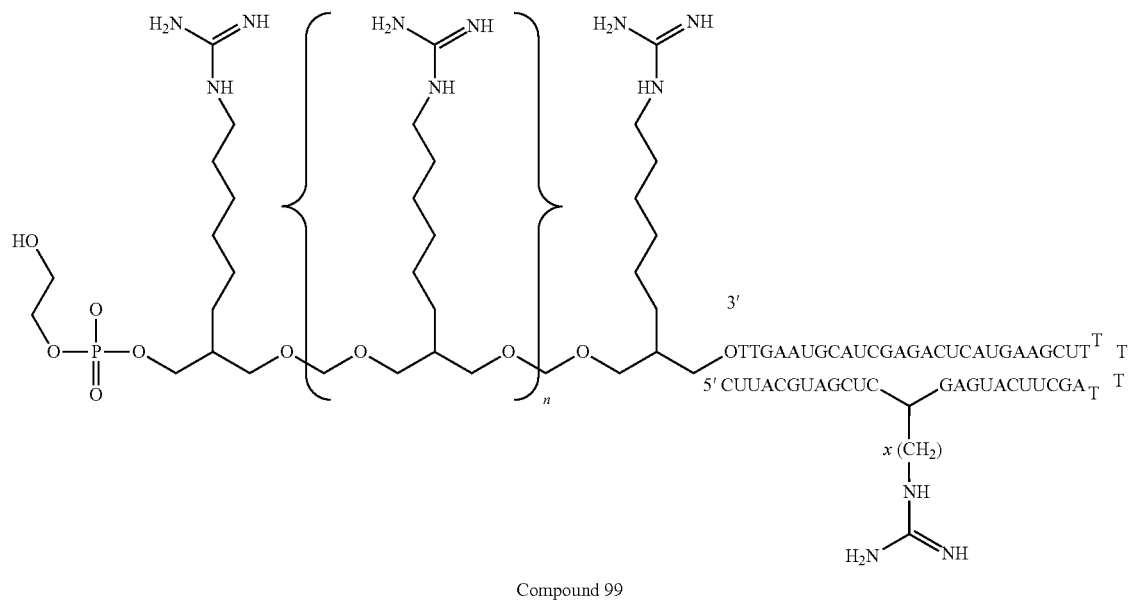

Compound 99 wherein x is an integer from 2-8 alkyl or alkylene moieties, preferably 6.

It is understood that this kind of mismatch modification can be introduced at any place along the RNA synthesis.

Similarly, using the solid support-bound polymeric Compound 96 depicted supra, DNA can be synthesized before and/or after the delivery moiety. In one example, a ssDNA sequence (SED ID NO: 14) is first synthesized, a delivery moiety is attached thereto and a ssDNA sequence (SEQ ID NO: 15) is then synthesized. The obtained conjugate can thereafter be subjected to annealing, as depicted in Scheme 71 below.

Scheme 71

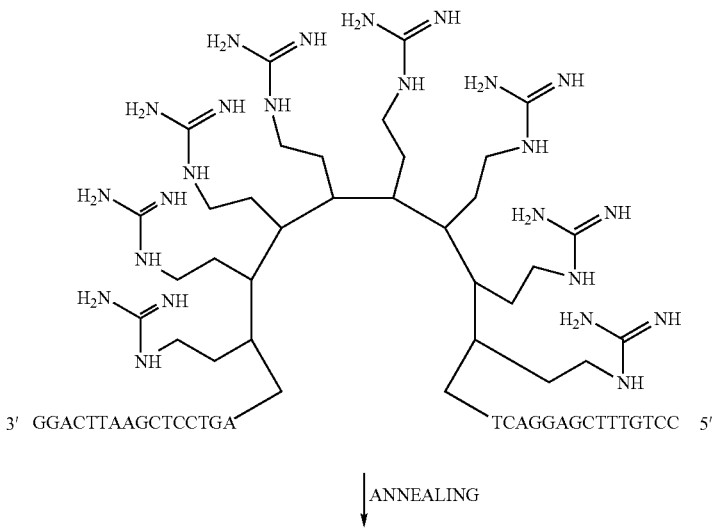

↓ ANNEALING

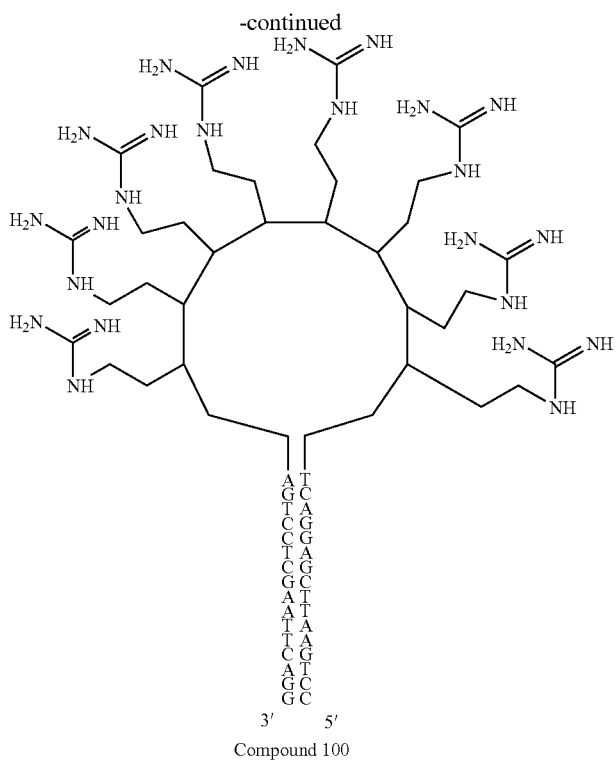

Compound 100

In this particular sequence, a restriction site EcoR1 is inserted, having the sequence (SEQ ID NO:16): 5'-GAATTC-3'

3'-CTTAAG-5'

Hence, this structure is subjected to breakage by EcoR1 restriction enzyme and can be ligated to any DNA sequence that have an EcoR1 restriction site.

Similarly to RNA, DNA sequences utilized in this context can also have the same guanido mismatch, as exemplified in Scheme 70.

Preparation of Drug-Containing Delivery Systems

The delivery moieties according to the present embodiments are used for conjugating thereto an active agent such as a drug, and thus serve as prodrugs that releases the drug upon exposure to physiological pH or other physiological conditions.

Herein, an exemplary general strategy for synthesizing prodrugs that have a delivery moiety (also referred to herein as "transporter") attached to a drug via a linker that releases the drug upon exposure to physiological pH is presented, as depicted in Scheme 72 below.

Thus, a drug is derivatized so as to carry an α-chloro or an α-bromo residue. Next, the chloride or the bromide is displaced with e.g., a thiol group of a cysteine residue that carries an unprotected amine (see, for example, Scheme 67 supra).

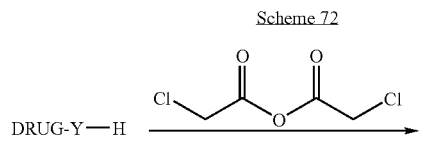

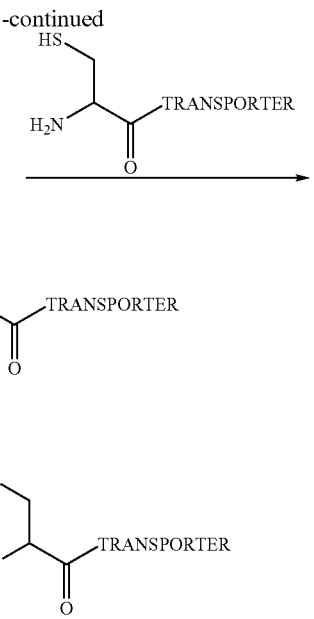

In an exemplary procedure, Taxol is attached to a delivery moiety as described herein as follows:

To a cooled (0° C.) solution of Taxol (179 mg, 209.8 μmol) in DCM (10 ml), under argon atmosphere, a solution of alpha-chloroacetic anhydride (36 mg, 210 μmol) was added, followed by addition of diisoprpylethyl amine (26.9 mg, 210 μmol). The reaction mixture was allowed to reach room temperature gradually.

TLC has shown that after 2 hours the Taxol starting material disappeared.

The solvent was thereafter evaporated to dryness and the product was purified by chromatography on silica-gel column using a 1:2 mixture of hexane:ethyl acetate as eluent, yielding 200 mg.

Preparation of Oligonucleotides-Containing Delivery Systems

Preparation, Via Chemical Synthesis, of an Exemplary Circular Single Stranded DNA Molecule Containing Delivery Moieties (Dcirc-1)

A 66 nucleotide long circular single stranded DNA template was designed to include: (i) two different 26 long oligonucleotides of a specific sequence, containing modified oligonucleotides and unmodified oligonucleotides and denoted Q1 and Q2, (ii) a 40 nucleotide long DNA template oligonucleotide, denoted S containing the 19 nucleotide long T7 promoter sequence linked to a 21 nucleotides long sequence, and being capable of producing a 21 nucleotides; and (iii) a complementary 40 nucleotide long DNA template oligonucleotide, denoted S', capable of hybridizing with the S sequence (see, Dcirc-1 below).

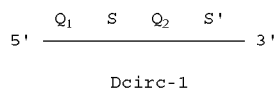

Dcirc-1

The S DNA template sequence was designed to produce a siRNA sequence having a guanosine (G) as the first nucleotide of the RNA so as to comply with the requirement for an efficient T7 RNA polymerase initiation (Milligan, J. F. et al., (1987) *Nucleic Acids Res* 15, 8783-98).

Dcirc-1 was synthesized using the phosphoramidite method described hereinabove on an Applied Biosystems Expedite 3900 DNA synthesizer, using standard phosphoramidites of unmodified nucleotides (by Glenn Research Inc.) and phosphoramidites of the modified nucleotides, Compound 4 as a modified deoxythymidine, Compound 5 as a modified deoxycytidine, and Compound 6 as a modified deoxycytidine.

The sequences of the Q1 (SEQ ID NO:3), Q2 (SEQ ID NO:4), S (SEQ ID NO:5), and S' (SEQ ID NO:6) oligonucleotides are presented in Scheme 73 below, wherein a letter having the symbol * represents a modified nucleotide, as described herein.

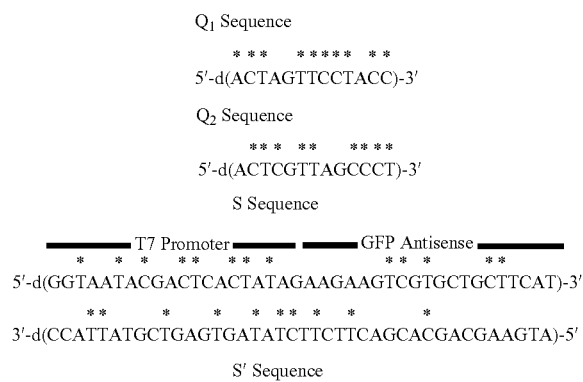

The total sequence of the resulting Dcirc-1 (SEQ ID NO:7) is presented in Scheme 74 below, wherein the order of appearance going from the 5' end to the 3' end is Q1-S-Q2-S'.

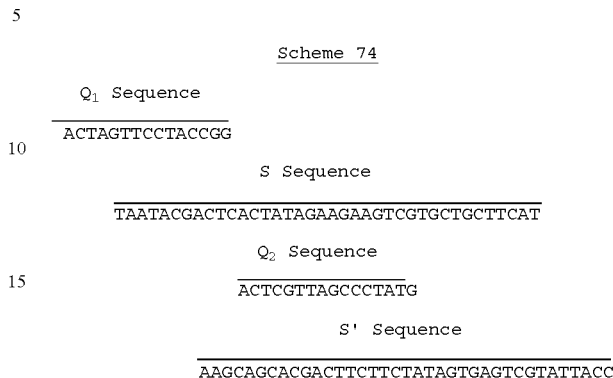

The synthesis of pre-cyclic Dcirc-1 was performed on a single controlled pore glass (CPG) column (Applied Biosystems). Once prepared, the linear, pre-cyclic oligonucleotide was cleavaged from the CPG column and was treated with concentrated ammonium hydroxide for 18 hours at 55° C., so as to remove the protecting groups. The continuous oligonucleotide was thereafter purified twice by precipitation in 0.5 M NaCl and 2.5 volumes of ethanol, followed by purification on a reverse phase HPLC column. Analytical gel electrophoresis was performed in 20% acrylamide, 8 M urea and 45 mM Tris-borate buffer set to pH 7.

The cyclization ligation of the linear oligonucleotide corresponding to Dcirc-1 was performed by combining one nanomole of the linear oligonucleotide and one nanomole of the ligation oligonucleotide (SEQ ID NO:8, see, Scheme 75 below) in 300 µl of a ligation buffer which included 40 mM Tris-HCl, 10 mM MgCl$_2$, 0.5 mM dithiothreitol (DTT) and 2 mM adenosine triphosphate (ATP) set to pH 7.8. The reaction mixture was boiled for 2 minutes and allowed to cool slowly to 4° C. Thereafter three units of T4 DNA ligase (Epicentre) were added to complete the ligation reaction. The mixture was kept at 4° C. for 18 hours, and purified on HPLC Sephadex column G25, so as to provide Dcirc-1.

Scheme 75

5'-d(GAACTAGTGGTAATAC)-3'

Dcirc-1 was purified on gel electrophoresis in 20% acrylamide, 8 M urea and 45 mM Tris-borate buffer set to pH 7, followed by purification on an HPLC Sephadex column G25 (Pharmacia), collected and lyophilized to dryness.

Dcirc-1 (0.1 nmole) was dissolved in 50 µl of an annealing buffer (10 mM Tris-HCl and 100 mM NaCl) and the solution was heated for 5 minutes at 95° C., then gradually cooled to room temperature, to afford the partly paired circular DNA molecule (see, Scheme 77 below).

Thus, as illustrated in Scheme 76 below, the complementary sequences, S and S', hybridize to form a double stranded DNA, while the random sequences, Q1 and Q2, remain as open loops, flanking the dsDNA.

Scheme 76

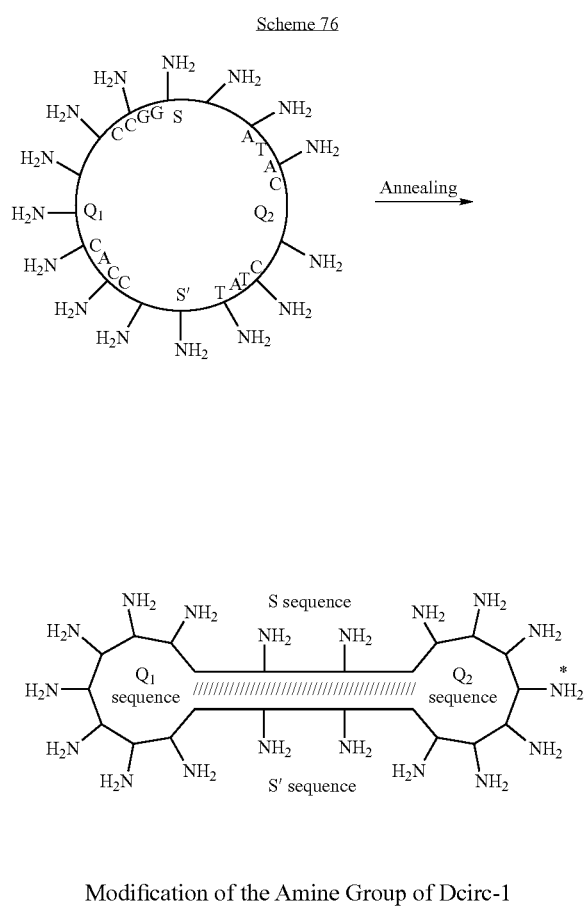

Modification of the Amine Group of Dcirc-1

Dcirc-1 (0.1 nmole) was dissolved in 0.5 ml of deionized water to yield a solution having pH 5.5. A solution of N-alpha-FMOC-L-arginine (5 mg) (Reanal Co.) in DMF (200 µl) was added to the dissolved Dcirc-1 followed by addition of 1-ethyl-3-(3-dimethyl-aminopropyl)carbodiimide hydrochloride (5 mg) and the reaction mixture was incubated at room temperature for 24 hours. The solvent was then removed under reduced pressure, and the residue was treated with concentrated ammonium hydroxide (1 ml) for 12 hours at room temperature. The product (see, Scheme 77 below) was purified on an HPLC Sephadex column G25 (Pharmacia), collected and lyophilized to dryness.

Scheme 77

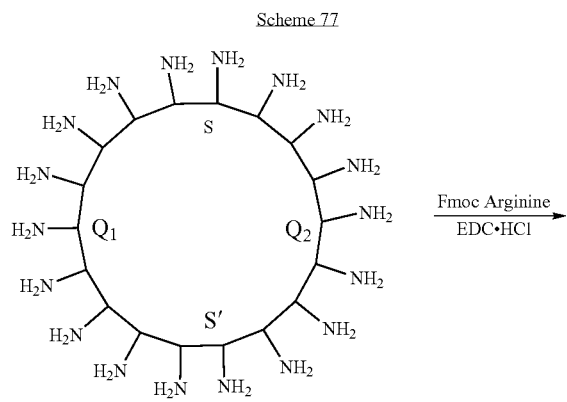

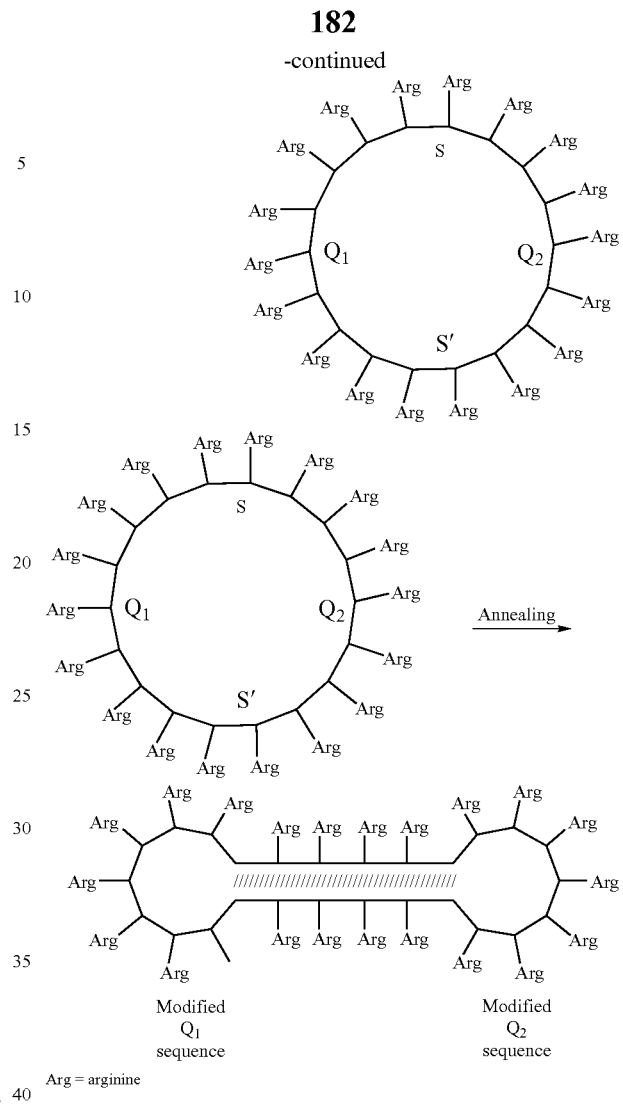

Arg = arginine

The product (0.1 nmole) was dissolved in 50 µl annealing buffer (10 mM Tris-HCl and 100 mM NaCl) and was heated for 5 minutes at 95° C., then gradually cooled to room temperature to afford the partly paired circular DNA molecule (see, Scheme 78 below).

As can be seen in Scheme 77, similarly as in the case of the amino-modified Dcirc-1, annealing of the arginine-modified compound also affords a partly paired circular DNA molecule.

Preparation, Via Enzymatic Synthesis, of a DNA Peptoid Conjugate

Compound 52a (1 nanomole) was dissolved in 300 µl of a ligation buffer which included 40 mM Tris-HCl, 10 mM MgCl$_2$, 0.5 mM dithiothreitol (DTT) and 2 mM adenosine triphosphate (ATP) set to pH 7.8. To this solution was added a solution of 0.4 nanomole of a dsDNA molecule having an oligonucleotide having SEQ ID NO:10 and an oligonucleotide having SEQ ID NO:11 being annealed to one another. The reaction mixture was boiled for 2 minutes and allowed to cool slowly to 4° C. Thereafter three units of T4 DNA ligase (Epicentre) were added to complete the ligation reaction. The mixture was kept at 4° C. for 18 hours, and purified on HPLC Sephadex column G25 so as to provide DNA-peptoid conjugate (see Scheme 78 below).

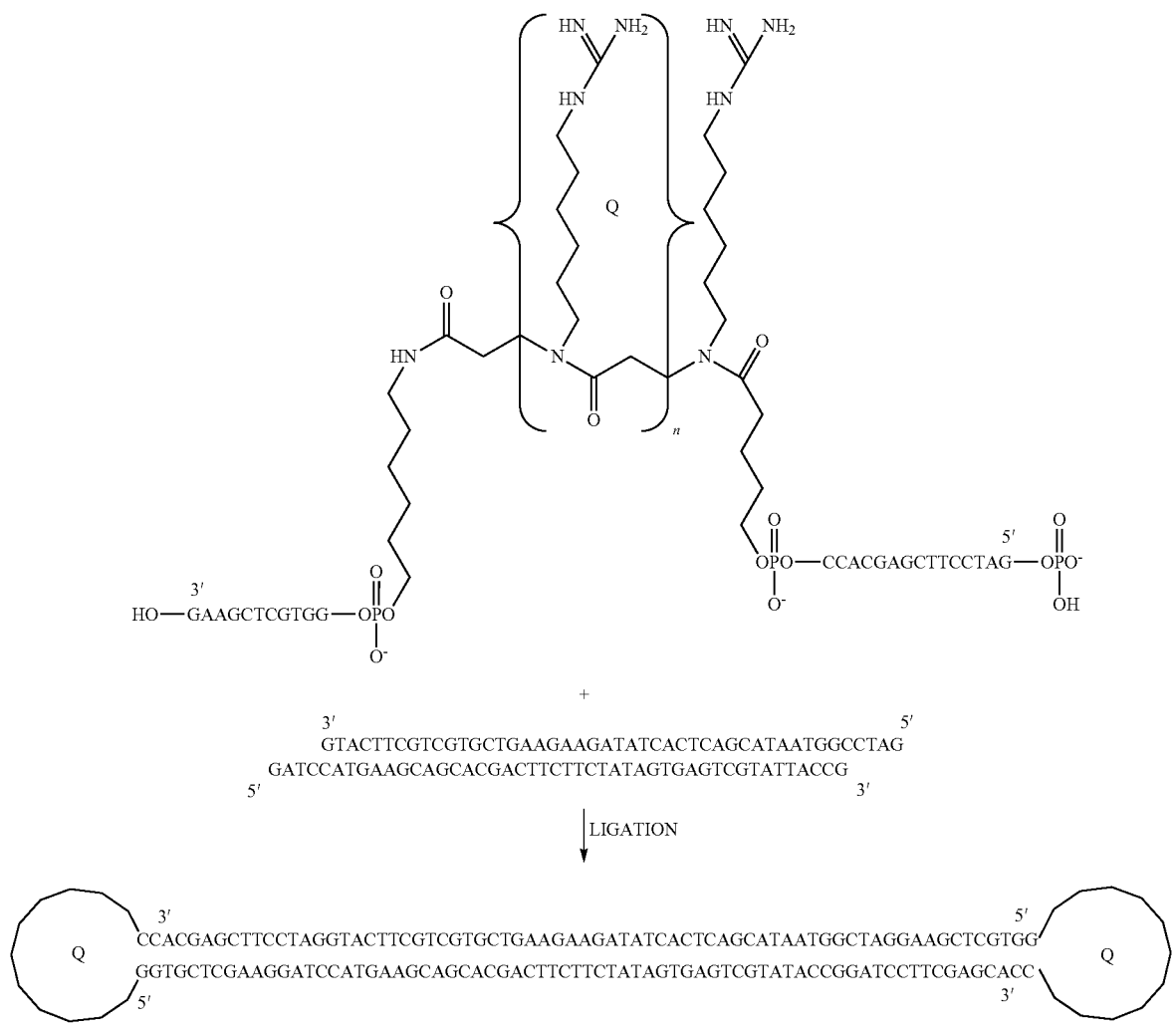

Scheme 78

Preparation of a Fluoresceinated Delivery Moiety

A Merrifield resin controlled pore glass (CPG) solid support was derivatized so as to be cleaved by at basic conditions and form Compound 53.

Compound 53

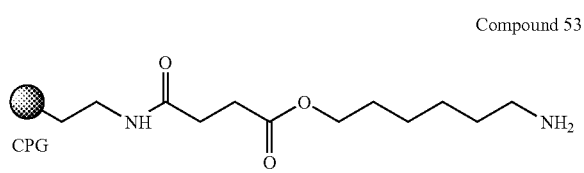

As depicted in Scheme 79 below, the synthesis of Compound 54 (see, Scheme 36 below) was carried out using a controlled pore glass (CPG) support of 1000 Å pore size, loaded at 35 mmol per gram with 6-aminohexylsuccinate. A solution of Compound 44 (20 mole equivalents with respect to Compound 53) was dissolved in dry dichloromethane (1 ml) and added through the ABI DNA synthesizer to the column containing Compound 53, followed by addition of a solution of diisopropyl carbodiimide (20 equivalents) in dichloromethane (1 ml). The mixture was allowed to react for 30 minutes and then the polymeric support was washed with methanol (5 ml) and dichloromethane (5 ml), treated with a solution of 2% dichloroacetic acid in didhloromethane (3×1 ml) for 30 seconds each time, followed by washings with methanol (10 ml) and dichloromethane (10 ml).

The addition reaction of Compound 44 was repeated to afford Compound 54, in which the number of repeating residues of Compound 44 corresponds to the number of times the addition reaction was carried out as desired. Typically, n equals 1-12, and preferably 9.

After addition of the last residue, the terminus free amine was treated with a solution of fluorescein yisothiocyanate (FITC, 5 mg) in DMSO (1 ml). To this mixture a solution of NaHCO$_3$ (1 ml) pH 8.5 was added. The reaction mixture was agitated at room temperature for 4 hours in the dark.

The polymeric support was washed with water (20 ml), methanol (20 ml) and dried with ether (20 ml). The residue was treated with concentrated ammonium hydroxide (10 ml) at 60° C. for 8 hours and the product was collected and purified on HPLC.

Scheme 79

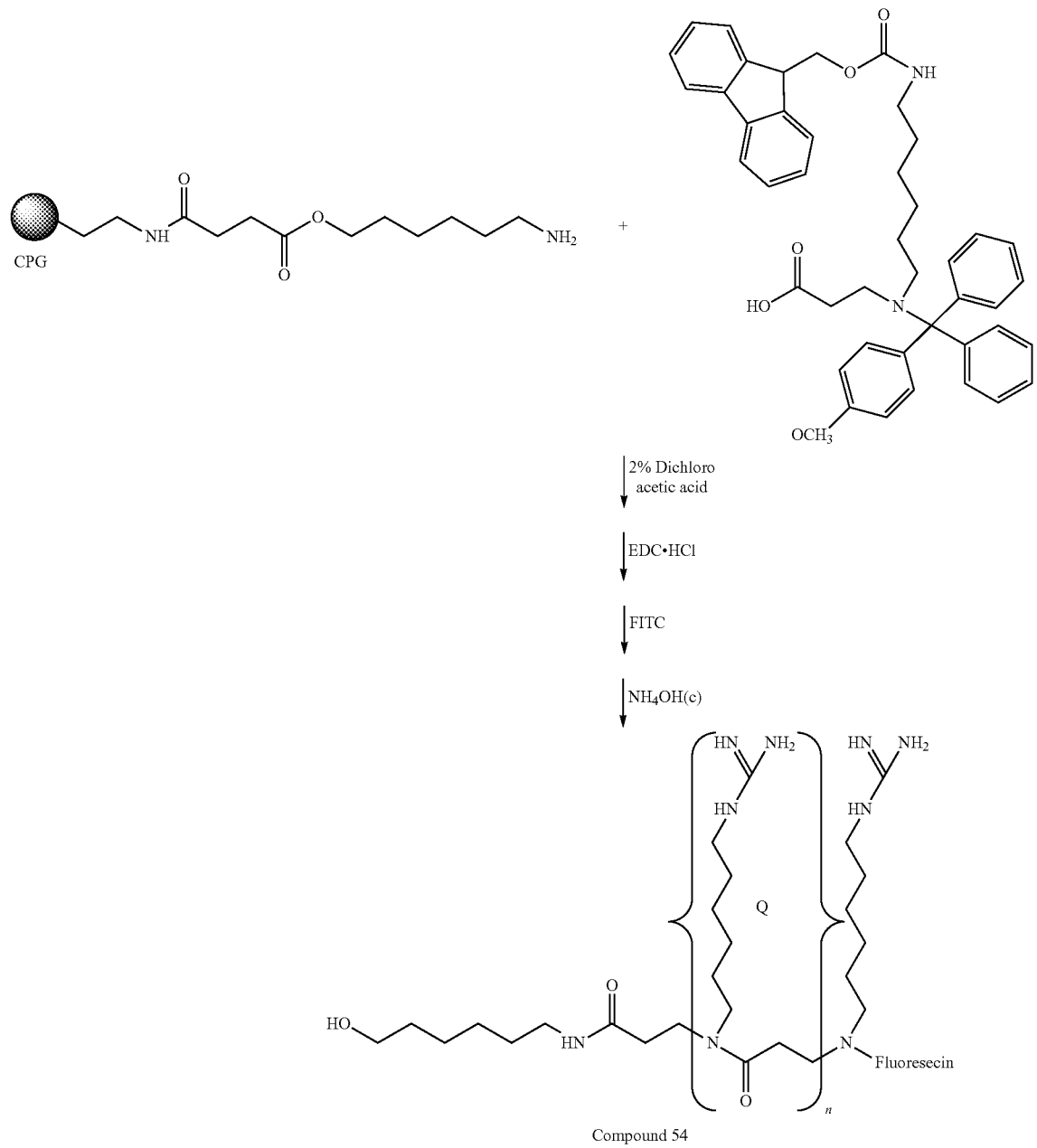

Compound 54

Preparation, Via Enzymatic Synthesis, of a DNA Plasmid Incorporating Modified Deoxynucleotides The modified deoxynucleotides for enzymatic synthesis, Compound 7-37, prepared as described hereinabove, were incorporated into a plasmid DNA using the BRL Nick Translation System.

Thus, a typical 400 µl reaction mixture contained 50 mM Tris-HCl (pH 7.8), 5 mM $MgCl_2$, 10 mM 2-mercaptoethanol, 10 µg/ml BSA, 20 µM of each of dGTP, dCTP, dTTP and Compound 8 (modified-dUTP) and/or Compound 11 (modified-dCTP) and/or Compound 29 (modified-dATP), 4 µg of a 5.4 Kb plasmid, 10 µCi of 3H-dGTP (12 Ci/mmol), 8 units of DNA polymerase I and 0.8 nanograms of DNase I. The reaction was carried out at 15° C.

At each time point of interest, 2 µl from the reaction mixture were withdrawn, spotted on glass fiber filters (GF/C), washed once with 10% trichloroacetic acid (TCA) and twice with 5% TCA, and with alcohol and was thereafter dried. The filters were loaded to a liquid scintillation counter for measurements of the progression of the polymerase reaction and the relative level of incorporation.

The plasmid was closed in the presence of three units of T4 DNA ligase (Epicentre) while cooling the reaction mixture slowly to 4° C.

The relative levels of incorporation of the modified deoxynucleotides at the 90 minute time point were 70% for $N^6$-aminohexyl dATP, 54% for Compound 8 (urocanic acid modified dUTP), 74% for Compound 29 (N$^4$-(6-aminohexyl)dCTP) and 44% for Compound 11 (urocanic acid modified dCTP).

Construction a pSDLuc Plasmid Containing Modified Nucleotides

The plasmid pSDLuc, a 5.0 kb DNA molecule in which the firefly luciferase reporter gene is under control of the SV40 early region promoter (Brasier, 1989, *Biotechniques* 7: 1116-1123), containing the modified nucleotides prepared as described above was constructed. The following modified nucleotides were used: allylamine-dUTP/dCTP (e.g., Compound 7), urocanic acid modified dUTP/dCTP (Compounds 8 and 11), histidine modified dUTP/dCTP (Compounds 10 and 13), urocanic acid modified N$^6$-aminoalkyldATP (Compound 26), histidine modified N$^6$ aminoalkyldATP (Compound 31), urocanic acid modified N$^8$-aminoalkyldGTP (Compound 23) and histidine modified N$^8$-aminoalkyldGTP (Compound 25).

Briefly, 5×105 cells per well were plated on day 0 into 12-well tissue culture plates. On day 1, after removing the medium, the solution (2 ml) containing the plasmid with the modified nucleotides was added into the cells in the well. After 4 hours of incubation at 37° C., the supernatant was removed and 2 ml of DMEM medium (GIBCO, Reufrewshire, U.K.) was added and cells were further incubated for 48 hours at 37° C.

Delivery and Activity Assays

In Vitro Transcription of the S Sequence in Dcirc-1

The in vitro transcription of the arginine-modified Dcirc-1 was carried out using the AmpliScribe T7 High Yield Transcription Kit (Epicentre Ltd.). The resulting siRNAs were isolated and purified using a 4% NuSieve GTG agarose gel (BMA Co.). The RNA duplexes were identified on the gel by co-migration with a chemically synthesized RNA duplex of the same length, and recovered from the gel by β-agarase digestion (New England Biolabs Inc.).

In Vitro Inhibition of Gene Expression by Co-Transcription of the Product of Dcirc-1

As a rapid assay for the transcribed siRNA product inhibitory function, the ability of arginine-modified Dcirc-1 to inhibit the expression of green fluorescent protein (GFP) in a transient transfection was tested. A plasmid vector containing a GFP expression vector (100 nanograms) was added to a solution of the annealed form of the arginine-modified Dcirc-1. In vitro co-transcription was carried out using the AmpliScribe. T7 High Yield Transcription Kit (Epicentre Ltd.). The expression of GFP was assessed by epifluorescence microscopy (UV excitation wavelength of 380-400 nm).

The results of the inhibitory function assay for arginine-modified Dcirc-1, which was co-transcribed by the T7 polymerase to afford the siRNAs, clearly showed the effectiveness of the siRNA to efficiently reduced GFP expression.

Cellular Uptake Assay for Compound 54 and Compounds Having Structure A

The tested compound (e.g., Compound 54 or Structure A) was dissolved in PBS buffer (pH 7.2) and its concentration was determined by absorption of fluorescein at 490 nm (ε=67,000). The accuracy of this method for determining transporter concentration was established by weighing selected samples and dissolving them in known amount of PBS buffer. The concentrations were determined by UV spectroscopy correlated with the manually weighed standards.

Jurkat cells (human T cell lines) and murine B cells (CH27) were grown in 10% FCS and DMEM and were used for the cellular uptake experiments. Varying amounts of the tested compound were added to approximately 3×106 cells in 2% FCS/PBS (combined total of 200 µl) and the cells were placed into microtiter 96-well plates and incubated for varying times at 23° C. or 4° C. The microtiter plates were thereafter centrifuged and the cells were isolated, washed with cold PBS (3×250 µl), incubated with 0.05% trypsin/0.53 mM EDTA at 37° C. for 5 minutes, washed with cold PBS, and resuspended in PBS containing 0.1% propidium iodide. The cells were analyzed using fluorescent flow cytometry (FACScan; Becton Dickinson).

Delivery of a pSDLuc Plasmid Containing Modified Nucleotides

Transfection of the modified plasmid pSDLuc, constructed as described hereinabove, (see, Scheme 80 below) into *E. coli* cells was performed by the classical DEAE dextran method, using 2.5 µg of the plasmid with 250 µg DEAE dextran in 1 ml DMEM at 37° C. One hour after transfection, the cells were washed and further incubated for 48 hours at 37° C.

Luciferase gene expression was measured by luminescence according to De Wet et al., 1987, *Mol. Cell. Biol.* 7: 725-737. The culture medium was discarded and cells were harvested upon incubation at 37° C. in PBS containing 0.2 mg/ml EDTA and 2.5 µg/ml trypsine (GIBCO) and washed three times with PBS. The homogenization buffer (200 µl; 8 mM MgCl$_2$, 1 mM dithiothreitol, 1 mM EDTA, 1% Triton X 100, 10 mg/ml bovine serum albumin and 15% glycerol, 25 mM Tris phosphate buffer, pH 7.8) was added onto the pellet, the suspension was agitated by vortex and kept for 10 minutes at 20° C., and the solution was spun down for 5 minutes at 800 g. ATP (95 µl of a 2 mM solution in the homogeneization buffer without Triton X 100) was thereafter added to 60 µl supernatant and the luminescence was recorded for 4 seconds using a luminometer (Lumat LB 9501, Berthold, Wildbach, Germany) upon automatic addition of 150 µl of a 167 µM luciferin in water.

Scheme 80

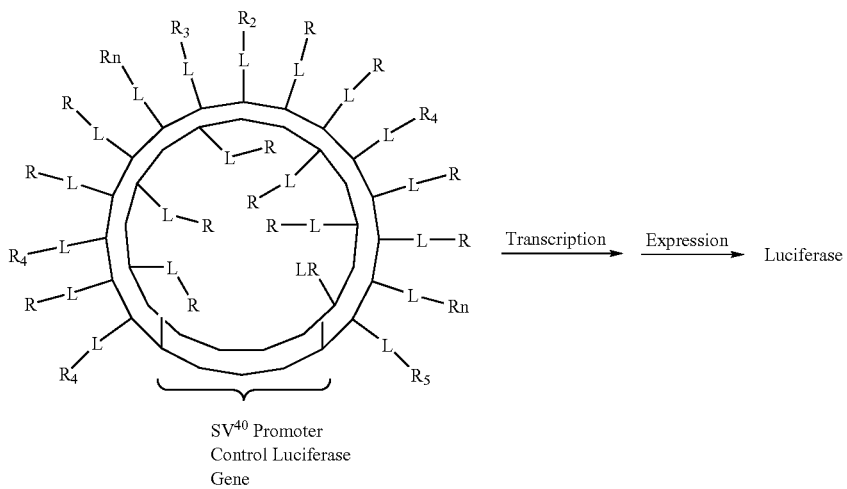

Materials for PCR

Primer: Telenius 6MW 5'-CCGACTCGAGNNNNNNNAT-GTGG-3' (SEQ ID No. 9);
Polymerase: Taq (5 U/μl, Promega, M1861);
Buffer 10×PCR buffer (Promega);
Nucleotides: 100 mM dNTPs (Boehringer, 1277049);
Dyes: Spectrum Green dUTP (1 mM, Vysis, 30-803200), Spectrum Orange dUTP (1 mM, Vysis, 30-803000);
Nucleotides stock solution for DNA amplification (Table 7):

TABLE 7

| Nucleotide | Volume (μl) | Final Concentration (mM) |
| --- | --- | --- |
| dGTP | 5 | 0.1 |
| dCTP | 5 | 0.1 |
| dATP | 5 | 0.1 |
| DTTP | 5 | 0.1 |
| dH20 | 480 | |
| Total | 500 | |

Nucleotides stock solution for DNA labeling (Table 8):

TABLE 8

| Nucleotide | Volume (μl) | Final Concentration (mM) |
| --- | --- | --- |
| dGTP | 5 | 0.1 |
| dCTP | 5 | 0.1 |
| dATP | 5 | 0.1 |
| DTTP | 3.75 | 0.075 |
| dH20 | 482.25 | 0.075 |
| Total | 500 | |

Materials for Pretreatment of Chromosome Slides $MgCl_2$, 1M (Sigma, M-1028);
Formaldehyde (Merck, 4003);
Pepsin: 10% enzyme stock solution (100 mg enzyme in 1 ml pepsin buffer);
Pepsin buffer: 50 ml of 1M $MgCl_2$ in 950 ml PBS (phosphate buffer saline).

Materials for Denaturation and Detection

Tween 20 (Merck, 109280);
Stock solution: 1 mg/ml, 2-(4-Amidinophenyl)-6-indole-carbamidine dihydrochloride (DAPI dihydrochloride, Sigma, D-9542) 1 mg, stock solution 10 mg/ml;
Anti-fade solution: Vectrashield (Vector, H-1000).

Assay of the Incorporation of a Modified Nucleotide into a Human Chromosome by Probe Labeling In order to verify the usability of the modified nucleotides of the present invention in enzymatic reactions, a DNA sequence containing the same was incorporated into a human chromosome and the ability to amplify the chromosome was assayed as described hereinbelow.

Flow sorted human chromosomes from chromosome 1 and chromosome 3 were amplified and labeled using DOP-PCR (Telenious 1992) with Spectrum Green dye conjugation to dUTP nucleotides.

For the two labeling PCR reaction 4 μl of DNA (100 ng/.mu.l) were combined with 2.5 μl of Spetrum Green dUTP. The PCR mixture for the four PCR tubes (two amplified and two amplified plus labeled) containing 1×PCR buffer (2 mM $MgCl_2$; 10 μl dNTP; 2 μM primer and 10 units of Taq DNA polymerase) was added.

The PCR was conducted at 95° C. for 2 minutes, 25 cycles of 95° C. for 1 minute, 56° C. for 1 minute and 72° C. for 4 minutes, final extension was conducted for 10 minutes at 72° C.

In the next step the two amplified unlabeled chromosomes (see, chromosome 1 in sample C and chromosome 3 in sample D in FIG. 10) and the two amplified chromosomes that were labeled with FITC dUTP (see, chromosome 1 in sample A and chromosome 3 in sample B in FIG. 10), were amplified (see, samples I, J, K and L respectively in FIG. 10) and labeled with Spectrum Orange dUTP as described before (see samples E, F, G and H respectively in FIG. 10).

For each hybridization 4 μl PCR product from each chromosome labeled in FITC (see, samples C and D in FIG. 10) and the 4 chromosomes that were labeled with Spectrum Orange dUTP (see, samples E and F in FIG. 1 from the amplified DNA without labeling) and samples G and H in FIG. 1 from the DNA that was labeled first with FITC dUTP, were combined together in a tube and precipitated in the presence of sodium acetate and 100% ethanol without the addition of suppression or carrier DNA. The dry pellet was dissolved in 5 µl of formamide and 5 µl of hybridization solution. Final concentration of the hybridization solution was: 50% formamide, 10% dexran sulfate and 2×SSC.

Denaturation, Hybridization and Washing of Chromosome Slides

Pretreatment of the chromosome slides was carried out according to standard techniques. Briefly, slides were incubated in a 10% pepsin solution for five minutes at 37° C., washed in PBS, fixed in 1% formaldehyde in a PBS/MgCl$_2$ buffer and dehydrated with a series of washes with ethanol.

The chromosomes were denatured in 70% formamide/2× SSC at 70° C. for 2 minutes, and then dehydrated with a series of washes with ethanol and air dried.

The six probes were denatured at 75° C. for five minute and then incubated at 37° C. for one hour to allow spontaneous annealing of the repetitive sequences.

Ten µl of the probe mixture were then applied to the denatured chromosome preparation, covered with a 18×18 mm cover-slip, and hybridized for 24 hours at 37° C.

The slides were washed in 0.5×SSC at 45° C. for 10 minutes and in 4×SSC/0.1% Tween 20 for 4 minutes at room temperature and then mounted in DAPI/antifade solution.

Images of the obtained slides are presented in FIGS. 11-14 and demonstrate the unrestricted hydridization of the amplified oligonucleotides incorporating modified nucleotides to chromosome 1 and 3.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An oligomeric compound having the general Formula I:

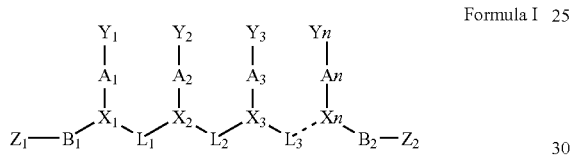

Formula I wherein:

n is an integer from 3 to 20;

each of $X_1$-$Xn$ is independently a residue of a building block of the oligomer, wherein said residue or building block is represented by the general structure:
-J-O—P(=O)(Ra)—O—;

wherein:

J is alkyl, cycloalkyl, aryl, ether, amide or carboxy;

Ra is hydrogen, hydroxyl, alkoxy, aryloxy, alkyl, phenyl, aryl, cycloalkyl, thiohydroxy, thioalkoxy or thiaryloxy;

each of $L_1$-$Ln$ is independently a first linking group or absent, wherein said first linking group is methylene, substituted or unsubstituted saturated or unsaturated $C_4$-$C_{10}$ hydrocarbon chain, or substituted or unsubstituted saturated or unsaturated $C_4$-$C_{10}$ hydrocarbon chain interrupted by at least one heteroatom selected from oxygen, nitrogen and sulfur;

each of $A_1$-$An$ is independently a second linking group attached to J or absent, wherein said second linking group is methylene, substituted or unsubstituted saturated or unsaturated $C_2$-$C_{10}$ hydrocarbon chain, or substituted or unsubstituted saturated or unsaturated $C_2$-$C_{10}$ hydrocarbon chain interrupted by at least one heteroatom selected from oxygen, nitrogen and sulfur;

each of $Y_1$-$Yn$ is independently a delivering group, wherein said delivering group is amine; guanidine, histidine or imidazole;

each of $B_1$ and $B_2$ is independently a spacer or absent, wherein said spacer is allylamine, diaminoethane, diaminohexane, substituted or unsubstituted saturated or unsaturated $C_2$-$C_{10}$ hydrocarbon chain, or substituted or unsubstituted saturated or unsaturated $C_2$-$C_{10}$ hydrocarbon chain interrupted by at least one heteroatom selected from oxygen, nitrogen and sulfur; and each of $Z_1$ and $Z_2$ is independently a reactive group capable of binding a biologically active moiety or hydrogen, provided that at least one of $Z_1$ and $Z_2$ is amine, halide, hydroxy, amide, amide, carboxy, thiol, thioamide, thiocarboxy, alkoxy, thioalkoxy, aryloxy, thioaryloxy, hydrazine, hydrazide, phosphoramidite, phosphate, phosphonate, phosphine or any combination thereof; and wherein $Z_1$, $Z_2$ and/or $Y_1$-$Y_n$ can each independently be protected by an amine protecting group selected from formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxycarbonyl ("FMOC"), nitro-veratryloxycarbonyl ("NVOC"); hydroxy protecting groups selected from benzyl, and trityl ethers as well as alkyl ethers, tetrahydropyranyl ethers, trialkylsilyl ethers, allyl ethers, monomethoxytrityl and dimethoxytrityl.

2. The compound of claim 1, wherein n is an integer from 6 to 12.

3. The compound of claim 1, wherein each of said first linking moieties is methylene ($CH_2$).

4. The compound of claim 1, comprising at least four delivering groups.

5. The compound of claim 1, wherein said biologically active moiety is selected from the group consisting of a therapeutically active agent, a labeling moiety, or any combination thereof.

6. A conjugate comprising at least one delivery moiety and at least one biologically active moiety being linked thereto, said delivery moiety being an oligomeric compound having the general Formula II:

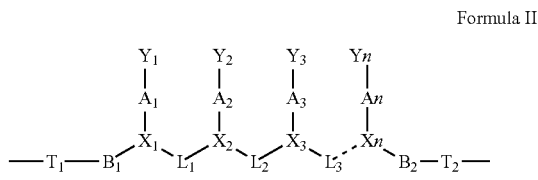

Formula II wherein:

n is an integer from 4 to 20;

each of $X_1$-Xn is independently a residue of a building block of said oligomer, wherein said residue or building block is represented by the general structure: -J-O—P(=O)(Ra)—O—;

wherein:

J is alkyl, cycloalkyl, aryl, ether, amide or carboxy;

Ra is hydrogen, hydroxyl, alkoxy, aryloxy, alkyl, phenyl, aryl, cycloalkyl, thiohydroxy, thioalkoxy or thiaryloxy;

each of $L_1$-Ln is independently a first linking group or absent, wherein said first linking group is methylene, substituted or unsubstituted saturated or unsaturated $C_4$-$C_{10}$ hydrocarbon chain, or substituted or unsubstituted saturated or unsaturated $C_4$-$C_{10}$ hydrocarbon chain interrupted by at least one heteroatom selected from oxygen, nitrogen and sulfur;

each of $A_1$-An is independently a second linking group attached to J or absent, wherein said second linking group is methylene, substituted or unsubstituted saturated or unsaturated $C_2$-$C_{10}$ hydrocarbon chain, or substituted or unsubstituted saturated or unsaturated $C_2$-$C_{10}$ hydrocarbon chain interrupted by at least one heteroatom selected from oxygen, nitrogen and sulfur;

each of $Y_1$-Yn is independently a delivering group, wherein said delivering group is amine; guanidine, histidine or imidazole;

each of $B_1$ and $B_2$ is independently a spacer or absent, wherein said spacer is allylamine, diaminoethane, diaminohexane, substituted or unsubstituted saturated or unsaturated $C_2$-$C_{10}$ hydrocarbon chain, or substituted or unsubstituted saturated or unsaturated $C_2$-$C_{10}$ hydrocarbon chain interrupted by at least one heteroatom selected from oxygen, nitrogen and sulfur; and each of $T_1$ and $T_2$ is independently a binding group binding said biologically active moiety or absent, wherein said binding group is a covalent bond selected from: amide bond, ester bond, ether bond, thioether bond, phosphate bond, or phosphodiester bond;

wherein at least one of said $T_1$ and $T_2$ is said binding group; and wherein said biologically active moiety is selected from: oligonucleotide, labeling moiety, and oligonucleotide attached to a labeling moiety.

7. The conjugate of claim 6, comprising at least one delivery moiety and at least two biologically active moieties being linked thereto via said binding groups.

8. The conjugate of claim 6, comprising at least two delivery moieties and at least two biologically active moieties being linked thereto via said binding groups.

9. The conjugate of claim 8, wherein each of said at least two biologically active moieties is attached to each of said at least two delivery moieties.

10. The conjugate of claim 8, wherein at least one of said at least two biologically active moieties is an oligonucleotide.

11. The conjugate of claim 10, wherein at least one of said at least two biologically active moieties is a second oligonucleotide being capable of hybridizing said oligonucleotide.

12. The conjugate of claim 11, wherein said second oligonucleotide is hybridized to said oligonucleotide.

13. The conjugate of claim 6, wherein at least one of said at least biologically active moieties comprises a labeling moiety.

14. A method of delivering a biologically active moiety to a cell, the method comprising:

contacting said cell with the conjugate of claim 6, thereby delivering the biologically active moiety to the cell.

15. A pharmaceutical composition comprising the conjugate of claim 6 and a pharmaceutically acceptable carrier.

16. The pharmaceutical composition of claim 15, being packaged in a packaging material and identified in print, in or on said packaging material, for use in the treatment and/or diagnosis of a condition in which delivering said biologically active moiety to a cell is beneficial.

17. A process of preparing the conjugate of claim 6, the process comprising:

providing at least one oligomeric compound having the general Formula III:

$$Z_1-B_1\underset{X_1}{\overset{\underset{V_1}{|}}{\underset{A_1}{|}}}\diagdown_{L_1}\underset{X_2}{\overset{\underset{V_2}{|}}{\underset{A_2}{|}}}\diagdown_{L_2}\underset{X_3}{\overset{\underset{V_3}{|}}{\underset{A_3}{|}}}\diagdown_{L_3}\cdots\underset{Xn}{\overset{\underset{Vn}{|}}{\underset{An}{|}}}B_2-Z_2 \qquad \text{Formula III}$$

wherein:

n is an integer from 4 to 20;

each of $X_1$-Xn is independently a residue of a building block of the oligomer, wherein said residue or building block is represented by the general structure: -J-O—P(=O)(Ra)—O—;

wherein:

J is alkyl, cycloalkyl, aryl, ether, amide or carboxy;

Ra is hydrogen, hydroxyl, alkoxy, aryloxy, alkyl, phenyl, aryl, cycloalkyl, thiohydroxy, thioalkoxy or thiaryloxy;

each of $L_1$-Ln is independently a first linking group or absent, wherein said first linking group is methylene, substituted or unsubstituted saturated or unsaturated $C_4$-$C_{10}$ hydrocarbon chain, or substituted or unsubstituted saturated or unsaturated $C_4$-$C_{10}$ hydrocarbon chain interrupted by at least one heteroatom selected from oxygen, nitrogen and sulfur;

each of $A_1$-An is independently a second linking group attached to J or absent, wherein said second linking group is methylene, substituted or unsubstituted saturated or unsaturated $C_2$-$C_{10}$ hydrocarbon chain, or substituted or unsubstituted saturated or unsaturated $C_2$-$C_{10}$ hydrocarbon chain interrupted by at least one heteroatom selected from oxygen, nitrogen and sulfur;

each of $V_1$-$Vn$ is independently a delivering group or a group capable of being converted to a delivering group, wherein said delivering group is amine, guanidine, histidine or imidazole;

each of $B_1$ and $B_2$ is independently a spacer or absent, wherein said spacer is allylamine, diaminoethane, diaminohexane, substituted or unsubstituted saturated or unsaturated $C_2$-$C_{10}$ hydrocarbon chain, or substituted or unsubstituted saturated or unsaturated $C_2$-$C_{10}$ hydrocarbon chain interrupted by at least one heteroatom selected from oxygen, nitrogen and sulfur; and each of $Z_1$ and $Z_2$ is independently a reactive group capable of binding said biologically active moiety, or hydrogen, provided that at least one of $Z_1$ and $Z_2$ is amine, halide, hydroxy, amide, amide, carboxy, thiol, thioamide, thiocarboxy, alkoxy, thioalkoxy, aryloxy, thioaryloxy, hydrazine, hydrazide, phosphoramidite, phosphate, phosphonate, phosphine or any combination thereof;

providing at least one biologically active compound having at least one functional group capable of reacting with said reactive group; and coupling said at least one biologically active compound and said compound having said Formula III, thereby obtaining the conjugate.

18. The process of claim 17, wherein said coupling is effected by reacting at least one of said reactive groups and at least one of said functional groups.

19. The process of claim 17, wherein at least one of said $V_1$-$Vn$ is a group capable of being converted to said delivering group, the process further comprising, prior to, during or subsequent to said coupling:
converting said group to a delivering group.

20. The process of claim 17, wherein at least one of said biologically active moiety and said oligomeric compound is attached to a solid support.

21. The process of claim 20, further comprising, subsequent to said coupling, detaching the conjugate from said solid support.

22. The process of claim 17, wherein providing said oligomeric compound having said general formula III comprises:
providing an oligomeric compound having a plurality of said building blocks linked therebetween; and
attaching at least one delivering group and/or a group capable of being converted to said delivering group to at least one of said building blocks.

23. The process of claim 17, wherein providing said oligomeric compound having said general formula III comprises:
providing a plurality of compounds each independently having the general formula IV:

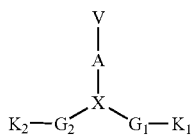

Formula IV wherein:
X is a residue of a building block of the oligomer, wherein said residue or building block is represented by the general structure: -J-O—P(=O)(Ra)—O—;
wherein:

J is alkyl, cycloalkyl, aryl, ether, amide or carboxy;

Ra is hydrogen, hydroxyl, alkoxy, aryloxy, alkyl, phenyl, aryl, cycloalkyl, thiohydroxy, thioalkoxy or thiaryloxy;

A is a linking group attached to J or absent, wherein said linking group is methylene, substituted or unsubstituted saturated or unsaturated $C_2$-$C_{10}$ hydrocarbon chain, or substituted or unsubstituted saturated or unsaturated $C_2$-$C_{10}$ hydrocarbon chain interrupted by at least one heteroatom selected from oxygen, nitrogen and sulfur;

V is a delivering group, or a group capable of being converted to said delivering group, wherein said delivering group is amine, guanidine, histidine or imidazole;

each of $G_1$ and $G_2$ is independently a linking group or absent;

$K_1$ is a first reactive group; and $K_2$ is a second reactive being capable of reacting with said first reactive group, provided that in at least one of said compounds having said general Formula III Vn is said delivering group or said group capable of being converted to said delivering group; and reacting said first reactive group and said second reactive group, thereby obtaining said oligomeric compound.

24. The process of claim 23, wherein said residue of said building block and said first reactive group form together a phosphoramidite residue.

25. The compound of claim 1, wherein said compound is represented by the following structure:

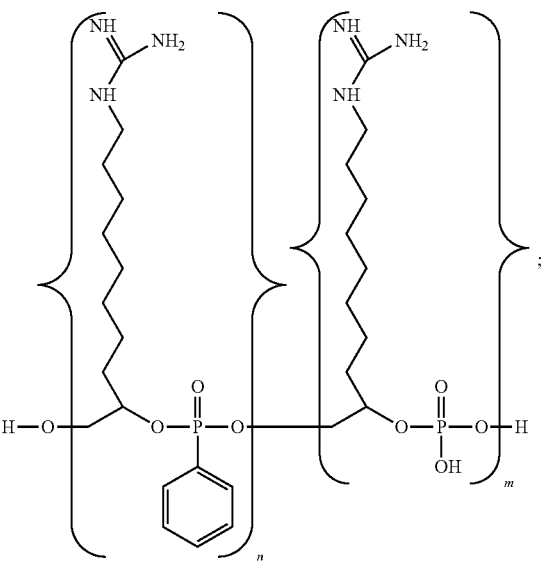

wherein each of m and n is independently an integer ranging from 0-20, and n and m cannot be both 0.

26. The conjugate according to claim 6, said conjugate is represented by the following structure:
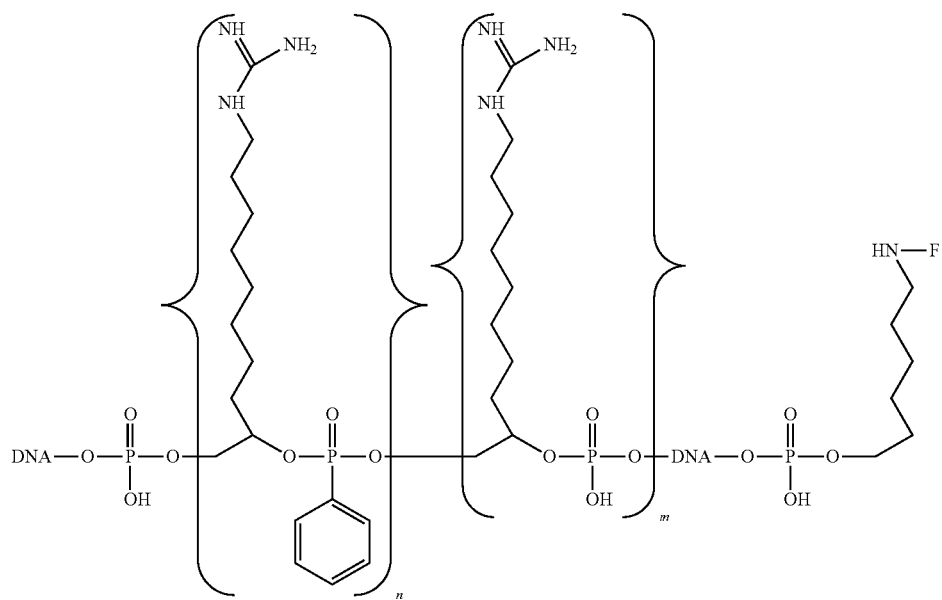
wherein each of m and n is independently an integer ranging from 0-20, and n and m cannot be both 0.
* * * * *

SEQUENCE LISTING

```
<160> NUMBER OF SEQ ID NOS: 17

<210> SEQ ID NO 1
<211> LENGTH: 11
<212> TYPE: DNA
<213> ORGANISM: Artificial sequence
<220> FEATURE:
<223> OTHER INFORMATION: Synthetic single strand olligonucleotide

<400> SEQUENCE: 1
ggtgctcgaa g                                                          11

<210> SEQ ID NO 2
<211> LENGTH: 15
<212> TYPE: DNA
<213> ORGANISM: Artificial sequence
<220> FEATURE:
<223> OTHER INFORMATION: Synthetic single strand olligonucleotide

<400> SEQUENCE: 2
gatccttcga gcacc                                                      15

<210> SEQ ID NO 3
<211> LENGTH: 13
<212> TYPE: DNA
<213> ORGANISM: Artificial sequence
<220> FEATURE:
<223> OTHER INFORMATION: Synthetic single strand olligonucleotide
<220> FEATURE:
<221> NAME/KEY: misc_feature
<222> LOCATION: (1)..(3)
<223> OTHER INFORMATION: Can be modified according to spec
<220> FEATURE:
<221> NAME/KEY: misc_feature
<222> LOCATION: (6)..(10)
<223> OTHER INFORMATION: Can be modified according to spec
<220> FEATURE:
<221> NAME/KEY: misc_feature
<222> LOCATION: (12)..(13)
```

```
<223> OTHER INFORMATION: Can be modified according to spec

<400> SEQUENCE: 3
actagttcct acc                                                          13

<210> SEQ ID NO 4
<211> LENGTH: 13
<212> TYPE: DNA
<213> ORGANISM: Artificial sequence
<220> FEATURE:
<223> OTHER INFORMATION: Synthetic single strand olligonucleotide
<220> FEATURE:
<221> NAME/KEY: misc_feature
<222> LOCATION: (2)..(4)
<223> OTHER INFORMATION: Can be modified according to spec
<220> FEATURE:
<221> NAME/KEY: misc_feature
<222> LOCATION: (6)..(7)
<223> OTHER INFORMATION: Can be modified according to spec
<220> FEATURE:
<221> NAME/KEY: misc_feature
<222> LOCATION: (10)..(13)
<223> OTHER INFORMATION: Can be modified according to spec

<400> SEQUENCE: 4
actcgttagc cct                                                          13

<210> SEQ ID NO 5
<211> LENGTH: 40
<212> TYPE: DNA
<213> ORGANISM: Artificial sequence
<220> FEATURE:
<223> OTHER INFORMATION: Synthetic single strand olligonucleotide
<220> FEATURE:
<221> NAME/KEY: misc_feature
<222> LOCATION: (3)..(3)
<223> OTHER INFORMATION: Can be modified according to spec
<220> FEATURE:
<221> NAME/KEY: misc_feature
<222> LOCATION: (6)..(6)
<223> OTHER INFORMATION: Can be modified according to spec
<220> FEATURE:
<221> NAME/KEY: misc_feature
<222> LOCATION: (8)..(8)
<223> OTHER INFORMATION: Can be modified according to spec
<220> FEATURE:
<221> NAME/KEY: misc_feature
<222> LOCATION: (11)..(12)
<223> OTHER INFORMATION: Can be modified according to spec
<220> FEATURE:
<221> NAME/KEY: misc_feature
<222> LOCATION: (15)..(16)
<223> OTHER INFORMATION: Can be modified according to spec
<220> FEATURE:
<221> NAME/KEY: misc_feature
<222> LOCATION: (18)..(18)
<223> OTHER INFORMATION: Can be modified according to spec
<220> FEATURE:
<221> NAME/KEY: misc_feature
<222> LOCATION: (27)..(28)
<223> OTHER INFORMATION: Can be modified according to spec
<220> FEATURE:
<221> NAME/KEY: misc_feature
<222> LOCATION: (30)..(30)
<223> OTHER INFORMATION: Can be modified according to spec
<220> FEATURE:
<221> NAME/KEY: misc_feature
<222> LOCATION: (35)..(36)
<223> OTHER INFORMATION: Can be modified according to spec

<400> SEQUENCE: 5
ggtaatacga ctcactatag aagaagtcgt gctgcttcat                             40

<210> SEQ ID NO 6
```

```
<211> LENGTH: 40
<212> TYPE: DNA
<213> ORGANISM: Artificial sequence
<220> FEATURE:
<223> OTHER INFORMATION: Synthetic single strand olligonucleotide
<220> FEATURE:
<221> NAME/KEY: misc_feature
<222> LOCATION: (10)..(10)
<223> OTHER INFORMATION: Can be modified according to spec
<220> FEATURE:
<221> NAME/KEY: misc_feature
<222> LOCATION: (16)..(16)
<223> OTHER INFORMATION: Can be modified according to spec
<220> FEATURE:
<221> NAME/KEY: misc_feature
<222> LOCATION: (19)..(19)
<223> OTHER INFORMATION: Can be modified according to spec
<220> FEATURE:
<221> NAME/KEY: misc_feature
<222> LOCATION: (21)..(22)
<223> OTHER INFORMATION: Can be modified according to spec
<220> FEATURE:
<221> NAME/KEY: misc_feature
<222> LOCATION: (24)..(24)
<223> OTHER INFORMATION: Can be modified according to spec
<220> FEATURE:
<221> NAME/KEY: misc_feature
<222> LOCATION: (27)..(27)
<223> OTHER INFORMATION: Can be modified according to spec
<220> FEATURE:
<221> NAME/KEY: misc_feature
<222> LOCATION: (31)..(31)
<223> OTHER INFORMATION: Can be modified according to spec
<220> FEATURE:
<221> NAME/KEY: misc_feature
<222> LOCATION: (36)..(37)
<223> OTHER INFORMATION: Can be modified according to spec

<400> SEQUENCE: 6
atgaagcagc acgacttctt ctatagtgag tcgtattacc                              40

<210> SEQ ID NO 7
<211> LENGTH: 106
<212> TYPE: DNA
<213> ORGANISM: Artificial sequence
<220> FEATURE:
<223> OTHER INFORMATION: Synthetic single strand olligonucleotide

<400> SEQUENCE: 7
actagttcct accggtaata cgactcacta tagaagaagt cgtgctgctt catactcgtt         60
agccctatga agcagcacga cttcttctat agtgagtcgt attacc                      106

<210> SEQ ID NO 8
<211> LENGTH: 16
<212> TYPE: DNA
<213> ORGANISM: Artificial sequence
<220> FEATURE:
<223> OTHER INFORMATION: Synthetic single strand olligonucleotide

<400> SEQUENCE: 8
gaactagtgg taatac                                                        16

<210> SEQ ID NO 9
<211> LENGTH: 22
<212> TYPE: DNA
<213> ORGANISM: Artificial sequence
<220> FEATURE:
<223> OTHER INFORMATION: Synthetic single strand olligonucleotide
<220> FEATURE:
<221> NAME/KEY: misc_feature
<222> LOCATION: (11)..(16)
<223> OTHER INFORMATION: n is a, c, g, or t
```

```
<400> SEQUENCE: 9
ccgactcgag nnnnnnatgt gg                                        22

<210> SEQ ID NO 10
<211> LENGTH: 46
<212> TYPE: DNA
<213> ORGANISM: Artificial sequence
<220> FEATURE:
<223> OTHER INFORMATION: Synthetic single strand olligonucleotide

<400> SEQUENCE: 10
gatccggtaa tacgactcac tatagaagaa gtcgtgctgc ttcatg               46

<210> SEQ ID NO 11
<211> LENGTH: 46
<212> TYPE: DNA
<213> ORGANISM: Artificial sequence
<220> FEATURE:
<223> OTHER INFORMATION: Synthetic single strand olligonucleotide

<400> SEQUENCE: 11
gatccatgaa gcagcacgac ttcttctata gtgagtcgta ttaccg               46

<210> SEQ ID NO 12
<211> LENGTH: 55
<212> TYPE: DNA
<213> ORGANISM: Artificial sequence
<220> FEATURE:
<223> OTHER INFORMATION: A synthetic polyether-polyacetal-RNA conjugate
<220> FEATURE:
<221> NAME/KEY: misc_feature
<222> LOCATION: (1)..(24)
<223> OTHER INFORMATION: Ribonucleic acid residue
<220> FEATURE:
<221> NAME/KEY: misc_feature
<222> LOCATION: (25)..(29)
<223> OTHER INFORMATION: Deoxyribonucleic acid residue
<220> FEATURE:
<221> NAME/KEY: misc_feature
<222> LOCATION: (30)..(53)
<223> OTHER INFORMATION: Ribonucleic acid residue
<220> FEATURE:
<221> NAME/KEY: misc_feature
<222> LOCATION: (54)..(55)
<223> OTHER INFORMATION: dT

<400> SEQUENCE: 12
cuuacguagc ucugaguacu ucgattttu cgaaguacuc agagcuacgu aagtt      55

<210> SEQ ID NO 13
<211> LENGTH: 55
<212> TYPE: DNA
<213> ORGANISM: Artificial sequence
<220> FEATURE:
<223> OTHER INFORMATION: A synthetic polyether-polyacetal-RNA conjugate
<220> FEATURE:
<221> NAME/KEY: misc_feature
<222> LOCATION: (1)..(24)
<223> OTHER INFORMATION: Ribonucleic acid residue
<220> FEATURE:
<221> NAME/KEY: misc_feature
<222> LOCATION: (13)..()
<223> OTHER INFORMATION: An uracyl base is replaced by an alkyl guanido
      group
<220> FEATURE:
<221> NAME/KEY: misc_feature
<222> LOCATION: (25)..(29)
<223> OTHER INFORMATION: Deoxyribonucleic acid residue
<220> FEATURE:
<221> NAME/KEY: misc_feature
<222> LOCATION: (30)..(53)
<223> OTHER INFORMATION: Ribonucleic acid residue
```

```
<220> FEATURE:
<221> NAME/KEY: misc_feature
<222> LOCATION: (54)..(55)
<223> OTHER INFORMATION: Deoxyribonucleic acid residue

<400> SEQUENCE: 13
cuuacguagc ucngaguacu ucgatttttu cgaaguacuc agagcuacgu aagtt          55

<210> SEQ ID NO 14
<211> LENGTH: 16
<212> TYPE: DNA
<213> ORGANISM: Artificial sequence
<220> FEATURE:
<223> OTHER INFORMATION: Synthetic single strand olligonucleotide

<400> SEQUENCE: 14
agtcctcgaa ttcagg                                                    16

<210> SEQ ID NO 15
<211> LENGTH: 16
<212> TYPE: DNA
<213> ORGANISM: Artificial sequence
<220> FEATURE:
<223> OTHER INFORMATION: Synthetic single strand olligonucleotide

<400> SEQUENCE: 15
cctgaattcg aggact                                                    16

<210> SEQ ID NO 16
<211> LENGTH: 6
<212> TYPE: DNA
<213> ORGANISM: Artificial sequence
<220> FEATURE:
<223> OTHER INFORMATION: EcoRI restriction site

<400> SEQUENCE: 16 gaattc                                                                6

<210> SEQ ID NO 17
<211> LENGTH: 55
<212> TYPE: DNA
<213> ORGANISM: Artificial sequence
<220> FEATURE:
<223> OTHER INFORMATION: A synthetic polyether-polyacetal-RNA conjugate
<220> FEATURE:
<221> NAME/KEY: misc_feature
<222> LOCATION: (1)..(24)
<223> OTHER INFORMATION: Ribonucleic acid residue
<220> FEATURE:
<221> NAME/KEY: misc_feature
<222> LOCATION: (4)..(4)
<223> OTHER INFORMATION: Can be modified according to spec
<220> FEATURE:
<221> NAME/KEY: misc_feature
<222> LOCATION: (11)..(11)
<223> OTHER INFORMATION: Can be modified according to spec
<220> FEATURE:
<221> NAME/KEY: misc_feature
<222> LOCATION: (18)..(18)
<223> OTHER INFORMATION: Can be modified according to spec
<220> FEATURE:
<221> NAME/KEY: misc_feature
<222> LOCATION: (25)..(29)
<223> OTHER INFORMATION: Deoxyribonucleic acid residue
<220> FEATURE:
<221> NAME/KEY: misc_feature
<222> LOCATION: (30)..(53)
<223> OTHER INFORMATION: Ribonucleic acid residue
<220> FEATURE:
<221> NAME/KEY: misc_feature
<222> LOCATION: (34)..(34)
<223> OTHER INFORMATION: Can be modified according to spec
```

```
<220> FEATURE:
<221> NAME/KEY: misc_feature
<222> LOCATION: (40)..(40)
<223> OTHER INFORMATION: Can be modified according to spec
<220> FEATURE:
<221> NAME/KEY: misc_feature
<222> LOCATION: (46)..(46)
<223> OTHER INFORMATION: Can be modified according to spec
<220> FEATURE:
<221> NAME/KEY: misc_feature
<222> LOCATION: (50)..(50)
<223> OTHER INFORMATION: Can be modified according to spec
<220> FEATURE:
<221> NAME/KEY: misc_feature
<222> LOCATION: (54)..(55)
<223> OTHER INFORMATION: Deoxyribonucleic acid residue

<400> SEQUENCE: 17
cuuacguagc ucugaguacu ucgatttttu cgaaguacuc agagcuacgu aagtt          55
```